United States Patent
Saltzman et al.

(10) Patent No.: US 11,136,597 B2
(45) Date of Patent: Oct. 5, 2021

(54) COMPOSITIONS FOR ENHANCING TARGETED GENE EDITING AND METHODS OF USE THEREOF

(71) Applicants: Yale University, New Haven, CT (US); Carnegie Mellon University, Pittsburgh, PA (US)

(72) Inventors: W. Mark Saltzman, New Haven, CT (US); Peter Glazer, Guilford, CT (US); Raman Bahal, Hamden, CT (US); Nicole Ali McNeer, Westport, CT (US); Danith H. Ly, Pittsburgh, PA (US); Elias Quijano, New Haven, CT (US)

(73) Assignees: Yale University, New Haven, CT (US); Carnegie Mellon University, Pittsburgh, PA (US)

( * ) Notice: Subject to any disclaimer, the term of this patent is extended or adjusted under 35 U.S.C. 154(b) by 318 days.

(21) Appl. No.: 15/434,978

(22) Filed: Feb. 16, 2017

(65) Prior Publication Data
US 2017/0283830 A1 Oct. 5, 2017

Related U.S. Application Data

(60) Provisional application No. 62/295,789, filed on Feb. 16, 2016.

(51) Int. Cl.
| | |
|---|---|
| *C07H 21/04* | (2006.01) |
| *C12N 15/90* | (2006.01) |
| *C07K 14/00* | (2006.01) |
| *C12N 15/10* | (2006.01) |
| *C12N 15/11* | (2006.01) |
| *A61K 9/16* | (2006.01) |
| *A61K 48/00* | (2006.01) |
| *C12N 15/113* | (2010.01) |

(52) U.S. Cl.
CPC .......... *C12N 15/907* (2013.01); *A61K 9/1647* (2013.01); *A61K 48/005* (2013.01); *C07K 14/003* (2013.01); *C12N 15/102* (2013.01); *C12N 15/11* (2013.01); *C12N 15/111* (2013.01); *C12N 15/113* (2013.01); *C12N 2310/15* (2013.01); *C12N 2310/152* (2013.01); *C12N 2310/318* (2013.01); *C12N 2310/3181* (2013.01); *C12N 2310/334* (2013.01); *C12N 2310/351* (2013.01); *C12N 2310/3519* (2013.01)

(58) Field of Classification Search
None
See application file for complete search history.

(56) References Cited

U.S. PATENT DOCUMENTS

| | | |
|---|---|---|
| 3,266,987 A | 8/1966 | Crowley |
| 3,832,253 A | 8/1974 | Palma |
| 3,854,480 A | 12/1974 | Zaffaroni |
| 4,452,775 A | 6/1984 | Kent |
| 4,460,563 A | 7/1984 | Calanchi |
| 4,667,013 A | 5/1987 | Reichle |
| 4,675,189 A | 6/1987 | Kent |
| 4,714,680 A | 12/1987 | Civin |
| 4,748,034 A | 5/1988 | Rham |
| 4,794,000 A | 12/1988 | Ecanow |
| 4,883,666 A | 11/1989 | Sabel |
| 4,965,204 A | 10/1990 | Civin |
| 5,034,506 A | 7/1991 | Summerton |
| 5,061,620 A | 10/1991 | Tsukamoto |
| 5,075,109 A | 12/1991 | Tice |
| 5,114,719 A | 5/1992 | Sabel |
| 5,118,528 A | 6/1992 | Fessi |
| 5,133,974 A | 7/1992 | Paradissis |
| 5,142,047 A | 8/1992 | Summerton |
| 5,176,996 A | 1/1993 | Hogan |
| 5,185,444 A | 2/1993 | Summerton |
| 5,239,660 A | 8/1993 | Ooi |
| 5,354,670 A | 10/1994 | Nickoloff |
| 5,356,802 A | 10/1994 | Chandrasegaran |

(Continued)

FOREIGN PATENT DOCUMENTS

| | | |
|---|---|---|
| EP | 0253193 | 1/1988 |
| EP | 0266099 | 5/1988 |

(Continued)

OTHER PUBLICATIONS

Agrawal, et al., "Pharmacokinetics, biodistribution, and stability of oligoeoxynucleotide phosphorothioates in mice," Proc Natl Acad Sci U S A. 88(17):7595-9 (1991).

Allison, et al., "The C-Terminal Domain of the Largest Subunit of RNA Polymerase II of *Saccharomyces cerevisiae, Drosophila melanogaster*, and Mamals: A Conserved Structure with an Essential Function," Molecular and Cellular Biology, 8(1):321-329 (1988).

(Continued)

*Primary Examiner* — Kimberly Chong
(74) *Attorney, Agent, or Firm* — PABST Patent Group LLP

(57) ABSTRACT

Compositions and methods for enhancing targeted gene editing and methods of use thereof are disclosed. In the most preferred embodiments, gene editing is carried out utilizing a gene editing composition such as triplex-forming oligonucleotides, CRISPR, zinc finger nucleases, TALENS, or others, in combination with a gene modification potentiating agent such as stem cell factor (SCF), a CHK1 or ATR inhibitor, or a combination thereof. A particular preferred gene editing composition is triplex-forming peptide nucleic acids (PNAs) substituted at the γ position for increased DNA binding affinity. Nanoparticle compositions for intracellular delivery of the gene editing composition are also provided and particular advantageous for use with in vivo applications.

30 Claims, 21 Drawing Sheets
Specification includes a Sequence Listing.

(56) References Cited

U.S. PATENT DOCUMENTS

| | | |
|---|---|---|
| 5,407,686 A | 4/1995 | Patel |
| 5,422,251 A | 6/1995 | Fresco |
| 5,436,150 A | 7/1995 | Chandrasegaran |
| 5,487,994 A | 1/1996 | Chandrasegaran |
| 5,527,675 A | 6/1996 | Coull |
| 5,539,082 A | 7/1996 | Nielsen |
| 5,601,835 A | 2/1997 | Sabel |
| 5,623,049 A | 4/1997 | Lobberding |
| 5,643,741 A | 7/1997 | Tsukamoto |
| 5,665,541 A | 9/1997 | Miller |
| 5,677,136 A | 10/1997 | Simmons |
| 5,698,546 A | 12/1997 | Bridger |
| 5,714,331 A | 2/1998 | Buchardt |
| 5,716,827 A | 2/1998 | Tsukamoto |
| 5,736,152 A | 4/1998 | Dunn |
| 5,736,336 A | 4/1998 | Buchardt |
| 5,739,308 A | 4/1998 | Kandimalla |
| 5,750,397 A | 5/1998 | Tsukamoto |
| 5,759,793 A | 6/1998 | Schwartz |
| 5,773,571 A | 6/1998 | Nielsen |
| 5,776,744 A | 7/1998 | Glazer |
| 5,786,461 A | 7/1998 | Buchardt |
| 5,786,571 A | 7/1998 | Bethel |
| 5,854,033 A | 12/1998 | Lizardi |
| 5,866,361 A | 2/1999 | Dujon |
| 5,932,711 A | 8/1999 | Boles |
| 5,945,337 A | 8/1999 | Brown |
| 5,962,426 A | 10/1999 | Glazer |
| 6,010,908 A | 1/2000 | Gruenert |
| 6,140,081 A | 10/2000 | Barbas |
| 6,261,841 B1 | 7/2001 | Cohen |
| 6,303,376 B1 | 10/2001 | Glazer |
| 6,326,479 B1 | 12/2001 | Gildea |
| 6,331,617 B1 | 12/2001 | Weeks |
| 6,363,746 B1 | 4/2002 | Wei |
| 6,422,251 B1 | 7/2002 | Tseng |
| 6,441,130 B1 | 8/2002 | Egholm |
| 6,453,242 B1 | 9/2002 | Eisenberg |
| 6,509,323 B1 | 1/2003 | Davis |
| 6,534,261 B1 | 3/2003 | Cox |
| 6,610,512 B1 | 8/2003 | Barbas |
| 6,632,919 B1 | 10/2003 | Nielsen |
| 6,686,463 B2 | 2/2004 | Beigelman |
| 6,746,838 B1 | 6/2004 | Choo |
| 6,770,442 B2 | 8/2004 | Gildea |
| 6,866,997 B1 | 3/2005 | Choo |
| 6,919,208 B2 | 7/2005 | Levy |
| 7,067,617 B2 | 6/2006 | Barbas |
| 7,078,389 B2 | 7/2006 | Glazer |
| 7,256,275 B2 | 8/2007 | Coull |
| 7,279,463 B2 | 10/2007 | Glazer |
| 7,534,448 B2 | 5/2009 | Saltzman |
| 7,534,449 B2 | 5/2009 | Saltzman |
| 7,550,154 B2 | 6/2009 | Saltzman |
| 7,566,535 B2 | 7/2009 | Kmiec |
| 8,309,356 B2 | 11/2012 | Glazer |
| 8,658,608 B2 | 2/2014 | Glazer |
| 8,889,117 B2 | 11/2014 | Mellman |
| 9,193,758 B2 | 11/2015 | Ly |
| 9,220,698 B2 | 12/2015 | Ault |
| 9,272,043 B2 | 3/2016 | Saltzman |
| 9,317,102 B2 | 4/2016 | Kanchana |
| 9,501,364 B1 | 11/2016 | Bushman |
| 9,501,365 B2 | 11/2016 | Parab |
| 9,526,136 B1 | 12/2016 | Ramabhadran |
| 9,617,074 B2 | 4/2017 | Hellenbrand |
| 9,834,945 B2 | 12/2017 | Crumley |
| 2002/0165356 A1 | 11/2002 | Barbas |
| 2003/0044978 A1 | 3/2003 | Young |
| 2003/0113894 A1 | 6/2003 | Selden |
| 2003/0148352 A1 | 8/2003 | Glazer |
| 2003/0211612 A1* | 11/2003 | Seidman ............ C12N 15/01 435/455 |
| 2004/0006035 A1 | 1/2004 | Macejak |
| 2004/0197892 A1 | 10/2004 | Moore |
| 2004/0241651 A1 | 12/2004 | Olek |
| 2006/0045874 A1 | 3/2006 | Bedwell |
| 2007/0154989 A1 | 7/2007 | Barbas |
| 2007/0213269 A1 | 9/2007 | Barbas |
| 2007/0219122 A1 | 9/2007 | Glazer |
| 2008/0050920 A1 | 2/2008 | Kawahara |
| 2009/0239789 A1 | 9/2009 | Saltzman |
| 2009/0269397 A1 | 10/2009 | Saltzman |
| 2010/0151436 A1 | 6/2010 | Fong |
| 2010/0172882 A1 | 7/2010 | Glazer |
| 2011/0008451 A1 | 1/2011 | Saltzman |
| 2011/0145940 A1 | 6/2011 | Voytas |
| 2011/0262406 A1* | 10/2011 | del Campo ............ C12N 15/111 424/93.7 |
| 2011/0268810 A1 | 11/2011 | Saltzman |
| 2011/0293585 A1 | 12/2011 | del Campo |
| 2014/0128570 A1* | 5/2014 | Ly ............ C07D 239/47 530/326 |
| 2014/0255384 A1 | 9/2014 | Frey, II |
| 2014/0342003 A1 | 11/2014 | Saltzman |
| 2015/0057505 A1 | 2/2015 | Bangera |
| 2015/0073041 A1 | 3/2015 | Saltzman |
| 2015/0118311 A1 | 4/2015 | Zhou |
| 2015/0125384 A1 | 5/2015 | Mellman |
| 2016/0251477 A1 | 9/2016 | Cui |
| 2016/0263875 A1 | 9/2016 | Ueno |
| 2017/0000737 A1 | 1/2017 | Deng |
| 2017/0266119 A1 | 9/2017 | Deng |
| 2017/0283830 A1 | 10/2017 | Saltzman |
| 2020/0113821 A1 | 4/2020 | Saltzman |
| 2020/0308590 A1 | 10/2020 | Glazer |

FOREIGN PATENT DOCUMENTS

| | | |
|---|---|---|
| EP | 0375408 | 6/1990 |
| EP | 2754684 | 7/2014 |
| EP | 3388517 | 10/2018 |
| GB | 929 401 | 6/1963 |
| GB | B929401 | 6/1963 |
| WO | 0375408 | 6/1990 |
| WO | 92/20698 | 11/1992 |
| WO | 9220698 | 11/1992 |
| WO | 93/012096 | 6/1993 |
| WO | 93012096 | 6/1993 |
| WO | 93/17102 | 9/1993 |
| WO | 9317102 | 9/1993 |
| WO | 95/001364 | 1/1995 |
| WO | 95/013650 | 1/1995 |
| WO | 1995/001364 | 1/1995 |
| WO | 95001364 | 1/1995 |
| WO | 95013650 | 1/1995 |
| WO | 1995001364 | 1/1995 |
| WO | 95/26136 | 10/1995 |
| WO | 9526136 | 10/1995 |
| WO | 96/02558 | 2/1996 |
| WO | 9602558 | 2/1996 |
| WO | 96039195 | 2/1996 |
| WO | 1996004000 | 2/1996 |
| WO | 96/17074 | 6/1996 |
| WO | 9617074 | 6/1996 |
| WO | 96/039195 | 12/1996 |
| WO | 96/040271 | 12/1996 |
| WO | 96/040898 | 12/1996 |
| WO | 96040271 | 12/1996 |
| WO | 96040898 | 12/1996 |
| WO | 98/34945 | 8/1998 |
| WO | 9834945 | 8/1998 |
| WO | 98/053059 | 11/1998 |
| WO | 98053059 | 11/1998 |
| WO | 1996/004000 | 2/2000 |
| WO | 0022113 | 4/2000 |
| WO | 0022114 | 4/2000 |
| WO | 0125419 | 4/2001 |
| WO | 2002/010142 | 2/2002 |
| WO | 2002010142 | 2/2002 |
| WO | 2003016496 | 2/2003 |
| WO | 2003/052071 | 6/2003 |
| WO | 2003052071 | 6/2003 |
| WO | 2003/016496 | 12/2003 |

(56) References Cited

FOREIGN PATENT DOCUMENTS

| WO | 2005/108622 | 11/2005 |
|---|---|---|
| WO | 2005108622 | 11/2005 |
| WO | 2008/086529 | 7/2008 |
| WO | 2008086529 | 7/2008 |
| WO | 2010/123983 | 10/2010 |
| WO | 2010123983 | 10/2010 |
| WO | 2011/053989 | 5/2011 |
| WO | 2011053989 | 5/2011 |
| WO | 2011/072246 | 6/2011 |
| WO | 2011072246 | 6/2011 |
| WO | 2011/133802 | 10/2011 |
| WO | 2011/133803 | 10/2011 |
| WO | 2011133802 | 10/2011 |
| WO | 2011133803 | 10/2011 |
| WO | 2012/085554 | 6/2012 |
| WO | 2012085554 | 6/2012 |
| WO | 2012/138955 | 10/2012 |
| WO | 2012138955 | 10/2012 |
| WO | 2013/082529 | 6/2013 |
| WO | 2013082529 | 6/2013 |
| WO | 2013/176772 | 11/2013 |
| WO | 2013176772 | 11/2013 |
| WO | 2014/018423 | 1/2014 |
| WO | 2014018423 | 6/2014 |
| WO | 2014/110020 | 7/2014 |
| WO | 2014110020 | 7/2014 |
| WO | 2015/148716 | 10/2015 |
| WO | 2015148716 | 10/2015 |
| WO | 2015/172149 | 11/2015 |
| WO | 2015/172153 | 11/2015 |
| WO | 2015172149 | 11/2015 |
| WO | 2015172153 | 11/2015 |
| WO | 2016/081621 | 5/2016 |
| WO | 2016081621 | 5/2016 |
| WO | 2016/183209 | 11/2016 |
| WO | 2016/183217 | 11/2016 |
| WO | 2016183209 | 11/2016 |
| WO | 2016183217 | 11/2016 |
| WO | 2017/143042 | 8/2017 |
| WO | 2017/143061 | 8/2017 |
| WO | 2017143042 | 8/2017 |
| WO | 2017143061 | 8/2017 |
| WO | 2018/175927 | 9/2018 |
| WO | 2018175927 | 9/2018 |
| WO | 2018/187493 | 10/2018 |
| WO | 2018187493 | 10/2018 |

OTHER PUBLICATIONS

Asensio, et al. "Thermodynamic, kinetic, and conformational properties of a parallel intermolecular DNA triplex containing 5' and 3' junctions", Biochemistry, 37(43):15188-98 (1998).
Asensio, et al., "The Contribution of Cytosine Protonation to the Stability of Parallel DNA Triple Helices," J. Mol. Biol., 275(5): 811-822 (1998).
Baron, et al., "Localization of the Centrin-Related 165,000—M.sub.r Protein of PtK.sub.2 Cells During the Cell Cycle," Cell Motil. and the Cytoskel. 18:1-14 (1991).
Barre, et al., "Unambiguous demonstration of triple-helix-directed gene modification," Proc. Natl. Acad. Sci. USA 97, 3084 (2000).
Baumann, et al., "Role of the human RAD51 protein in homologous recombination and double-stranded-break repair," Trends Biochem Sci 23(7):247-251 (1998).
Beal & Dervan ,"Second Structural Motif for Recognition of DNA by Oligonucleotide-Directed Triple-Helix Formation," Science 251:1360-1363 (1991).
Beal & Dervan, "The Influence of Single Base Triplet Changes on the Stability of a Pur.Pur.Pyr Triple Helix Determined by Affinity Cleaving," Nucleic Acids Res. 20(11): 2773-2776 (1992).
Beesley, et al., "Mutational analysis of 85 mucopolysaccharidosis type I families: frequency of known mutations, identification of 17 novel mutations and in vitro expression of missense mutations", Human Genetics, 109(5):503-511 (2001).

Belousov, et al., "Triplex targeting of a native gene in permeabilized intact cells: covalent modification of the gene for the chemokine receptor CCR5," Nucleic Acids Res., 26(5):1324-8 (1998).
Bennett & Davis, "Erythrocyte ankyrin: Immunoreactive analogues are associated with mitotic structures in cultured cells and with microtubules in brain," Proc. Natl. Acad. Sci. USA. 78: 7550-7554 (1981).
Bindra & Glazer, "Co-repression of mismatch repair gene expression by hypoxia in cancer cells: role of the Myc/Max network", Cancer Lett, 252(1):93-103 (2007).
Bindra et al., "Hypoxia-induced down-regulation of BRCA1 expression by E2Fs", Cancer Res, 65(24):11597-604, (2005).
Blume, et al., "Triple helix formation by purine-rich oligonucleotides targeted to the human dihydrofolate reductase promoter", Nucleic Acids Res., 20(7):1777-84 (1992).
Bramlage, et al., "Designing ribozymes for the inhibition of gene expression," Trends Biotechnol. 16, 434 (1998).
Bredberg, et al., "Psoralen adducts in a shuttle vector plasmid propagated in primate cells: high mutagenicity of DNA cross-links", Carcinogenesis 8(12):1923-27 (1987).
Bregman et al., "Cytostellin distributes to nuclear regions enriched with splicing factors," J Cell Sci. 107 (Pt 3):387-96 (1994).
Brenneman, et al., "Stimulation of intrachromosomal homologous recombination in human cells by electroporation with site-specific endonucleases," Proc. Natl. Acad. Sci. USA 93(8): 3608-12 (1996).
Campbell, et al., "Homologous recombination involving small single-stranded oligonucleotides in human cells," New Biol. 1(2):223-7 (1989).
Capecchi, "Altering the genome by homologous recombination," Science 244(4910): 1288-1292 (1989).
Carrington, et al., "Novel alleles of the chemokine-receptor gene CCR5.", Am. J. Hum. Genet., 61:1261-1267 (1997).
Chan, et al., "Targeted correction of an episomal gene in mammalian cells by a short DNA fragment tethered to a triplex-forming oligonucleotide," J. Biol. Chem. 274(17): 11541-11548 (1999).
Chan, et al., "Triplex DNA: Fundamentals, Advances, and Potential Applications for Gene Therapy," J. Mol. Med. 75: 267-282 (1997).
Chen, et al., "Ethyl carbamate metabolism: in vivo inhibitors and in vitro enzymatic systems." Drug Metab. Dispos. 18, 815 (1990).
Chen, et al., "In Vivo Expression of Single-Stranded DNA in Mammalian Cells with DNA Enzyme Sequences Targeted to C-raf," Antisense Nucleic Acid Drug Dev. 10: 415-422 (2000).
Cole-Strauss, et al., "Correction of the mutation responsible for sickle cell anemia by an RNA-DNA oligonucleotide.", Science, 273(5280): 1386-1389.
Connell, et al., "Automated DNA sequence analysis." BioTechniques 5:342 (1987).
Cooney, et al., "Site-Specific Oligonucleotide Binding Represses Transcription of the Human c-myc Gene in Vitro," Science 241:456 (1988).
Cuenoud, et al., "Dual recognition of double-stranded DNA by 2'-aminoethoxy-modified oligonucleotides", Angew. Chem. Int. Ed., 37:1288-1291 (1998).
Culver et al., "Correction of chromosomal point mutations in human cells with bifunctional oligonucleotides", Nature Biotechnology, 17(10):989-993 (1999).
Dagle, et al., "Positively charged oligonucleotides overcome potassium-mediated inhibition of triplex DNA formation", Nucleic Acids Res., 24(11):2143-9 (1996).
Dahmus, "Phosphorylation of Eukaryotic DNA-dependent RNA Polymerase," J. Biol. Chem. 256:3332-3339 (1981).
Di Domenico, et al., "Gene Therapy for a Mucopolysaccharidosis Type I Murine Model with Lentiviral-IDUA Vector", Human Gene Therapy, 16(1):81-90 2005).
Duval-Valentin, et al., "Specific Inhibition of Transcription by Triple Helix-Forming Oligonucleotides," Proc. Natl. Acad. Sci. USA 89:504 (1992).
Egholm, et al., "Efficient pH-independent sequence-specific DNA binding by pseudoisocytosine-containing bis-PNA.", Nucl. Acids Res., 23(2):217-222 (1995).
Fakan & Bernhard, "Localization of Rapidly and Slowly Labelled Nuclear RNA as Visualized by High Resolution Autoradiography," Exp. Cell Res. 67:129-141 (1971).

(56) References Cited

OTHER PUBLICATIONS

Fakan & Nobis, "Ultrastructural Localization of Transcription Sites and of RNA Distribution During the Cell Cycle of Synchronized Cho Cells," Exp. Cell Res. 113:327-337 (1978).
Fakan & Puvion, "The Ultrastructural Visualization of Nucleolar and Extranucleolar RNA Synthesis and Distribution," Int. Rev. Cytol.. 65:255-99 (1980).
Fakan, et al., "Localization and Characterization of Newly Synthesized Nuclear RNA in Isolated Rat Hepatocytes," Exp. Cell. Res. 99:155-164 (1976).
Famulok, "Oligonucleotide aptamers that recognize small molecules," Curr. Opin. Struct. Biol. 9, 324 (1999).
Faria, et al., "Targeted Inhibition of Transcription Elongation in Cells Mediated by Triplex-Forming Oligonucleotides," Proc. Natl. Acad. Sci. USA, 97: 3862-3867 (2000).
Faruqi, et al., "Triple-helix formation induces recombination in mammalian cells via a nucleotide excision repair-dependent pathway," Mol Cell Biol 20(3): 990-1000 (2000).
Faruqi, et al., "Recombination induced by triple helix-targeted DNA damage in mammalian cells", Mol. Cell. Biol. 16: 6820-6828, (1996).
Francois et al., "Sequence-Specific Recognition and Cleavage of Duplex DNA via Triple-Helix Formation by Oligonucleotides Covalently Linked to a Phenanthroline-Copper Chelate," Proc. Natl. Acad. Sci. USA 86:9702 (1989).
Galderisi, et al., "Antisense oligonucleotides as therapeutic agents," J. Cell Physiol. 181, 251 (1999).
Gasparro, et al., "Site-specific targeting of Psoralen Photoadducts with a Triple Helix-Forming Oligonucleotide: Characterization of Psoralen Monoadduct and Crosslink Formation," Nucleic Acids Research, 22(14):2845-2852 (1994).
Gasparro, et al., "Photoactivatable antisense DNA: suppression of ampicillin resistance in normally resistant *Escherichia coli*.," Antisense Res. Dev. 1:117-140 (1991).
Gasparro, et al.,"Rapid and sensitive analysis of 8-methoxypsoralen in plasma," J. Invest. Derm. 90:234-236 (1988).
Gerace, et al., "Immunocytochemical Localization of the Major Polypeptides of the Nuclear Pore Complex—Lamina Fraction," J. Cell Biol. 79:546-566 (1978).
Gia, et al., "Sequence specificity of psoralen photobinding to DNA: a quantitative approach," Biochemistry 31:11818-11822 (1992).
Giovannangeli, et al., "Oligodeoxynucleotide-directed photo-induced cross-linking of HIV proviral DNA via triple-ihelix formation," Nucleic Acids Res. 20:4275-4281 (1992).
Giovannangeli, et al., "Triple-helix formation by oligonucleotides containing the three bases thymine, cytosine, and guanine," Proc. Natl. Acad. Sci. USA 89:8631-8635 (1992B).
Giovannangeli, et al., "Triplex-forming molecules for modulation of DNA information processing," Curr. Opin. Mol. Ther. 2(3): 288-296 (2000).
Glazer, et al., "Detection and Analysis of UV-induced Mutations in Mammalian Cell DNA Using a Phage Suttle Vector," Proc. Natl. Acad. Sci. 83:1041-1044 (1986).
Glazer, et al., "DNA mismatch repair detected in human cell extracts," Mol. Cell. Biol. 7:218 (1987).
Goncz, et al., "Site-directed alteration of genomic DNA by small-fragment homologous replacement," Methods Mol. Biol. 133:85-89 (2000).
Good, et al., "Progress in developing PNA as a gene-targeted drug," Antisense Nucleic Acid Drug Dev. 7(4):431-7 (1997).
Gordenin, et al., "Yeast ARMs (DNA at-risk motifs) can reveal sources of genome instability," Mutat. Res. 400(1-2)45-58 (1998).
Gorman and Glazer, "Directed gene modification via triple helix formation," Curr. Mol. Med., 1(3): 391-399 (2001).
Gorman, et al., "Stable Alteration of Pre-mRNA Splicing Patterns by Modified U7 Small Nuclear RNAs," Proc. Natl. Acad. Sci. USA, 95: 4929-4934 (1998).
Gottesfeld, et al., "Regulation of gene expression by small molecules" Nature 387(6629):202-5 (1997).
Grigoriev, et al., "A Triple-Helix-Forming Oligonucleotide-Intercalator Conjugate Acts as a Transcriptional Repressor via Inhibition of NF kB Binding to Interleukin-2 Receptor ☐ Regulatory Sequence," J. of Biological Chem. 267:3389 (1992B).
Grigoriev, et al., "Inhibition of Gene Expression by Triple Helix-directed DNA Cross-linking at Specific Sites," Proceedings of the National Academy of Sciences of USA, 90(8):3501-3505 (1993).
Grigoriev, et al., "Oligodeoxynucleotide-directed Photo-induced Cross-linking of HIV Proviral DNA via Triple-helix Formation," Nucleic Acids Research, 20(16):4275-4281 (1992A).
Gura, "Antisense has growing pains," Science 270:575-77 (1995).
Hanawalt, "Transcription-coupled repair and human diseases," Science 266(5193): 1957-1958 (1994).
Hanson, et al., "Analysis of biological selections for high-efficiency gene targeting," Mol. Cell. Biol. 15(1):45-51 (1995).
Harding, "NMR Studies on YSPTSPSY: Implications for the Design of DNA Bisintercalators," Journal of Medicinal Chemistry, 35:4658-4664 (1992).
Hartley, et al., "Electrophoretic and chromatographic separation methods used to reveal interstrand crosslinking of nucleic acids", J. Chromatogr., 618(1-2):277-88 (1993).
Havre & Glazer, "Targeted mutagenesis of simian virus 40 DNA mediated by a triple helix-forming oligonucleotide," J. Virol. 67(12):7324-31 (1993A).
Havre, et al., "Targed Mutagenesis of DNA Using Triple Helix-forming Oligonucleotides Linked to Psoralen," Proc. Natl. Acad. Sci. USA, 90(16):7879-7883 (1993).
Helene, "Sequence-selective recognition and cleavage of double-helical DNA," Curr. Opinion Biotechnology 4:29-36 (1993).
Helene, et al., "The anti-gene strategy: control of gene expression by triplex-forming-oligonucleotides," Anticancer Drug Des. 6(6):569-84 (1991).
Henry & Hodge, "Nuclear Matrix: A Cell-Cycle-Dependent Site of Increased Intranuclear Protein Phosphorylation," Eur. J. Biochem. 133:23-29 (1983).
Hirt, et al., "Selective extraction of polyoma DNA from infected mouse cell cultures" J. Mol. Biol. 26:365-369 (1967).
Horne, et al., "Recognition of Mixed-Sequence Duplex DNA by Alternate-Strand Triple-Helix Formation", J. Am. Chem. Soc., 112:2435-2437 (1990).
Hu, et al., "Reaction parameters pf targeted gene repair in mammalian cells", Mol. Biotech., 29:197-210 (2005).
Huang & Spector, "Nascent pre-mRNA transcripts are associated with nuclear regions enriched in splicing factors," Genes and Dev. 5:2288 (1991).
Igoucheva, et al., "Transcription affects formation and processing of intermediates in oligonucleotide-mediated gene alteration", Nucleic Acid Res., 31:2659-2670 (2003).
Ito, et al., "Sequence-specific DNA purification by triplex affinity capture," Proc. Natl. Acad. Sci. USA 89:495 (1992).
Iverson, et al., "In vivo studies with phosphorothioate oligonucleotides: pharmacokinetics prologue," Anticancer Drug Des. 6(6):531-8 (1991).
Izvolsky, et al., "Sequence-specific protection of duplex DNA against restriction and methylation enzymes by pseudocomplementary PNAs", Biochemistry, 10908-10913 (2000).
Jackson, et al., "Visualization of focal sites of transcription within human nuclei," EMBO 12:1059-1065 (1993).
Jagodzinski, "Enhanced human immunodeficiency virus infection in macrophages by high-molecular-weight dextran sulfate is associated with conformational changes of gp120 and expression of the CCR5 receptor", Viral Immunol, 12:23 (1999).
Jakubczak, et al., "Analysis of genetic instability during mammary tumor progression using a novel selection-based assay for in vivo mutations in a bacteriophage lambda transgene target," Proc. Natl. Acad. Sci. USA 93:9073-9078 (1996).
James, et al., "Towards gene-inhibition therapy: a review of progress and prospects in the field of antiviral antisense nucleic acids and ribozymes," Antiviral Chemistry & Chemotherapy 2:191-214 (1991).
Jasin "Genetic manipulation of genomes with rare-cutting endonucleasis", Trends Genet., 12:224-228 (1996).
Jepsen, et al., "LNA-antisense rivals siRNA for gene silencing", Curr. Opin. Drug Discov. Devel., 7(2):188-94 (2004).

(56) References Cited

OTHER PUBLICATIONS

Jones & Wood, "Preferential binding of the xeroderma pigmentosum group A complementing protein to damaged DNA," Biochemistry 32(45):12096-104 (1993).
Karen, et al., "Angiokeratoma corporis diffusum (Fabry disease)", Dermatol. Online J., 11(4): 8 (2005).
Khiat, et al., "Structural Differences Between the Free and Bound States of DNA-Bisintercalating Peptide YSPTSPSY," Journal of Medicinal Chemistry, 39(21):2495 (1996).
Kim, et al., "Efficient sequence-directed psoralen targeting using pseudocomplementary peptide nucleic acids", Bioconjug. Chem., 18:567-572 (2007).
Kim, et al., "Inhibition of Transcription of the Human c-myc Protooncogene by Intermolecular Triplex," Biochemistry 37: 2299-304 (1998).
Kim, et al., "Site-directed gene mutation at mixed sequence targets by psoralen-conjugated pseudo-complementary peptide nucleic acids", Nucleic Acids, 35:7604-7613 (2007B).
Kitagawa, et al., "Enzyme coupled immunoassay of insulin using a novel coupling reagent." J. Biochem. 79:233-236 (1976).
Knauert, et al., "Distance and affinity dependence of triplex-induced recombination." Biochemistry, 44:3856-3864 (2005).
Knauert, et al., "Triplex-stimulated intermolecular recombination at a single-copy genomic target", Mol. Therapy, 14:392-400 (2006).
Kong, "Btrim: a fast, lightweight adapter and quality trimming program for next-generation sequencing technologies," Genomics, 98:152-153 (2011).
Konopka & Duzgunes, "Expression of CD4 controls the susceptibility of THP-1 cells to infection by R5 and X4 HIV type 1 isolates", AIDS Res Hum Retroviruses, 18(2):123-31 (2002).
Kramer, et al., "Monoclonal Antibody Directed Against RNA Polymerase II of *Drosophila melanogaster*," Molec. Gen. Genet. 180:193-199 (1980).
Kuhn, et al., "An experimental study of mechanism and specificity of peptide nucleic acid (PNA) binding to duplex DNA.", J. Mol. Biol., 286(5): 1337-1345 (1999).
Kukreti, et al., "Extension of the range of DNA sequences available for triplex helix formation: stabilization of mismatched triplexes by acridine-containing oligonucleotides," (Nucl. Acid. Resc 25(21): 4264-4270, (1997).
Lacroix, et al., "Triplex formation by oligonucleotides containing 5-(1-propynyl)-2'-deoxyuridine: decreased magnesium dependence and improved intracellular gene targeting", Biochemistry, 38(6):1893-901(1999).
Laemmli, "Cleavage of Structural Proteins during the Assembly of the Head of Bacteriophage T4," Nature. 227:680-685 (1970).
Lahoud, et al., "Properties of pseudo-complementary DNA substituted with weakly pairing analogs of guanine or cytosine", Nucleic Acid Research, 36(22):6999-7008 (2008).
Lassner, et al., "Targeting of T7 RNA polymerase to tobacco nuclei mediated by an SV40 nuclear location signal," Plant Mol Biol. 17(2):29-34 (1991).
Lee & Greenleaf, "A protein kinase that phosphorylates the C-terminal repeat domain of the largest subunit of RNA polymerase II," Proc. Natl. Acad. Sci. U.S.A. 86:3624-28 (1989).
Letai, et al., "Specificity in formation of triple-stranded nucleic acid helical complexes: studies with agarose-linked polyribonucleotide affinity columns," Biochemistry 27:9108 (1988).
Lin et al., "Stability of DNA triplexes on shuttle vector plasmids in the replication pool in Mammalian cells", J. Biol. Chem., 275(50):39117-39124 (2000).
Lin, et al., "Extrachromosomal recombination in mammalian cells as studied with single- and double-stranded DNA substrates," Mol. Cell Biol 7(1):129-140 (1987).
Lin, et al., "Repair of double-stranded DNA breaks by homologous DNA fragments during transfer of DNA into mouse L Cells," Molecular and Cellular Biology 10:113-119 (1990).
Lin, et al., "Use of EDTA derivatization to characterize interactions between oligodeoxyribonucleoside methylphosphonates and nucleic acids," Biochemistry 28:1054 (1989).
Lind, et al., "Structural characteristics of 2'-O-(2-methoxyethyl)-modified nucleic acids from molecular dynamics simulations", Nucleic Acids Res., 26(16):3694-799 (1998).
Liu, et al., "New procedures for preparation and isolation of conjugates of proteins and a synthetic copolymer of D-amino acids and immunochemical characterization of such conjugates" Biochem. 18:690-697 (1979).
Lohse, et al., "Double duplex invasion by peptide nucleic acid: a general principle for sequence-specific targeting of double-stranded DNA", Proc. Natl. Acad. Sci. USA, 96:11804-11808 (1999).
Luo, et al., "High-frequency intrachromosomal gene conversion induced by triplex-forming oligonucleotides microinjected into mouse cells," Proc. Natl. Acad. Sci. USA 97(16): 9003-9008 (2000).
Ma, et al., "Nuclease-resistant external guide sequence-induced cleavage of target RNA by human ribonuclease P", Antisense Nucleic Acid Drug Dev., 8(5):415-26 (1998).
Magzoub, et al., "N-terminal peptides from unprocessed prion proteins enter cells by micropinocytosis", Biochem Biophys Res Commun., 348:379-85 (2006).
Maher, et al., "Analysis of Promoter-Specific Repression by Triple Helical DNA Complexes in a Eukarvotic Cell-Free Transcription System," Biochemistry 31:70 (1992).
Maher, et al., "Inhibition of DNA binding proteins by oligonucleotide-directed triple helix formation," Science 245:725 (1989).
Majumdar, et al., "Cell cycle modulation of gene targeting by a triple helix-forming oligonucleotide", J. Biol. Chem., 278(13):11072-7 (2003A).
Majumdar, et al., "Gene targeting by triple helix-forming oligonucleotides", Ann. N.Y. Acad. Sci., 1002:141-53 (2003B).
Mayer, "Synthesis and triplex forming properties of pyrrolidino pseudoisoccytidine containing oligodeoxynucleotides.", Org. Biomol. Chem., 3(9):1653-1658 (2005).
Mergny, et al., "Sequence specificity in triple-helix formation: experimental and theoretical studies of the effect of mismatches on triplex stability," Biochemistry 30:9791 (1991).
Mirabelli, et al., "In Vitro and in vivo pharmacologic activities of antisense oligonucleotides," Anticancer Design 6:647-661 (1991).
Moser & Dervan, "Sequence-specific cleavage of double helical DNA by triple helix formation," Science 238:645-650 (1987).
Myhr, "Validation studies with Muta Mouse: a transgenic mouse model for detecting mutations in vivo," Environ. Mol. Mutagen, 18:308-315(1991).
Narayanan, et al., "Elevated levels of mutation in multiple tissues of mice deficient in the DNA mismatch repair gene Pms2," Proc. Natl. Acad. Sci. USA 94:3122-3127 (1997).
Nickerson, et al., "A Normally Masked Nuclear Matrix Antigen That Appears at Mitosis on Cytoskeleton Filaments Adjoining Chromosomes, Centrioles, and Midbodies," J. Cell. Biol. 116:977-987 (1992).
Noonberg, et al., "In Vivo Generation of Highly Abundant Sequence-Specific Oligonucleotides for Antisense and Triplex Gene Regulation," Nucleic Acids Res. 22: 2830-2836 (1994).
O'Keefe, et al., Disruption of Pre-mRNA Splicing In Vivo Results in Reorganization of Slicing Factors, J. Cell Biol. 124:249-260 (1994).
Obika, et al., "2'-O,4'-C-Methylene bridged nucleic acid (2',4'-BNA): synthesis and triplex-forming properties", Bioorg. Med. Chem., 9(4):1001-11 (2001).
Olsen, et al., "Genomic sequence correction by single-stranded DNA oligonucleotides: role of DNA, synthesis and chemical modifications of the oligonucleotide ends", J. Gene Med., 7:1534-1544 (2005).
Orson, et al., "Oligonucleotide inhibition of IL2R alpha mRNA transcription by promoter region collinear triplex formation in lymphocytes," Nucleic Acids Res. 19:3435-3441 (1991).
Park, et al., "Formation of a ternary complex by human XPA, ERCC1, and ERCC4(XPF) excision repair proteins," Proc. Natl. Acad. Sci. USA 91:5017-5021 (1994).
Parris, et al., "Proximal and distal effects of sequence context on ultraviolet mutational hotspots in a shuttle vector replicated in xeroderma cells," J mol Biol. 236(2):491-502 (1994).

(56) References Cited

OTHER PUBLICATIONS

Pattanayek, et al., "Structural rationalization of a large difference in RNA affinity despite a small difference in chemistry between two 2'-O-modified nucleic acid analogues", J. Am. Chem. Soc., 126(46):15006-7 (2004).
Pei et al, "Site Specific Cleavage of Duplex DNA by a Semisynthetic Nuclease via Triple-Helix Formation," Proc. Natl. Acad. Sci. USA 87:9858 (1990).
Perroualt, et al., "Sequence-specific artificial photo-induced ndonucleases based on triple helix-forming oligonucleotides," Nature 344:358 (1990).
Pierce et al., "Oligonucleotide-directed single-base DNA alterations in mouse embryonic stem cells", Gene Therapy, 10(1):24-33 (2003).
Postel, et al., "Evidence that a triplex-forming oligodeoxyribonucleotide binds to the c-myc promoter in HeLa cells, thereby reducing c-myc mRNA levels," Proc. Natl. Acad. Sci. USA 88:8227 (1991).
Posvic, et al., "Sequence-Specific Alkylation of Double Helical DNA by Oligonucleotide Directed Triple-Helix Formation," J. Am. Chem. Soc. 112:9428 (1992).
Prakash, et al., "2'-O[2-(guanidinium)ethyl]-modified oligonucleotides: stabilizing effect on duplex and triplex structures", Org. Lett., 6(12):1971-4 (2004).
Praseuth, et al., "Sequence-Specific Binding and Photocrosslinking of ☐ and ☐ Oligodeoxynucleotides to the Major Groove of DNA via Triple-Helix Formation," Proc. Natl. Acad. Sci. USA 85:1349 (1988).
Price & Pettijohn, "Redistribution of the Nuclear Mitotic Apparatus Protein (NuMA) during Mitosis and Nuclear Assembly," Exp. Cell Res. 166:292-311 (1986).
Puri, et al., "Minimum number of 2'-O-(2-aminoethyl) residues required for gene knockout activity by triple helix forming oligonucleotides", Biochemistry, 41(24):7716-24 (2002).
Puri, et al., "Targeted gene knockout by 2'-O-aminoethyl modified triplex forming oligonucleotides", J.Biol. Chem. (2001) 276(31):28991-28998.
Raha, et al., "Mutagenesis by Third-Strand-Directed Psoralen Adducts in Repair-Deficient Human Cells: High Frequency and Altered Specgrum in a Xeroderma Pigmentosum Variant," Proc. Natl. Acad. Sci. USA, 93(7):2941-2942 (1996).
Reardon, et al., "Removal of psoralen monoadducts and crosslinks by human cell free extracts," Nucleic Acids Res. 19: 4623 (1991).
Reza et al., "Triplex-mediated genome targeting and editing," Methods Mol Biol, 1114:115-142 (2014).
Roberts, et al., "Stability and Properties of Double and Triple Helices: Dramatic Effects of RNA or DNA Backbone Composition," Science 258: 1463-1466 (1992).
Rooney & Moore, "Antiparallel, intramolecular triplex DNA stimulates homologous recombination in human cells," Proc. Natl. Acad. Sci. USA 92:2141-2144 (1995).
Sambrook, et al., Molecular Cloning: A Laboratory Manual, second edition, Cold Spring Harbor Laboratory Press, New York (1990).
Sancar, "DNA excision repair," Annu. Rev. Biochem. 65: 43-81 (1996).
Schleifman, et al., "Triplex-mediated gene modification", Methods in Molecular Biology, 175-190 (2008).
Schneider, et al., "Optimal design of parallel triplex forming oligonucleotides containing Twisted Intercalating Nucleic Acids—TINA," Nucl. Acids Res. 38(13):4394-4403, (2010).
Seidman, et al., "The potential for gene repair via triple helix formation", The Clinical Journal of Investigation 112(4):487-94 (2003).
Seipel, et al, "Basal Components of the Transcription Apparatus (RNA Polymerase II, TATA-binding Protein) Contain Activation Domains: Is Repetitive C-Terminal Domain (CTD) of RNA Polymerase II a" Portable Enhancer Domain?, Chemical Abstracts, 122(17), Abstract No. 206769 (1994).
Seksek, et al., "Nuclear pH gradient in mammalian cells revealed by laser microspectrofluorimetry", Journal of Cell Science 109, 257-262 (1996)).

Semerad & Maher, "Exclusion of RNA Strands from a Purine Motif Triple Helix," Nucleic Acids Res. 22: 5321-5325 (1994).
Shahid, et al., "Targeted cross-linking of the human beta-globin gene in living cells mediated by a triple helix forming oligonucleotide.", Biochemistry, 45 (6): 1970-1978 (2006).
Shen et al., "Intrinsic human immunodeficiency virus type 1 resistance of hematopoietic stem cells despite coreceptor expression", J Virol, 73:728 (1999).
Shevelev, et al., "Potential Triple Helix-Mediated Inhibition of IGF-I Gene Expression Significantly Reduces Tumorigenicity of Gliolastoma in an Animal Model," Cancer Gene Therapy 4: 105-112 (1997).
Shimizu, et al., "Oligo(2'-O-methypribonucleotides. Effective probes for duplex DNA", FEBS Lett., 302(2):155-8 (1992).
Shivji, et al., "Proliferating cell nuclear antigen is required for DNA excision repair," Cell 69: 367 (1992).
Sibghat-Ullah, et al., "Human nucleotide excision repair in vitro: repair of pyrimidine dimers, psoralen and cisplatin adducts by HeLa cell-free extract," Nucleic Acids Res. 17(12):4471-84 (1989).
Sidransky, et al., "Identification of p53 gene mutations in bladder cancers and urine samples" Science 252:706-709 (1991).
Singleton & Dervan, "Influence of pH on the Equilibrium Association Constants for Oligodeoxyribonucleotide-Directed Triple Helix Formation at Single DNA Sites," Biochemistry 31: 10995-1003 (1992).
Smith, et al., "Alterations in chromatic Conformation Are Accompanies by Reorganization of Nonchromatin Domains That Contain U-snRNP Protein p28 and Nuclear Protein p107," J. Cell Biol. 101:560-567 (1985).
Spector, "Higher order nuclear organization: Three-dimensional distribution of small nuclear ribonucleoprotein particles," Proc. Natl. Acad. Sci. 87:147-151 (1990).
Streisinger, et al., "Frameshift mutations and the genetic code," Cold Spring harbor Symp. Quant. Biol. 31:77-84 (1966).
Strobel, et al., "Site-specific cleavage of human chromosome 4 mediated by triple-helix formation", Science, 254(5038):1639-42 (1991).
Summerton, et al., "Morpholino antisense oligomers: design, preparation, and properties", Antisense Nucleic Acid Drug Dev., 7(3):187-95 (1997).
Sung, et al., "Recombination factors of *Saccharomyces cerevisiae*," Mutat Res 451:257-75 (2000).
Takasugi, et al., "Sequence-specific photo-induced cross-linking of the two strands of double-helical DNA by a psoralen covalently linked to a triple helix-forming oligonucleotide," Proc. Natl. Acad. Sci. USA 88:5602-5606 (1991).
Talmadge, "The pharmaceutics and delivery of therapeutic polypeptides and proteins," Adv. Drug Del. Rev. 10:247-299 (1993).
Thacker, "A surfeit of RAD51-like genes?," Trends Genet 15(5):166-8 (1999).
Thacker, "The photoprotective effect of ascorbic acid, acetylsalicylic acid, and indomethacin evaluated by the photo hen's egg test," Trends Genet 15(5): 166-8 (1999B).
Thibodeau & Vincent, "Monoclonal Antibody CC-3 Recognizes Phosphorproteins in Interphase and Mitotic Cells," Experimental Cell Research 195:145-153 (1991).
Towbin, et al., "Electrophoretic transfer of proteins from polyacrylamide gels to nitrocellulose sheets: Procedure and some applications," Proc. Natl. Acad. Sci USA., 76:4350-4354 (1979).
Treisman, et al., "A single-base change at a splice site in a beta 0-thalassemic gene causes abnormal RNA splicing." Cell, 29(3): 903-911, (1982).
Uhlman, et al., "Antisense Oligonucleotides: A New Therapeutic Principle," Chem. Reviews 90(4):544-584 (1990).
Urnov, et al., "Highly efficient endogenous human gene correction using designed zinc-finger nucleases", Nature, 435:646-651 (2005).
Vasquez, et al., "Chromosomal mutations induced by triplex-forming oligonucleotides in mammalian cells," Nucleic Acids Res. 27: 1176 (1999).
Vasquez, et al., "Manipulating the mammalian genome by homologous recombination" Proc. Natl. Acad. Sci. USA, 98:8403-8410 (2001).

(56) References Cited

OTHER PUBLICATIONS

Vasquez, et al., "Triplex-directed modification of genes and gene activity.", Trends Biochem. Sci., 23(1):4-9 (1998).
Wang, et al., "Altered Repair of Targeted Psoralen Photoadducts in the Context of an Oligonucleotide-mediated Triple Helix" J. Biol. Chem. 270(22):22595-22601(1996).
Wang, et al., "Mutagenesis in mammalian cells induced by triple helix formation and transcription-coupled repair," Science 271: 802-805 (1996B).
Wang, et al., "Targeted Mutagenesis in Mammalian Cells Mediated by Intracellular Triple Helix Formation," Molecular and Cellular Biology, 15(32), 1759-1768 (1995).
Wansink, et al., "Fluorescent Labeling of Nascent RNA Reveals Transcription by RNA Polymerase II in Domains Scattered Throughout the Nucleus," J. Cell. Biol. 122:283-293 (1993).
Warren & Nelson, "Nonmitogenic Morphoregulatory Action of pp60.sup.v-src on Multicellular Epithelial Structures," Mol. Cell. Biol. 7:1326-1337 (1987).
Warren, et al., "Cytostellin: a novel. highly conserved protein that undergoes continuous redistribution during the cell cycle," J. Cell Sci. 103:381-388 (1992).
Warren, et al., Coordinated Transcription-Dependent Redistribution, Journal of Cellular Biochemistry, Supplement 21B:141 (1995).
White, et al., "Cell killing by the *Drosophila* gene reaper," Science 271(5250): 805-807 (1996).
Whitesell, et al., "Stability, clearance, and disposition of intraventricularly administered oligodeoxynucleotides: implications for therapeutic application within the central nervous system," Proc Natl Acad Sci U S A. 90(10):4665-9 (1993).
Wood, et al., "Complementation of the xeroderma pigmentosum DNA repair defect in cell-free extracts," Cell 53:97 (1988).
Wood, et al., "The Effect of Volume and Temperature on the Energy and Entropy of Pure Liquids," J. Am. Chem. Soc. 79:2023 (1957).
Wu, et al., "Increased efficiency of oligonucleotide-mediated gene repair through slowing replication fork progression", Proc. Natl. Acad. Sci. USA, 102:2508-2513 (2005).
Xing & Lawrence, "Higher Level Organization of Individual Gene Transcription and RNA Splicing," Science 259:1326-1330 (1993).
Yang, et al., "Nu-MA: An Unusually Long Coiled-Coil Related Protein in the Mammalian Nucleus," J. Cell Biol. 116:1303-1317 (1992).
Yang, et al., "Blocking the CC Chemokine Receptor 5 Pathway by Antisense Peptide Nucleic Acid Prolongs Islet Allograft Survivals", Transplantation Proceedings, 39(1):185-190 (2007).
Young et al., "Triple Helix Formation Inhibits Transcription Elongation in vitro," Proc. Natl. Sci. USA 88:10023 (1991).
Zendegui, et al., "In vivo stability and kinetics of absorption and disposition of 3' phosphopropyl amine oligonucleotides," Nucleic Acids Res. 20(2):307-14 (1992).
Zon & Geiser, "Phosphorothioate oligonucleotides: chemistry, purification, analysis, scale-up and future directions," Anticancer Drug Des. 6(6):539-68 (1991).
Grigoriev, et al., "A Triple-Helix-Forming Oligonucleotide-Intercalator Conjugate Acts as a Transcriptional Repressor via Inhibition of NF$_K$B Binding to Interleukin-2 Receptor α-Regulatory Sequence," J. of Biological Chem. 267:3389 (1992B).
Iversen, et al., "In vivo studies with phosphorothioate oligonucleotides: pharmacokinetics prologue," Anticancer Drug Des. 6(6):531-8 (1991).
Kim, et al., "Efficient sequence-directed psoralen targeting using pseudocomplementary peptide nucleic acids", Bioconjug. Chem., 18:567-572 (2007B).
Kim, et al., "Site-directed gene mutation at mixed sequence targets by psoralen-conjugated pseudo-complementary peptide nucleic acids", Nucleic Acids, 35:7604-7613 (2007).
Puri, et al., "Targeted gene knockout by 2'-O-aminoethyl modified triplex forming oligonucleotides", J.Biol. Chem., 276(31):28991-28998 (2001).

Seksek, et al., "Nuclear pH gradient in mammalian cells revealed by laser microspectrofluorimetry", Journal of Cell Science 109(1):257-262 (1996).
Shimizu, et al., "Oligo(2'-O-methyl)ribonucleotides. Effective probes for duplex DNA", FEBS Lett., 302(2):155-8 (1992).
Thacker, "The photoprotective effect of ascorbic acid, acetylsalicylic acid, and indomethacin evaluated by the photo hen's egg test," Trends Genet 15(5): 166-8 (1999).
Wang, et al., "Mutagenesis in mammalian cells induced by triple helix formation and transcription-coupled repair," Science 271(5250): 802-805 (1996B).
Abes, et al., "Endosome trapping limits the efficiency of splicing correction by PNA-oligolysine conjugates", J. Controll. Rel., 110:595-604 (2006).
Agata, et al., Expression of the PD-1 antigen on the surface of stimulated mouse T and B lymphocytes Int. Immunol., 8:765-772 (1996).
Aguado, et al., "Controlled-release vaccines—biodegradable polylactide/polyglycolide (PL/PG) microspheres as antigen vehicles," Immunobiology, 184(2-3):113-25 (1992).
Aiuti, et al., "Gene therapy for immunodeficiency due to adenosine deaminase deficiency", N Engl J Med., 360(5):447-458 (2009).
Akinc, et al., "Synthesis of poly(beta-amino ester)s optimized for highly effective gene delivery", Bioconjug Chem., 14:979-88 (2003).
Alshamsan, "Nanoprecipitation is more efficient than emulsion solvent evaporation method to encapsulate cucurbitacin I in PLGA nanoparticles", Saudi Pharma J., 22(3):219-222 (2014).
Alton, et al., "A randomised, double-blind, placebo-controlled phase IIB clinical trial of repeated application of gene therapy in patients with cystic fibrosis", Thorax, 68(11):1075-7 (2013).
Alton, et al., "Repeated nebulisation of non-viral CFTR gene therapy in patients with cystic fibrosis: a randomised, double-blind, placebo-controlled, phase 2b trial", Lancet Respir Med., 3(9):684-91 (2015).
Anandalingam, et al., "Nanoparticles with triplex-forming oligonucleotides for site specific editing of the human CFTR gene", Poster, Dept of Bioeng, Yale Univ School of Med.and School of Eng and Applied Sci., 2012.
Andreani, et al., "Persistence of mixed chimerism in class 3 thalassemic patients following BMT", Bone Marrow Transplant, 7(Suppl 2):75 (1991).
Armstrong, et al., "Gene therapy in cystic fibrosis", Arch Dis Child., 99(5):465-8 (2014).
Arnould, et al., "The I-CreI meganuclease and its engineered derivatives: applications from cell modification to gene therapy", Protein Eng. Des. Sel., 24(1-2):27-31 (2011).
Babar, et al., "Nanoparticle-based therapy in an in vivo microRNA-155 (miR-155)-dependent mouse model of lymphoma", PNAS, 109:E1695-E1704 (2012).
Bahal, et al. "Nanoparticle for delivery of antisense γPNA oligomers targeting CCR5", Artificial DNA: PNA & XNA, 4:2, 49-57(2013).
Bahal, et al., "In vivo correction of anaemia in β-thalassemic mice by γPNA-mediated gene editing with nanoparticle delivery", Nat Commun., 7:13304. doi: 10.1038 (2016).
Bahal, et al., "Sequence-Unrestricted, Watson-Crick Recognition of Double Helical B-DNA by (R)-MiniPEG-gPNAs", ChemBioChem, 13:56-60 (2012).
Bahal, et al., "Single-Stranded γPNAs for In Vivo Site-Specific Genome Editing via Watson-Crick Recognition", Curr. Gene Ther., 14:331-42 (2014).
Bahal, et al., "Site-specific genome editing of hematopoietic stem cells for beta thalassemia gene therapy", Mol Ther., 22:S290-91 (2014b).
Barkalina, et al., "Nanotechnology in reproductive medicine: emerging applications of nanomaterials", Nanomedicine, 10:921-38 (2014).
Beer, et al., "Genome-edited human stem cell-derived beta cells: a powerful tool for drilling down om type 2 diabetes GWAS biology {version1:referees:2 approve]", https://f1000research.com/articles/5-1711/v1 (2016).
Bentin, et al., "Combined triplex/duplex invasion of double-stranded DNA by "tail-clamp" peptide nucleic acid", Biochemistry 42(47):13987-95 (2003).

(56) References Cited

OTHER PUBLICATIONS

Bentin, et al., "Structural diversity of target-specific homopyrimidine peptide nucleic acid-dsDNA complexes", Nucleic Acids Res, 34(20): 5790-5799 (2006).
Bertram, "Functionalized poly(lactic-co-glycolic acid) enhances drug delivery and provides chemical moieties for surface engineering while preserving biocompatibility", Acta Biomater. 5:2860-71 (2009).
Beumer, et al., "Efficient gene targeting in *Drosophila* with zinc-finger nucleases", Genetics, 172:2391-2403 (2006).
Braasch, et al., "Locked nucleic acid (LNA): fine-tuning the recognition of DNA and RNA", Chem. Biol., 8(1):1-7 (2001).
Braden, et al., "Polymeric nanoparticles for sustained down-regulation of annexin A2 lead to reduction in proliferation and migration of prostate cancer cells", Journal of Biomedical Nanotechnology 3:148-159 (2007).
Bramwell, et al., "Particulate delivery systems for biodefense subunit vaccines", Adv. Drug Deliv. Rev., 57(9):1247-65 (2005).
Bruscia, et al., "Isolation of CF cell lines corrected at DeltaF508-CFTR locus by SFHR-mediated targeting", Gene Ther., 9:683-5 (2002).
Cai, et al., "In utero delivery of oligodeoxynucleotides for gene correction", Gene Correction Methods and Protocols, Methods in Molecular Biology vol. 1114, Chapter 26:399-411, Francesca Storici, editor Springer Science-Business Media (2014).
Cartier, et al., "Hematopoietic stem cell gene therapy with a lentiviral vector in X-linked adrenoleukodystrophy", Science, 326(5954):818-23 (2009).
Cartiera, et al., "Partial correction of cystic fibrosis defects with PLGA nanoparticles encapsulating curcumin", Mol Pharm, 7:86-93 (2010).
Cermak, et al, "Efficient design and assembly of custom TALEN and other TAL effector-based constructs for DNA targeting", Nucl. Acids Res., 39(12):e82 (2011).
Cheng, et al., "Enhanced siRNA delivery into cells by exploiting the synergy between targeting ligands and cell-penetrating peptides", Biomaterials, 32(26):6194-203 (2011).
Chin, et al., "Correction of a splice-site mutation in the beta-globin gene stimulated by triplex-forming peptide nucleic acids", PNAS. ,105(36):13514-19 (2008).
Chin, et al., "Repair of DNA lesions associated with triplex-forming oligonucleotides", Mol Carcinog., 48:389-399 (2009).
Chin, et al., "Triplex-forming Peptide Nucleic Acids Induce Heritable Elevations in Gamma-globin Expression in Hematopoietic Progenitor Cells", Mol. Ther., 21(3):580-7 (2013).
Choi, et al., "Applicastion of chitosan amd cjitosan derivastives as biomaterials", J Ind Eng Chem., 33:1-10 (2016).
Cong, et al., "Multiplex genome engineering using CRISPR/Cas systems", Science, 15:339(6121):819-23 (2013).
Conner and Schmid, "Regulated portals of entry into the cell", Nature 422:37-44 (2003).
Cradick, et al., "CRISPR/Cas9 systems targeting β-globin and CCR5 genes have substantial off-target activity", Nucleic Acids Res., 41:9584-92 (2013).
Cruz, et al., "Targeted PLGA nano- but not microparticles specifically deliver antigen to human dendritic cells via DC-SIGN in vitro", J Control Release, 144:118-126 (2010).
Cu, et al., "In vivo distribution of surface-modified PLGA nanoparticles following intravaginal delivery", J Control Release, 156:258-264 (2011).
Cu, et al., "Ligand-modified gene carriers increased uptake in target cells but reduced DNA release and transfection efficiency", Nanomedicine, 6:334-343 (2010).
Datta, et al., "Triplex-induced Recombination in Human Cell-free Extracts," J. Biol. Chem., 276:18018-18023 (2001).
Davis, et al., "Cystic fibrosis since 1938", Am J Respir Crit Care Med., 173(5):475-82 (2006).
Davis, et al., "Cystic fibrosis", Pediatr Rev., 22(8):257-64 (2001).

Depreaux, et al., "Antisense oligonucleotides delivered to the amniotic cavity in utero modulate gene expression in the postnatal mouse," Nucleic Acids Res. 44(20):9519-9529 (2016).
Desai, et al., "The mechanism of uptake of biodegradable microparticles in Caco-2 cells is size dependent", Pharm. Res., 14:1568-73 (1997).
Dib and Pastories, "Laronidase for treating mucopolysaccharidosis type I", Genet. Mol. Res., 6(3):667-74 (2007).
Doudna, et al., "Genome editing. The new frontier of genome engineering with CRISPR-Cas9", Science, 346:1258096 (2014).
Durland, et al., "Binding of triple helix forming oligonucleotides to sites in gene promoters.", Biochemistry, 30(38):9246-9255 (1991).
Egan, et al., "Calcium-pump inhibitors induce functional surface expression of Delta F508-CFTR protein in cystic fibrosis epithelial cells", Nat Med., 8:485-92 (2002).
Egholm, et al., "PNA hybridizes to complementary oligonucleotides obeying the Watson-Crick hydrogen-bonding rules", Nature, 365:566-8 (1993).
Endoh, et al., "Cellular siRNA delivery using cell-penetrating peptides modified for endosomal escape", Adv Drug Deliv Rev., 61:704-9 (2009).
Fahmy, et al., "Surface modification of biodegradable polyesters with fatty acid conjugates for improved drug targeting", Biomaterials, 26: 5727-36 (2005).
Faruqi, et al., "Peptide nucleic acid-targeted mutagenesis of a chromosomal gene in mouse cells", PNAS, 95:1398-1403 (1998).
Felfly, et al., "Long-term correction of beta-thalassemia with minimal cellular requirement and transplantation modalities", Mol Ther, 15:1701-9 (2007).
Fields, et al., "Modified poly(lactic-co-glycolic acid) nanoparticles for enhanced cellular uptake and gene editing in the lung", Adv Healthc Mater., 4(3):361-6 (with supporting information) (2015).
Fields, et al., "Surface modified poly(β amino ester)-containing nanoparticles for plasmid DNA delivery", J Control Release, 164(1):41-8 (2012).
Gabbianelli, et al., "Role of stem cell factor in the reactivation of human fetal hermoglobin", Mediter J Hemo Infect Dis., 1(1):e2009009 (2009).
Gaj, et al., "ZFN, TALEN, and CRISPER/cas-based methods dor genome engineering", Trends in Biotech., 31(7):397-405 (2013).
Genbank accession No. U01317.1—"Human beta globin region on chromosome 11",42 pages, first appeared Feb. 18, 1994, updated Jan. 9, 2012, accessed Aug. 9, 2017.
Genbank accession No. NM_000579, "CCR5 chemokine (C-C motif) receptor 5 (*Homo sapiens*)", 8 pages, first appeared Mar. 24, 1999, updated Aug. 22, 2010, accessed Aug. 9, 2201.
Genbank accession No. AH006034.1, "Human cystic fibrosis transmembrane conductance regulator (CFTR) gene", 24 pages, first appeared Jul. 26, 1993, updated Jun. 10, 2016, accessed Aug. 9, 2017.
Goncz, et al., "Expression of DeltaF508 CFTR in normal mouse lung after site-specific modification of CFTR sequences by SFHR", Gene Ther., 8:961-965 (2001).
Goncz, et al., "Targeted replacement of normal and mutant CFTR sequences in human airway epithelial cells using DNA fragments", Hum Mol Genet., 7:1913-9 (1998).
Goncz, et al., "Small fragment homologous replacement-mediated modification of genomic beta-globin sequences in human hematopoietic stem/progenitor cells", Oligonucleotides, 16:213-24 (2006).
Grafmueller, et al., "Bidirectional transfer study of polystyrene nanoparticles across the placental barrier in an ex vivo human placental perfusion model", Enviro Health Perspectives, 123(12):1280-6 (2015).
Granio, et al., "Adenovirus 5-fiber 35 chimeric vector mediates efficient apical correction of the cystic fibrosis transmembrane conductance regulator defect in cystic fibrosis primary airway epithelia", Human Gene Therapy, 21:251-69 (2010).
Green, "A combinatorial polymer library approach yields insight into nonviral gene delivery", Acc Chem Res., 41(6):749-59 (2008).
Griesenbach, et al., "Gene transfer to the lung: Lessons learned from more than 2 decades of CF gene therapy", Advanced Drug Delivery Reviews, 61:128-139 (2009).
Gruenert, et al., "Established cell lines used in cystic fibrosis research", J Cystic Fibros, 3 (Suppl 2):191-6 (2004).

(56) References Cited

OTHER PUBLICATIONS

Gupta, et al., "Nanotechnology for delivery of peptide nucleic acids (PNAs)", J Control Release, 240:302-11 (2016).
Haendel, et al., "Zinc-finger nuclease based genome surgery: it's all about specificity", Gene Ther., 11:28-37 (2011).
Hanna, et al., "Treatment of Sickle Cell Anemia Mouse Model with iPS Cells Generated from Autologous Skin", Science, 318:1920-3 (2007).
Hansen, et al., "High-affinity triplex targeting of double stranded DNA using chemically modified peptide nucleic acid oligomers", Nucleic Acids Research, 37(13): doi:10.1093/nar/gkp437.
Hollingsworth, et al., "A nuclear factor that binds purine-rich, single-stranded oligonucleotides derived from S1-sensitive elements upstream of the CFTR gene and the MUC1 gene", Nucleic Acids Res., 22(7):1138-46 (1994).
Holt, et al., "Human hematopoietic stem/progenitor cells modified by zinc-finger nucleases targeted to CCR5 control HIV-1 in vivo", Nature biotechnology, 28(8):839-47 (2010).
Hrkach, et al., "Preclinical Development and Clinical Translation of a PSMA-Targeted Docetaxel Nanoparticle with a Differentiated Pharmacological Profile", Sci Transl Med., 4:128ra139 (2012).
Hu, et al., "ELDA: extreme limiting dilution analysis for comparing depleted and enriched populations in stem cell and other assays", J Immunol Methods, 347:70-8 (2009).
Huang, et al., "Functional silencing of hepatic microsomal glucose-6-phosphatase gene expression in vivo by adenovirus-mediated delivery of short hairpin RNA", FEBS Lett., 558(1-3):69-73 (2004).
Huang, et al., "Preparation and determination of optical purity of γ-lysine modified peptide nucleic acid analogues", Arch Pharm Res, 35(3):51722 (2012).
Hubbell, et al., "Chemistry. Nanomaterials for drug delivery", Science, 337:303-5 (2012).
Hutt, et al., "Reduced histone deacetylase 7 activity restores function to misfolded CFTR in cystic fibrosis", Nat Chem Biol., 6:25-33 (2010).
Jain, et al., "Influence of pendant chiral C(γ)-(alkylideneamino/guanidino) cationic side-chains of PNA backbone on hybridization with complementary DNA/RNA and cell permeability", J. Org. Chem., 79(20): 9567-9577 (2014).
Jia, et al., "Bacterial delivery of TALEN proteins for human genome editing", PlosOne, 9(3):e91547 1-9 (2014).
Jiang, et al., "Biodegradable poly(lactic-co-glycolic acid) microparticles for injectable delivery of vaccine antigens", Adv. Drug Deliv. Rev., 57(3):391-410 (2005).
Jinek, et al., "A programmable dual-RNA-guided DNA endonuclease in adaptive bacterial immunity", Science, 337(6096):816-21 (2012).
Johnson, et al., "Efficiency of gene transfer for restoration of normal airway epithelial function in cystic fibrosis", Nature Genetics, 2:21-25 (1992).
Juch, et al., "Nanomaterial interference with early human placenta: Sophisticated matter meets sophisticated tissues", Reproductive Toxicology, 41:73-79 (2013).
Kaihatsu, et al., "Extending recognition by peptide nucleic acids (PNAs): binding to duplex DNA and inhibition of transcription by tail-clamp PNA-peptide conjugates", Biochemistry, 42(47):13996-4003 (2003).
Kamei, et al., "Mechanistic study of the uptake/permeation of cell-penetrating peptides across a caco-2 monolayer and their stimulatory effect on epithelial insulin transport", J Pharm Sci., 102(11):3998-4008 (2013).
Kayali, et al., "Site-directed gene repair of the dystrophin gene mediated by PNA-ssODNs", Human Molecular Genetics, 19(16):3266-3281 (2010).
Kenesei, et al., "Enhanced detection with spectral imaging fluorescence microscopy reveals tissue-and cell-type-specific compartmentalization of surface-modified polystyrene nanoparticles," J.Nanobiotechnol, 14:55 (2016).
Khan, A. et al., "Sustained polymeric delivery of gene silencing antisense ODNs, siRNA, DNAzymes and ribozymes: in vitro and in vivo studies", J Drug Target, 12:393-404 (2004).
Kim, et al. "Insertion and deletion mutants of FokI restriction endonuclease", J. Biol. Chem. 269:31978-82 (1994b).
Kim, et al., "Chimeric restriction endonuclease", PNAS, 91:883-7 (1994a).
Kim, et al., "USP17- and SCFβTrCP-Regulated Degradation of DEC1 Controls the DNA Damage Response",Mol Cell Biol., 34(22):4177-85 (2014c).
Konstan, et al., "Compacted DNA Nanoparticles Administered to the Nasal Mucosa of Cystic Fibrosis Subjects Are Safe and Demonstrate Partial to Complete Cystic Fibrosis Transmembrane Regulator Reconstitution", Human Gene Therapy, 15(12):1255-69 (2004).
Koppelhus, et al., "Cellular delivery of peptide nucleic acid (PNA)" Adv. Drug Deliv. Rev., 55(2): 267-280 (2003).
Kuhn, et al., "Sequence specificity at targeting double-stranded DNA with a γ-PNA oligomer modified with guanidinium G-clamp nucleobases", Artificial DNA, PNA & XNA, 1(1):45-53(2010).
Lee, et al., "Correction of the ΔF508 Mutation in the Cystic Fibrosis Transmembrane Conductance Regulator Gene by Zinc-Finger Nuclease Homology-Directed Repair", BioResearch Open Access, 1:99-108 (2012).
Lewis, et al., "A common human beta globin splicing mutation modeled in mice", Blood, 91:2152-6 (1998).
Li, et al., "Alteration of the cleavage distance of Fok I restriction endonuclease by insertion mutagenesis", PNAS, 90:2764-8 (1993).
Li, et al., "Functional domains in Fok I restriction endonuclease", PNAS, 89:4275-9 (1992).
Lin, et al., "Enhanced homology-directed human genome engineering by controlled timing of CRISPR/Cas9 delivery", eLife, 3:e04766. doi: 10.7554 (2014).
Little, et al., "Formulation and characterization of poly (beta amino ester) microparticles for genetic vaccine delivery", J Control Release, 107:449-62 (2005).
Little, et al., "Poly-beta amino ester-containing microparticles enhance the activity of nonviral genetic vaccines", PNAS, 101:9534-9 (2004).
Lorenz, et al., "Steroid and lipid conjugates of siRNAs to enhance cellular uptake and gene silencing in liver cells", Bioorg. Med. Chem. Lett., 14(19):4975-4977 (2004).
Luens, et al., "Thrombopoietin, kit ligand, and flk2/flt3 ligand together induce increased numbers of primitive hematopoietic progenitors from human CD34+Thy-1+Lin-cells with preserved ability to engraft SCID-hu bone", Blood 91:1206-15 (1998).
Luo, et al., "Controlled DNA delivery systems", Pharm Res, 16:1300-08 (1999).
Lynn, et al., "Degradable Poly(β-amino esters): Synthesis, Characterization, and Self-Assembly with Plasmid DNA", J Am Chem Soc., 122(44):10761-10768 (2000).
Majumdar, et al., "Targeted gene knockout mediated by triple helix forming oligonucleotides", Nat. Genet., 20:212-214 (1998).
Mali, et al., "RNA-guided human genome engineering via Cas9", Science, 339:823-6 (2013).
Martz, "Triplex solution for a monogenic problem", Science-Business eXchange, 1(33); doi:10.1038/scibx.2008.794, Published online Sep. 18, 2008 (http://www.nature.com/scibx/journal/v1/n33/full/scibx.2008.794.html), 4 pages.
McClain, et al., "In utero stem cell transplantation and gene therapy: Recent progress and the potential for clinical application," Best Practice & Research Clinical Obstetrics and Gynaecology, 31:88-98 (2016).
McNeer et al., "Nanoparticles that deliver triplex-forming peptide nucleic acid molecules correct F508del CFTR in airway epithelium", Nat Commun., doi: 10.1098/ncomms7952 (2015).
McNeer, "Nanoparticles for site specific genome editing", Dissertation presented to the Facility of Graduate School of Yale University, 154 pages, May 2013.
McNeer, et al., "Correction of F508DEL CFTR using nanoparticles delivering triplex-forming peptide nucleic acid molecules", Nat Commun. 6:(6925):1-25 (2015).
McNeer, et al., "Correction of F508DEL CFTR using nanoparticles delivering triplex-forming peptide nucleic acid molecules", poster presented at North American Cystic Fibrosis Meeting, Oct. 8-10, 2015.

(56) References Cited

OTHER PUBLICATIONS

McNeer, et al., "Correction of F508DEL CFTR using nanoparticles delivering triplex-forming peptide nucleic acid molecules", supplemental, Nat Commun. 6:(6925):1-25 (2015).
McNeer, et al., "Nanoparticles Deliver Triplex-forming PNAs for Site-specific Genomic Recombination in CD34+ Human Hematopoietic Progenitors", Mol Ther., 19(1):172-80 (2011).
McNeer, et al., "Nanoparticles for site-specific genome editing in cystic fibrosis", 16 pages, presented at 26th Annual North American Cystic Fibrosis Conference, Orlando, Fl, Oct. 11-13, 2012.
McNeer, et al., "Polymer delivery systems for site-specific genome editing", J Control Release, 155(2): 312-316 (2011b).
McNeer, et al., "Systemic delivery of triplex-forming PNA and donor DNA by nanoparticles mediates site-specific genome editing of human hematopoietic cells in vivo", Gene Therapy, 20:658-669 (2013).
Miccio, et al., "In vivo selection of genetically modified erythroblastic progenitors leads to longterm correction of beta-thalassemia", PNAS, 105:10547-52 (2008).
Miller, et al., "A TALE nuclease architecture for efficient genome editing", Nature Biotechnol 29: 143 (2011).
Murata, et al., "Anti-tumor effects of anti-VEGF siRNA encapsulated with PLGA microspheres in mice", J. Control. Release, 126(3):246-54 (2008).
Nansen, et al., "The role of CC chemokine receptor 5 in antiviral immunity.", Blood, 99(4):1237-1245 (2002).
NCBI Reference Sequence: NG_007119.1), "*Homo sapiens* galactosidase alpha (GLA), RefSeqGene (LRG_672) on chromosome X", 10 pages first appeared Nov. 27, 2007, updated Jul. 12, 2017, accessd Aug. 10, 2017.
NCBI Reference Sequence: NG_008103.1), "*Homo sapiens* iduronidase, alpha-L- (IDUA), RefSeqGene on chromosome 4", 14 pages, first appeared Nov. 27, 2008, updated Jul. 12, 2017, accessed Aug. 10, 2017.
NCBI Reference Sequence: NG_009783.1 "*Homo sapiens* glucosylceramidase beta (GBA), RefSeqGene on chromosome 1)", 11 pages, first appeared Feb. 19, 2009, updated Jul. 12, 2017, accessed Aug. 10, 2017.
Nie, et al., "Lysine-based peptide-functionalized PLGA foams for controlled DNA delivery", J Control Release, 138:64-70 (2009).
Nielsen, et al., "Sequence-Selective Recognition of DNA by Strand Displacement with a Thymine-Substituted Polyamide", Science (Washington, D.C., 1883-), 254:1497-1500 (1991).
Nyce and Metzger, "DNA antisense therapy for asthma in an animal model", Nature, 385(6618):721-5 (1997).
Oakland, et al., "Advances in cell and gene-based therapies for cystic fibrosis lung disease", Mol Ther., 20:1108-15 (2012).
Oliveria, et al., "Enhancement of chitosan-mediated gene delivery through combination witj phiC31 integrase", Acta Biomaterialia, 17:89-97 (2015).
Pászty, et al., "Transgenic knockout mice with exclusively human sickle hemoglobin and sickle cell disease." Science, 278(5339):876-8 (1997).
Preprotech, Recombinant Human SCF Catalog No. 250-03, Stem Cell Factor, c-Kit Ligand, Mast Cell Growth Factor (MGF), Steel Factor, 2 pages, accessed Aug. 11, 2017.
Preprotech, Recombinant Human SCF Catalog No. 300-07, Stem Cell Factor, c-Kit Ligand, Mast Cell Growth Factor (MGF), Steel Factor, 2 pages, accessed Aug. 11, 2017.
Ramachandran, et al., "A microRNA network regulates expression and biosynthesis of wild-type and DeltaF508 mutant cystic fibrosis transmembrane conductance regulator", PNAS, 109:13362-7 (2012).
Rapireddy, et al., "Strand invasion of mixed-sequence, double-helical B-DNA by γ-peptide nucleic acids containing G-clamp nucleobases under physiological conditions", Biochemistry, 50(19):3913-8 (2011).
Reay, et al., "Full-length dystrophin gene transfer to the mdx mouse in utero", Gene Therapy, 15:531-6 (2008).
Recombinant Rat SCF (Stem Cell Factor) Accession No. P2158,1 Catalog No. 300-32) accessed Aug. 11, 2017.

Rivera-Torres, et al., "The position of DNA cleavage by TALENs and cell synchronization influences the frequency of gene editing directed by single-stranded oligonucleotides", Plos One, 9(5):e96483 1-8 (2014).
Rodriguez, et al., "Minimal "Self" peptides that inhibit phagocytic clearance and enhance delivery of nanoparticles", Science, 339:971-5 (2013).
Rogers, et al., "Local delivery of gene-modifying triplex-forming molecules to the epidermis", J Ivest Dermatol., 133(3):685-91(2013).
Rogers, et al., "Site-directed recombination via bifunctional PNA-DNA conjugates", PNAS., 99(26):16695-16700 (2002).
Rump, et al., "Modification of the plasma clearance and liver uptake of steroid ester-conjugated oligodeoxynucleotides by association with (lactosylated) low-density lipoprotein", Biochem. Pharmacol., 59(11):1407-1416 (2000).
Ryan, et al., "Knockout-transgenic mouse model of sickle cell disease." Science., 278(5339):873-6 (1997).
Sahu, et al., "Synthesis and characterization of conformationally preorganized, (R)-diethylene glycol-containing γ-peptide nucleic acids with superior hybridization properties and water solubility", J. Org. Chem., 76:5614-27 (2011).
Sangamo Bioscience, Triple forming peptide nucleic acids (TFPs)-SGMO, http://www.investorvillage.com/mbthread.asp?mb=1933&=13823114&showall, accessed Jul. 13, 2016.
Sargent, et al., "Oligo/polynucleotide-based gene modification: strategies and therapeutic potential", Oligonucleotides, 21(2):55-75 (2011).
Sazani, et al., "Systemically delivered antisense oligomers upregulate gene expression in mouse tissues", Nat. Biotechnol., 20:1228-33 (2002).
Schleifman, et al., "Site-specific Genome Editing in PBMCs With PLGA Nanoparticle-delivered PNAs Confers HIV-1 Resistance in Humanized Mice", Mol. Ther Nucleic Acids, 2:e135 (2013).
Schleifman, et al., Targeted disruption of the CCR5 gene in human hematopoietic stem cells stimulated by peptide nucleic acids Chem Biol., 18:1189-98 (2011).
Schwank, et al., "Functional repair of CFTR by CRISPR/Cas9 in intestinal stem cell organoids of cystic fibrosis patients", Cell Stem Cell, 13:653-8 (2013).
Scott et al., "Molecular genetics of mucopolysaccharidosis type I: diagnostic, clinical, and biological implications", Hum. Mutat. 6:288-302 (1995).
Shenoy, et al., "Calcium-modulated chloride pathways contribute to chloride flux in murine cystic fibrosis-affected macrophages", Pediatr Res., 70:447-52 (2011).
Singer, et al., "Electronic barcoding of a viral gene at the single-molecule lever", Nano Ltrs., 12:1722-8 (2012).
Sinn, et al., "Lentiviral vector gene transfer to porcine airways", Mol Ther Nucleic Acids, 1:e56 (2012).
Smith, et al., "The ATM-Chk2 and ATR-Chk1 pathways in DNA damage signaling and cancer", Adv Cancer Res., 108:73-112 (2010).
Song, et al., "Evidence against the rescue of defective DeltaF508-CFTR cellular processing by curcumin in cell culture and mouse models", Science, 304:600-2 (2004).
Soutschek, et al., "Therapeutic silencing of an endogenous gene by systemic administration of modified siRNAs", Nature, 432(7014):173-8 (2004).
Staretz-Chacham, et al., "Lysosomal storage disorders in the newborn", Pediatrics, 123(4):1191-207 (2009).
Steinberger, et al., "Functional deletion of the CCR5 receptor by intracellular immunization produces cells that are refractory to CCR5-dependent HIV-1 infection and cell fusion", PNAS, 97:805-10 (2000).
Sterchak, et al., "Uncharged stereoregular nucleic acid analogs. 1. Synthesis of a cytosine-containing oligomer with carbamate internucleoside linkages", Organic Chem., 52:4202-06, (1987).
Strouse, et al., "Combinatorial gene editing in mammalian cells using ssODNs and TALENs", Scientific Reports, 4:3791-9 (2014).
UniProtKB—P20826 (SCF_MOUSE), 8 pages, first appeared Feb. 1, 1991, updated May 10, 2017, accessed Aug. 11, 2017.
Sugiyama and Kittaka, "Chiral peptide nucleic acids with a substituent in the N-(2-aminoethy)glycine backbone", Molecules, 18:287-310 (2013).

(56) References Cited

OTHER PUBLICATIONS

Svasti, et al., "RNA repair restores hemoglobin expression in IVS2-654 thalassemic mice", PNAS, 106:1205-10 (2009).
Tatokoro, et al., "Heat shock protein 90 targeting therapy: state of the art and future perspective", EXCLI J., 14:48-58 (2015).
Thompson and Eastman, "The cancer therapeutic potential of Chk1 inhibitors: how mechanistic studies impact on clinical trial design", Br J Clin Pharmacol., 76(3):358-69 (2013).
UniProtKB—21581(SCF_RAT), 7 pages, first appeared May 1, 1991, updated May 10, 2017, accessed Aug. 11, 2017.
UniProtKB—P20826 (SCF_MOUSE), 8 pages, first appeared Feb. 1, 1991, updated May 10, 2017, accessed Aug. 11, 2017.
UniProtKB—P21583 (SCF_HUMAN), 10 pages, first appeared May 1, 1991, updated May 10, 2017, accessed Aug. 11, 2017.
Vasquez, et al., "Human XPA and RPA DNA repair proteins participate in specific recognition of triplex-induced helical distortions", PNAS, 99:5848-53 (2002).
Vasquez, et al., "Specific mutations induced by triplex-forming oligonucleotides in mice", Science, 290:530-533 (2000).
Von Bismarck, et al., "IKK NBD peptide inhibits LPS induced pulmonary inflammation and alters sphingolipid metabolism in a murine model", Pulm Pharmacol Ther., 25(3):228-35 (2012).
Walkley, "Pathogenic cascades in lysosomal disease—Why so complex", J. Inherit. Metab. Dis., 32(2):181-9 (2009).
Wang, et al., "The sustained-release behavior and in vitro and in vivo transfection of pEGFP-loaded core-shell-structured chitosan-based composite particles", Intl J Namomed., 9:4965-78 (2014).
Weber and Ryan, "ATM and ATR as therapeutic targets in cancer", Pharmacol Ther., 149:124-38 (2015).
Wick, et al., "Barrier capacity of human placenta for nanosized materials", Enviro Health Perspectives, 118(3):432-6 (2010).
Woodrow, et al., "Intravaginal gene silencing using biodegradable polymer nanoparticles densely loaded with small-interfering RNA", Nat Mater, 8:526-33 (2009).
Yamano, et al., "Modified Tat peptide with cationic lipids enhances gene transfection efficiency via temperature-dependent and caveolae-mediated endocytosis", J Control Release, 152:278-85 (2011).
Yang, et al., "In utero gene delivery using chitosan-DNA nanoparticles in mice", J Surgical Res., 171:691-9 (2011).
Yin, "Genome editing with Cas9 in adult mice corrects a disease mutation and phenotype", Nat Biotechnol., 32(6):551-3 (2014).
Yu, et al., "Novel aptamer-nanoparticle bioconjugates enhances delivery of anticancer drug to MUC1-positive cancer cells in vitro", PLoS One., 6:e24077 (2011).
Yuan, et al., "siRNA drug delivery by biodegradable polymeric nanoparticles", J. Nanosci. Nanotechnol., 6:2821-8 (2006).
Zeiher, et al., "A mouse model for the delta F508 allele of cystic fibrosis", J Clin Invest., 96:2051-64 (1995).
Zhou, et al., "Biodegradable poly(amine-co-ester) terpolymers for targeted gene delivery", Nat Mater.,11:82-90 (2012).
Zielke, et al., "Repetitive synchronization of human lymphoblast cultures with excess thymidine", Methods Cell Biol., 8:107-121 (1974).
International Search Report PCT/US2017/018142, dated Sep. 15, 2017.
Arnould, et al., "The I-CreI meganuclease and its engineered derivatives: applications from cell modification to gene therapy", *Protein Eng. Des. Sel.*, 24(1-2):27-31 (2011).
Gaj, et al., "ZFN, TALEN, and CRISPER/cas-based methods for genome engineering", *Trends in Biotech.*, 31(7):397-405 (2013).
Oliveria, et al., "Enhancement of chitosan-mediated gene delivery through combination with phiC31 integrase", *Acta Biomaterialia*, 17:89-97 (2015).
Sangamo Bioscience, Triple forming peptide nucleic acids (TFPs)-SGMO, http://www.investorvillage.com/mbthread.asp?mb=1933&=13823114&showall, post dated May 13, 2014, accessed Jul. 13, 2016.
Strouse, et al., "Combinatorial gene editing in mammalian cells using ssODNs and TALENs", *Scientific Reports*, 4:3791-9 (2014).
Abramova, et al., "Solid-phase-supported synthesis of morpholinoglycine oligonucleotide mimics", Beilstein J. Org. Chem., 10: 1151-1158 (2014).
Avitabile, et al., "[gamma] sulphate ONA (PNA S): Highly Selective DNA Binding Molecule Showing Promising Antigene Activity", PLOS ONE, 7(5): e35774 (2012).
Banal, et al., "In vivo correction of anaemia in b-thalassemic mice by gPNA-mediated gene editing with nanoparticle delivery", Nature Communications, 7:1-14 (2016).
Bahal, et al., "Site specific genome editing of hematopoietic stem cells for beta thalassemia gene therapy," American Society of Gene and Cell Therapy, Annual Meeting, May 21-24, (2014).
Budke, et al., "RI-1: a chemical inhibitor of RAD51 that disrupts homologous recombination in human cells", Nucleic Acids Research, 40(15):7347-7357 (2012).
Cantin, et al., "Synthesis of the monomeric building blocks of Z-olefinic PNA (Z-OPA) containing the bases adenine and thymine", Tetrahedron Lett., 38:4211-4214 (1997).
Carrington, et al., "Novel Alleles of the Chemokine-Receptor Gene CCR5," Am. J. Hum. Genet., 61(6):1261-7(1997).
Cavazzana-Calvo, et al., "Gene therapy of human severe combined immunodeficiency (SCID)-X1 disease", Science, 288:669-672 (2000).
Chapman, et al., "Playing the end game: DNA double-strand break repair pathway choice," Mol. Cell, 47:497-510 (2012).
Chenna, et al., "A simple cytosine to G-clamp nucleobase substitution enables chiral gamma-PNAs to invade mixed-sequence double-helical B-form DNA", Chembiochem., 9:2388-2391 (2008).
Chung, et al., "Generation of ΔF508-CFTR T84 cell lines by CRISPR/Cas9-mediated genome editing", Biotechnol. Lett., 38:2023-2034 (2016).
Ciapetti, et al., "Synthesis of N-Fmoc-α-amino acids carrying the four DNA nucleobases in the side chain", Tetrahedron, 53:1167-1176 (1997).
Ciccia, et al., "The DNA damage response: making it safe to the play with knives," Mol. Cell., 40:179-204 (2010).
Coskun, et al., "Development of the fetal bone marrow niche and regulation of HSC quiescence and homing ability by emerging osteolineage cells", Cell Rep., 9:581-590 (2014).
Crane, et al., "Targeted Correction and Restored Function of the CFTR Gene in Cystic Fibrosis Induced Pluripotent Stem Cells", Stem Cell Reports, 4:569-577 (2015).
Cui, et al., "Ex vivo pretreatment of human vessels with siRNA nanoparticles provides protein silencing in endothelial cells", Nature Communications, 8:(191):1-11 (2017).
Daksis, et al., "Heteropolymeric Triplex-Based Genomic Assay to Detect Pathogens or Single-Nucleotide Polymorphisms in Human Genomic Samples", PLOS ONE, 2:3 (2007).
Deng, et al., "Improved i.p. drug delivery with bioadhesive nanoparticles", Proc. Natl. Acad. Sci., 113:11453-11458 (2016).
Deng, et al., "The Effect of Hyperbranched Polyglycerol Coatings on Drug Delivery Using Degradable Polymer Nanoparticles", Biomaterials, 35(24): 6595-6602 (2014).
Diderichsen, et al., "Self-pairing PNA with alternating alanyl/homoalanyl backbone", Tetrahedron Lett., 37:475-478 (1996).
Diedrichsen, et al., "Alanyl-PNA homoduplex: A-T pairing with the N7-regioisomer of adenine", Bioorg. Med. Chem. Lett., 8:165-168 (1998).
Doe, et al., "Generating CRISPR/Cas9-Derived Mutant Mice by Zygote Cytoplasmic Injection Using an Automatic Microinjector", Methods and Protocols, 1(5):1-12 (2018).
Dragulescu-Andrasi, et al., "A Simple γ-Backbone Modification Preorganizes Peptide Nucleic Acid into a Helical Structure", Journal of the American Chemical Society, 128(31):10258-67 (2006).
Efimov, et al., "Hydroxyproline-based DNA mimics provide an efficient gene silencing in vitro and in vivo", Nucleic Acids Res., 34(8):2247-2257 (2006).
Egan, et al., "Curcumin, a Major Constituent of Turmeric, Corrects Cystic Fibrosis Defects", Science, 304:600-602 (2004).
Eriksson, et al., "PNA-nucleic acid complexes. Structure, stability and dynamics", Quart. Rev. Biophys., 29(4):369-394 (1996).
Ezzati, et al., "Tubal transport of gametes and embryos: a review of physiology and pathophysiology", J. Assist. Reprod. Genet., 31(10):1337-47 (2014).

(56) References Cited

OTHER PUBLICATIONS

Fanen, et al., "Genetics of cystic fibrosis: CFTR mutation classifications toward genotype-based CF therapies", Int. J. Biochem. Cell Biol., 52:94-102 (2014).
Firth, et al., "Functional Gene Correction for Cystic Fibrosis in Lung Epithelial Cells Generated From Patient iPSCs", Cell Rep., 12:1385-1390 (2015).
Fujii, et al., "Nucleic acid analog peptide (NAAP) 2. Syntheses and properties of novel DNA analog peptides containing nucleobase linked β-aminoalanine" Bioorg. Med. Chem. Lett. 7:637-627 (1997).
Gamble, et al., "Development of Cu+2-Based Distance Methods and force Field Parameters for the Determination of PNA Conformations and Dynamics by EPR and MD Simulations", Journal of Physical Chemistry Part B, 124(35):7544-7556 (2020).
Gaspar, et al., "Gene therapy of X-linked severe combined immunodeficiency by use of a pseudotyped gammaretroviral vector", Lancet, 364:2181-2187 (2004).
Govindaraju, et al., "(1S,2R/1R,2S)-cis-Cyclopentyl PNAs (cpPNAs) as Constrained PNA Analogues: Synthesis and Evaluation of aeg-cpPNA Chimera and Stereopreferences in Hybridization with DNA/RNA", J. Org. Chem. 69(17):5725-34 (2004).
Gupta, et al., "Triple Helical Recognition of Pyrimidine Inversions in Polypurine Tracts of RNA by Nucleobase-modified PNA", Chem. Comm., 47:11125-11127 (2011).
Hacein-Bey-Abina, et al., "Sustained correction of X-linked severe combined immunodeficiency by ex vivo gene therapy", N. Engl. J. Med., 346:1185-1193 (2002).
He, et al., "The Structure of a y-modified peptide nucleic acid duplex", Mol. BioSyst. 6:1619-1629 (2010).
Hoban, et al., "Correction of the sickle cell disease mutation in human hematopoietic stem/progenitor cells", Blood, 125:2597-2604 (2015).
Johnson, et al., "Efficiency of gene transfer for restoration of normal airway epithelial function in cystic fibrosis", Nat. Genet. 2:21-25 (1992).
Jordan, et al., "New hetero-oligomeric peptide nucleic acids with improved binding properties to complementary DNA", Bioorg. Med. Chem. Lett., 7:687-690 (1997).
Keshet, et al., "Embryonic RNA expression patterns of the c-kit receptor and its cognate ligand suggest multiple functional roles in mouse development", EMBO J. 10:2425-2435 (1991).
Kirillova, et al., "Polyanionic Carboxyethyl Peptide Nucleic Acids (ce-PNAs): Synthesis and DNA Binding", PLOS ONE, 10(10):e0140468 (2015).
Krishnendu, et al., "Core/shell nanoparticles in biomedical applications", Advances in Colloid and Interface Science, 209:8-39 (2014).
Krotz, et al., "Synthesis of 'retro-inverso' peptide nucleic acids: 2. Oligomerization and stability", Tetrahedron Lett. 36:6941-6944 (1995).
Lagriffoul, et al., "The synthesis, co-oligomerization and hybridization of a thymine-thymine heterodimer containing PNA", Bioorg. Med. Chem. Lett. 4:1081-1082 (1994).
Lagriffoule, et al., "Peptide Nucleic Acids with a Conformationally Constrained Chiral Cyclohexyl☐Derived Backbone", Chem. Eur. J., 3:912-919 (1997).
Larson, et al., "In Utero Gene Therapy", Ochsner J., 2(2):107-110 (2000).
Lennartsso, et al., "Stem Cell Factor Receptor/C-Kit: From Basic Science to Clinical Implications", Physiological Reviews, 92(4):1619-1649 (2012).
Lowe, et al., "Amino acids bearing nucleobases for the synthesis of novel peptide nucleic acids", J. Chem. Soc. Perkin Trans., 1:539-546 (1997).
Maeder, et al., "Genome-editing Technologies for Gene and Cell," Therapy Molecular Therapy, 24(3): 430-446 (2016).
Matsui, et al., "Embryonic expression of a haematopoietic growth factor encoded by the SI locus and the ligand for c-kit", Nature, 347:667-669 (1990).

Nielsen, et al., "Peptide nucleic acid (PNA). A DNA mimic with a peptide backbone", Bioconjug. Chem., 5:3-7 (1994).
Nielsen, et al., "Sequence-selective targeting of duplex DNA by peptide nucleic acids", Current opinion in molecular therapeutics, 12:184-191 (2010).
Orr-Urtreger, et al., "Developmental expression of c-kit, a proto-oncogene encoded by the W locus", Development, 109:911-923 (1990).
Papaioannou, et al., "Oligonucleotide-directed gene-editing technology: mechanisms and future prospects", Expert Opin. Biol. Ther., 12(3):329-342 (2012).
Papaioannou, et al., "Oligonucleotide-directed gene-editing technology: mechanisms and future prospects", Expert Opinion on Biological, The Informa Healthcare, UK., 12(3):329-342 (2012).
Patel, et al., "Polymeric nanoparticles for drug delivery to the central nervous system", Advanced drug delivery reviews, 64(7):701-5 (2012).
Petersen, et al., "Synthesis and oligomerization of Nδ-Boc-Nα-(thymin-1-ylacetyl)ornithine", Bioorg. Med. Chem. Lett., 6(7):793-796 (1996).
Quijano, et al., "Therapeutic Peptide Nucleic Acids: Principles, Limitations, and Opportunities", Yale J. Biol. Med., 90:583-598 (2017).
Reyes, et al., "Towards a CRISPR view of early human development: applications, limitations and ethical concerns of genome editing in human embryos," Development, 144: 3-7 (2017).
Ricciardi, et al., "Targeted genome modification via triple helix formation", Methods Mol. Biol., 1176:89-106 (2014).
Richardson, et al., "Gene Repair in the New Age of Gene Therapy", Hepatology, 35(3):512-518 (2002).
Roos, et al., "The multifaceted influence of histone deacetylases on DNA damage signalling and DNA repair", Nucleic Acids Research, 44(21):10017-10030 (2016).
Roybal, et al., "Stem cell and genetic therapies for the fetus", Semin. Fetal Neonatal. Med., 15:46-51 (2010).
Sanz, et al., "Cas9/gRNA targeted excision of cystic fibrosis-causing deep-intronic splicing mutations restores normal splicing of CFTR mRNA", PLoS One 12:e0184009 (2017).
Schaefer, et al., "Unexpected mutations after CRISPR-Cas9 editing in vivo", Nat. Methods, 14:547-548 (2017).
Shenoy, et al., "Calcium Modulated Chloride Pathways Contribute to Chloride Flux in Murine CF-Affected Macrophages", Pediatric research, 70:447-452 (2011).
Song, et al., "Surface chemistry governs cellular tropism of nanoparticles in the brain", Nat. Commun, 8:15322 (2017).
Sugiyama, et al., "PNA monomers fully compatible with standard Fmoc-based solid-phase synthesis of pseudocomplementary PNA", Bioorg. Med. Chem. Lett., 27(15):3337-3341 (2017).
Tan, et al., "Homopolymeric pyrrolidine-amide oligonucleotide mimics: Fmoc-synthesis and DNA/RNA binding properties", Org. Biomol. Chem., 5: 239-248 (2007).
Van Der Laan, et al., "An approach towards the synthesis of oligomers containing a N-2-hydroxyethyl-aminomethylphosphonate backbone: A novel PNA analogue", Tetrahedron Lett. 37:7857-7860 (1996).
Waddington, et al., "In Utero gene therapy: current challenges and perspectives," Molecular Therapy, 11(5): 661-676 (2005).
Walsh, "Fetal Gene Therapy," Gene Therapy, 6(7):1200-1 (1999).
Wefers, et al., "Gene editing in mouse zygotes using the CRISPR/Cas9 system," Methods, 121-122:55-67 (2017).
Yeh, et al., "Self-assembled Monothiol-Terminated Hyperbranched Polyglycerols on a Gold Surface: A Comparative Study on the Structure, Morphology, and Protein Adsorption Characteristics With Linear Poly(ethylene Glycol)s", Langmuir, 24(9):4907-16(2008).
Zhou, et al., "Highly penetrative, drug-loaded nanocarriers improve treatment of glioblastoma", PNAS, 110(29):11751-6 (2013).
Bahal, et al., "In vivo correction of anaemia in b-thalassemic mice by gPNA-mediated gene editing with nanoparticle delivery", *Nature Communications*, 7:1-14 (2016).
He, et al., "The Structure of a γ-modified peptide nucleic acid duplex", *Mol. BioSyst.* 6:1619-1629 (2010).

(56) References Cited

OTHER PUBLICATIONS

Lennartsson, et al., "Stem Cell Factor Receptor/C-Kit: From Basic Science to Clinical Implications", *Physiological Reviews*, 92(4):1619-1649 (2012).
Matsui, et al., "Embryonic expression of a haematopoietic growth factor encoded by the Sl locus and the ligand for c-kit", *Nature*, 347:667-669 (1990).

\* cited by examiner

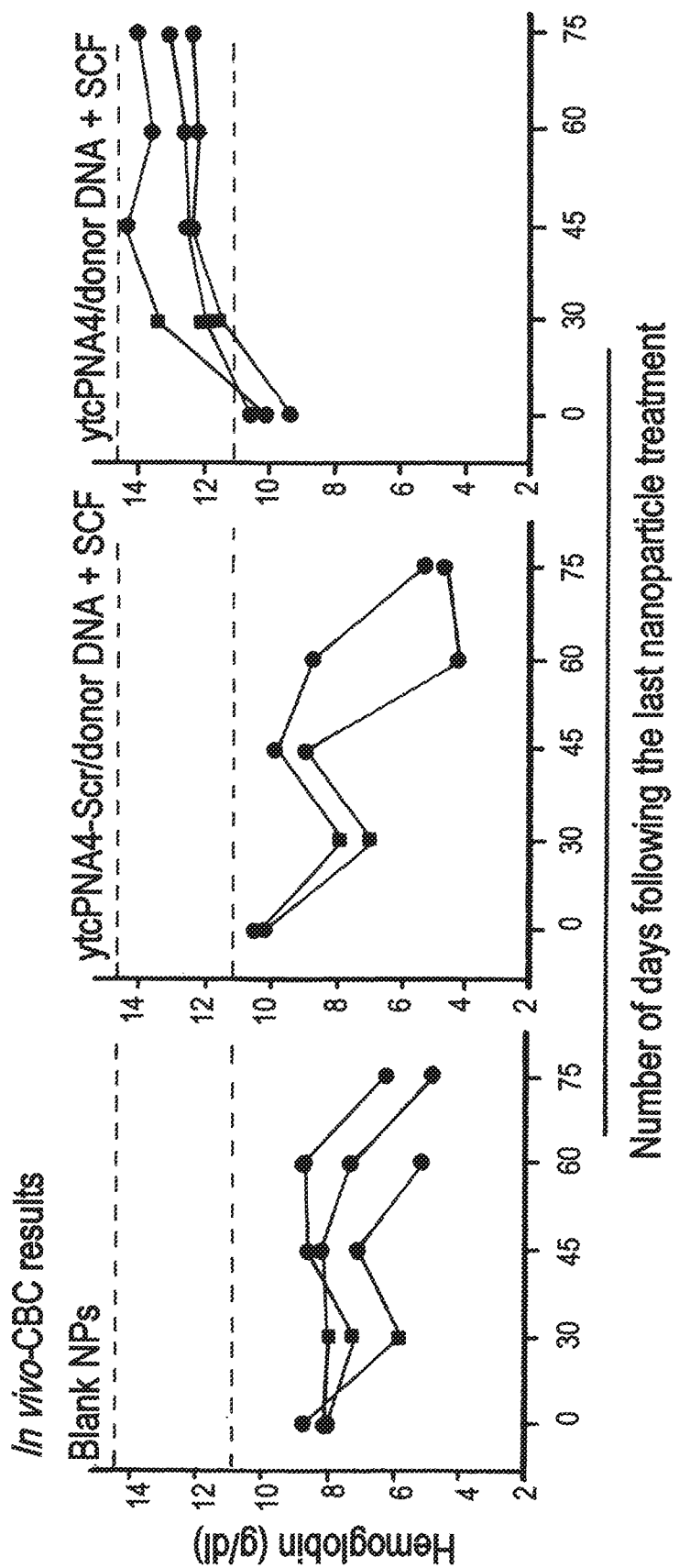

*In vivo* deep sequencing results: Bone marrow

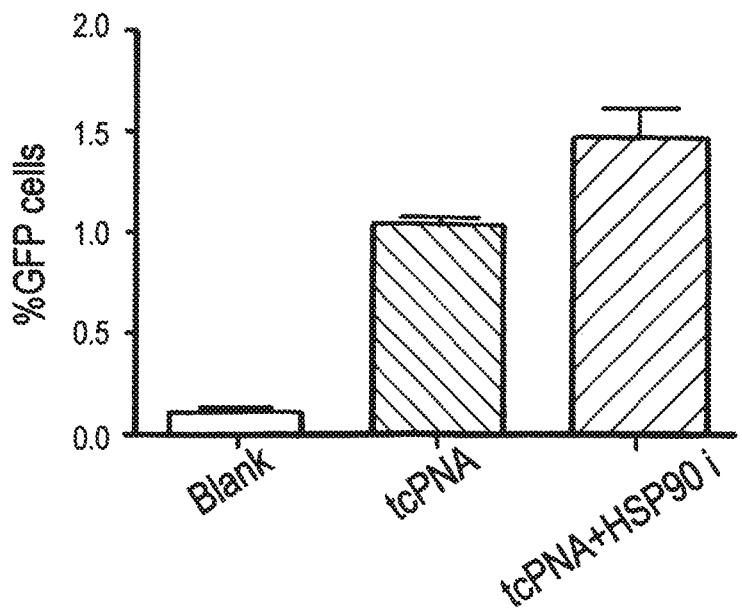
FIG. 5D
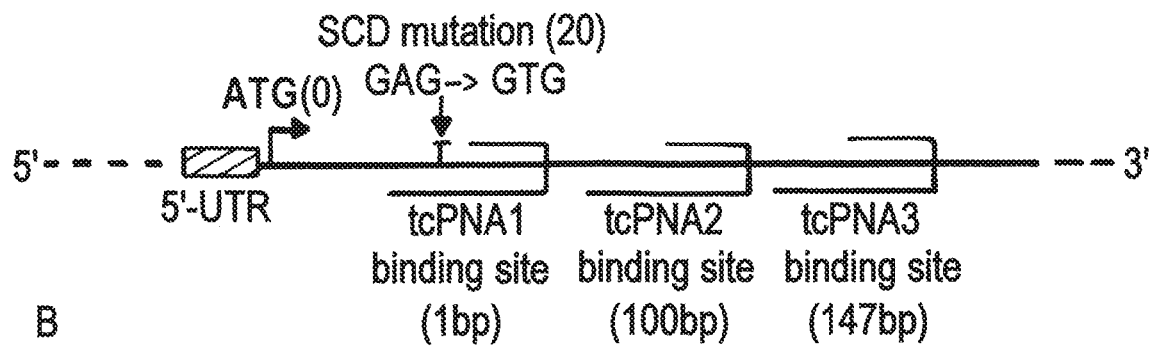
FIG. 6A
tcPNA 1: H-KKK-JJTJTTJ-OOO-CTTCTCCAAAGGAGT-KKK-NH$_2$
tcPNA 2: H-KKK-TTJJTJT-OOO-TCTCCTTAAACCTGT-KKK-NH$_2$
tcPNA 3: H-KKK-TJTJTTJT-OOO-TCTTCTCTGTCTCCAC-KKK-NH$_2$
FIG. 6B
Sense donor DNA. 5'-ACAGACACCATGGTGCACCTGACTCCTGAGGAGAAGTCTGCCGTTACTGCC-3'
FIG. 6C tc PNA-1236: H-KKK-JTTJTJTJTTT-OOO-TTTCTCCTTCAGTGTTCA-KKK-NH$_2$
tc PNA-1314: H-KKK-TTTTJJT-OOO-TCCTTTTGCTCACCTGTGGT-KKK-NH$_2$
tc PNA-1329: H-KKK-TJTTTTTJ-OOO-CCTTTTTCTGGCTAAGT-KKK-NH$_2$ 5'-T(s)C(s)T(s)TGGGATTCAATAACCT̲TGCAGACAGTGG̲AGGAAG̲GCCTTTGGC̲GTGATACCACAG(s)T(s)G(s)-3'

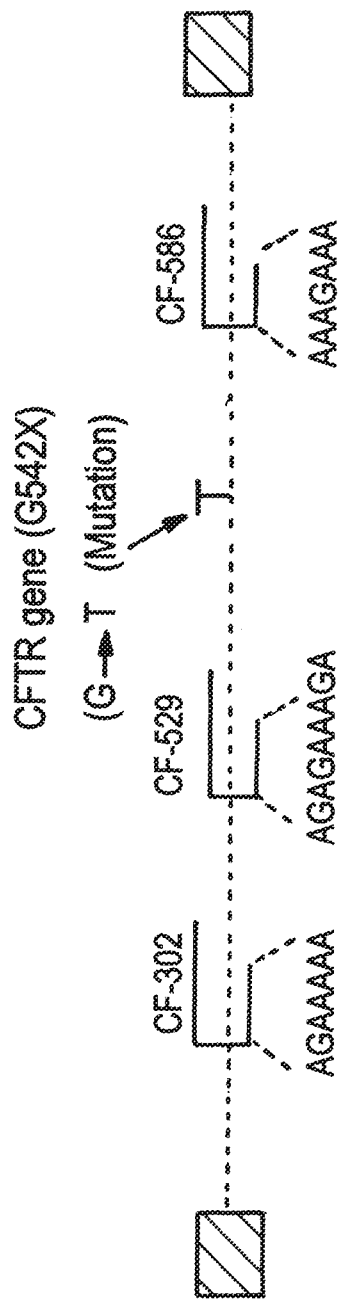

COMPOSITIONS FOR ENHANCING TARGETED GENE EDITING AND METHODS OF USE THEREOF

CROSS-REFERENCE TO RELATED APPLICATIONS

This application claims the benefit of and priority to U.S. Ser. No. 62/295,789 filed Feb. 16, 2016 and which is incorporated by reference in its entirety.

STATEMENT REGARDING FEDERALLY SPONSORED RESEARCH

This invention was made with government support under AI112443 awarded by National Institutes of Health and under 1012467 awarded by National Science Foundation. The government has certain rights in the invention.

REFERENCE TO SEQUENCE LISTING

The Sequence Listing submitted as a text file named "YU_6876_5_ST25.txt," created on Nov. 3, 2020, and having a size of 93,350 bytes is hereby incorporated by reference pursuant to 37 C.F.R § 1.52(e)(5).

FIELD OF THE INVENTION

The field of the invention is generally related to gene editing technology used in combination with a gene modification potentiating agent, and compositions and methods of use thereof for ex vivo and in vivo gene editing.

BACKGROUND OF THE INVENTION

Gene editing in hematopoietic stem/progenitor cells (HSPCs) provides an attractive strategy for treatment of inherited disorders such as sickle cell anemia and β-thalassemia. Genes can be selectively edited by several methods, including targeted nucleases such as zinc finger nucleases (ZFNs) (Haendel, et al., *Gene Ther.*, 11:28-37 (2011)) and CRISPRs (Yin, et al., *Nat. Biotechnol.*, 32:551-553 (2014)), short fragment homologous recombination (SFHR) (Goncz, et al., *Oligonucleotides*, 16:213-224 (2006)), or triplex-forming oligonucleotides (TFOs) (Vasquez, et al., *Science*, 290:530-533 (2000)). Recent excitement has focused on CRISPR/Cas9 technology because of its ease of use and facile reagent design (Doudna, et al., *Science*, 346:1258096 (2014)). However, like ZFNs, the CRISPR approach introduces an active nuclease into cells, which can lead to off-target cleavage in the genome (Cradick, et al., *Nucleic Acids Res.*, 41:9584-9592 (2013)), a problem that so far has not been eliminated.

One alternative is triplex-forming peptide nucleic acid (PNA) oligomers designed to bind site-specifically to genomic DNA via strand invasion and formation of PNA/DNA/PNA triplexes via both Watson-Crick and Hoogsteen binding) with a displaced DNA strand (Egholm, et al., *Nature* (London), 365:566-568 (1993); Nielsen, et al., *Science* (Washington, D.C., 1883-), 254:1497-1500 (1991); Faruqi, et al., *Proc Natl Acad Sci USA*, 95:1398-1403 (1998)). PNAs have a charge-neutral peptide-like backbone and nucleobases enabling hybridization with DNA and RNA with high affinity. PNA/DNA/PNA triplexes recruit the cell's endogenous DNA repair systems to initiate site-specific modification of the genome when single-stranded "donor DNAs" are co-delivered as templates containing the desired sequence modification (Rogers, et al., *Proc. Natl. Acad. Sci. USA*, 99:16695-16700 (2002)).

PNA-induced genome modification is believed to be mediated in part by the nucleotide excision repair (NER) and homology-dependent repair (HDR) pathways (Rogers, et al., *Proc. Natl. Acad. Sci. USA*, 99:16695-16700 (2002); Chin, et al., *Molecular Carcinogenesis*, 48:389-399 (2009)). Both NER and HDR are high fidelity pathways, and the PNAs lack any intrinsic nuclease activity. Together these features may account for the very low frequencies of off-target genotoxicity seen with PNA-mediated gene editing compared to nuclease based approaches (McNeer, et al., *Gene Therapy*, 20:658-669 (2013); Schleifinan, et al., *Chem. Biol.* (Cambridge, Mass., U.S.), 18:1189-1198 (2011); Schleifman, et al., *Mol. Ther.—Nucleic Acids*, 2:e135 (2013)). Tail-clamp PNAs (tcPNAs) with an extended Watson-Crick binding domain can enhance gene editing in human hematopoietic cells with increased efficiency and specificity (Schleifman, et al., *Chem. Biol.* (Cambridge, Mass., U.S.), 18:1189-1198 (2011)) and that polymer nanoparticles (NPs) can effectively deliver these molecules into human HSPCs both ex vivo and in vivo in a humanized mouse model (McNeer, et al., *Gene Therapy*, 20:658-669 (2013); Bahal, et al., *Curr. Gene Ther.*, 14:331-342 (2014)).

Nonetheless, compositions and methods for improved gene editing are needed.

It is an object of the invention to provide potentiating agents that increase gene modification induced or enhanced by gene editing technology.

It is another object of the invention to provide triplex forming molecules with enhanced DNA binding.

It is a further object of the invention to provide gene modification formulations that achieve therapeutically significant target site modification with reduced low off-target modification.

SUMMARY OF THE INVENTION

Highly elevated levels of gene editing in hematopoietic stem/progenitor cells are achieved using triplex-forming peptide nucleic acids (PNAs) substituted at the γ position for increased DNA binding affinity in combination with stimulation of the stem cell factor (SCF)/c-Kit pathway. The SCF/c-Kit pathway is believed to boost DNA repair gene expression and homology-dependent repair activity as evidence shows that stimulation is correlated with elevated DNA repair, specifically increased HDR activity and increased levels of HDR gene expression, including BRCA2 and Rad51. In a mouse model of human β-thalassemia, injection with SCF plus nanoparticles containing γPNAs and donor DNAs yielded amelioration of the disease phenotype, with clinically relevant β-globin gene correction frequencies (4% in bone marrow) and extremely low off-target effects. The mice showed alleviation of anemia with sustained elevation of blood hemoglobin levels into the normal range, reduced reticulocyte counts, and reversal of splenomegaly.

Compositions and methods for enhancing targeted gene editing and methods of use thereof are disclosed. In the most preferred embodiments, gene editing is carried out utilizing a gene editing composition such as triplex-forming oligonucleotides, CRISPR, zinc finger nucleases, TALENS, or others, in combination with a gene modification potentiating agent such as SCF, a CHK1 or ATR inhibitor, a DNA polymerase alpha inhibitor, a heat shock protein 90 inhibitor (HSP90i) or a combination thereof. A particularly preferred gene editing composition is triplex-forming peptide nucleic acids (PNAs) substituted at the γ position for increased DNA binding affinity. Nanoparticle compositions for intracellular delivery of the gene editing composition are also provided and particularly advantageous for use with in vivo applications.

For example, an exemplary method of modifying the genome of a cell can include contacting the cell with an effective amount of (i) a gene editing potentiating agent selected from the group consisting of tyrosine kinase C-kit ligands, ATR-Chk1 cell cycle checkpoint pathway inhibitors, DNA polymerase alpha inhibitors, and heat shock protein 90 inhibitors (HSP90i), and (ii) a gene editing technology that can induce genomic modification of the cell selected from the group consisting of triplex forming molecules, pseudocomplementary oligonucleotides, a CRISPR system, zinc finger nucleases (ZFN), and transcription activator-like effector nucleases (TALEN); wherein genomic modification occurs at a higher frequency in a population of cells contacted with both (i) and (ii), then in an equivalent population contacted with (ii) in the absence of (i). The method can further include contacting the cells with a donor oligonucleotide including, for example, a sequence that corrects or induces a mutation(s) in the cell's genome by insertion or recombination of the donor induced or enhanced by the gene editing technology.

A preferred C-kit ligand is a stem cell factor protein or fragment thereof sufficient to cause dimerization of C-kit and activate its tyrosine kinase activity. In some embodiments, the C-kit ligand is a nucleic acid such as an mRNA or an expression vector encoding a stem cell factor protein or fragment thereof sufficient to cause dimerization of C-kit and activate its tyrosine kinase activity.

ATR-Chk1 cell cycle checkpoint pathway inhibitors are typically small molecules though they can also be inhibitory nucleic acids such as siRNA that target and reduce expression a gene in the pathway. Inhibitors include, for example, AZD7762, SCH900776/MK-8776, IC83/LY2603618, LY2606368, GDC-0425, PF-00477736, XL844, CEP-3891, SAR-020106, CCT-244747, Arry-575, SB218075, Schisandrin B, NU6027, NVP-BEZ235, VE-821, VE-822 (VX-970), AZ20, AZD6738, MIRIN, KU5593, VE-821, NU7441, LCA, and L189.

In some embodiments, the cell's genome has a mutation underlying a disease or disorder, for example a genetic disorder such as hemophilia, globinopathies, cystic fibrosis, xeroderma pigmentosum, muscular dystrophy, and lysosomal storage diseases. The globinopathy can be sickle cell anemia or beta-thalassemia. The lysosomal storage disease can be Gaucher's disease, Fabry disease, or Hurler syndrome. In some embodiments, the method induces a mutation that reduces HIV infection, for example, by reducing an activity of a cell surface receptor that facilitates entry of HIV into the cell.

The contacting of the compositions with the cell can occur ex vivo. In some embodiments, the ex vivo-treated cells are hematopoietic stem cells. The modified cells can be administered to a subject in need thereof in an effective amount to treat one or more symptoms of a disease or disorder such as hemophilia, a globinopathy, cystic fibrosis, xeroderma pigmentosum, muscular dystrophy, a lysosomal storage disease, or HIV.

In vivo applications are also provided. For example in some embodiments, the potentiating agent, gene editing technology and optionally the donor oligonucleotide are administered to a subject in need thereof. Each of the foregoing can be in the same or different pharmaceutical compositions and can be administered to the subject in any order. In preferred embodiments, the compositions induce or enhance in vivo gene modification in an effective amount to reduce one or more symptoms of the disease or disorder, for example, hemophilia, a globinopathy, xeroderma pigmentosum, a lysosomal storage disease, or HIV in the subject.

Any of the disclosed compositions including potentiating agent, gene editing technology, and/or donor oligonucleotide can be packaged together or separately in nanoparticles. In preferred embodiments, the nanoparticles include poly(lactic-co-glycolic acid) (PLGA) alone or in a blend with poly(beta-amino) esters (PBAEs). In particular embodiments, the nanoparticles include a blend of PLGA and PBAE having between about 10 and about 20 percent PBAE (wt %). In preferred embodiments, the nanoparticles are prepared by double emulsion. In some embodiments the gene editing technology, the donor oligonucleotide or a combination thereof are complexed with a polycation prior to preparation of the nanoparticles.

Functional molecules such as targeting moieties, a cell penetrating peptides, or a combination thereof can be associated with, linked, conjugated, or otherwise attached directly or indirectly to the potentiating agent, the gene editing technology, the nanoparticle, or a combination thereof. In particularly preferred embodiments, a cell penetrating peptide including the sequence GALFLGFL-GAAGSTMGAWS QPKKKRKV (SEQ ID NO:12) (MPG (Synthetic chimera: SV40 Lg T. Ant.+HIV gb41 coat)) is conjugated to the surface of the nanoparticles.

Improved DNA-binding triplex forming molecules are also provided. The triplex forming molecules can be utilized in all manners of gene modification including those methods both with and without a potentiating agent. The triplex forming composition typically includes a Hoogsteen binding peptide nucleic acid (PNA) segment and a Watson-Crick binding PNA segment collectively totaling no more than about 50 nucleobases in length, wherein the two segments can bind or hybridize to a target region having a polypurine stretch in a cell's genome to induce strand invasion, displacement, and formation of a triple-stranded molecule among the two PNA segments and the polypurine stretch. The Hoogsteen binding segment binds to the target duplex by Hoogsteen binding for a length of at least five nucleobases, and the Watson-Crick binding segment typically binds to the target duplex by Watson-Crick binding for a length of least five nucleobases.

In preferred embodiments, one or more of the PNA monomers are γPNA. The side chain at the γ position of the γPNA monomer(s) can be, for example, the side chain of an amino acid selected from the group consisting of alanine, serine, threonine, cysteine, valine, leucine, isoleucine, methionine, proline, phenylalanine, tyrosine, aspartic acid, glutamic acid, asparagine, glutamine, histidine, lysine, arginine, and the derivatives thereof. In some embodiments, the side chain at the γ position of the γPNA monomer(s) is a diethylene glycol ("miniPEG"). In some embodiments, all of the peptide nucleic acid monomers in the Hoogsteen-binding portion only, all of the peptide nucleic acid monomers in the Watson-Crick-binding portion only, or all of the peptide nucleic monomers in the PNA oligomer are γPNA monomers. In some embodiments, alternating residues in the Hoogsteen-binding portion only, the Watson-Crick-binding portion only, or across the entire PNA are PNA and γPNA. Specific exemplary sequences are provided below.

In some embodiments, one or more of the cytosines is replaced with a clamp-G (9-(2-guanidinoethoxy) phenoxazine). In preferred embodiments, the Hoogsteen binding segment includes one or more chemically modified cytosines selected from the group consisting of pseudocytosine, pseudoisocytosine, and 5-methylcytosine. The Watson-Crick binding segment preferably includes a tail sequence of up to fifteen nucleobases that binds to the target duplex by Watson-Crick binding outside of the triplex. In preferred embodiments, the two segments are linked by a linker, for example, between 1 and 10 units of 8-amino-3,6-dioxaoctanoic acid.

BRIEF DESCRIPTION OF THE DRAWINGS

FIGS. 4A-4C are line graphs showing blood hemoglobin levels (g/dl) of thalassemic mice treated with blank NPs, SCF plus scrambled γtcPNA4-Scr/donor DNA (SEQ ID NOS:158 and 65) NPs, or with SCF plus γtcPNA4/donor DNA (SEQ ID NOS:162 and 65) NPs performed at the indicated times after treatment. Each line represents an individual mouse followed over time.

FIG. 5D is a bar graph showing gene correction of control (blank), and cells treated with nanoparticles containing tcPNA1 (SEQ ID NO:191) and donor DNA (SEQ ID NO:76) alone, or in combination with a heat shock protein 90 inhibitor (HSP90i) (STA-9090 (ganetespib)).

FIG. 6A is an illustration of a Sickle Cell Disease mutation (GAG→GTG) in the human beta globin gene, relative to the ATG transcriptional start site and exemplary tcPNAs. FIG. 6B shows the sequences of exemplary PNAs: tcPNA1: lys-lys-lys-JJTJTTJ-OOO-CTTCTCCAAAGGAGT-lys-lys-lys (SEQ ID NO:66); tcPNA2: lys-lys-lys-TTJJTJT-OOO-TCTCCTTAAACCTGT-lys-lys-lys (SEQ ID NO:67); and tcPNA3: lys-lys-lys-TJTJTTJT-OOO-TCTTCTC-TGTCTCCAC-lys-lys-lys (SEQ ID NO:68). FIG. 6C shows the sequence of a DNA donor (SEQ ID NO:64).

FIG. 9A is an illustration of a mutation (G→T) in the CFTR gene (G542X) relative to three exemplary tcPNAs. FIG. 9B provides the sequences of the tcPNAs: CF-302 lys-lys-lys-TJTTTTT-OOO-TTTTTCTGTAATTTTTAA-lys-lys-lys (SEQ ID NO:172), CF-529 lys-lys-lys-TJTJTTTJT-OOO-TCTTTCTCTGCAAACTT-lys-lys-lys (SEQ ID NO:173), and CF-586 lys-lys-lys-TTTJTTT-OOO-TTTCTTTAAGAACGAGCA-lys-lys-lys (SEQ ID NO:174). FIG. 9C provides the sequence of an exemplary donor DNA: T(s)C(s)C(s)-AAGTTTGCAGAGAAAGA TAATATAGTCCTTGGAGAAGGAGGAATCA CCCTG-AGTGGA-G(s)G(s)T(s) (SEQ ID NO:124).

DETAILED DESCRIPTION OF THE INVENTION

I. Definitions

Figure 1A:
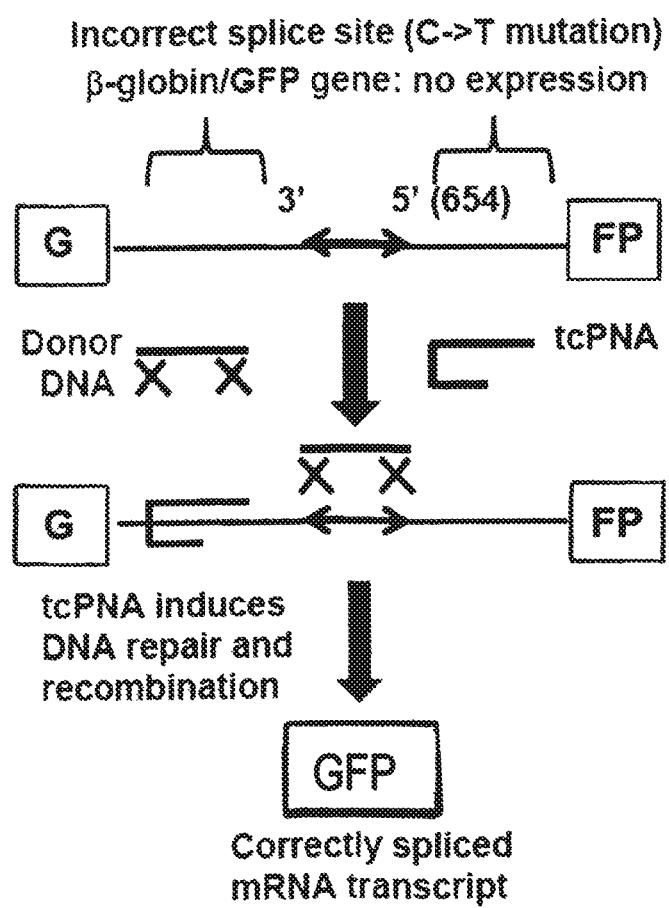
FIG. 1A is a schematic showing a strategy for targeted correction of a β-globin gene IVS2-654 (C→T) mutation in β-globin/GFP transgenic mice using triplex-forming tail clamp PNAs (tcPNAs) and donor DNAs.

As used herein, "affinity tags" are defined herein as molecular species which form highly specific, non-covalent, physiochemical interactions with defined binding partners. Affinity tags which form highly specific, non-covalent, physiochemical interactions with one another are defined herein as "complementary".

As used herein, "coupling agents" are defined herein as molecular entities which associate with polymeric nanoparticles and provide substrates that facilitate the modular assembly and disassembly of functional elements onto the nanoparticle. Coupling agents can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Coupling agents can also be covalently coupled to functional elements in the absence of affinity tags.

As used herein, the term "isolated" describes a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a nucleic acid can be introduced.

As used herein, "transformed" and "transfected" encompass the introduction of a nucleic acid into a cell by one of a number of techniques known in the art.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ M$^{-1}$. Affinities greater than $10^8$M$^{-1}$ are preferred.

As used herein, "targeting molecule" is a substance which can direct a nanoparticle to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.*, 79:315-321 (1990); Kostelny, et al., *J. Immunol.*, 148, 1547-1553 (1992). As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10, amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke, et al., *J. Inf. Dis.*, 170:1110-19 (1994)), by antigen-dependent killing (cytotoxic T lymphocyte assay, Tigges, et al., *J. Immunol.*, 156, 3901-3910) or by cytokine secretion.

As used herein, the term "small molecule," as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

II. Gene Editing Potentiating Factors

It has been discovered that certain potentiating factors can be used to increase the efficacy of gene editing technologies. Gene expression profiling on SCF-treated CD117+ cells versus untreated CD117+ cells discussed in the Examples below showed additional up-regulation of numerous DNA repair genes including RAD51 and BRCA2. These results and others discussed below indicate that a functional c-Kit signaling pathway mediates increased HDR and promotes gene editing, rather than CD117 simply being a phenotypic marker. When CD117+ cells were treated with SCF, expression of these DNA repair genes was increased even more, correlating with a further increase in gene editing.

Accordingly, compositions and methods of increasing the efficacy of gene editing technology are provided. As used herein a "gene editing potentiating factor" or "gene editing potentiating agent" or "potentiating factor or "potentiating agent" refers a compound that increases the efficacy of editing (e.g., mutation, including insertion, deletion, substitution, etc.) of a gene, genome, or other nucleic acid) by a gene editing technology relative to use of the gene editing technology in the absence of the compound. Preferred gene editing technologies suitable for use alone or more preferably in combination with the disclosed potentiating factors are discussed in more detail below. In certain preferred embodiments, the gene editing technology is a triplex-forming γPNA and donor DNA, optionally, but preferably in a nanoparticle composition.

Potentiating factors include, for example, DNA damage or repair-stimulating or -potentiating factors. Preferably the factor is one that engages one or more endogenous high fidelity DNA repair pathways. In some embodiments, the factor is one that increases expression of Rad51, BRCA2, or a combination thereof.

As discussed in more detail below, the preferred methods typically include contacting cells with an effective amount of a gene editing potentiating factor. The contacting can occur ex vivo, for example isolated cells, or in vivo following, for example, administration of the potentiating factor to a subject.

A. C-Kit Ligands

In some embodiments, the factor is an activator of the receptor tyrosine kinase c-Kit. CD117 (also known as mast/stem cell growth factor receptor or proto-oncogene c-Kit protein) is a receptor tyrosine kinase expressed on the surface of hematopoietic stem and progenitor cells as well as other cell types. Stem cell factor (SCF), the ligand for c-Kit, causes dimerization of the receptor and activates its tyrosine kinase activity to trigger downstream signaling pathways that can impact survival, proliferation, and differentiation. SCF and c-Kit are reviewed in Lennartsson and Ronnstrand, *Physiological Reviews,* 92(4):1619-1649 (2012)).

The human SCF gene encodes for a 273 amino acid transmembrane protein, which contains a 25 amino acid N-terminal signal sequence, a 189 amino acid extracellular domain, a 23 amino acid transmembrane domain, and a 36 amino acid cytoplasmic domain. A canonical human SCF amino acid sequence is:

(SEQ ID NO: 1, UniProtKB-P21583 (SCF_HUMAN))
MKKTQTWILTCIYLQLLLFNPLVKTEGICRNRVTNNNKDVTKLVANLPK

DYMITLKYVPGMDVLPSHCWISEMVVQLSDSLTDLLDKFSNISEGLSNY

SIIDKLVNIVDDLVECVKENSSKDLKKSFKSPEPRLFTPEEFFRIFNRSI

DAFKDFVVASETSDCVVSSTLSPEKDSRVSVTKPFMLPPVAASSLRNDSS

SSNRKAKNPPGDSSLHWAAMALPALFSLIIGFAFGALYWKKR

QPSLTRAVENIQINEEDNEISMLQEKEREFQEV.

The secreted soluble form of SCF is generated by proteolytic processing of the membrane-anchored precursor. A cleaved, secreted soluble form of human SCF is underlined in SEQ ID NO:1, which corresponds to SEQ ID NO:2 without the N-terminal methionine.

MEGICRNRVTNNVKDVTKLVANLPKDYMITLKYVPGMDVLPSHCWISE

MVVQLSDSLTDLLDKFSNISEGLSNYSIIDKLVNIVDDLVECVKENSSKD

LKKSFKSPEPRLFTPEEFFRIFNRSIDAFKDFVVASETSDCVVSSTLSPE

KDSRVSVTKPFMLPPVA (SEQ ID NO: 2, Preprotech

Recombinant Human SCF Catalog Number: 300-07).

Murine and rat SCF are fully active on human cells. A canonical mouse SCF amino acid sequence is:

(SEQ ID NO: 3, UniProtKB-P20826 (SCF_MOUSE))
MKKTQTWIITCIYLQLLLENPLVKTKEICGNPVTDNVKDITKLVANLPND

YMITLNYVAGMDVLPSHCWLRDMVIQLSLSLTTLLDKFSNISEGLSNYSI

IDKLGKIVDDLVLCMEENAPKNIKESPKRPETRSFTPEEFFSIFNRSIDA

FKDFMVASDTSDCVLSSTLGPEKDSRVSVTKPFMLPPVAASSLRNDSSSS

NRKAAKAPEDSGLQWTAMALPALISLVIGFAFGALYWKKKQSSLTRAVEN

IQINEEDNEISMLQQKEREFQEV.

A cleaved, secreted soluble form of mouse SCF is underlined in SEQ ID NO:3, which corresponds to SEQ ID NO:4 without the N-terminal methionine.

MKEICGNPVTDNVKDITKLVANLPNDYMITLNYVAGMDVLPSHCWLRD

MVIQLSLSLTTLLDKFSNISEGLSNYSIIDKLGKIVDDLVLCMEENAPKN

IKESPKRPETRSFTPEEFFSIFNRSIDAFKDFMVASDTSDCVLSSTLGPE

KDSRVSVTKPFMLPPVA (SEQ ID NO: 4, Preprotech

Recombinant Murine SCF Catalog Number: 250-03)

A canonical mouse SCF amino acid sequence is:

(SEQ ID NO: 5, UniProtKB-P21581 (SCF_RAT))
MKKTQTWIITCIYLQLLLFNPLVKTQEICRNPVTDNVKDITKLVANLPND

YMITLNYVAGMDVLPSHCWLRDMVTHLSVSLTTLLDKFSNISEGLSNYS

IIDKLGKIVDDLVACMEENAPKNVKESLKKPETRNFTPEEFFSIFNRSID

AFKDFMVASDTSDCVLSSTLGPEKDSRVSVTKPFMLPPVAASSLRNDSSS

SNRKAAKSPEDPGLQWTAMALPALISLVIGFAFGALYWKKKQSSLTRAV

ENIQINEEDNEISMLQQKEREFQEV.

A cleaved, secreted soluble form of rat SCF is underlined in SEQ ID NO:5, which corresponds to SEQ ID NO:6 without the N-terminal methionine.

MQEICRNPVTDNVKDITKLVANLPNDYMITLNYVAGMDVLPSHCWLRD

MVTHLSVSLTTLLDKFSNISEGLSNYSIIDKLGKIVDDLVACMEENAPKN

VKESLKKPETRNFTPEEFFSIFNRSIDAFKDFMVASDTSDCVLSSTLGPE

KDSRVSVTKPFMLPPVA (SEQ ID NO: 6, Shenandoah

Biotechnology, Inc., Recombinant Rat SCF (Stem

Cell Factor) Catalog Number: 300-32).

In some embodiments, the factor is a SCF such as any of SEQ ID NO:1-6, with or without the N-terminal methionine, or a functional fragment thereof, or a variant thereof with at least 60, 65, 70, 75, 80, 85, 90, 95, 96, 97, 98, 99, or more sequence identity to any one of SEQ ID NO:1-6.

It will be appreciated that SCF can be administered to cells or a subject as SCF protein, or as a nucleic acid encoding SCF (transcribed RNA, DNA, DNA in an expression vector). Accordingly, nucleic acid sequences, including RNA (e.g., mRNA) and DNA sequences, encoding SEQ ID NOS:1-6 are also provided, both alone and inserted into expression cassettes and vectors. For example, a sequence encoding SCF can be incorporated into an autonomously replicating plasmid, a virus (e.g., a retrovirus, lentivirus, adenovirus, or herpes virus), or into the genomic DNA of a prokaryote or eukaryote.

The observed effect of SCF indicates that other cytokines or growth factors including, but not limited to, erythropoietin, GM-CSF, EGF (especially for epithelial cells; lung epithelia for cystic fibrosis), hepatocyte growth factor etc., could similarly serve to boost gene editing potential in bone marrow cells or in other tissues. In some embodiments, gene editing is enhanced in specific cell types using cytokines targeted to these cell types.

B. Replication Modulators

In some embodiments, the potentiating factor is a replication modulator that can, for example, manipulate replication progression and/or replication forks. For example, the ATR-Chk1 cell cycle checkpoint pathway has numerous roles in protecting cells from DNA damage and stalled replication, one of the most prominent being control of the cell cycle and prevention of premature entry into mitosis (Thompson and Eastman, *Br J Clin Pharmacol.*, 76(3): 358-369 (2013), Smith, et al., *Adv Cancer Res.*, 108:73-112 (2010)). However, Chk1 also contributes to the stabilization of stalled replication forks, the control of replication origin firing and replication fork progression, and homologous recombination. DNA polymerase alpha also known as Pol α is an enzyme complex found in eukaryotes that is involved in initiation of DNA replication. Hsp90 (heat shock protein 90) is a chaperone protein that assists other proteins to fold properly, stabilizes proteins against heat stress, and aids in protein degradation.

Experimental results show that inhibitors of CHK1 and ATR in the DNA damage response pathway, as well as DNA polymerase alpha inhibitors and HSP90 inhibitors, substantially boost gene editing by triplex-forming PNAs and single-stranded donor DNA oligonucleotides. Accordingly, in some embodiments, the potentiating factor is a CHK1 or ATR pathway inhibitor, a DNA polymerase alpha inhibitor, or an HSP90 inhibitor. The inhibitor can be a functional nucleic acid, for example siRNA, miRNA, aptamers, ribozymes, triplex forming molecules, RNAi, or external guide sequences that targets CHK1, ATR, or another molecule in the ATR-Chk1 cell cycle checkpoint pathway; DNA polymerase alpha; or HSP90 and reduces expression or active of ATR, CHK1, DNA polymerase alpha, or HSP90.

Preferably, the inhibitor is a small molecule. For example, the potentiating factor can be a small molecule inhibitor of ATR-Chk1 Cell Cycle Checkpoint Pathway Inhibitor. Such inhibitors are known in the art, and many have been tested in clinical trials for the treatment of cancer. Exemplary CHK1 inhibitors include, but are not limited to, AZD7762, SCH900776/MK-8776, IC83/LY2603618, LY2606368, GDC-0425, PF-00477736, XL844, CEP-3891, SAR-020106, CCT-244747, Arry-575 (Thompson and Eastman, *Br J Clin Pharmacol.*, 76(3): 358-369 (2013)), and SB218075. Exemplary ATR pathway inhibitors include, but are not limited to Schisandrin B, NU6027, NVP-BEZ235, VE-821, VE-822 (VX-970), AZ20, AZD6738, MIRIN, KU5593, VE-821, NU7441, LCA, and L189 (Weber and Ryan, *Pharmacology & Therapeutics*, 149:124-138 (2015)).

In some embodiments, the potentiating factor is a DNA polymerase alpha inhibitor, such as aphidicolin.

In some embodiments, the potentiating factor is a heat shock protein 90 inhibitor (HSP90i) such as STA-9090 (ganetespib). Other HSP90 inhibitors are known in the art and include, but are not limited to, benzoquinone ansamycin antibiotics such as geldanamycin (GA); 17-AAG (17-Allylamino-17-demethoxy-geldanamycin); 17-DMAG (17-dimethylaminoethylamino-17-demethoxy-geldanamycin) (Alvespimycin); IPI-504 (Retaspimycin); and AUY922 (Tatokoro, et al., *EXCLI J.*, 14:48-58 (2015)).

III. Gene Editing Technology

Gene editing technologies can be used alone or preferably in combination with a potentiating agent. Exemplary gene editing technologies include, but are not limited to, triplex-forming, pseudocomplementary oligonucleotides, CRISPR/Cas, zinc finger nucleases, and TALENs, each of which are discussed in more detail below. As discussed in more detail below, some gene editing technologies are used in combination with a donor oligonucleotide. In some embodiments, the gene editing technology is the donor oligonucleotide, which can be used be used alone to modify genes. Strategies include, but are not limited to, small fragment homologous replacement (e.g., polynucleotide small DNA fragments (SDFs)), single-stranded oligodeoxynucleotide-mediated gene modification (e.g., ssODN/SSOs) and other described in Sargent, *Oligonucleotides*, 21(2): 55-75 (2011)), and elsewhere. Other suitable gene editing technologies include, but are not limited to intron encoded meganucleases that are engineered to change their target specificity. See, e.g., Arnould, et al., *Protein Eng. Des. Sel.*, 24(1-2):27-31 (2011)).

A. Triplex-Forming Molecules

1. Compositions

Compositions containing "triplex-forming molecules," that bind to duplex DNA in a sequence-specific manner to form a triple-stranded structure include, but are not limited to, triplex-forming oligonucleotides (TFOs), peptide nucleic acids (PNA), and "tail clamp" PNA (tcPNA). The triplex-forming molecules can be used to induce site-specific homologous recombination in mammalian cells when combined with donor DNA molecules. The donor DNA molecules can contain mutated nucleic acids relative to the target DNA sequence. This is useful to activate, inactivate, or otherwise alter the function of a polypeptide or protein encoded by the targeted duplex DNA. Triplex-forming molecules include triplex-forming oligonucleotides and peptide nucleic acids. Triplex forming molecules are described in U.S. Pat. Nos. 5,962,426, 6,303,376, 7,078,389, 7,279,463, 8,658,608, U.S. Published Application Nos. 2003/0148352, 2010/0172882, 2011/0268810, 2011/0262406, 2011/0293585, and published PCT application numbers WO 1995/001364, WO 1996/040898, WO 1996/039195, WO 2003/052071, WO 2008/086529, WO 2010/123983, WO 2011/053989, WO 2011/133802, WO 2011/13380, Rogers, et al., *Proc Natl Acad Sci USA*, 99:16695-16700 (2002), Majumdar, et al., *Nature Genetics*, 20:212-214 (1998), Chin, et al., *Proc Natl Acad Sci USA*, 105:13514-13519 (2008), and Schleifman, et al., *Chem Biol.*, 18:1189-1198 (2011). As discussed in more detail below, triplex forming molecules are typically single-stranded oligonucleotides that bind to polypyrimidine:polypurine target motif in a double stranded nucleic acid molecule to form a triple-stranded nucleic acid molecule. The single-stranded oligonucleotide typically includes a sequence substantially complementary to the polypurine strand of the polypyrimidine:polypurine target motif.

a. Triplex-Forming Oligonucleotides (TFOs)

Triplex-forming oligonucleotides (TFOs) are defined as oligonucleotides which bind as third strands to duplex DNA in a sequence specific manner. The oligonucleotides are synthetic or isolated nucleic acid molecules which selectively bind to or hybridize with a predetermined target sequence, target region, or target site within or adjacent to a human gene so as to form a triple-stranded structure.

Preferably, the oligonucleotide is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition may be homopurine or homopyrimidine. Alternatively, the base composition may be polypurine or polypyrimidine. However, other compositions are also useful.

The oligonucleotides are preferably generated using known DNA synthesis procedures. In one embodiment, oligonucleotides are generated synthetically. Oligonucleotides can also be chemically modified using standard methods that are well known in the art.

The nucleotide sequence of the oligonucleotides is selected based on the sequence of the target sequence, the physical constraints imposed by the need to achieve binding of the oligonucleotide within the major groove of the target region, and the need to have a low dissociation constant ($K_d$) for the oligonucleotide/target sequence. The oligonucleotides have a base composition which is conducive to triple-helix formation and is generated based on one of the known structural motifs for third strand binding. The most stable complexes are formed on polypurine:polypyrimidine elements, which are relatively abundant in mammalian genomes. Triplex formation by TFOs can occur with the third strand oriented either parallel or anti-parallel to the purine strand of the duplex. In the anti-parallel, purine motif, the triplets are G.G:C and A.A:T, whereas in the parallel pyrimidine motif, the canonical triplets are $C^+$.G:C and T.A:T. The triplex structures are stabilized by two Hoogsteen hydrogen bonds between the bases in the TFO strand and the purine strand in the duplex. A review of base compositions for third strand binding oligonucleotides is provided in U.S. Pat. No. 5,422,251.

Preferably, the oligonucleotide binds to or hybridizes to the target sequence under conditions of high stringency and specificity. Most preferably, the oligonucleotides bind in a sequence-specific manner within the major groove of duplex DNA. Reaction conditions for in vitro triple helix formation of an oligonucleotide probe or primer to a nucleic acid sequence vary from oligonucleotide to oligonucleotide, depending on factors such as oligonucleotide length, the number of G:C and A:T base pairs, and the composition of the buffer utilized in the hybridization reaction. An oligonucleotide substantially complementary, based on the third strand binding code, to the target region of the double-stranded nucleic acid molecule is preferred.

As used herein, a triplex forming molecule is said to be substantially complementary to a target region when the oligonucleotide has a heterocyclic base composition which allows for the formation of a triple-helix with the target region. As such, an oligonucleotide is substantially complementary to a target region even when there are non-complementary bases present in the oligonucleotide. As stated above, there are a variety of structural motifs available which can be used to determine the nucleotide sequence of a substantially complementary oligonucleotide.

b. Peptide Nucleic Acids (PNA)

In another embodiment, the triplex-forming molecules are peptide nucleic acids (PNAs). Peptide nucleic acids are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that are similar to oligonucleotides, but are achiral and neutrally charged molecules. Peptide nucleic acids are comprised of peptide nucleic acid monomers. The heterocyclic bases can be any of the standard bases (uracil, thymine, cytosine, adenine and guanine) or any of the modified heterocyclic bases described below.

PNAs can bind to DNA via Watson-Crick hydrogen bonds, but with binding affinities significantly higher than those of a corresponding nucleotide composed of DNA or RNA. The neutral backbone of PNAs decreases electrostatic repulsion between the PNA and target DNA phosphates. Under in vitro or in vivo conditions that promote opening of the duplex DNA, PNAs can mediate strand invasion of duplex DNA resulting in displacement of one DNA strand to form a D-loop.

Highly stable triplex PNA:DNA:PNA structures can be formed from a homopurine DNA strand and two PNA strands. The two PNA strands may be two separate PNA molecules, or two PNA molecules linked together by a linker of sufficient flexibility to form a single bis-PNA molecule. In both cases, the PNA molecule(s) forms a triplex "clamp" with one of the strands of the target duplex while displacing the other strand of the duplex target. In this structure, one strand forms Watson-Crick base pairs with the DNA strand in the anti-parallel orientation (the Watson-Crick binding portion), whereas the other strand forms Hoogsteen base pairs to the DNA strand in the parallel orientation (the Hoogsteen binding portion). A homopurine strand allows formation of a stable PNA/DNA/PNA triplex. PNA clamps can form at shorter homopurine sequences than those required by triplex-forming oligonucleotides (TFOs) and also do so with greater stability.

Suitable molecules for use in linkers of bis-PNA molecules include, but are not limited to, 8-amino-3,6-dioxaoctanoic acid, referred to as an O-linker, and 6-aminohexanoic acid. Poly(ethylene) glycol monomers can also be used in bis-PNA linkers. A bis-PNA linker can contain multiple linker molecule monomers in any combination.

PNAs can also include other positively charged moieties to increase the solubility of the PNA and increase the affinity of the PNA for duplex DNA. Commonly used positively charged moieties include the amino acids lysine and arginine, although other positively charged moieties may also be useful. Lysine and arginine residues can be added to a bis-PNA linker or can be added to the carboxy or the N-terminus of a PNA strand.

c. Tail Clamp Peptide Nucleic Acids (tcPNA)

Although polypurine:polypyrimidine stretches do exist in mammalian genomes, it is desirable to target triplex formation in the absence of this requirement. In some embodiments such as PNA, triplex-forming molecules include a "tail" added to the end of the Watson-Crick binding portion. Adding additional nucleobases, known as a "tail" or "tail clamp", to the Watson-Crick binding portion that bind to the target strand outside the triple helix further reduces the requirement for a polypurine:polypyrimidine stretch and increases the number of potential target sites. The tail is most typically added to the end of the Watson-Crick binding sequence furthest from the linker. This molecule therefore mediates a mode of binding to DNA that encompasses both triplex and duplex formation (Kaihatsu, et al., *Biochemistry*, 42(47):13996-4003 (2003); Bentin, et al., *Biochemistry*, 42(47):13987-95 (2003)). For example, if the triplex-forming molecules are tail clamp PNA (tcPNA), the PNA/DNA/PNA triple helix portion and the PNA/DNA duplex portion both produce displacement of the pyrimidine-rich strand, creating an altered helical structure that strongly provokes the nucleotide excision repair pathway and activating the site for recombination with a donor DNA molecule (Rogers, et al., *Proc. Natl. Acad. Sci. USA.*, 99(26):16695-700 (2002)).

Tails added to clamp PNAs (sometimes referred to as bis-PNAs) form tail-clamp PNAs (referred to as tcPNAs) that have been described by Kaihatsu, et al., *Biochemistry*, 42(47):13996-4003 (2003); Bentin, et al., *Biochemistry*, 42(47):13987-95 (2003). tcPNAs are known to bind to DNA more efficiently due to low dissociation constants. The addition of the tail also increases binding specificity and binding stringency of the triplex-foiming molecules to the target duplex. It has also been found that the addition of a tail to clamp PNA improves the frequency of recombination of the donor oligonucleotide at the target site compared to PNA without the tail.

d. PNA Modifications

PNAs can also include other positively charged moieties to increase the solubility of the PNA and increase the affinity of the PNA for duplex DNA. Commonly used positively charged moieties include the amino acids lysine and arginine, although other positively charged moieties may also be useful. Lysine and arginine residues can be added to a bis-PNA linker or can be added to the carboxy or the N-terminus of a PNA strand. Common modifications to PNA are discussed in Sugiyama and Kittaka, *Molecules*, 18:287-310 (2013)) and Sahu, et al., *J. Org. Chem.*, 76, 5614-5627 (2011), each of which are specifically incorporated by reference in their entireties, and include, but are not limited to, incorporation of charged amino acid residues, such as lysine at the termini or in the interior part of the oligomer; inclusion of polar groups in the backbone, carboxymethylene bridge, and in the nucleobases; chiral PNAs bearing substituents on the original N-(2-aminoethyl)glycine backbone; replacement of the original aminoethyl-glycyl backbone skeleton with a negatively-charged scaffold; conjugation of high molecular weight polyethylene glycol (PEG) to one of the termini; fusion of PNA to DNA to generate a chimeric oligomer, redesign of the backbone architecture, conjugation of PNA to DNA or RNA. These modifications improve solubility but often result in reduced binding affinity and/or sequence specificity. In some embodiments, the some or all of the PNA monomers are modified at the gamma position in the polyamide backbone (γPNAs) as illustrated below (wherein "B" is a nucleobase and "R" is a substitution at the gamma position).

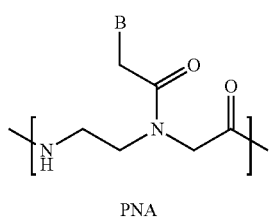

PNA

-continued

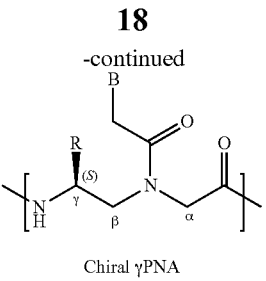

Chiral γPNA

Substitution at the gamma position creates chirality and provides helical pre-organization to the PNA oligomer, yielding substantially increased binding affinity to the target DNA (Rapireddy, et al., *Biochemistry*, 50(19):3913-8 (2011)). Other advantageous properties can be conferred depending on the chemical nature of the specific substitution at the gamma position (the "R" group in the chiral γPNA above).

One class of γ substitution, is miniPEG, but other residues and side chains can be considered, and even mixed substitutions can be used to tune the properties of the oligomers. "MiniPEG" and "MP" refers to diethylene glycol. Mini-PEG-containing γPNAs are conformationally preorganized PNAs that exhibit superior hybridization properties and water solubility as compared to the original PNA design and other chiral γPNAs. γPNAs prepared from L-amino acids adopt a right-handed helix, while those prepared from D-amino acids adopt a left-handed helix; however, only the right-handed helical γPNAs hybridize to DNA or RNA with high affinity and sequence selectivity. In the most preferred embodiments, some or all of the PNA monomers are mini-PEG-containing γPNAs (Sahu, et al., *J. Org. Chem.*, 76, 5614-5627 (2011). In the embodiments, tcPNAs are prepared wherein every other PNA monomer on the Watson-Crick binding side of the linker is a miniPEG-containing γPNA. Accordingly, the tail clamp side of the PNA has alternating PNA and miniPEG-containing γPNA monomers.

In some embodiments PNA-mediated gene editing are achieved via additional or alternative γ substitutions or other PNA chemical modifications including but limited to those introduced above and below. Examples of γ substitution with other side chains include that of alanine, serine, threonine, cysteine, valine, leucine, isoleucine, methionine, proline, phenylalanine, tyrosine, aspartic acid, glutamic acid, asparagine, glutamine, histidine, lysine, arginine, and the derivatives thereof. The "derivatives thereof" herein are defined as those chemical moieties that are covalently attached to these amino acid side chains, for instance, to that of serine, cysteine, threonine, tyrosine, aspartic acid, glutamic acid, asparagine, glutamine, lysine, and arginine.

In addition to γPNAs showing consistently improved gene editing potency the level of off-target effects in the genome remains extremely low. This is in keeping with the lack of any intrinsic nuclease activity in the PNAs (in contrast to ZFNs or CRISPR/Cas9 or TALENS), and reflects the mechanism of triplex-induced gene editing, which acts by creating an altered helix at the target-binding site that engages endogenous high fidelity DNA repair pathways. As discussed above, the SCF/c-Kit pathway also stimulates these same pathways, providing for enhanced gene editing without increasing off-target risk or cellular toxicity.

Additionally, any of the triplex forming sequences can be modified to include guanidine-G-clamp ("G-clamp") PNA monomer(s) to enhance PNA binding. γPNAs with substitution of cytosine by clamp-G (9-(2-guanidinoethoxy) phenoxazine), a cytosine analog that can form five H-bonds with guanine, and can also provide extra base stacking due to the expanded phenoxazine ring system and substantially increased binding affinity. In vitro studies indicate that a single clamp-G substitution for C can substantially enhance the binding of a PNA-DNA duplex by 23° C. (Kuhn, et al., *Artificial DNA, PNA & ANA*, 1(1):45-53(2010)). As a result, γPNAs containing G-clamp substitutions can have further increased activity.

The structure of a clamp-G monomer-to-G base pair (clamp-G indicated by the "X") is illustrated below in comparison to C-G base pair.

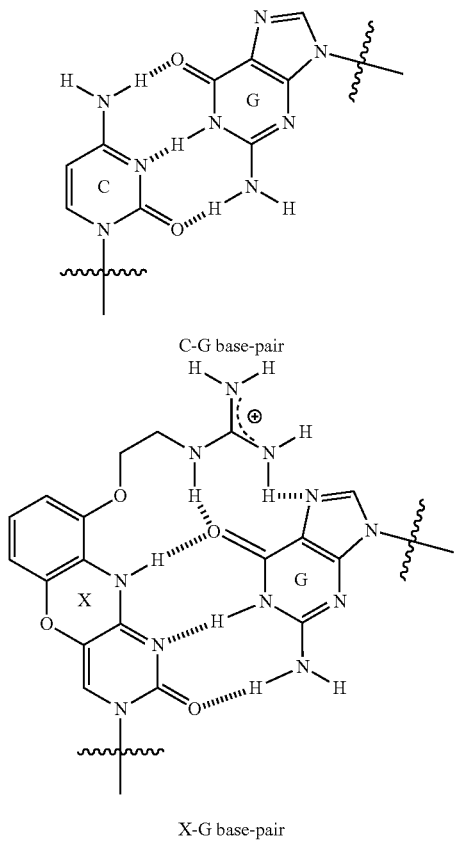

Some studies have shown improvements using D-amino acids in peptide synthesis.

2. Triplex-Forming Target Sequence Considerations

The triplex-forming molecules bind to a predetermined target region referred to herein as the "target sequence," "target region," or "target site." The target sequence for the triplex-forming molecules can be within or adjacent to a human gene encoding, for example the beta globin, cystic fibrosis transmembrane conductance regulator (CFTR) or other gene discussed in more detail below, or an enzyme necessary for the metabolism of lipids, glycoproteins, or mucopolysaccharides, or another gene in need of correction. The target sequence can be within the coding DNA sequence of the gene or within an intron. The target sequence can also be within DNA sequences which regulate expression of the target gene, including promoter or enhancer sequences or sites that regulate RNA splicing.

The nucleotide sequences of the triplex-forming molecules are selected based on the sequence of the target sequence, the physical constraints, and the need to have a low dissociation constant ($K_d$) for the triplex-forming molecules/target sequence. As used herein, triplex-forming molecules are said to be substantially complementary to a target region when the triplex-forming molecules has a heterocyclic base composition which allows for the formation of a triple-helix with the target region. As such, a triplex-forming molecules is substantially complementary to a target region even when there are non-complementary bases present in the triplex-forming molecules.

There are a variety of structural motifs available which can be used to determine the nucleotide sequence of a substantially complementary oligonucleotide. Preferably, the triplex-forming molecules bind to or hybridize to the target sequence under conditions of high stringency and specificity. Reaction conditions for in vitro triple helix formation of an triplex-forming molecules probe or primer to a nucleic acid sequence vary from triplex-forming molecules to triplex-forming molecules, depending on factors such as the length triplex-forming molecules, the number of G:C and A:T base pairs, and the composition of the buffer utilized in the hybridization reaction.

a. Target Sequence Considerations for TFOs

Preferably, the TFO is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition may be homopurine or homopyrimidine. Alternatively, the base composition may be polypurine or polypyrimidine. However, other compositions are also useful. Most preferably, the oligonucleotides bind in a sequence-specific manner within the major groove of duplex DNA. An oligonucleotide substantially complementary, based on the third strand binding code, to the target region of the double-stranded nucleic acid molecule is preferred. The oligonucleotides will have a base composition which is conducive to triple-helix formation and will be generated based on one of the known structural motifs for third strand binding. The most stable complexes are formed on polypurine:polypyrimidine elements, which are relatively abundant in mammalian genomes. Triplex formation by TFOs can occur with the third strand oriented either parallel or anti-parallel to the purine strand of the duplex. In the anti-parallel, purine motif, the triplets are G.G:C and A.A:T, whereas in the parallel pyrimidine motif, the canonical triplets are C$^+$.G:C and T.A:T. The triplex structures are stabilized by two Hoogsteen hydrogen bonds between the bases in the TFO strand and the purine strand in the duplex. A review of base compositions for third strand binding oligonucleotides is provided in U.S. Pat. No. 5,422,251.

The oligonucleotides are preferably generated using known DNA synthesis procedures. In one embodiment, oligonucleotides are generated synthetically. Oligonucleotides can also be chemically modified using standard methods that are well known in the art.

b. Target Sequence Considerations for PNAs

Some triplex-forming molecules, such as PNA and tcPNA invade the target duplex, with displacement of the polypyrimidine strand, and induce triplex formation with the polypurine strand of the target duplex by both Watson-Crick and Hoogsteen binding. Preferably, both the Watson-Crick and Hoogsteen binding portions of the triplex forming molecules are substantially complementary to the target sequence. Although, as with triplex-forming oligonucleotides, a homopurine strand is needed to allow formation of a stable PNA/DNA/PNA triplex, PNA clamps can form at shorter homopurine sequences than those required by triplex-forming oligonucleotides and also do so with greater stability.

Preferably, PNAs are between 6 and 50 nucleotides in length. The Watson-Crick portion should be 9 or more nucleobases in length, optionally including a tail sequence. More preferably, the Watson-Crick binding portion is between about 9 and 30 nucleobases in length, optionally including a tail sequence of between 0 and about 15 nucleobases. More preferably, the Watson-Crick binding portion is between about 10 and 25 nucleobases in length, optionally including a tail sequence of between 0 and about 10 nucleobases. In the most preferred embodiment, the Watson-Crick binding portion is between 15 and 25 nucleobases in length, optionally including a tail sequence of between 5 and 10 nucleobases. The Hoogsteen binding portion should be 6 or more nucleobases in length. Most preferably, the Hoogsteen binding portion is between about 6 and 15 nucleobases, inclusive.

The triplex-forming molecules are designed to target the polypurine strand of a polypurine:polypyrimidine stretch in the target duplex nucleotide. Therefore, the base composition of the triplex-forming molecules may be homopyrimidine. Alternatively, the base composition may be polypyrimidine. The addition of a "tail" reduces the requirement for polypurine:polypyrimidine run. Adding additional nucleobases, known as a "tail," to the Watson-Crick binding portion of the triplex-forming molecules allows the Watson-Crick binding portion to bind/hybridize to the target strand outside the site of polypurine sequence for triplex formation. These additional bases further reduce the requirement for the polypurine:polypyrimidine stretch in the target duplex and therefore increase the number of potential target sites. Triplex-forming oligonucleotides (TFOs) also require a polypurine:polypyrimidine sequence to a form a triple helix. TFOs may require stretch of at least 15 and preferably 30 or more nucleotides. Peptide nucleic acids require fewer purines to a form a triple helix, although at least 10 or preferably more may be needed. Peptide nucleic acids including a tail, also referred to tail clamp PNAs, or tcPNAs, require even fewer purines to a form a triple helix. A triple helix may be formed with a target sequence containing fewer than 8 purines. Therefore, PNAs should be designed to target a site on duplex nucleic acid containing between 6-30 polypurine:polypyrimidines, preferably, 6-25 polypurine:polypyrimidines, more preferably 6-20 polypurine:polypyrimidines.

The addition of a "mixed-sequence" tail to the Watson-Crick-binding strand of the triplex-forming molecules such as PNAs also increases the length of the triplex-forming molecule and, correspondingly, the length of the binding site. This increases the target specificity and size of the lesion created at the target site and disrupts the helix in the duplex nucleic acid, while maintaining a low requirement for a stretch of polypurine:polypyrimidines. Increasing the length of the target sequence improves specificity for the target, for example, a target of 17 base pairs will statistically be unique in the human genome. Relative to a smaller lesion, it is likely that a larger triplex lesion with greater disruption of the underlying DNA duplex will be detected and processed more quickly and efficiently by the endogenous DNA repair machinery that facilitates recombination of the donor oligonucleotide.

The triple-forming molecules are preferably generated using known synthesis procedures. In one embodiment, triplex-forming molecules are generated synthetically. Triplex-forming molecules can also be chemically modified using standard methods that are well known in the art.

B. Pseudocomplementary Oligonucleotides

The gene editing technology can be pseudocomplementary oligonucleotides such as those disclosed in U.S. Pat. No. 8,309,356. "Double duplex-forming molecules," are oligonucleotides that bind to duplex DNA in a sequence-specific manner to form a four-stranded structure. Double duplex-forming molecules, such as a pair of pseudocomplementary oligonucleotides, can induce recombination with a donor oligonucleotide at a chromosomal site in mammalian cells. Pseudocomplementary oligonucleotides are complementary oligonucleotides that contain one or more modifications such that they do not recognize or hybridize to each other, for example due to steric hindrance, but each can recognize and hybridize to its complementary nucleic acid strands at the target site. Preferred pseudocomplementary oligonucleotides include Pseudocomplementary peptide nucleic acids (pcPNAs). A pseudocomplementary oligonucleotide is said to be substantially complementary to a target region when the oligonucleotide has a base composition which allows for the formation of a double duplex with the target region. As such, an oligonucleotide is substantially complementary to a target region even when there are non-complementary bases present in the oligonucleotide.

This strategy can be more efficient and provides increased flexibility over other methods of induced recombination such as triple-helix oligonucleotides and bis-peptide nucleic acids which prefer a polypurine sequence in the target double-stranded DNA. The design ensures that the pseudocomplementary oligonucleotides do not pair with each other but instead bind the cognate nucleic acids at the target site, inducing the formation of a double duplex.

The predetermined region that the double duplex-forming molecules bind to can be referred to as a "double duplex target sequence," "double duplex target region," or "double duplex target site." The double duplex target sequence (DDTS) for the double duplex-forming oligonucleotides can be, for example, within or adjacent to a human gene in need of induced gene correction. The DDTS can be within the coding DNA sequence of the gene or within introns. The DDTS can also be within DNA sequences which regulate expression of the target gene, including promoter or enhancer sequences.

The nucleotide sequence of the pseudocomplementary oligonucleotides is selected based on the sequence of the DDTS. Therapeutic administration of pseudocomplementary oligonucleotides involves two single stranded oligonucleotides unlinked, or linked by a linker. One pseudocomplementary oligonucleotide strand is complementary to the DDTS, while the other is complementary to the displaced DNA strand. The use of pseudocomplementary oligonucleotides, particularly pcPNAs are not subject to limitation on sequence choice and/or target length and specificity as are triplex-forming oligonucleotides, helix-invading peptide nucleic acids (bis-PNAs) and side-by-side minor groove binders. Pseudocomplementary oligonucleotides do not require third-strand Hoogsteen-binding, and therefore are not restricted to homopurine targets. Pseudocomplementary oligonucleotides can be designed for mixed, general sequence recognition of a desired target site. Preferably, the target site contains an A:T base pair content of about 40% or greater. Preferably pseudocomplementary oligonucleotides are between about 8 and 50 nucleobases, more preferably 8 to 30, even more preferably between about 8 and 20 nucleobases.

The pseudocomplementary oligonucleotides should be designed to bind to the target site (DDTS) at a distance of between about 1 to 800 bases from the target site of the donor oligonucleotide. More preferably, the pseudocomplementary oligonucleotides bind at a distance of between about 25 and 75 bases from the donor oligonucleotide. Most preferably, the pseudocomplementary oligonucleotides bind at a distance of about 50 bases from the donor oligonucleotide. Preferred pcPNA sequences for targeted repair of a mutation in the β-globin intron IVS2 (G to A) are described in U.S. Pat. No. 8,309,356.

Preferably, the pseudocomplementary oligonucleotides bind/hybridize to the target nucleic acid molecule under conditions of high stringency and specificity. Most preferably, the oligonucleotides bind in a sequence-specific manner and induce the formation of double duplex. Specificity and binding affinity of the pseudocomplementary oligonucleotides may vary from oligonucleotide to oligonucleotide, depending on factors such as oligonucleotide length, the number of G:C and A:T base pairs, and the formulation.

C. CRISPR/Cas

In some embodiments, the gene editing composition is the CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (transactivating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as precrRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct can also be referred to as a guide RNA or gRNA (or single-guide RNA (sgRNA)). Within an sgRNA, the crRNA portion can be identified as the "target sequence" and the tracrRNA is often referred to as the "scaffold."

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as CTPS1) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

D. Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and β nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/

0154989; 2007/0213269; and International Patent Application Publication Nos. WO 98/53059 and WO 2003/016496.

E. Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). U.S. Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246.

IV. Donor Oligonucleotides

In some embodiments, the gene editing composition includes or is administered in combination with a donor oligonucleotide. Generally, in the case of gene therapy, the donor oligonucleotide includes a sequence that can correct a mutation(s) in the host genome, though in some embodiments, the donor introduces a mutation that can, for example, reduce expression of an oncogene or a receptor that facilitates HIV infection. In addition to containing a sequence designed to introduce the desired correction or mutation, the donor oligonucleotide may also contain synonymous (silent) mutations (e.g., 7 to 10). The additional silent mutations can facilitate detection of the corrected target sequence using allele-specific PCR of genomic DNA isolated from treated cells.

A. Preferred Donor Oligonucleotide Design for Triplex and Double-Duplex based Technologies The triplex forming molecules including peptide nucleic acids may be administered in combination with, or tethered to, a donor oligonucleotide via a mixed sequence linker or used in conjunction with a non-tethered donor oligonucleotide that is substantially homologous to the target sequence. Triplex-forming molecules can induce recombination of a donor oligonucleotide sequence up to several hundred base pairs away. It is preferred that the donor oligonucleotide sequence is between 1 to 800 bases from the target binding site of the triplex-forming molecules. More preferably the donor oligonucleotide sequence is between 25 to 75 bases from the target binding site of the triplex-forming molecules. Most preferably that the donor oligonucleotide sequence is about 50 nucleotides from the target binding site of the triplex-forming molecules.

The donor sequence can contain one or more nucleic acid sequence alterations compared to the sequence of the region targeted for recombination, for example, a substitution, a deletion, or an insertion of one or more nucleotides. Successful recombination of the donor sequence results in a change of the sequence of the target region. Donor oligonucleotides are also referred to herein as donor fragments, donor nucleic acids, donor DNA, or donor DNA fragments. This strategy exploits the ability of a triplex to provoke DNA repair, potentially increasing the probability of recombination with the homologous donor DNA. It is understood in the art that a greater number of homologous positions within the donor fragment will increase the probability that the donor fragment will be recombined into the target sequence, target region, or target site. Tethering of a donor oligonucleotide to a triplex-forming molecule facilitates target site recognition via triple helix formation while at the same time positioning the tethered donor fragment for possible recombination and information transfer. Triplex-forming molecules also effectively induce homologous recombination of non-tethered donor oligonucleotides. The term "recombinagenic" as used herein, is used to define a DNA fragment, oligonucleotide, peptide nucleic acid, or composition as being able to recombine into a target site or sequence or induce recombination of another DNA fragment, oligonucleotide, or composition.

Non-tethered or unlinked fragments may range in length from 20 nucleotides to several thousand. The donor oligonucleotide molecules, whether linked or unlinked, can exist in single stranded or double stranded form. The donor fragment to be recombined can be linked or un-linked to the triplex forming molecules. The linked donor fragment may range in length from 4 nucleotides to 100 nucleotides, preferably from 4 to 80 nucleotides in length. However, the unlinked donor fragments have a much broader range, from 20 nucleotides to several thousand. In one embodiment the oligonucleotide donor is between 25 and 80 nucleobases. In a further embodiment, the non-tethered donor nucleotide is about 50 to 60 nucleotides in length.

The donor oligonucleotides contain at least one mutated, inserted or deleted nucleotide relative to the target DNA sequence. Target sequences can be within the coding DNA sequence of the gene or within introns. Target sequences can also be within DNA sequences which regulate expression of the target gene, including promoter or enhancer sequences or sequences that regulate RNA splicing.

The donor oligonucleotides can contain a variety of mutations relative to the target sequence. Representative types of mutations include, but are not limited to, point mutations, deletions and insertions. Deletions and insertions can result in frameshift mutations or deletions. Point mutations can cause missense or nonsense mutations. These mutations may disrupt, reduce, stop, increase, improve, or otherwise alter the expression of the target gene.

Compositions including triplex-forming molecules such as tcPNA may include one or more than one donor oligonucleotides. More than one donor oligonucleotides may be administered with triplex-forming molecules in a single transfection, or sequential transfections. Use of more than one donor oligonucleotide may be useful, for example, to create a heterozygous target gene where the two alleles contain different modifications.

Donor oligonucleotides are preferably DNA oligonucleotides, composed of the principal naturally-occurring nucleotides (uracil, thymine, cytosine, adenine and guanine) as the heterocyclic bases, deoxyribose as the sugar moiety, and phosphate ester linkages. Donor oligonucleotides may include modifications to nucleobases, sugar moieties, or backbone/linkages, as described above, depending on the desired structure of the replacement sequence at the site of recombination or to provide some resistance to degradation by nucleases. Modifications to the donor oligonucleotide should not prevent the donor oligonucleotide from successfully recombining at the recombination target sequence in the presence of triplex-forming molecules.

B. Preferred Donor Oligonucleotides Design for Nuclease-based Technologies

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

V. Oligonucleotide Composition

Any of the gene editing technologies, components thereof, donor oligonucleotides, or other nucleic acids disclosed herein can include one or more modifications or substitutions to the nucleobases or linkages. Although modifications are particularly preferred for use with triplex-forming technologies and typically discussed below with reference thereto, any of the modifications can be utilized in the construction of any of the disclosed gene editing compositions, donor, nucleotides, etc. Modifications should not prevent, and preferably enhance the activity, persistence, or function of the gene editing technology. For example, modifications to oligonucleotides for use as triplex-forming should not prevent, and preferably enhance duplex invasion, strand displacement, and/or stabilize triplex formation as described above by increasing specificity or binding affinity of the triplex-forming molecules to the target site. Modified bases and base analogues, modified sugars and sugar analogues and/or various suitable linkages known in the art are also suitable for use in the molecules disclosed herein. Several preferred oligonucleotide compositions including PNA, and modification thereof to include MiniPEG at the γ position in the PNA backbone, are discussed above. Additional modifications are discussed in more detail below.

A. Heterocyclic Bases

The principal naturally-occurring nucleotides include uracil, thymine, cytosine, adenine and guanine as the heterocyclic bases. Gene editing molecules can include chemical modifications to their nucleotide constituents. For example, target sequences with adjacent cytosines can be problematic. Triplex stability is greatly compromised by runs of cytosines, thought to be due to repulsion between the positive charge resulting from the $N^3$ protonation or perhaps because of competition for protons by the adjacent cytosines. Chemical modification of nucleotides including triplex-forming molecules such as PNAs may be useful to increase binding affinity of triplex-forming molecules and/or triplex stability under physiologic conditions.

Chemical modifications of heterocyclic bases or heterocyclic base analogs may be effective to increase the binding affinity of a nucleotide or its stability in a triplex. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D- ribofuranosyl)pyridine (2-aminopyridine), and various pyrrolo- and pyrazolopyrimidine derivatives. Substitution of 5-methylcytosine or pseudoisocytosine for cytosine in triplex-forming molecules such as PNAs helps to stabilize triplex formation at neutral and/or physiological pH, especially in triplex-forming molecules with isolated cytosines. This is because the positive charge partially reduces the negative charge repulsion between the triplex-forming molecules and the target duplex, and allows for Hoogsteen binding.

B. Backbone

The nucleotide subunits of the triplex-forming molecules such as PNAs are connected by an internucleotide bond that refers to a chemical linkage between two nucleoside moieties. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds, which allow them to form PNA-DNA or PNA-RNA duplexes via Watson-Crick base pairing with high affinity and sequence-specificity. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications, particularly those relating to PNAs, include peptide and amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Backbone modifications used to generate triplex-forming molecules should not prevent the molecules from binding with high specificity to the target site and creating a triplex with the target duplex nucleic acid by displacing one strand of the target duplex and foiming a clamp around the other strand of the target duplex.

C. Modified Nucleic Acids

Modified nucleic acids in addition to peptide nucleic acids are also useful as triplex-forming molecules. Oligonucleotides are composed a chain of nucleotides which are linked to one another. Canonical nucleotides typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds. As used herein "modified nucleotide" or "chemically modified nucleotide" defines a nucleotide that has a chemical modification of one or more of the heterocyclic base, sugar moiety or phosphate moiety constituents. Preferably the charge of the modified nucleotide is reduced compared to DNA or RNA oligonucleotides of the same nucleobase sequence. Most preferably the triplex-forming molecules have low negative charge, no charge, or positive charge such that electrostatic repulsion with the nucleotide duplex at the target site is reduced compared to DNA or RNA oligonucleotides with the corresponding nucleobase sequence.

Examples of modified nucleotides with reduced charge include modified internucleotide linkages such as phosphate analogs having achiral and uncharged intersubunit linkages (e.g., Sterchak, E. P. et al., *Organic Chem.*, 52:4202, (1987)), and uncharged morpholino-based polymers having achiral intersubunit linkages (see, e.g., U.S. Pat. No. 5,034,506). Some internucleotide linkage analogs include morpholidate, acetal, and polyamide-linked heterocycles. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

Molecules may also include nucleotides with modified heterocyclic bases, sugar moieties or sugar moiety analogs. Modified nucleotides may include modified heterocyclic bases or base analogs as described above with respect to peptide nucleic acids. Sugar moiety modifications include, but are not limited to, 2'-O-aminoethoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the triplex-forming molecule and the target duplex. This modification stabilizes the C3'-endo conformation of the ribose or deoxyribose and also forms a bridge with the i−1 phosphate in the purine strand of the duplex.

VI. Nanoparticle Delivery Vehicles

Any of the disclosed compositions including, but not limited to potentiating factors, gene editing molecules, donor oligonucleotides, etc., can be delivered to the target cells using a nanoparticle delivery vehicle. In some embodiments, some of the compositions are packaged in nanoparticles and some are not. For example, in some embodiments, the gene editing technology and/or donor oligonucleotide is incorporated into nanoparticles while the potentiating factor is not. In some embodiments, the gene editing technology and/or donor oligonucleotide, and the potentiating factor are packaged in nanoparticles. The different compositions can be packaged in the same nanoparticles or different nanoparticles. For example, the compositions can be mixed and packaged together. In some embodiments, the different compositions are packaged separately into separate nanoparticles wherein the nanoparticles are similarly or identically composed and/or manufactured. In some embodiments, the different compositions are packaged separately into separate nanoparticles wherein the nanoparticles are differentially composed and/or manufactured.

Nanoparticles generally refers to particles in the range of between 500 nm to less than 0.5 nm, preferably having a diameter that is between 50 and 500 nm, more preferably having a diameter that is between 50 and 300 nm. Cellular internalization of polymeric particles is highly dependent upon their size, with nanoparticulate polymeric particles being internalized by cells with much higher efficiency than microparticulate polymeric particles. For example, Desai, et al. have demonstrated that about 2.5 times more nanoparticles that are 100 nm in diameter are taken up by cultured Caco-2 cells as compared to microparticles having a diameter on 1 µM (Desai, et al., *Pharm. Res.*, 14:1568-73 (1997)). Nanoparticles also have a greater ability to diffuse deeper into tissues in vivo.

A. Polymer

The polymer that forms the core of the nanoparticle may be any biodegradable or non-biodegradable synthetic or natural polymer. In a preferred embodiment, the polymer is a biodegradable polymer. Nanoparticles are ideal materials for the fabrication of gene editing delivery vehicles: 1) control over the size range of fabrication, down to 100 nm or less, an important feature for passing through biological barriers; 2) reproducible biodegradability without the addition of enzymes or cofactors; 3) capability for sustained release of encapsulated, protected nucleic acids over a period in the range of days to months by varying factors such as the monomer ratios or polymer size, for example, the ratio of lactide to glycolide monomer units in poly(lactide-co-glycolide) (PLGA); 4) well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Examples of preferred biodegradable polymers include synthetic polymers that degrade by hydrolysis such as poly(hydroxy acids), such as polymers and copolymers of lactic acid and glycolic acid, other degradable polyesters, polyanhydrides, poly(ortho)esters, polyesters, polyurethanes, poly(butic acid), poly(valeric acid), poly(caprolactone), poly(hydroxyalkanoates), poly(lactide-co-caprolactone), and poly(amine-co-ester) polymers, such as those described in Zhou, et al., *Nature Materials*, 11:82-90 (2012) and WO 2013/082529, U.S. Published Application No. 2014/0342003, and PCT/US2015/061375.

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terepthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate). These materials may be used alone, as physical mixtures (blends), or as co-polymers.

The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

Release rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

In a preferred embodiment, the nanoparticles are formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)). These polymers have been used to encapsulate siRNA (Yuan, et al., *Jour. Nanoscience and Nanotechnology*, 6:2821-8 (2006); Braden, et al., *Jour. Biomed. Nanotechnology*, 3:148-59 (2007); Khan, et al., *Jour. Drug Target*, 12:393-404 (2004); Woodrow, et al., *Nature Materials*, 8:526-533 (2009)). Murata, et al., *J. Control. Release*, 126(3):246-54 (2008) showed inhibition of tumor growth after intratumoral injection of PLGA microspheres encapsulating siRNA targeted against vascular endothelial growth factor (VEGF). However, these microspheres were too large to be endocytosed (35-45 µm) (Conner and Schmid, *Nature*, 422(6927):37-44 (2003)) and required release of the anti-VEGF siRNA extracellularly as a polyplex with either polyarginine or PEI before they could be internalized by the cell. These microparticles may have limited applications because of the toxicity of the polycations and the size of the particles. Nanoparticles (100-300 nm) of PLGA can penetrate deep into tissue and are easily internalized by many cells (Conner and Schmid, *Nature*, 422(6927):37-44 (2003)).

The nanoparticles can be designed to release encapsulated nucleic acids over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity, affecting degradation rate. Specifically, the hydrophobic poly (lactic acid)

(PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Exemplary nanoparticles are described in U.S. Pat. Nos. 4,883,666, 5,114,719, 5,601,835, 7,534,448, 7,534,449, 7,550,154, and 8,889,117, and U.S. Published Application Nos. 2009/0269397, 2009/0239789, 2010/0151436, 2011/0008451, 2011/0268810, 2014/0342003, 2015/0118311, 2015/0125384, 2015/0073041, Hubbell, et al., *Science*, 337: 303-305 (2012), Cheng, et al., *Biomaterials*, 32:6194-6203 (2011), Rodriguez, et al., *Science*, 339:971-975 (2013), Hrkach, et al., *Sci Transl Med.*, 4:128ra139 (2012), McNeer, et al., *Mol Ther.*, 19:172-180 (2011), McNeer, et al., *Gene Ther.*, 20:658-659 (2013), Babar, et al., *Proc Natl Acad Sci USA*, 109:E1695-E1704 (2012), Fields, et al., *J Control Release* 164:41-48 (2012), and Fields, et al., *Advanced Healthcare Materials*, 361-366 (2015).

B. Polycations

In a preferred embodiment, the nucleic acids are complexed to polycations to increase the encapsulation efficiency of the nucleic acids into the nanoparticles. The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values.

Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quartemized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In one embodiment, the polycation is a polyamine. Polyamines are compounds having two or more primary amine groups. In a preferred embodiment, the polyamine is a naturally occurring polyamine that is produced in prokaryotic or eukaryotic cells. Naturally occurring polyamines represent compounds with cations that are found at regularly-spaced intervals and are therefore particularly suitable for complexing with nucleic acids. Polyamines play a major role in very basic genetic processes such as DNA synthesis and gene expression. Polyamines are integral to cell migration, proliferation and differentiation in plants and animals. The metabolic levels of polyamines and amino acid precursors are critical and hence biosynthesis and degradation are tightly regulated. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane) which is produced from L-omithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

In some embodiments, the particles themselves are a polycation (e.g., a blend of PLGA and poly(beta amino ester).

C. Coupling Agents or Ligands

The external surface of the polymeric nanoparticles may be modified by conjugating to, or incorporating into, the surface of the nanoparticle a coupling agent or ligand.

In a preferred embodiment, the coupling agent is present in high density on the surface of the nanoparticle. As used herein, "high density" refers to polymeric nanoparticles having a high density of ligands or coupling agents, which is preferably in the range of 1,000 to 10,000,000, more preferably 10,000-1,000,000 ligands per square micron of nanoparticle surface area. This can be measured by fluorescence staining of dissolved particles and calibrating this fluorescence to a known amount of free fluorescent molecules in solution.

Coupling agents associate with the polymeric nanoparticles and provide substrates that facilitate the modular assembly and disassembly of functional elements to the nanoparticles. Coupling agents or ligands may associate with nanoparticles through a variety of interactions including, but not limited to, hydrophobic interactions, electrostatic interactions and covalent coupling.

In a preferred embodiment, the coupling agents are molecules that match the polymer phase hydrophile-lipophile balance. Hydrophile-lipophile balances range from 1 to 15. Molecules with a low hydrophile-lipophile balance are more lipid loving and thus tend to make a water in oil emulsion while those with a high hydrophile-lipophile balance are more hydrophilic and tend to make an oil in water emulsion. Fatty acids and lipids have a low hydrophile-lipophile balance below 10.

Any amphiphilic polymer with a hydrophile-lipophile balance in the range 1-10, more preferably between 1 and 6, most preferably between 1 and up to 5, can be used as a coupling agent. Examples of coupling agents which may associate with polymeric nanoparticles via hydrophobic interactions include, but are not limited to, fatty acids, hydrophobic or amphipathic peptides or proteins, and polymers. These classes of coupling agents may also be used in any combination or ratio. In a preferred embodiment, the association of adaptor elements with nanoparticles facilitates a prolonged presentation of functional elements which can last for several weeks.

Coupling agents can also be attached to polymeric nanoparticles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

Functionality may be introduced into the particles in two ways. The first is during the preparation of the nanoparticles, for example during the emulsion preparation of nanoparticles by incorporation of stabilizers with functional chemical groups. Suitable stabilizers include hydrophobic or amphipathic molecules that associate with the outer surface of the nanoparticles.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. The "coupling" of the molecule to the "activated" polymer matrix is maximal in the pH range of 9-10 and normally requires at least 24 hrs. The resulting molecule-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

A useful coupling procedure for attaching molecules with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of molecules and polymers with double bonds, including the use of UV crosslinking, may be used for attachment of molecules to the polymer.

In one embodiment, coupling agents can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$, GFP, DIG, biotin and avidin. Antibodies (both monoclonal and polyclonal and antigen-binding fragments thereof) which bind to these epitopes are well known in the art.

Affinity tags that are conjugated to coupling agents allow for highly flexible, modular assembly and disassembly of functional elements which are conjugated to affinity tags which form highly specific, noncovalent, physiochemical interactions with complementary affinity tags which are conjugated to coupling agents. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In another embodiment, coupling agents are coupled directly to functional elements in the absence of affinity tags, such as through direct covalent interactions. Coupling agents can be covalently coupled to at least one species of functional element. Coupling agents can be covalently coupled to a single species of functional element or with any combination of species of functional elements in any ratio.

In a preferred embodiment, coupling agents are conjugated to at least one affinity tag that provides for assembly and disassembly of modular functional elements which are conjugated to complementary affinity tags. In a more preferred embodiment, coupling agents are fatty acids that are conjugated with at least one affinity tag. In a particularly preferred embodiment, the coupling agents are fatty acids conjugated with avidin or streptavidin. Avidin/streptavidin-conjugated fatty acids allow for the attachment of a wide variety of biotin-conjugated functional elements.

The coupling agents are preferably provided on, or in the surface of, nanoparticles at a high density. This high density of coupling agents allows for coupling of the polymeric nanoparticles to a variety of species of functional elements while still allowing for the functional elements to be present in high enough numbers to be efficacious.

1. Fatty Acids

The coupling agents may include fatty acids. Fatty acids may be of any acyl chain length and may be saturated or unsaturated. In a particularly preferred embodiment, the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

2. Hydrophobic or Amphipathic Peptides

The coupling agents may include hydrophobic or amphipathic peptides. Preferred peptides should be sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric nanoparticles through the hydrophobic end of the peptide and be conjugated on the hydrophilic end to a functional group.

3. Hydrophobic Polymers

Coupling agents may include hydrophobic polymers. Examples of hydrophobic polymers include, but are not limited to, polyanhydrides, poly(ortho)esters, and polyesters such as polycaprolactone.

VII. Functional Molecules

Functional molecules can be associated with, linked, conjugated, or otherwise attached directly or indirectly gene editing technology, potentiating agents, or nanoparticles utilized for delivery thereof.

A. Targeting Molecules

One class of functional elements is targeting molecules. Targeting molecules can be associated with, linked, conjugated, or otherwise attached directly or indirectly to the gene editing molecule, or to a nanoparticle or other delivery vehicle thereof.

Targeting molecules can be proteins, peptides, nucleic acid molecules, saccharides or polysaccharides that bind to a receptor or other molecule on the surface of a targeted cell. The degree of specificity and the avidity of binding to the graft can be modulated through the selection of the targeting molecule. For example, antibodies are very specific. These can be polyclonal, monoclonal, fragments, recombinant, or single chain, many of which are commercially available or readily obtained using standard techniques.

Examples of moieties include, for example, targeting moieties which provide for the delivery of molecules to specific cells, e.g., antibodies to hematopoietic stem cells, CD34+ cells, T cells or any other preferred cell type, as well as receptor and ligands expressed on the preferred cell type. Preferably, the moieties target hematopoeitic stem cells.

Examples of molecules targeting extracellular matrix ("ECM") include glycosaminoglycan ("GAG") and collagen. In one embodiment, the external surface of polymer particles may be modified to enhance the ability of the particles to interact with selected cells or tissue. The method described above wherein an adaptor element conjugated to a targeting molecule is inserted into the particle is preferred. However, in another embodiment, the outer surface of a polymer micro- or nanoparticle having a carboxy terminus may be linked to targeting molecules that have a free amine terminus.

Other useful ligands attached to polymeric micro- and nanoparticles include pathogen-associated molecular patterns (PAMPs). PAMPs target Toll-like Receptors (TLRs) on the surface of the cells or tissue, or signal the cells or tissue internally, thereby potentially increasing uptake. PAMPs conjugated to the particle surface or co-encapsulated may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

In another embodiment, the outer surface of the particle may be treated using a mannose amine, thereby mannosylating the outer surface of the particle. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins that can be covalently attached to micro- and nanoparticles to render them target specific to the mucin and mucosal cell layer include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus*.

The choice of targeting molecule will depend on the method of administration of the nanoparticle composition and the cells or tissues to be targeted. The targeting molecule may generally increase the binding affinity of the particles for cell or tissues or may target the nanoparticle to a particular tissue in an organ or a particular cell type in a tissue. Avidin increases the ability of polymeric nanoparticles to bind to tissues. While the exact mechanism of the enhanced binding of avidin-coated particles to tissues has not been elucidated, it is hypothesized it is caused by electrostatic attraction of positively charged avidin to the negatively charged extracellular matrix of tissue. Non-specific binding of avidin, due to electrostatic interactions, has been previously documented and zeta potential measurements of avidin-coated PLGA particles revealed a positively charged surface as compared to uncoated PLGA particles.

The attachment of any positively charged ligand, such as polyethyleneimine or polylysine, to any polymeric particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most particles with the appropriate chemistry and be expected to influence the binding of particles to the gut. For example, polyclonal antibodies raised against components of mucin or else intact mucin, when covalently coupled to particles, would provide for increased bioadhesion. Similarly, antibodies directed against specific cell surface receptors exposed on the lumenal surface of the intestinal tract would increase the residence time of beads, when coupled to particles using the appropriate chemistry. The ligand affinity need not be based only on electrostatic charge, but other useful physical parameters such as solubility in mucin or else specific affinity to carbohydrate groups.

The covalent attachment of any of the natural components of mucin in either pure or partially purified form to the particles would decrease the surface tension of the bead-gut interface and increase the solubility of the bead in the mucin layer. The list of useful ligands includes, but is not limited to the following: sialic acid, neuraminic acid, n-acetylneuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range yields chains of 120 to 425 amino acid residues attached to the surface of the particles. The polyamino chains increase bioadhesion by means of chain entanglement in mucin strands as well as by increased carboxylic charge.

The efficacy of the nanoparticles is determined in part by their route of administration into the body. For orally and topically administered nanoparticles, epithelial cells constitute the principal barrier that separates an organism's interior from the outside world. Epithelial cells such as those that line the gastrointestinal tract form continuous monolayers that simultaneously confront the extracellular fluid compartment and the extracorporeal space.

Adherence to cells is an essential first step in crossing the epithelial barrier by any of these mechanisms. Therefore, in one embodiment, the nanoparticles disclosed herein further include epithelial cell targeting molecules. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificites, dipeptidyl peptidase, and E-cadherin.

B. Protein Transduction Domains and Fusogenic Peptides

Other functional elements that can be associated with, linked, conjugated, or otherwise attached directly or indirectly to the gene editing molecule, potentiating agent, or to a nanoparticle or other delivery vehicle thereof, include protein transduction domains and fusogenic peptides.

For example, the efficiency of nanoparticle delivery systems can also be improved by the attachment of functional ligands to the NP surface. Potential ligands include, but are not limited to, small molecules, cell-penetrating peptides (CPPs), targeting peptides, antibodies or aptamers (Yu, et al., *PLoS One.*, 6:e24077 (2011), Cu, et al., *J Control Release*, 156:258-264 (2011), Nie, et al., *J Control Release*, 138:64-70 (2009), Cruz, et al., *J Control Release*, 144:118-126 (2010)). Attachment of these moieties serves a variety of different functions; such as inducing intracellular uptake, endosome disruption, and delivery of the plasmid payload to the nucleus. There have been numerous methods employed to tether ligands to the particle surface. One approach is direct covalent attachment to the functional groups on PLGA NPs (Bertram, *Acta Biomater.* 5:2860-2871 (2009)). Another approach utilizes amphiphilic conjugates like avidin palmitate to secure biotinylated ligands to the NP surface (Fahmy, et al., *Biomaterials*, 26:5727-5736 (2005), Cu, et al., *Nanomedicine*, 6:334-343 (2010)). This approach produces particles with enhanced uptake into cells, but reduced pDNA release and gene transfection, which is likely due to the surface modification occluding pDNA release. In a similar approach, lipid-conjugated polyethylene glycol (PEG) is used as a multivalent linker of penetratin, a CPP, or folate (Cheng, et al., *Biomaterials*, 32:6194-6203 (2011)).

These methods, as well as other methods discussed herein, and others methods known in the art, can be combined to tune particle function and efficacy. In some preferred embodiments, PEG is used as a linker for linking functional molecules to nanoparticles. For example, DSPE-PEG(2000)-maleimide is commercially available and can be used utilized for covalently attaching functional molecules such as CPP.

"Protein Transduction Domain" or PTD refers to a polypeptide, polynucleotide, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. PTA can be short basic peptide sequences such as those present in many cellular and viral proteins. Exemplary protein transduction domains that are well-known in the art include, but are not limited to, the Antennapedia PTD and the TAT (transactivator of transcription) PTD, poly-arginine, poly-lysine or mixtures of arginine and lysine, HIV TAT (YGRKKRRQRRR (SEQ ID NO:7) or RKKRRQRRR (SEQ ID NO:8), 11 arginine residues, VP22 peptide, and an ANTp peptide (RQIKIWFQNRRMKWKK) (SEQ ID NO:9) or positively charged polypeptides or polynucleotides having 8-15 residues, preferably 9-11 residues. Short, non-peptide polymers that are rich in amines or guanidinium groups are also capable of carrying molecules crossing biological membranes. Penetratin and other derivatives of peptides derived from antennapedia (Cheng, et al., *Biomaterials*, 32(26):6194-203 (2011) can also be used. Results show that penetratin in which additional Args are added, further enhances uptake and endosomal escape, and IKK NBD, which has an antennapedia domain for permeation as well as a domain that blocks activation of NFkB and has been used safely in the lung for other purposes (von Bismarck, et al., *Pulmonary Pharmacology & Therapeutics,* 25(3):228-35 (2012), Kamei, et al., *Journal Of Pharmaceutical Sciences,* 102(11):3998-4008 (2013)).

A "fusogenic peptide" is any peptide with membrane destabilizing abilities. In general, fusogenic peptides have the propensity to form an amphiphilic alpha-helical structure when in the presence of a hydrophobic surface such as a membrane. The presence of a fusogenic peptide induces formation of pores in the cell membrane by disruption of the ordered packing of the membrane phospholipids. Some fusogenic peptides act to promote lipid disorder and in this way enhance the chance of merging or fusing of proximally positioned membranes of two membrane enveloped particles of various nature (e.g. cells, enveloped viruses, liposomes). Other fusogenic peptides may simultaneously attach to two membranes, causing merging of the membranes and promoting their fusion into one. Examples of fusogenic peptides include a fusion peptide from a viral envelope protein ectodomain, a membrane-destabilizing peptide of a viral envelope protein membrane-proximal domain from the cytoplasmic tails.

Other fusogenic peptides often also contain an amphiphilic-region. Examples of amphiphilic-region containing peptides include: melittin, magainins, the cytoplasmic tail of HIV1 gp41, microbial and reptilian cytotoxic peptides such as bomolitin 1, pardaxin, mastoparan, crabrolin, cecropin, entamoeba, and staphylococcal .alpha.-toxin; viral fusion peptides from (1) regions at the N terminus of the transmembrane (TM) domains of viral envelope proteins, e.g. HIV-1, SIV, influenza, polio, rhinovirus, and coxsackie virus; (2) regions internal to the TM ectodomain, e.g. semliki forest virus, sindbis virus, rota virus, rubella virus and the fusion peptide from sperm protein PH-30: (3) regions membrane-proximal to the cytoplasmic side of viral envelope proteins e.g. in viruses of avian leukosis (ALV), Feline immunodeficiency (FIV), Rous Sarcoma (RSV), Moloney murine leukemia virus (MoMuLV), and spleen necrosis (SNV).

In particular embodiments, a functional molecule such as a CPP is covalently linked to DSPE-PEG-maleimide functionalized nanoparticles such as PBAE/PLGA blended particles using known methods such as those described in Fields, et al., *J Control Release*, 164(1):41-48 (2012). For example, DSPE-PEG-function molecule can be added to the 5.0% PVA solution during formation of the second emulsion. In some embodiments, the loading ratio is about 5 nmol/mg ligand-to-polymer ratio.

In some embodiments, the functional molecule is a CPP such as those above, or mTAT (HIV-1 (with histidine modification) HHHHRKKRRQRRRRHHHHH (SEQ ID NO:10) (Yamano, et al., J Control Release, 152:278-285 (2011)); or bPrPp (Bovine prion) MVKSKIGSWILVLFVAMWS DVGLCKKRPKP (SEQ ID NO:11) (Magzoub, et al., *Biochem Biophys Res Commun.*, 348:379-385 (2006)); or MPG (Synthetic chimera: SV40 Lg T. Ant.+ HIV gb41 coat) GALFLGFLGAAGSTMGAWS QPKKKRKV (SEQ ID NO:12) (Endoh, et al., *Adv Drug Deliv Rev.*, 61:704-709 (2009)).

VIII. Methods of Manufacture

A. Methods of Making Nanoparticles

The nanoparticle compositions described herein can be prepared by a variety of methods.

1. Polycations

In some embodiments, the nucleic acid is first complexed to a polycation. Complexation can be achieved by mixing the nucleic acids and polycations at an appropriate molar ratio. When a polyamine is used as the polycation species, it is useful to determine the molar ratio of the polyamine nitrogen to the polynucleotide phosphate (N/P ratio). In a preferred embodiment, nucleic acids and polyamines are mixed together to form a complex at an N/P ratio of between approximately 8:1 to 15:1. The volume of polyamine solution required to achieve particular molar ratios can be determined according to the following formula:

$$V_{NH2} = \frac{C_{nucacid,final} \times M_{w,nucacid} / C_{nucacid,final} \times M_{w,P} \times \Phi_{N:P} \times \Phi V_{final}}{C_{NH2} / M_{w,NH2}}$$

where $M_{w,nucacid}$=molecular weight of nucleic acid, $M_{w,P}$=molecular weight of phosphate groups of the nucleic acid, $\Phi_{N:P}$=N:P ratio (molar ratio of nitrogens from polyamine to the ratio of phosphates from the nucleic acid), $C_{NH2}$, stock=concentration of polyamine stock solution, and $M_{w,NH2}$=molecular weight per nitrogen of polyamine.

Polycation complexation with nucleic acids can be achieved by mixing solutions containing polycations with solutions containing nucleic acids. The mixing can occur at any appropriate temperature. In one embodiment, the mixing occurs at room temperature. The mixing can occur with mild agitation, such as can be achieved through the use of a rotary shaker.

2. Exemplary Preferred Methods of Manufacture

In preferred embodiments, the nanoparticles are formed by a double-emulsion solvent evaporation technique, such as is disclosed in U.S. Published Application No. 2011/0008451 or U.S. Published Application No. 2011/0268810, each of which is a specifically incorporated by reference in its entirety, or Fahmy, et al., *Biomaterials*, 26:5727-5736, (2005), or McNeer, et al., *Mol.* Ther. 19, 172-180 (2011)). In this technique, the nucleic acids or nucleic acid/polycation complexes are reconstituted in an aqueous solution. Nucleic acid and polycation amounts are discussed in more detail below and can be chosen, for example, based on amounts and ratios disclosed in U.S. Published Application No. 2011/0008451 or U.S. Published Application No. 2011/0268810, or used by McNeer, et al., (McNeer, et al., *Mol. Ther.* 19, 172-180 (2011)), or by Woodrow et al. for small interfering RNA encapsulation (Woodrow, et al., *Nat Mater,* 8:526-533 (2009)). This aqueous solution is then added dropwise to a polymer solution of a desired polymer dissolved in an organic solvent to form the first emulsion.

This mixture is then added dropwise to solution containing a surfactant, such as polyvinyl alcohol (PVA) and sonicated to form the double emulsion. The final emulsion is then poured into a solution containing the surfactant in an aqueous solution and stirred for a period of time to allow the dichloromethane to evaporate and the particles to harden. The concentration of the surfactant used to form the emulsion, and the sonication time and amplitude can been optimized according to principles known in the art for formulating particles with a desired diameter. The particles can be collected by centrifugation. If it is desirable to store the nanoparticles for later use, they can be rapidly frozen, and lyophilized.

In preferred embodiments the nanoparticles are PLGA nanoparticles. In a particular exemplary protocol, nucleic acid (such as PNA, DNA, or PNA-DNA) with or without a polycation (such as spermidine) are dissolved in DNAse/RNAse free H$_2$O. Encapsulant in H$_2$O can be added dropwise to a polymer solution of 50:50 ester-terminated PLGA dissolved in dichloromethane (DCM), then sonicated to form the first emulsion. This emulsion can then be added dropwise to 5% polyvinyl alcohol, then sonicated to form the second emulsion. This mixture can be poured into 0.3% polyvinyl alcohol, and stirred at room temperature to form nanoparticles. Nanoparticles can then be collected and washed with, for example H$_2$O, collected by centrifugation, and then resuspended in H$_2$O, frozen at −80° C., and lyophilized. Particles can be stored at −20° C. following lyophilization.

Additional techniques for encapsulating the nucleic acid and polycation complex into polymeric nanoparticles are described below.

3. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

4. Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

5. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of nanoparticles that have a more optimized release of the encapsulated material.

6. Hot Melt Microencapsulation

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting particles are washed by decantation with petroleum ether to give a free-flowing powder. Particles with sizes between 0.5 to 1000 microns are obtained with this method. The external surfaces of spheres prepared with this technique are usually smooth and dense. This procedure is used to prepare particles made of polyesters and polyanhydrides. However, this method is limited to polymers with molecular weights between 1,000-50,000.

7. Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

8. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

9. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

10. Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

11. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

12. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=-24° C., outlet temperature=13-15° C., aspirator setting=15, pump setting=10 mL/minute, spray flow=600 Nl/hr, and nozzle diameter=0.5 mm. Particles ranging between 1-10 microns are obtained with a morphology which depends on the type of polymer used.

13. Nanoprecipitation

In nanoprecipitation, the polymer and nucleic acids are co-dissolved in a selected, water-miscible solvent, for example DMSO, acetone, ethanol, acetone, etc. In a preferred embodiment, nucleic acids and polymer are dissolved in DMSO. The solvent containing the polymer and nucleic acids is then drop-wise added to an excess volume of stirring aqueous phase containing a stabilizer (e.g., poloxamer, Pluronic®, and other stabilizers known in the art). Particles are formed and precipitated during solvent evaporation. To reduce the loss of polymer, the viscosity of the aqueous phase can be increased by using a higher concentration of the stabilizer or other thickening agents such as glycerol and others known in the art. Lastly, the entire dispersed system is centrifuged, and the nucleic acid-loaded polymer nanoparticles are collected and optionally filtered. Nanoprecipitation-based techniques are discussed in, for example, U.S. Pat. No. 5,118,528.

Advantages to nanoprecipitation include: the method can significantly increase the encapsulation efficiency of drugs that are polar yet water-insoluble, compared to single or double emulsion methods (Alshamsan, *Saudi Pharmaceutical Journal*, 22(3):219-222 (2014)). No emulsification or high shear force step (e.g., sonication or high-speed homogenization) is involved in nanoprecipitation, therefore preserving the conformation of nucleic acids. Nanoprecipitation relies on the differences in the interfacial tension between the solvent and the nonsolvent, rather than shear stress, to produce nanoparticles. Hydrophobicity of the drug will retain it in the instantly-precipitating nanoparticles; the un-precipitated polymer due to equilibrium is "lost" and not in the precipitated nanoparticle form.

B. Molecules to be Encapsulated or Attached to the Surface of the Particles

There are two principle groups of molecules to be encapsulated or attached to the polymer, either directly or via a coupling molecule: targeting molecules, attachment molecules and therapeutic, nutritional, diagnostic or prophylactic agents. These can be coupled using standard techniques. The targeting molecule or therapeutic molecule to be delivered can be coupled directly to the polymer or to a material such as a fatty acid which is incorporated into the polymer.

Functionality refers to conjugation of a ligand to the surface of the particle via a functional chemical group (carboxylic acids, aldehydes, amines, sulfhydryls and hydroxyls) present on the surface of the particle and present on the ligand to be attached. Functionality may be introduced into the particles in two ways. The first is during the preparation of the particles, for example during the emulsion preparation of particles by incorporation of stabilizers with functional chemical groups. Example 1 demonstrates this type of process whereby functional amphiphilic molecules are inserted into the particles during emulsion preparation.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

In the preferred embodiment, the surface is modified to insert amphiphilic polymers or surfactants that match the polymer phase HLB or hydrophile-lipophile balance, as demonstrated in the following example. HLBs range from 1 to 15. Surfactants with a low HLB are more lipid loving and thus tend to make a water in oil emulsion while those with a high HLB are more hydrophilic and tend to make an oil in water emulsion. Fatty acids and lipids have a low HLB below 10. After conjugation with target group (such as hydrophilic avidin), HLB increases above 10. This conjugate is used in emulsion preparation. Any amphiphilic polymer with an HLB in the range 1-10, more preferably between 1 and 6, most preferably between 1 and up to 5, can be used. This includes all lipids, fatty acids and detergents.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as strepavidin and biotin. It may also be by electrostatic attraction by dip-coating.

The molecules to be delivered can also be encapsulated into the polymer using double emulsion solvent evaporation techniques, such as that described by Luo et al., Controlled DNA delivery system, *Phar. Res.*, 16: 1300-1308 (1999).

C. Particularly Preferred Nanoparticle Formulations

The nanoparticle formulation can be selected based on the considerations including the targeted tissue or cells. For example, in embodiments directed to treatment of treating or correcting beta-thalassemia (e.g. when the target cells are, for example, hematopoietic stem cells), a preferred nanoparticle formulation is PLGA.

Other preferred nanoparticle formulations, particularly preferred for treating cystic fibrosis, are described in McNeer, et al., *Nature Commun.*, 6:6952. doi: 10.1038/ncomms7952 (2015), and Fields, et al., *Adv Healthc Mater.*, 4(3):361-6 (2015). doi: 10.1002/adhm.201400355 (2015) Epub 2014. Such nanoparticles are composed of a blend of Poly(beta-amino) esters (PBAEs) and poly(lactic-co-glycolic acid) (PLGA). Poly(beta-amino) esters (PBAEs) are degradable, cationic polymers synthesized by conjugate (Michael-like) addition of bifunctional amines to diacrylate esters (Lynn, Langer R, editor. *J Am Chem Soc*. 2000. pp. 10761-10768). PBAEs appear to have properties that make them efficient vectors for gene delivery. These cationic polymers are able to condense negatively charged pDNA, induce cellular uptake, and buffer the low pH environment of endosomes leading to DNA escape (Lynn, Langer R, editor. *J Am Chem Soc*. 2000. pp. 10761-10768, and Green, *Acc Chem Res.*, 41(6):749-759 (2008)). PBAEs have the ability to form hybrid particles with other polymers, which allows for production of solid, stable and storable particles. For example, blending cationic PBAE with PLGA produced highly loaded pDNA particles. The addition of PBAE to PLGA resulted in an increase in gene transfection in vitro and induced antigen-specific tumor rejection in a murine model (Little, et al. *Proc Natl Acad Sci USA.*, 101:9534-9539 (2004), Little, et al., *J Control Release*, 107:449-462 (2005)).

Therefore, in some embodiments, the nanoparticles utilized to deliver the disclosed compositions are composed of a blend of PBAE and a second polymer one of those discussed above. In some embodiments, the nanoparticles are composed of a blend of PBAE and PLGA.

PLGA and PBAE/PLGA blended nanoparticles loaded with gene editing technology can be formulated using a double-emulsion solvent evaporation technique such as that described in detail above, and in McNeer, et al., *Nature Commun.*, 6:6952. doi: 10.1038/ncomms7952 (2015), and Fields, et al., *Adv Healthc Mater.*, 4(3):361-6 (2015). doi: 10.1002/adhm.201400355 (2015) Epub 2014. Poly(beta amino ester) (PBAE) can synthesized by a Michael addition reaction of 1,4-butanediol diacrylate and 4,4'-trimethylene-dipiperidine as described in Akinc, et al., *Bioconjug Chem.*, 14:979-988 (2003). In some embodiments, PBAE blended particles such as PLGA/PBAE blended particles, contain between about 1 and 99, or between about 1 and 50, or between about 5 and 25, or between about 5 and 20, or between about 10 and 20, or about 15 percent PBAE (wt %). In particular embodiments, PBAE blended particles such as PLGA/PBAE blended particles, contain about 50, 45, 40, 35, 30, 25, 20, 15, 10, or 5% PBAE (wt %). Solvent from these particles in PVA as discussed above, and in some cases may continue overnight. PLGA/PBAE/MPG nanoparticles was shown to produce significantly greater nanoparticle association with airway epithelial cells than PLGA nanoparticles (Fields, et al., *Advanced Healthcare Materials*, 4:361-366 (2015)).

IX. Methods of Use

A. Methods of Treatment

The disclosed compositions can be used to ex vivo or in vivo gene editing. The methods typically include contacting a cell with an effective amount of gene editing composition, preferably in combination with a potentiating agent, to modify the cell's genome. As discussed in more detail below, the contacting can occur ex vivo or in vivo. In preferred embodiments, the method includes contacting a population of target cells with an effective amount of gene editing composition, preferably in combination with a potentiating agent, to modify the genomes of a sufficient number of cells to achieve a therapeutic result.

For example, the effective amount or therapeutically effective amount can be a dosage sufficient to treat, inhibit, or alleviate one or more symptoms of a disease or disorder, or to otherwise provide a desired pharmacologic and/or physiologic effect, for example, reducing, inhibiting, or reversing one or more of the underlying pathophysiological mechanisms underlying a disease or disorder.

In some embodiments, when the gene editing technology is triplex forming molecules, the molecules can be administered in an effective amount to induce formation of a triple helix at the target site. An effective amount of gene editing technology such as triplex-forming molecules may also be an amount effective to increase the rate of recombination of a donor fragment relative to administration of the donor fragment in the absence of the gene editing technology. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids. The precise dosage will vary according to a variety of factors such as subject-dependent variables (e.g., age, immune system health, clinical symptoms etc.). Exemplary symptoms, pharmacologic, and physiologic effects are discussed in more detail below.

The disclosed compositions can be administered or otherwise contacted with target cells once, twice, or three time daily; one, two, three, four, five, six, seven times a week, one, two, three, four, five, six, seven or eight times a month. For example, in some embodiments, the composition is administered every two or three days, or on average about 2 to about 4 times about week.

In some embodiments, the potentiating agent is administered to the subject prior to administration of the gene editing technology to the subject. The potentiating agent can be administered to the subject, for example, 1, 2, 3, 4, 5, 6, 8, 10, 12, 18, or 24 hours, or 1, 2, 3, 4, 5, 6, or 7 days, or any combination thereof prior to administration of the gene editing technology to the subject.

In some embodiments, the gene editing technology is administered to the subject prior to administration of the potentiating agent to the subject. The gene editing technology can be administered to the subject, for example, 1, 2, 3, 4, 5, 6, 8, 10, 12, 18, or 24 hours, or 1, 2, 3, 4, 5, 6, or 7 days, or any combination thereof prior to administration of the potentiating agent to the subject.

In preferred embodiments, the compositions are administered in an amount effective to induce gene modification in at least one target allele to occur at frequency of at least 0.1, 0.2. 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25% of target cells. In some embodiments, particularly ex vivo applications, gene modification occurs in at least one target allele at a frequency of about 0.1-25%, or 0.5-25%, or 1-25% 2-25%, or 3-25%, or 4-25% or 5-25% or 6-25%, or 7-25%, or 8-25%, or 9-25%, or 10-25%, 11-25%, or 12-25%, or 13%-25% or 14%-25% or 15-25%, or 2-20%, or 3-20%, or 4-20% or 5-20% or 6-20%, or 7-20%, or 8-20%, or 9-20%, or 10-20%, 11-20%, or 12-20%, or 13%-20% or 14%-20% or 15-20%, 2-15%, or 3-15%, or 4-15% or 5-15% or 6-15%, or 7-15%, or 8-15%, or 9-15%, or 10-15%, 11-15%, or 12-15%, or 13%-15% or 14%-15%.

In some embodiments, particularly in vivo applications, gene modification occurs in at least one target allele at a frequency of about 0.1% to about 10%, or about 0.2% to about 10%, or about 0.3% to about 10%, or about 0.4% to about 10%, or about 0.5% to about 10%, or about 0.6% to about 10%, or about 0.7% to about 10%, or about 0.8% to about 10%, or about 0.9% to about 10%, or about 1.0% to about 10%, or about 1.1% to about 10%, or about 1.1% to about 10%, 1.2% to about 10%, or about 1.3% to about 10%, or about 1.4% to about 10%, or about 1.5% to about 10%, or about 1.6% to about 10%, or about 1.7% to about 10%, or about 1.8% to about 10%, or about 1.9% to about 10%, or about 2.0% to about 10%, or about 2.5% to about 10%, or about 3.0% to about 10%, or about 3.5% to about 10%, or about 4.0% to about 10%, or about 4.5% to about 10%, or about 5.0% to about 10%.

In some embodiments, gene modification occurs with low off-target effects. In some embodiments, off-target modification is undetectable using routine analysis such as those described in the Examples below. In some embodiments, off-target incidents occur at a frequency of 0-1%, or 0-0.1%, or 0-0.01%, or 0-0.001%, or 0-0.0001%, or 0-0000.1%, or 0-0.000001%. In some embodiments, off-target modification occurs at a frequency that is about $10^2$, $10^3$, $10^4$, or $10^5$-fold lower than at the target site.

Gene Editing Technology

In general, by way of example only, dosage forms useful in the disclosed methods can include doses in the range of about $10^2$ to about $10^{50}$, or about $10^5$ to about $10^{40}$, or about $10^{10}$ to about $10^{30}$, or about $10^{12}$ to about $10^{20}$ copies of the gene editing technology per dose. In particular embodiments, about $10^{13}$, $10^{14}$, $10^{15}$, $10^{16}$, or $10^{17}$ copies of gene editing technology are administered to a subject in need thereof.

In other embodiments, dosages are expressed in moles. For example, in some embodiments, the dose of gene editing technology is about 0.1 nmol to about 100 nmol, or about 0.25 nmol to about 50 nmol, or about 0.5 nmol to about 25 nmol, or about 0.75 nmol to about 7.5 nmol.

In other embodiments, dosages are expressed in molecules per target cells. For example, in some embodiments, the dose of gene editing technology is about $10^2$ to about $10^{50}$, or about $10^5$ to about $10^{15}$, or about $10^7$ to about $10^{12}$, or about $10^8$ to about $10^{11}$ copies of the gene editing technology per target cell.

In other embodiments, dosages are expressed in mg/kg, particularly when the expressed as an in vivo dosage of gene editing composition packaged in a nanoparticle with or without functional molecules. Dosages can be, for example 0.1 mg/kg to about 1,000 mg/kg, or 0.5 mg/kg to about 1,000 mg/kg, or 1 mg/kg to about 1,000 mg/kg, or about 10 mg/kg to about 500 mg/kg, or about 20 mg/kg to about 500 mg/kg per dose, or 20 mg/kg to about 100 mg/kg per dose, or 25 mg/kg to about 75 mg/kg per dose, or about 25, 30, 35, 40, 45, 50, 55, 60, 65, 70, or 75 mg/kg per dose.

In other embodiments, dosages are expressed in mg/ml, particularly when the expressed as an ex vivo dosage of gene editing composition packaged in a nanoparticle with or without functional molecules. Dosages can be, for example 0.01 mg/ml to about 100 mg/ml, or about 0.5 mg/ml to about 50 mg/ml, or about 1 mg/ml to about 10 mg/ml per dose to a cell population of $10^6$ cells.

As discussed above, gene editing technology can be administered without, but is preferably administered with at least one donor oligonucleotide. Such donors can be administered at similar dosages as the gene editing technology. Compositions should include an amount of donor fragment effective to recombine at the target site in the presence of a gene editing technology such as triplex forming molecules.

Potentiating Agents

The methods can include contacting cells with an effective amount potentiating agents. Preferably the amount of potentiating agent is effective to increase gene modification when used in combination with a gene modifying technology, compared to using the gene modifying technology in the absence of the potentiating agent.

Exemplary dosages for SCF include, about 0.01 mg/kg to about 250 mg/kg, or about 0.1 mg/kg to about 100 mg/kg, or about 0.5 mg/kg to about 50 mg/kg, or about 0.75 mg/kg to about 10 mg/kg.

Dosages for CHK1 inhibitors are known in the art, and many of these are in clinical trial. Accordingly, the dosage can be selected by the practitioner based on known, preferred humans dosages. In preferred embodiments, the dosage is below the lowest-observed-adverse-effect level (LOAEL), and is preferably a no observed adverse effect level (NOAEL) dosage.

1. Ex Vivo Gene Therapy

In some embodiments, ex vivo gene therapy of cells is used for the treatment of a genetic disorder in a subject. For ex vivo gene therapy, cells are isolated from a subject and contacted ex vivo with the compositions to produce cells containing mutations in or adjacent to genes. In a preferred embodiment, the cells are isolated from the subject to be treated or from a syngenic host. Target cells are removed from a subject prior to contacting with a gene editing composition and preferably a potentiating factor. The cells can be hematopoietic progenitor or stem cells. In a preferred embodiment, the target cells are CD34+ hematopoietic stem cells. Hematopoietic stem cells (HSCs), such as CD34+ cells are multipotent stem cells that give rise to all the blood cell types including erythrocytes. Therefore, CD34+ cells can be isolated from a patient with, for example, thalassemia, sickle cell disease, or a lysosomal storage disease, the mutant gene altered or repaired ex-vivo using the disclosed compositions and methods, and the cells reintroduced back into the patient as a treatment or a cure.

Stem cells can be isolated and enriched by one of skill in the art. Methods for such isolation and enrichment of CD34+ and other cells are known in the art and disclosed for example in U.S. Pat. Nos. 4,965,204; 4,714,680; 5,061,620; 5,643,741; 5,677,136; 5,716,827; 5,750,397 and 5,759,793. As used herein in the context of compositions enriched in hematopoietic progenitor and stem cells, "enriched" indicates a proportion of a desirable element (e.g. hematopoietic progenitor and stem cells) which is higher than that found in the natural source of the cells. A composition of cells may be enriched over a natural source of the cells by at least one order of magnitude, preferably two or three orders, and more preferably 10, 100, 200 or 1000 orders of magnitude.

In humans, CD34+ cells can be recovered from cord blood, bone marrow or from blood after cytokine mobilization effected by injecting the donor with hematopoietic growth factors such as granulocyte colony stimulating factor (G-CSF), granulocyte-monocyte colony stimulating factor (GM-CSF), stem cell factor (SCF) subcutaneously or intravenously in amounts sufficient to cause movement of hematopoietic stem cells from the bone marrow space into the peripheral circulation. Initially, bone marrow cells may be obtained from any suitable source of bone marrow, e.g. tibiae, femora, spine, and other bone cavities. For isolation of bone marrow, an appropriate solution may be used to flush the bone, which solution will be a balanced salt solution, conveniently supplemented with fetal calf serum or other naturally occurring factors, in conjunction with an acceptable buffer at low concentration, generally from about 5 to 25 mM. Convenient buffers include Hepes, phosphate buffers, lactate buffers, etc.

Cells can be selected by positive and negative selection techniques. Cells can be selected using commercially available antibodies which bind to hematopoietic progenitor or stem cell surface antigens, e.g. CD34, using methods known to those of skill in the art. For example, the antibodies may be conjugated to magnetic beads and immunogenic procedures utilized to recover the desired cell type. Other techniques involve the use of fluorescence activated cell sorting (FACS). The CD34 antigen, which is found on progenitor cells within the hematopoietic system of non-leukemic individuals, is expressed on a population of cells recognized by the monoclonal antibody My-10 (i.e., express the CD34 antigen) and can be used to isolate stem cell for bone marrow transplantation. My-10 deposited with the American Type Culture Collection (Rockville, Md.) as HB-8483 is commercially available as anti-HPCA 1. Additionally, negative selection of differentiated and "dedicated" cells from human bone marrow can be utilized, to select against substantially any desired cell marker. For example, progenitor or stem cells, most preferably CD34+ cells, can be characterized as being any of CD3−, CDT, CD8−, CD10−, CD14−, CD15−, CD19−, CD20−, CD33−, Class II HLA+ and Thy-1+.

Once progenitor or stem cells have been isolated, they may be propagated by growing in any suitable medium. For example, progenitor or stem cells can be grown in conditioned medium from stromal cells, such as those that can be obtained from bone marrow or liver associated with the secretion of factors, or in medium including cell surface factors supporting the proliferation of stem cells. Stromal cells may be freed of hematopoietic cells employing appropriate monoclonal antibodies for removal of the undesired cells.

The isolated cells are contacted ex vivo with a combination of triplex-forming molecules and donor oligonucleotides in amounts effective to cause the desired mutations in or adjacent to genes in need of repair or alteration, for example the human beta-globin or α-L-iduronidase gene. These cells are referred to herein as modified cells. Methods for transfection of cells with oligonucleotides and peptide nucleic acids are well known in the art (Koppelhus, et al., *Adv. Drug Deliv. Rev.*, 55(2): 267-280 (2003)). It may be desirable to synchronize the cells in S-phase to further increase the frequency of gene correction. Methods for synchronizing cultured cells, for example, by double thymidine block, are known in the art (Zielke, et al., *Methods Cell Biol.*, 8:107-121 (1974)).

The modified cells can be maintained or expanded in culture prior to administration to a subject. Culture conditions are generally known in the art depending on the cell type. Conditions for the maintenance of CD34+ in particular have been well studied, and several suitable methods are available. A common approach to ex vivo multi-potential hematopoietic cell expansion is to culture purified progenitor or stem cells in the presence of early-acting cytokines such as interleukin-3. It has also been shown that inclusion, in a nutritive medium for maintaining hematopoietic progenitor cells ex vivo, of a combination of thrombopoietin (TPO), stem cell factor (SCF), and flt3 ligand (Flt-3L; i.e., the ligand of the flt3 gene product) was useful for expanding primitive (i.e., relatively non-differentiated) human hematopoietic progenitor cells in vitro, and that those cells were capable of engraftment in SCID-hu mice (Luens et al., 1998, Blood 91:1206-1215). In other known methods, cells can be maintained ex vivo in a nutritive medium (e.g., for minutes, hours, or 3, 6, 9, 13, or more days) including murine prolactin-like protein E (mPLP-E) or murine prolactin-like protein F (mPIP-F; collectively mPLP-E/IF) (U.S. Pat. No. 6,261,841). It will be appreciated that other suitable cell culture and expansion method can be used in accordance with the invention as well. Cells can also be grown in serum-free medium, as described in U.S. Pat. No. 5,945,337.

In another embodiment, the modified hematopoietic stem cells are differentiated ex vivo into CD4+ cells culture using specific combinations of interleukins and growth factors prior to administration to a subject using methods well known in the art. The cells may be expanded ex vivo in large numbers, preferably at least a 5-fold, more preferably at least a 10-fold and even more preferably at least a 20-fold expansion of cells compared to the original population of isolated hematopoietic stem cells.

In another embodiment cells for ex vivo gene therapy, the cells to be used can be dedifferentiated somatic cells.

Somatic cells can be reprogrammed to become pluripotent stem-like cells that can be induced to become hematopoietic progenitor cells. The hematopoietic progenitor cells can then be treated with triplex-forming molecules and donor oligonucleotides as described above with respect to CD34+ cells to produce recombinant cells having one or more modified genes. Representative somatic cells that can be reprogrammed include, but are not limited to fibroblasts, adipocytes, and muscles cells. Hematopoietic progenitor cells from induced stem-like cells have been successfully developed in the mouse (Hanna, J. et al. *Science,* 318:1920-1923 (2007)).

To produce hematopoietic progenitor cells from induced stem-like cells, somatic cells are harvested from a host. In a preferred embodiment, the somatic cells are autologous fibroblasts. The cells are cultured and transduced with vectors encoding Oct4, Sox2, Klf4, and c-Myc transcription factors. The transduced cells are cultured and screened for embryonic stem cell (ES) morphology and ES cell markers including, but not limited to AP, SSEA1, and Nanog. The transduced ES cells are cultured and induced to produce induced stem-like cells. Cells are then screened for CD41 and c-kit markers (early hematopoietic progenitor markers) as well as markers for myeloid and erythroid differentiation.

The modified hematopoietic stem cells or modified induced hematopoietic progenitor cells are then introduced into a subject. Delivery of the cells may be effected using various methods and includes most preferably intravenous administration by infusion as well as direct depot injection into periosteal, bone marrow and/or subcutaneous sites.

The subject receiving the modified cells may be treated for bone marrow conditioning to enhance engraftment of the cells. The recipient may be treated to enhance engraftment, using a radiation or chemotherapeutic treatment prior to the administration of the cells. Upon administration, the cells will generally require a period of time to engraft. Achieving significant engraftment of hematopoietic stem or progenitor cells typically takes weeks to months.

A high percentage of engraftment of modified hematopoietic stem cells is not envisioned to be necessary to achieve significant prophylactic or therapeutic effect. It is expected that the engrafted cells will expand over time following engraftment to increase the percentage of modified cells. In some embodiments, the modified cells have a corrected α-L-iduronidase gene. Therefore, in a subject with Hurler syndrome, the modified cells are expected to improve or cure the condition. It is expected that engraftment of only a small number or small percentage of modified hematopoietic stem cells will be required to provide a prophylactic or therapeutic effect.

In preferred embodiments, the cells to be administered to a subject will be autologous, e.g. derived from the subject, or syngenic.

2. In Vivo Gene Therapy

The disclosed compositions can be administered directly to a subject for in vivo gene therapy.

a. Pharmaceutical Formulations

The disclosed compositions are preferably employed for therapeutic uses in combination with a suitable pharmaceutical carrier. Such compositions include an effective amount of the composition, and a pharmaceutically acceptable carrier or excipient.

It is understood by one of ordinary skill in the art that nucleotides administered in vivo are taken up and distributed to cells and tissues (Huang, et al., *FEBS Lett.,* 558(1-3):69-73 (2004)). For example, Nyce, et al. have shown that antisense oligodeoxynucleotides (ODNs) when inhaled bind to endogenous surfactant (a lipid produced by lung cells) and are taken up by lung cells without a need for additional carrier lipids (Nyce, et al., *Nature,* 385:721-725 (1997)). Small nucleic acids are readily taken up into T24 bladder carcinoma tissue culture cells (Ma, et al., *Antisense Nucleic Acid Drug Dev.,* 8:415-426 (1998)).

The disclosed compositions including triplex-forming molecules, such as TFOs and PNAs, and donor fragments may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles, nanoparticles, or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example, in Sambrook et al., *Molecular Cloning: A Laboratory Manual*, Cold Spring Harbor Laboratory, New York (1989); and Ausubel, et al., *Current Protocols in Molecular Biology*, John Wiley & Sons, New York (1994). Such nucleic acid delivery systems include the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, optionally with an added preservative. The compositions may take such forms as sterile aqueous or non-aqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil including synthetic mono- or di-glycerides may be employed. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The disclosed compositions alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and air. For administration by inhalation, the compounds are delivered in the form of an aerosol spray presentation from pressurized packs or a nebulizer, with the use of a suitable propellant.

In some embodiments, the compositions include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the triplex-forming molecules and/or donor oligonucleotides are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.*, 14(19):4975-4977 (2004)) and in vivo (Soutschek, et al., *Nature*, 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.*, 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

b. Methods of Administration

In general, methods of administering compounds, including oligonucleotides and related molecules, are well known in the art. In particular, the routes of administration already in use for nucleic acid therapeutics, along with formulations in current use, provide preferred routes of administration and formulation for the triplex-forming molecules described above. Preferably the compositions are injected into the organism undergoing genetic manipulation, such as an animal requiring gene therapy.

The disclosed compositions can be administered by a number of routes including, but not limited to, oral, intravenous, intraperitoneal, intramuscular, transdermal, subcutaneous, topical, sublingual, rectal, intranasal, pulmonary, and other suitable means. The compositions can also be administered via liposomes. Such administration routes and appropriate formulations are generally known to those of skill in the art.

Administration of the formulations may be accomplished by any acceptable method which allows the gene editing compositions to reach their targets.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The compositions may be delivered in a manner which enables tissue-specific uptake of the agent and/or nucleotide delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the composition, over a certain time period, for example, hours, days, weeks, months or years. This may be accomplished, for example, by repeated administrations of a formulation or by a sustained or controlled release delivery system in which the compositions are delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include non-polymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the oligonucleotides are contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the triplex-forming molecules and donor oligonucleotides. In addition, a pump-based hardware delivery system may be used to deliver one or more embodiments.

Examples of systems in which release occurs in bursts include systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

c. Preferred Formulations for Mucosal and Pulmonary Administration

Active agent(s) and compositions thereof can be formulated for pulmonary or mucosal administration. The administration can include delivery of the composition to the lungs, nasal, oral (sublingual, buccal), vaginal, or rectal mucosa.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

C. Diseases to be Treated

Gene therapy is apparent when studied in the context of human genetic diseases, for example, cystic fibrosis, hemophilia, globinopathies such as sickle cell anemia and beta-thalassemia, xeroderma pigmentosum, and lysosomal storage diseases, though the strategies are also useful for treating non-genetic disease such as HIV, in the context of ex vivo-based cell modification and also for in vivo cell modification. The disclosed compositions are especially useful to treat genetic deficiencies, disorders and diseases caused by mutations in single genes, for example, to correct genetic deficiencies, disorders and diseases caused by point mutations. If the target gene contains a mutation that is the cause of a genetic disorder, then the disclosed compositions can be used for mutagenic repair that may restore the DNA sequence of the target gene to normal. The target sequence can be within the coding DNA sequence of the gene or within an intron. The target sequence can also be within DNA sequences that regulate expression of the target gene, including promoter or enhancer sequences.

If the target gene is an oncogene causing unregulated proliferation, such as in a cancer cell, then the oligonucleotide is useful for causing a mutation that inactivates the gene and terminates or reduces the uncontrolled proliferation of the cell. The oligonucleotide is also a useful anti-cancer agent for activating a repressor gene that has lost its ability to repress proliferation. The target gene can also be a gene that encodes an immune regulatory factor, such as PD-1, in order to enhance the host's immune response to a cancer.

Programmed cell death protein 1, also known as PD-1 and CD279 (cluster of differentiation 279), is a protein encoded by the PDCD1 gene. PD-1 has two ligands: PD-L1 and PD-L2. PD-1 is expressed on a subset of thymocytes and up-regulated on T, B, and myeloid cells after activation (Agata, et al., *Int. Immunol.,* 8:765-772 (1996)). PD-1 acts to antagonize signal transduction downstream of the TCR after it binds a peptide antigen presented by the major histocompatibility complex (MHC). It can function as an immune checkpoint, by preventing the activation of T-cells, which in turn reduces autoimmunity and promotes self-tolerance, but can also reduce the body's ability to combat cancer. The inhibitory effect of PD-1 to act through twofold mechanism of promoting apoptosis (programmed cell death) in antigen specific T-cells in lymph nodes while simultaneously reducing apoptosis in regulatory T cells (suppressor T cells). Compositions that block PD-1, the PD-1 inhibitors, activate the immune system to attack tumors and are therefore used with varying success to treat some types of cancer.

Therefore, in some embodiments, compositions are used to treat cancer. The gene modification technology can be designed to reduce or prevent expression of PD-1, and administered in an effective amount to do so.

The compositions can be used as antiviral agents, for example, when designed to modify a specific a portion of a viral genome necessary for proper proliferation or function of the virus.

Variants, Substitutions, and Exemplary PNAs

Preferred diseases and sequences of exemplary targeting sites, triplex forming molecules, and donor oligonucleotides are discussed in more detail below. Any of the sequences can also be modified as disclosed herein or otherwise known in the art. For example, in some embodiments, any of the triplex-forming sequences herein can have one or more mutations (e.g., substitutions, deletions, or insertions), such that the triplex-forming molecules still bind to the target sequence.

Any of the triplex-forming sequences herein can be manufactured using canonical nucleic acids or other suitable substitutes including those disclosed herein (e.g., PNAs), without or without any of the base, sugar, or backbone modifications discussed herein or in WO 1996/040271, WO/2010/123983, and U.S. Pat. No. 8,658,608.

Any of the triplex-forming sequences herein can be peptide nucleic acids. In some embodiments, one or more of the cytosines of any of triplex-forming sequences herein is substituted with a pseudoisocytosine. In some embodiments, all of the cytosines in the Hoogsteen-binding portion of a triplex forming molecule are substituted with pseudoisocytosine. In some embodiments, any of the triplex-forming sequences herein, includes one or more of peptide nucleic acid monomers substituted with a γPNA. In some embodiments all of the peptide nucleic acid monomers in the Hoogsteen-binding portion only, the Watson-Crick-binding portion only, or across the entire PNA are substituted with γPNA monomers. In particular embodiments, alternating residues are PNA and γPNA in the Hoogsteen-binding portion only, the Watson-Crick-binding portion only, or across the entire PNA are substituted. In some embodiments, the γPNAs are miniPEG γPNA, methyl γPNA, another γ substitution discussed above. In some embodiments, the PNA oligomer includes two or more different γPNAs.

For example, in some embodiments, (1) some or all of the residues in the Watson-Crick binding portion are γPNA (e.g., miniPEG-containing γPNA); (2) some or all of the residues in the Hoogsteen binding portion are γPNA (e.g., miniPEG-containing γPNA); or (3) some or all of the residue (in the Watson-Crick and/or Hoogsteen binding portions) are γPNA (e.g., miniPEG-containing γPNA). Therefore, in some embodiments any of the triplex foiming nucleic acid sequence herein is a peptide nucleic acid wherein (1) all of the residues in the Watson-Crick binding portion are γPNA (e.g., miniPEG-containing γPNA) and none of the residues is in Hoogsteen binding portion are γPNA (e.g., miniPEG-containing γPNA); (2) all of the residues in the Hoogsteen binding portion are γPNA (e.g., miniPEG-containing γPNA) and none of the residues is in Watson-Crick binding portion are γPNA (e.g., miniPEG-containing γPNA); or (3) all of the residues (in the Watson-Crick and Hoogsteen binding portions) are γPNA (e.g., miniPEG-containing γPNA).

Preferred triplex molecules are bis-peptide nucleic acids with pseudoisocytosine substituted for one or more cytosines, particularly in the Hoogsteen-binding portion, and wherein some or all of the PNA are γPNA.

Any of the triplex-forming sequences herein can have one or more G-clamp monomers. For example, one or more cytosines or variant thereof such as pseudoisocytosine in any of the triplex-forming sequences herein can be substituted or otherwise modified to be a clamp-G (9-(2-guanidinoethoxy) phenoxazine).

Any of the triplex-forming sequences herein can include a flexible linker, linking, for example, a Hoogsteen-binding domain and a Watson-Crick binding domain to form a bis-PNA. The sequences can be linked with a flexible linker. For example, in some embodiments the flexible linker includes about 1-10, more preferably 2-5, most preferably about 3 units such as 8-amino-2,6,10-trioxaoctanoic acid residues. Some molecules include N-terminal or C-terminal non-binding residues, preferably positively charged. For example, some molecules include 1-10, preferable 2-5, most preferably about 3 lysines at the N-terminus, the C-terminus, or a combination thereof of the PNA.

For the disclosed sequences, "J" is pseudoisocyto sine, "O" is flexible 8-amino-3,6-dioxaoctanoic acid, 6-aminohexanoic acid monomers, "K" and "lys" are lysine. PNA sequences are generally presented in an H-"nucleic acid sequence"-NH$_2$ orientation. For bis-PNA the Hoosten-binding portion is typically oriented up stream (e.g., at the "H" end) of the linker, while the Watson-Crick-binding portion is typically oriented downstream (e.g., at the NH$_2$ end) of the linker. Any of the donors can include optional phosphorothioate internucleoside linkages, particular between the three or four terminal 5' and three or four terminal 3' nucleotides. Thus, each of the donor oligonucleotide sequences disclosed herein is expressly disclosed without any phosphorothioate internucleoside linkages, and with phosphorothioate internucleoside linkages, preferably between the three or four terminal 5' and three or four terminal 3' nucleotides.

1. Globinopathies

Worldwide, globinopathies account for significant morbidity and mortality. Over 1,200 different known genetic mutations affect the DNA sequence of the human alpha-like (HBZ, HBA2, HBA1, and HBQ1) and beta-like (HBE1, HBG1, HBD, and HBB) globin genes. Two of the more prevalent and well-studied globinopathies are sickle cell anemia and β-thalassemia. Substitution of valine for glutamic acid at position 6 of the β-globin chain in patients with sickle cell anemia predisposes to hemoglobin polymerization, leading to sickle cell rigidity and vasoocclusion with resulting tissue and organ damage. In patients with β-thalassemia, a variety of mutational mechanisms results in reduced synthesis of β-globin leading to accumulation of aggregates of unpaired, insoluble α-chains that cause ineffective erythropoiesis, accelerated red cell destruction, and severe anemia.

Together, globinopathies represent the most common single-gene disorders in man. Triplex forming oligonucleotides are particularly well suited to treat globinopathies, as they are single gene disorders caused by point mutations. Triplex forming molecules disclosed herein are effective at binding to the human β-globin both in vitro and in living cells, both ex vivo and in vivo in animals. Experimental results also demonstrate correction of a thalassemia-associated mutation in vivo in a transgenic mouse carrying a human beta globin gene with the IVS2-654 thalassemia mutation (in place of the endogenous mouse beta globin) with correction of the mutation in 4% of the total bone marrow cells, cure of the anemia with blood hemoglobin levels showing a sustained elevation into the normal range, reversal of extramedullary hematopoiesis and reversal of splenomegaly, and reduction in reticulocyte counts, following systemic administration of PNA and DNA containing nanoparticles.

β-thalassemia is an unstable hemoglobinopathy leading to the precipitation of α-hemoglobin within RBCs resulting in a severe hemolytic anemia. Patients experience jaundice and splenomegaly, with substantially decreased blood hemoglobin concentrations necessitating repeated transfusions, typically resulting in severe iron overload with time. Cardiac failure due to myocardial siderosis is a major cause of death from β-thalassemia by the end of the third decade. Reduction of repeated blood transfusions in these patients is therefore of primary importance to improve patient outcomes.

a. Exemplary β-Globin Gene Target Sites

In the β-globin gene sequence, particularly in the introns, there are many good third-strand binding sites that may be utilized in the methods disclosed herein. A portion of the GenBank sequence of the chromosome-11 human-native hemoglobin-gene cluster (GenBank: U01317.1—Human beta globin region on chromosome 11—LOCUS HUMHBB, 73308 bp ds-DNA) from base 60001 to base 66060 is presented below. The start of the gene coding sequence at position 62187-62189 (or positions 2187-2189 of SEQ ID NO:13) is indicated by wave underlining. This portion of the GenBank sequence contains the native β globin gene sequence. In sickle cell hemoglobin the adenine base at position 62206 (or position 2206 as listed in SEQ ID NO:13, indicated in bold and heavy underlining) is mutated to a thymine. Other common point mutations occur in intron 2 (IVS2), which is highlighted in the sequence below by italics (SEQ ID NO:14) and corresponds with nucleotides 2,632-3,481 of SEQ ID NO:13. Mutations include IVS2-1, IVS2-566, IVS2-654, IVS2-705, and IVS2-745, which are also shown in bold and heavy underlining; numbering relative to the start of intron 2.

Exemplary triplex forming molecule binding sites, are provided in, for example, WO 1996/040271, WO/2010/123983, and U.S. Pat. No. 8,658,608, and in the working Examples below. Target regions can be reference based on the coding strand of genomic DNA, or the complementary non-coding sequence thereto (e.g., the Watson or Crick stand). Exemplary target regions are identified with reference to the coding sequence of the globin gene sequence in the sequence below by double underlining and a combination of underlining and double underlining (wherein the underlining is optional additional binding sequence). Additionally, for each targeting sequence identified, the complementary target sequence on the reverse non-coding strand is also explicitly disclosed as a triplex forming molecule binding sequence.

Accordingly, triplex forming molecules can be designed to bind a target region on either the coding or non-coding strand. However, as discussed above, triplex-forming molecules, such as PNA and tcPNA preferably invade the target duplex, displacement of the polypyrimidine, and induce triplex formation with the displaced polypurine.

(SEQ ID NO: 13 - full sequence;
SEQ ID NO: 14 - sequence in italics).

AAAGCTCTTGCTTTGACAATTTTGGTCTTTCAGAATACTATAAATATAACCTATATTATA

ATTTCATAAAGTCTGTGCATTTTCTTTGACCCAGGATATTTGCAAAAGACATATTCAAAC

TTCCGCAGAACACTTTATTTCACATATACATGCCTCTTATATCAGGGATGTGAAACAGGG

TCTTGAAAACTGTCTAAATCTAAAACAATGCTAATGCAGGTTTAAATTTAATAAAATAAA

ATCCAAAATCTAACAGCCAAGTCAAATCTGTATGTTTTAACATTTAAAATATTTTAAAGA

CGTCTTTTCCCAGGATTCAACATGTGAAATCTTTTCTCAGGGATACACGTGTGCCTAGAT

CCTCATTGCTTTAGTTTTTTACAGAGGAATGAATATAAAAAGAAAATACTTAAATTTTAT

CCCTCTTACCTCTATAATCATACATAGGCATAATTTTTTAACCTAGGCTCCAGATAGCCA

TAGAAGAACCAAACACTTTCTGCGTGTGTGAGAATAATCAGAGTGAGATTTTTTCACAAG

TACCTGATGAGGGTTGAGACAGGTAGAAAAAGTGAGAGATCTCTATTTATTTAGCAATAA

TAGAGAAAGCATTTAAGAGAATAAAGCAATGGAAATAAGAAATTTGTAAATTTCCTTCTG

ATAACTAGAAATAGAGGATCCAGTTTCTTTTGGTTAACCTAAATTTTATTTCATTTTATT

GTTTTATTTTATTTTATTTTATTTTATTTTGTGTAATCGTAGTTTCAGAGTGTTAGAGCT

GAAAGGAAGAAGTAGGAGAAACATGCAAAGTAAAAGTATAACACTTTCCTTACTAAACCG

ACTGGGTTTCCAGGTAGGGCAGGATTCAGGATGACTGACAGGGCCCTTAGGGAACACTG

AGACCCTACGCTGACCTCATAAATGCTTGCTACCTTTGCTGTTTTAATTACATCTTTTAA

TAGCAGGAAGCAGAACTCTGCACTTCAAAAGTTTTTCCTCACCTGAGGAGTTAATTTAGT

ACAAGGGGAAAAAGTACAGGGGGATGGGAGAAAGGCGATCACGTTGGGAAGCTATAGAGA

AAGAAGAGTAAATTTTAGTAAAGGAGGTTTAAACAAACAAATATAAAGAGAAATAGGAA

CTTGAATCAAGGAAATGATTTTAAAACGCAGTATTCTTAGTGGACTAGAGGAAAAAAATA

ATCTGAGCCAAGTAGAAGACCTTTTCCCCTCCTACCCCTACTTTCTAAGTCACAGAGGCT

TTTTGTTCCCCCAGACACTCTTGCAGATTAGTCCAGGCAGAAACAGTTAGATGTCCCCAG

TTAACCTCCTATTTGACACCACTGATTACCCCATTGATAGTCACACTTTGGGTTGTAAGT

GACTTTTTATTTATTTGTATTTTTGACTGCATTAAGAGGTCTCTAGTTTTTTATCTCTTG

TTTCCCAAAACCTAATAAGTAACTAATGCACAGAGCACATTGATTTGTATTTATTCTATT

TTTAGACATAATTTATTAGCATGCATGAGCAAATTAAGAAAAACAACAACAAATGAATGC

ATATATATGTATATGTATGTGTATATATACACATATATATATATATTTTTTTTCTTTT

CTTACCAGAAGGTTTTAATCCAAATAAGGAGAAGATATGCTTAGAACTGAGGTAGAGTTT

TCATCCATTCTGTCCTGTAAGTATTTTGCATATTCTGGAGACGCAGGAAGAGATCCATCT

ACATATCCCAAAGCTGAATTATGGTAGACAAAGCTCTTCCACTTTTAGTGCATCAATTTC

TTATTTGTGTAATAAGAAAATTGGGAAAACGATCTTCAATATGCTTACCAAGCTGTGATT

CCAAATATTACGTAAATACACTTGCAAAGGAGGATGTTTTTAGTAGCAATTTGTACTGAT

GGTATGGGGCCAAGAGATATATCTTAGAGGGAGGGCTGAGGGTTTGAAGTCCAACTCCTA

AGCCAGTGCCAGAAGAGCCAAGGACAGGTACGGCTGTCATCACTTAGACCTCACCCTGTG

GAGCCACACCCTAGGGTTGGCCAATCTACTCCCAGGAGCAGGGAGGGCAGGAGCCAGGGC

TGGGCATAAAAGTCAGGGCAGAGCCATCTATTGCTTACATTTGCTTCTGACACAACTGTG

TTCACTAGCAACCTCAAACAGACACCATGGTGCACCTGACTCCTGAGGAGAAGTCTGCCG

TTACTGCCCTGTGGGGCAAGGTGAACGTGGATGAAGTTGGTGGTGAGGCCCTGGGCAGGT

TGGTATCAAGGTTACAAGACAGGTTTAAGGAGACCAATAGAAACTGGGCATGTGGAGACA

GAGAAGACTCTTGGGTTTCTGATAGGCACTGACTCTCTCTGCCTATTGGTCTATTTTCCC

ACCCTTAGGCTGCTGGTGGTCTACCCTTGGACCCAGAGGTTCTTTGAGTCCTTTGGGGAT

CTGTCCACTCCTGATGCTGTTATGGGCAACCCTAAGGTGAAGGCTCATGGCAAGAAAGTG

CTCGGTGCCTTTAGTGATGGCCTGGCTCACCTGGACAACCTCAAGGGCACCTTTGCCACA

CTGAGTGAGCTGCACTGTGACAAGCTGCACGTGGATCCTGAGAACTTCAGGGTGAGTCTA

TGGGACCCTTGATGTTTCTTTCCCCTTCTTTTCTATGGTTAAGTTCATGTCATAGGAAG

GGGAGAAGTAACAGGGTACAGTTTAGAATGGGAAACAGACGAATGATTGCATCAGTGTGG

AAGTCTCAGGATCGTTTTAGTTTCTTTTATTTGCTGTTCATAACAATTGTTTTCTTTTGT

TTAATTCTTGCTTTCTTTTTTTTCTTCTCCGCAATTTTTACTATTATACTTAATGCCTT

AACATTGTGTATAACAAAGGAAATATCTCTGAGATACATTAAGTAACTTAAAAAAAAAC

TTTACACAGTCTGCCTAGTACATTACTATTTGGAATATATGTGTGCTTATTTGCATATTC

ATAATCTCCCTACTTTATTTTCTTTTATTTTTAATTGATACATAATCATTATACATATTT

ATGGGTTAAAGTGTAATGTTTTAATATGTGTACACATATTGACCAAATCAGGGTAATTTT

GCATTTGTAATTTTAAAAAATGCTTTCTTCTTTTAATATACTTTTTTGTTTATCTTATTT

CTAATACTTTCCCTAATCTCTTTCTTTCAGGGCAATAATGATACAATGTATCATGCCTCT**

TTGCACCATTCTAAAGAATAACAGTGATAATTTCTGGGTTAAGGCAATAGCAATATTTCT

GCATATAAATATTTCTGCATATAAATTGTAACTGATGTAAGAGGTTTCATATTGCTAATA

GCAGCTACAATCCAGCTACCATTCTGCTTTTATTTTATGGTTGGGATAAGGCTGGATTAT

TCTGAGTCCAAGCTAGGCCCTTTTGCTAATCATGTTCATACCTCTTATCTTCCTCCCACA

GCTCCTGGGCAACGTGCTGGTCTGTGTGCTGGCCCATCACTTTGGCAAAGAATTCACCCC

ACCAGTGCAGGCTGCCTATCAGAAAGTGGTGGCTGGTGTGGCTAATGCCCTGGCCCACAA

GTATCACTAAGCTCGCTTTCTTGCTGTCCAATTTCTATTAAAGGTTCCTTTGTTCCCTAA

GTCCAACTACTAAACTGGGGGATATTATGAAGGGCCTTGAGCATCTGGATTCTGCCTAAT

AAAAAACATTTATTTTCATTGCAATGATGTATTTAAATTATTTCTGAATATTTTACTAAA

AAGGGAATGTGGGAGGTCAGTGCATTTAAAACATAAAGAAATGAAGAGCTAGTTCAAACC

TTGGGAAAATACACTATATCTTAAACTCCATGAAAGAAGGTGAGGCTGCAAACAGCTAAT

GCACATTGGCAACAGCCCTGATGCCTATGCCTTATTCATCCCTCAGAAAAGGATTCAAGT

AGAGGCTTGATTTGGAGGTTAAAGTTTTGCTATGCTGTATTTTACATTACTTATTGTTTT

AGCTGTCCTCATGAATGTCTTTTCACTACCCATTTGCTTATCCTGCATCTCTCAGCCTTG

ACTCCACTCAGTTCTCTTGCTTAGAGATACCACCTTTCCCCTGAAGTGTTCCTTCCATGT

TTTACGGCGAGATGGTTTCTCCTCGCCTGGCCACTCAGCCTTAGTTGTCTCTGTTGTCTT

ATAGAGGTCTACTTGAAGAAGGAAAAACAGGGGGCATGGTTTGACTGTCCTGTGAGCCCT

TCTTCCCTGCCTCCCCCACTCACAGTGACCCGGAATCTGCAGTGCTAGTCTCCCGGAACT

ATCACTCTTTCACAGTCTGCTTTGGAAGGACTGGGCTTAGTATGAAAAGTTAGGACTGAG

AAGAATTTGAAAGGGGGCTTTTTGTAGCTTGATATTCACTACTGTCTTATTACCCTATCA

TAGGCCCACCCCAAATGGAAGTCCCATTCTTCCTCAGGATGTTTAAGATTAGCATTCAGG

```
AAGAGATCAGAGGTCTGCTGGCTCCCTTATCATGTCCCTTATGGTGCTTCTGGCTCTGCA

GTTATTAGCATAGTGTTACCATCAACCACCTTAACTTCATTTTTCTTATTCAATACCTAG

GTAGGTAGATGCTAGATTCTGGAAATAAAATATGAGTCTCAAGTGGTCCTTGTCCTCTCT

CCCAGTCAAATTCTGAATCTAGTTGGCAAGATTCTGAAATCAAGGCATATAATCAGTAAT

AAGTGATGATAGAAGGGTATATAGAAGAATTTTATTATATGAGAGGGTGAAACCTAAAAT

GAAATGAAATCAGACCCTTGTCTTACACCATAAACAAAAATAAATTTGAATGGGTTAAAG

AATTAAACTAAGACCTAAAACCATAAAAATTTTTAAAGAAATCAAAAGAAGAAAATTCTA

ATATTCATGTTGCAGCCGTTTTTTGAATTTGATATGAGAAGCAAAGGCAACAAAAGGAAA

AATAAAGAAGTGAGGCTACATCAAACTAAAAAATTTCCACACAAAAAAGAAAACAATGAA

CAAATGAAAGGTGAACCATGAAATGGCATATTTGCAAACCAAATATTTCTTAAATATTTT

GGTTAATATCCAAAATATATAAGAAACACAGATGATTCAATAACAAACAAAAAATTAAAA

ATAGGAAAATAAAAAAATTAAAAAGAAGAAAATCCTGCCATTTATGCGAGAATTGATGAA

CCTGGAGGATGTAAAACTAAGAAAAATAAGCCTGACACAAAAAGACAAATACTACACAAC

CTTGCTCATATGTGAAACATAAAAAAGTCACTCTCATGGAAACAGACAGTAGAGGTATGG

TTTCCAGGGGTTGGGGGTGGGAGAATCAGGAAACTATTACTCAAAGGGTATAAAATTTCA

GTTATGTGGGATGAATAAATTCTAGATATCTAATGTACAGCATCGTGACTGTAGTTAATT

GTACTGTAAGTATATTTAAAATTTGCAAAGAGAGTAGATTTTTTGTTTTTTAGATGGA

GTTTTGCTCTTGTTGTCCAGGCTGGAGTGCAATGGCAAGATCTTGGCTCACTGCAACCTC

CGCCTCCTGGGTTCAAGCAAATCTCCTGCCTCAGCCTCCCGAGTAGCTGGGATTACAGGC

ATGCGACACCATGCCCAGCTAATTTTGTATTTTTAGTAGAGACGGGGTTTCTCCATGTTG

GTCAGGCTGATCCGCCTCCTCGGCCACCAAAGGGCTGGGATTACAGGCGTGACCACCGGG

CCTGGCCGAGAGTAGATCTTAAAAGCATTTACCACAAGAAAAAGGTAACTATGTGAGATA

ATGGGTATGTTAATTAGCTTGATTGTGGTAATCATTTCACAAGGTATACATATATTAAAA

CATCATGTTGTACACCTTAAATATATACAATTTTTATTTGTGAATGATACCTCAATAAAG

TTGAAGAATAATAAAAAAGAATAGACATCACATGAATTAAAAAACTAAAAAATAAAAAAA

TGCATCTTGATGATTAGAATTGCATTCTTGATTTTTCAGATACAAATATCCATTTGACTG
``` b. Exemplary Triplex Forming Sequences i. Beta Thalassemia

Gene editing molecules can be designed based on the guidance provided herein and otherwise known in the art. Exemplary triplex forming molecule and donor sequences, are provided in, for example, WO 1996/040271, WO/2010/123983, and U.S. Pat. No. 8,658,608, and in the working Examples below, and can be altered to include one or more of the modifications disclosed herein.

Triplex forming molecules can include a sequence substantially complementary to the polypurine strand of the polypyrimidine:polypurine target motif. In some embodiments, the triplex forming molecules target a region corresponding to nucleotides 566-577, optionally 566-583 or more of SEQ ID NO:14; a region corresponding to nucleotides 807-813, optionally 807-824 or more of SEQ ID NO:14; or a region corresponding to nucleotides 605-611, optionally 605-621 of SEQ ID NO:14. Therefore in some embodiments, the triplex-forming molecules can form a triple-stranded molecule with the sequence including GAAAGAAAGAGA (SEQ ID NO:15) or TGCCCT-GAAAGAAAGAGA (SEQ ID NO:16) or GGAGAAA (SEQ ID NO:17) or AGAATGGTGCAAAGAGG (SEQ ID NO:18) or AAAAGGG (SEQ ID NO:19) or ACATGATT-AGCAAAAGGG (SEQ ID NO:20).

Accordingly, in some embodiments, the triplex-folining molecule includes the nucleic acid sequence CTTTCTTTCTCT (SEQ ID NO:21), preferable includes the sequence CTTTCTTTCTCT (SEQ ID NO:21) linked to the sequence TCTCTTTCTTTC (SEQ ID NO:22), or more preferable includes the sequence CTTTCTTTCTCT (SEQ ID NO:21) linked to the sequence TCTCTTTCTTTCAGGGCA (SEQ ID NO:23).

In some embodiments, the triplex-forming molecule includes the nucleic acid sequence TTTCCC (SEQ ID NO:24), preferable includes the sequence TTTCCC (SEQ ID NO:24) linked to the sequence CCCTTTT (SEQ ID NO:25), or more preferable includes the sequence TTTCCC (SEQ ID NO:24) linked to the sequence CCCTTTTGCTAATCATGT (SEQ ID NO:26).

In some embodiments, the triplex-forming molecule includes the nucleic acid sequence TTTCTCC (SEQ ID NO:27), preferable includes the sequence TTTCTCC (SEQ ID NO:27) linked to the sequence CCTCTTT (SEQ ID NO:28), or more preferable includes the sequence TTTCTCC (SEQ ID NO:27) linked to the sequence CCTCTTTGCACCATTCT (SEQ ID NO:29).

In some preferred embodiments, the triplex forming nucleic acid is a peptide nucleic acid including the sequence JTTTJTTTJTJT (SEQ ID NO:30) linked to the sequence TCTCTTTCTTTC (SEQ ID NO:22) or TCTCTTTCTTTCAGGGCA (SEQ ID NO:23); or a peptide nucleic acid including the sequence TTTTJJJ (SEQ ID NO:31) linked to the sequence CCCTTTT (SEQ ID NO:25) or CCCTTTTGCTAATCATGT (SEQ ID NO:26);

or a peptide nucleic acid including the sequence TTTJTJJ (SEQ ID NO:32) linked to the sequence CCTCTTT (SEQ ID NO:28) or CCTCTTTGCACCATTCT (SEQ ID NO:29), optionally, but preferably wherein one or more of the PNA monomers is a γPNA.

In specific embodiments, the triplex forming molecule is a peptide nucleic acid including the sequence lys-lys-lys-JTTTJTTTJTJT-OOO-TCTCTTTCTTTCAGGGC A-lys-lys-lys (SEQ ID NO:33), or lys-lys-lys-TTTTJJJ-OOO-CCCTTTGCTAATCATG T-lys-lys-lys (SEQ ID NO:34), or lys-lys-lys-TTTJTJJ-OOO-CCTCTTTGCACCATT CT-lys-lys-lys (SEQ ID NO:35);

optionally, but preferably wherein one or more of the PNA monomers is a γPNA. In even more specific embodiments, the bolded and underlined residues are miniPEG-containing γPNA.

In other embodiments, the triplex forming nucleic acid is a peptide nucleic acid including the sequence TJTTTTJTTJ (SEQ ID NO:36) linked to the sequence CTTCTTTTCT (SEQ ID NO:37); or TTJTTJTTTJ (SEQ ID NO:38) linked to the sequence CTTTCTTCTT (SEQ ID NO:39); or JJJTJTTJT (SEQ ID NO:40) linked to the sequence TCTTCCTCCC (SEQ ID NO:41); or optionally, but preferably wherein one or more of the PNA monomers is a γPNA.

In specific embodiments, the triplex forming nucleic acid is a peptide nucleic acid including the sequence lys-lys-lys-TJTTTTJTTJ-OOO-CTTCTTTTCT-lys-lys-lys (SEQ ID NO:42) (IVS2-24); or lys-lys-lys-TTJTTJTTTJ-OOO-CTTTCTTCT T-lys-lys-lys (SEQ ID NO:43) (IVS2-512); or lys-lys-lys-JJJTJJTTJT-OOO-TCTTCCTCCC-lys-lys-lys (SEQ ID NO:44) (IVS2-830);

optionally, but preferably wherein one or more of the PNA monomers is a γPNA. In even more specific embodiments, the bolded and underlined residues are miniPEG-containing γPNA.

ii. Sickle Cell Disease

Preferred sequences that target the sickle cell disease mutation (20) in the beta globin gene are also provided (see, e.g., FIG. 6). In some embodiments, the triplex-forming molecule includes the nucleic acid sequence CCTCTTC (SEQ ID NO:45), preferable includes the sequence CCTCTTC (SEQ ID NO:45) linked to the sequence CTTCTCC (SEQ ID NO:46), or more preferable includes the sequence CCTCTTC (SEQ ID NO:45) linked to the sequence CTTCTCCAAAGGAGT (SEQ ID NO:47) or CTTCTCCACAGGAGTCAG (SEQ ID NO:48) or CTTCTCCACAGGAGTCAGGTGC (SEQ ID NO:205).

In some embodiments, the triplex-forming molecule includes the nucleic acid sequence TTCCTCT (SEQ ID NO:49), preferable includes the sequence TTCCTCT (SEQ ID NO:49) linked to the sequence TCTCCTT (SEQ ID NO:50), or more preferable includes the sequence TTCCTCT (SEQ ID NO:49) linked to the sequence TCTCCTTAAACCTGT (SEQ ID NO:51) or TCTCCT-TAAACCTGTCTT (SEQ ID NO:212).

In some embodiments, the triplex-forming molecule includes the nucleic acid sequence TCTCTTCT (SEQ ID NO:52), preferable includes the sequence TCTCTTCT (SEQ ID NO:52) linked to the sequence TCTTCTCT (SEQ ID NO:53), or more preferable includes the sequence TCTCTTCT (SEQ ID NO:52) linked to the sequence TCTTCTCTGTCTCCAC (SEQ ID NO:54) or TCTTCTCTGTCTCCACAT (SEQ ID NO:55).

In some preferred embodiments for correction of Sickle Cell Disease Mutation (e.g., FIG. 6), the triplex forming nucleic acid is a peptide nucleic acid including the sequence JJTJTTJ (SEQ ID NO:56) linked to the sequence CTTCTCC (SEQ ID NO:46) or CTTCTCCAAAGGAGT (SEQ ID NO:47) or CTTCTCCACAGGAGTCAG (SEQ ID NO:48) or CTTCTCCACAGGAGTCAGGTGC (SEQ ID NO:205);

or a peptide nucleic acid including the sequence TTJJTJT (SEQ ID NO:214) linked to the sequence TCTCCTT (SEQ ID NO:50) or TCTCCTTAAACCTGT (SEQ ID NO:51) or TCTCCTTAAACCTGTCTT (SEQ ID NO:212);

or a peptide nucleic acid including the sequence TJTJTTJT (SEQ ID NO:215) linked to the sequence TCTTCTCT (SEQ ID NO:53) or TCTTCTCTGTCTCCAC (SEQ ID NO:54) or TCTTCTCTGTCTCCACAT (SEQ ID NO:55);

optionally, but preferably wherein one or more of the PNA monomers is a γPNA.

In specific embodiments for correction of Sickle Cell Disease Mutation (e.g., FIG. 6), the triplex forming nucleic acid is a peptide nucleic acid including the sequence

```
                                    (SEQ ID NO: 160)
lys-lys-lys-JJTJTTJ-OOO-CTTCTCCAAAGGAGTlys-lys-lys;
or
                                     (SEQ ID NO: 57)
lys-lys-lys-TTJJTJT-OOO-TCTCCTTAAACCTGT-lys-lyslys;
or
                                    (SEQ ID NO: 213)
lys-lys-lys-TTJJTJT-OOO-TCTCCTTAAACCTGTCTT-lyslys-lys
or
                                     (SEQ ID NO: 58)
lys-lys-lys-TJTJTTJT-OOO-TCTTCTCTGTCTCCAC-lys-lyslys (tc8 16);
or
                                     (SEQ ID NO: 59)
lys-lys-lys-JJTJTTJ-OOO-CTTCTCCACAGGAGTCAG-lyslys-lys;
or
                                     (SEQ ID NO: 59)
lys-lys-lys-JJTJTTJ-OOO-CTTCTCCACAGGAGTCAG-lyslys-lys (SCD-tcPNA 1A);
or
                                     (SEQ ID NO: 59)
lys-lys-lys-JJTJTTJ-OOO-CTTCTCCACAGGAGTCAG-lyslys-lys (SCD-tcPNA 1B);
or
```

-continued lys-lys-lys-JJTJTTJ-OOO-CTTCTCCACAGGAGTCAG-lys- (SEQ ID NO: 59)

lys-lys (SCD-tcPNA 1C);
or lys-lys-lys-JJTJTTJ-OOO-CTTCTCCACAGGAGTCAGGTGC- (SEQ ID NO: 209)

lys-lys-lys-NH₂(SCD-tcPNA 1D);
or lys-lys-lys-JJTJTTJ-OOO-CTTCTCCACAGGAGTCAGGTGC- (SEQ ID NO: 209)

lys-lys-lys (SCD-tcPNA 1E);
or lys-lys-lys-JJTJTTJ-OOO-CTTCTCCACAGGAGTCAGGTGC- (SEQ ID NO: 209)

lys-lys-lys (SCD-tcPNA 1F);
or lys-lys-lys-TJTJTTJT-OOO-TCTTCTCTGTCTCCACAT-lys- (SEQ ID NO: 60)

lys-lys;

optionally, but preferably wherein one or more of the PNA monomers is a γPNA. In even more specific embodiments, the bolded and underlined residues are miniPEG-containing γPNA.

c. Exemplary Donors

In some embodiments, the triplex forming molecules are used in combination with a donor oligonucleotide for correction of IVS2-654 mutation that includes the sequence 5' AAAGAATAACAGTGATAATTTCTGGGTTAAGG C̲AATAGCAATATCTCTGCATATAAATAT 3' (SEQ ID NO:65) with the correcting IVS2-654 nucleotide underlined, or a functional fragment thereof that is suitable and sufficient to correct the IVS2-654 mutation.

Other exemplary donor sequences include, but are not limited to, DonorGFP-IVS2-1 (Sense) 5'-GTTCAGCGTGTCCGGCGAGGGCGAGGTGAGTC-TATGGGACCCTTGATGTTT-3' (SEQ ID NO:61), DonorGFP-IVS2-1 (Antisense) 5'-AAACAT-CAAGGGTCCCATAGACTCACCTCGCCCTCGCCG-GACACGCTGAAC-3' (SEQ ID NO:62), and, or a functional fragment thereof that is suitable and sufficient to correct a mutation.

In some embodiments, a Sickle Cells Disease mutation can be corrected using a donor having the sequence

5' CTTGCCCCACAGGGCAGTAACGGCAGATTTTT[TTC]CGGCGTTAAATG (SEQ ID NO: 63)

CACCATGGTGTCTGTTTGAGGT 3', or a functional fragment thereof that is suitable and sufficient to correct a mutation, wherein the three boxed nucleotides represent the corrected codon 6 which reverts the mutant Valine (associated with human sickle cell disease) back to the wildtype Glutamic acid and nucleotides in bold font (without underlining) represent changes to the genomic DNA but not to the encoded amino acid; or 5ACAGACACCATGGTGCACCTGACTCCTGAG-GAGAAGTCTGC CGTTACTGCC 3' (SEQ ID NO:64), or a functional fragment thereof that is suitable and sufficient to correct a mutation, wherein the bolded and underlined residue is the correction (see, e.g., FIG. 6), or 5'T(s)T(s)G(s)CCCCACAGGGCAGTAACGGCA-GACTTCTCCTCAGGA̲GTCAGGTGCACC ATGGTGTCTGTT(s)T̲(s)G(s)3' (SEQ ID NO:204), or a functional fragment thereof that is suitable and sufficient to correct a mutation, wherein the bolded and underlined residue is the correction and "(s)" indicates an optional phosphorothioate internucleoside linkage.

2. Cystic Fibrosis

The disclosed compositions and methods can be used to treat cystic fibrosis. Cystic fibrosis (CF) is a lethal autosomal recessive disease caused by defects in the cystic fibrosis transmembrane conductance regulator (CFTR), an ion channel that mediates Cl– transport. Lack of CFTR function results in chronic obstructive lung disease and premature death due to respiratory failure, intestinal obstruction syndromes, exocrine and endocrine pancreatic dysfunction, and infertility (Davis, et al., *Pediatr Rev.,* 22(8):257-64 (2001)). The most common mutation in CF is a three base-pair deletion (F508del) resulting in the loss of a phenylalanine residue, causing intracellular degradation of the CFTR protein and lack of cell surface expression (Davis, et al., *Am J Respir Crit Care Med.,* 173(5):475-82 (2006)). In addition to this common mutation there are many other mutations that occur and lead to disease including a class of mutations due to premature stop codons, nonsense mutations. In fact nonsense mutations account for approximately 10% of disease causing mutations. Of the nonsense mutations G542X and W1282X are the most common with frequencies of 2.6% and 1.6% respectfully.

Although CF is one of the most rigorously characterized genetic diseases, current treatment of patients with CF focuses on symptomatic management rather than primary correction of the genetic defect. Gene therapy has remained an elusive target in CF, because of challenges of in vivo delivery to the lung and other organ systems (Armstrong, et al., *Archives of disease in childhood* (2014) doi: 10.1136/archdischild-2012-302158. PubMed PMID: 24464978). In recent years, there have been many advances in gene therapy for treatment of diseases involving the hematolymphoid system, where harvest and ex vivo manipulation of cells for autologous transplantation is possible: some examples include the use of zinc finger nucleases targeting CCR5 to produce HIV-1 resistant cells (Holt, et al., *Nature biotechnology,* 28(8):839-47 (2010)) correction of the ABCD1 gene by lentiviral vectors for treatment of adrenoleukodystrophy (Cartier, et al., *Science,* 326(5954):818-23 (2009)) and correction of SCID due to ADA deficiency using retroviral gene transfer (Aiuti, et al., *The New England Journal Of Medicine,* 360(5):447-58 (2009).

Unfortunately, harvest and autologous transplant is not an option in CF, due to the involvement of the lung and other internal organs. As one approach, the UK Cystic Fibrosis Gene Therapy Consortium has tested liposomes to deliver plasmids containing cDNA encoding CFTR to the lung (Alton, et al., Thorax, 68(11):1075-7 (2013)), Alton, et al., *The Lancet Respiratory Medicine,* (2015). doi: 10.1016/S2213-2600(15)00245-3. PubMed PMID: 26149841.) other clinical trials have used viral vectors for delivery of the CFTR gene or CFTR expression plasmids that are compacted by polyethylene glycol-substituted lysine 30-mer peptides with limited success (Konstan, et al., *Human Gene Therapy,* 15(12):1255-69 (2004)). Moreover, delivery of plasmid DNA for gene addition without targeted insertion does not result in correction of the endogenous gene and is not subject to normal CFTR gene regulation, and virus-mediated integration of the CFTR cDNA could introduce the risk of non-specific integration into important genomic sites.

However, it has been discovered that triplex-forming PNA molecules and donor DNA can be used to correct mutations leading to cystic fibrosis. In preferred embodiments, the compositions are administered by intranasal or pulmonary delivery. The compositions can be administered in an effective amount to induce or enhance gene correction in an amount effective to reduce one or more symptoms of cystic fibrosis. For example, in some embodiments, the gene correction occurs at an amount effective to improve impaired response to cyclic AMP stimulation, improve hyperpolarization in response to forskolin, reduction in the large lumen negative nasal potential, reduction in inflammatory cells in the bronchoalveolar lavage (BAL), improve lung histology, or a combination thereof. In some embodiments, the target cells are cells, particularly epithelial cells, that make up the sweat glands in the skin, that line passageways inside the lungs, liver, pancreas, or digestive or reproductive systems. In particular embodiments, the target cells are bronchial epithelial cells. While permanent genomic change using PNA/DNA is less transient than plasmid-based approaches and the changes will be passed on to daughter cells, some modified cells may be lost over time with regular turnover of the respiratory epithelium. In some embodiments, the target cells are lung epithelial progenitor cells. Modification of lung epithelial progenitors can induce more long-term correction of phenotype.

Sequences for the human cystic fibrosis transmembrane conductance regulator (CFTR) are known in the art, see, for example, GenBank Accession number: AH006034.1, and compositions and methods of targeted correction of CFTR are described in McNeer, et al., *Nature Communications*, 6:6952, (DOI 10.1038/ncomms7952), 11 pages.

a. Exemplary F508del Target Sites

In some embodiments, the triplex-forming molecules are designed to target the CFTR gene at nucleotides 9,152-9,159 (TTTCCTCT (SEQ ID NO:70)) or 9,159-9,168 (TTTCCTCTATGGGTAAG (SEQ ID NO:71) of accession number AH006034.1, or the non-coding strand (e.g., 3'-5' complementary sequence) corresponding to nucleotides 9,152-9,159 or 9,152-9,168 (e.g., 5'-AGAGGAAA-3' (SEQ ID NO:72), or 5'-CTTACCCATAGAGGAAA-3' (SEQ ID NO:73)).

In some embodiments, the triplex-forming molecules are designed to target the CFTR gene at nucleotides 9,039-9,046 (5'-AGAAGAGG-3' (SEQ ID NO:74), or 9,030-9,046 (5'-ATGCCAACTAGAAGAGG-3' (SEQ ID NO:75)) of accession number AH006034.1, or the non-coding strand (e.g., 3'-5' complementary sequence) corresponding to nucleotides (5' CCTCTTCT 3' (SEQ ID NO:76)) or (5' CCTCTTCTAGTTGGCAT 3' (SEQ ID NO:77).

In some embodiments, the triplex-forming molecules are designed to target the CFTR gene at nucleotides 8,665-8,683 (CTTTCCCTT (SEQ ID NO:78)) or 8,665-8,682 (CTTTCCCTTGTATCTTTT (SEQ ID NO:79) of accession number AH006034.1, or the non-coding strand (e.g., 3'-5' complementary sequence) corresponding to nucleotides 8,665-8,683 or 8,665-8,682 (e.g., 5'-AAGGGAAAG-3' (SEQ ID NO:80), or 5'-AAAAGATAC AAGGGAAAG-3' (SEQ ID NO:81)).

Figures 8A, 8B, 8C:
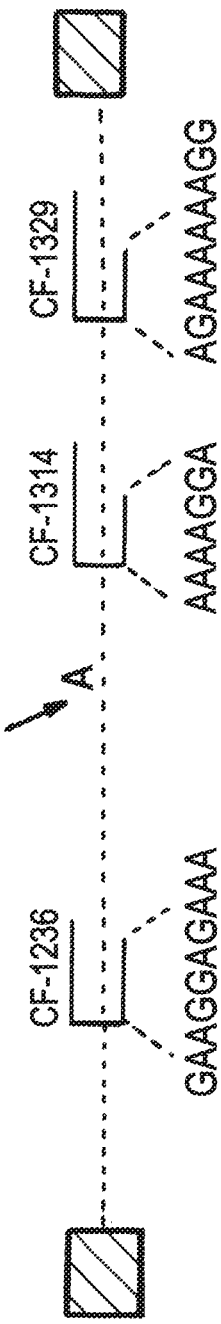
FIG. 8A is an illustration of a mutation (G→A) in the CFTR gene (W1282X) relative to three exemplary tcPNAs.
FIG. 8B provides the sequences of the tcPNAs: CF-1236 lys-lys-lys-JTTJJTJTTT-OOO-TTTCTCCTTCAGTG-TTCA-lys-lys-lys (SEQ ID NO:169), CF-1314 lys-lys-lys-TTTTJJT-OOO-TCCTTTTGCTCACCTGTGGT-lys-lys-lys (SEQ ID NO:170), and CF-1329: lys-lys-lys-TJTTTTTTJJ-OOO-CCTTTTTTCTGGCTAAGT-lys-lys-lys (SEQ ID NO:171).
FIG. 8C provides the sequence of an exemplary donor DNA: T(s)C(s)T(s)TGGGATTCAATAAC CTTGCAGACAGTGGAGGAAGGCCTT TGGCGTG-ATACCACAGG-(s)T(s)G(s) (SEQ ID NO:109).

In some embodiments, the triplex-forming molecules are designed to target the W1282X mutation in CFTR gene at the sequence GAAGGAGAAA (SEQ ID NO:163), AAAAGGAA (SEQ ID NO:164), or AGAAAAAAGG (SEQ ID NO:165), or the inverse complement thereof. See FIG. 8C.

In some embodiments, the triplex-forming molecules are designed to target the G542X mutation in CFTR gene at the sequence AGAAAAA (SEQ ID NO:166), AGAGAAAGA (SEQ ID NO:167), or AAAGAAA (SEQ ID NO:168), or the inverse complement thereof. See FIG. 9C.

b. Exemplary Triplex Forming Sequences and Donors
i. F508del

In some embodiments, the triplex-forming molecule includes the nucleic acid sequence includes TCTCCTTT (SEQ ID NO:82), preferably linked to the sequence TTTCCTCT (SEQ ID NO:83) or more preferably includes TCTCCTTT (SEQ ID NO:82) linked to the sequence TTTCCTCTATGGGTAAG (SEQ ID NO:84); or includes TCTTCTCC (SEQ ID NO:85) preferably linked to the sequence CCTCTTCT (SEQ ID NO:86), or more preferably includes TCTTCTCC (SEQ ID NO:85) linked to CCTCTTCTAGTTGGCAT (SEQ ID NO:87); or includes TTCCCTTTC (SEQ ID NO:88), preferable includes the sequence TTCCCTTTC (SEQ ID NO:88) linked to the sequence CTTTCCCTT (SEQ ID NO:89), or more preferable includes the sequence TTCCCTTTC (SEQ ID NO:89) linked to the sequence CTTTCCCTTGTATCTTTT (SEQ ID NO:90).

In some preferred embodiments, the triplex forming nucleic acid is a peptide nucleic acid including the sequence TJTJJTTT (SEQ ID NO:91), linked to the sequence TTTCCTCT (SEQ ID NO:83) or TTTCCTC-TATGGGTAAG (SEQ ID NO:84); or TJTTJTJJ (SEQ ID NO:216) linked to the sequence CCTCTTCT (SEQ ID NO:86), or CCTCTTCTAGTTGG-CAT (SEQ ID NO:87);

or TTJJJTTTJ (SEQ ID NO:92) linked to the sequence CTTTCCCTT (SEQ ID NO:89), or CTTTCCCTTGTATCTTTT (SEQ ID NO:90);

optionally, but preferably wherein one or more of the PNA monomers is a γPNA.

In specific embodiments the triplex forming nucleic acid is a peptide nucleic acid including the sequence is lys-lys-lys-TJTJJTTT-OOO-T̲T̲T̲C̲C̲T̲C̲T̲A̲T̲G̲G̲G̲T̲A̲ AG-lys-lys-lys (SEQ ID NO:93) (hCFPNA2); or lys-lys-lys-TJTJJTTT-OOO-TTTCCTCTATGGGTAAG-lys-lys-lys (SEQ ID NO:93); or lys-lys-lys-TJTTJTJJ-OOO-C̲C̲T̲C̲T̲T̲C̲T̲A̲G̲T̲T̲G̲G̲C̲ A̲T̲-lys-lys-lys (SEQ ID NO:94) (hCFPNA1); or lys-lys-lys-TTJJJTTTJ-OOO-C̲T̲T̲T̲C̲C̲C̲T̲T̲G̲T̲A̲T̲C̲T̲T̲T̲ T̲-lys-lys-lys (SEQ ID NO:95) (hCFPNA3);

optionally, but preferably wherein one or more of the PNA monomers is a γPNA. In even more specific embodiments, the bolded and underlined residues are miniPEG-containing γPNA.

In some embodiments, a donor that can be used for CFTR gene correction, particularly in combination with the foregoing triplex forming molecules, includes the sequence 5'TTCTGTATCTATATTCATCATAGGAAACACCAAA-GATAATGTTCTCC TTAATGGTGCCAGG3' (SEQ ID NO:96), or a functional fragment thereof that is suitable and sufficient to correct the F508del mutation in the cystic fibrosis transmembrane conductance regulator (CFTR) gene.

ii. W1282 Mutation Site

In some embodiments, the triplex-forming molecule includes the nucleic acid sequence CTTCCTCTTT (SEQ ID NO:97), preferable includes the sequence CTTCCTCTTT (SEQ ID NO:97) linked to the sequence TTTCTCCTTC (SEQ ID NO:98), or more preferable includes the sequence CTTCCTCTTT (SEQ ID NO:97) linked to the sequence TTTCTCCTTCAGTGTTCA (SEQ ID NO:99); or the triplex-forming molecule includes the nucleic acid sequence TTTTCCT (SEQ ID NO:100), preferable includes the sequence TTTTCCT (SEQ ID NO:100) linked to the sequence TCCTTTT (SEQ ID NO:101), or more preferable includes the sequence TTTTCCT (SEQ ID NO:100) linked to the sequence TCCTTTTGCTCACCTGTGGT (SEQ ID NO:102); or the triplex-forming molecule includes the nucleic acid sequence TCTTTTTTCC (SEQ ID NO:103), preferable includes the sequence TCTTTTTTCC (SEQ ID NO:103) linked to the sequence CCTTTTTTCT (SEQ ID NO:104), or more preferable includes the sequence TCTTTTTTCC (SEQ ID NO:103) linked to the sequence CCTTTTTTCTGGCTAAGT (SEQ ID NO:105).

In preferred embodiments, the triple forming nucleic acid is a peptide nucleic acid including the sequence JTTJJTJTTT (SEQ ID NO:106) linked to the sequence TTTCTCCTTC (SEQ ID NO:98) or TTTCTCCTTCAGTGTTCA (SEQ ID NO:99); or a peptide nucleic acid including the sequence TTTTJJT (SEQ ID NO:107) linked to the sequence TCCTTTT (SEQ ID NO:101) or linked to the sequence TCCTTTTGCTCACCTGTGGT (SEQ ID NO:102); or a peptide nucleic acid including the sequence TJTTTTTTJJ (SEQ ID NO:108) linked to the sequence CCTTTTTTCT (SEQ ID NO:104) or linked to the sequence CCTTTTTTCTGGCTAAGT (SEQ ID NO:105);

optionally, but preferably wherein one or more of the PNA monomers is a γPNA.

In specific embodiments, the triplex forming nucleic acid is a peptide nucleic acid including the sequence lys-lys-lys-JTTJJTJTTT-OOO-T<u>TT</u>CTCCTT<u>C</u>AGTGTT<u>C</u>A-lys-lys-lys (SEQ ID NO:155) (tcPNA-1236); or lys-lys-lys-TTTTJJT-OOO-T<u>CC</u>TTTTGCT<u>C</u>ACCTGT<u>GG</u>T-lys-lys-lys (SEQ ID NO:156) (tcPNA-1314); or lys-lys-lys-TJTTTTTTJJ-OOO-C<u>C</u>TTTTTT<u>C</u>TGGCT<u>A</u>AGT-lys-lys-lys (SEQ ID NO:157) (tcPNA-1329);

optionally, but preferably wherein one or more of the PNA monomers is a γPNA. In even more specific embodiments, the bolded and underlined residues are miniPEG-containing γPNA.

In some embodiments, a donor that can be used for CFTR gene correction, particularly in combination with the foregoing triplex forming molecules, includes the sequence T(s)C(s)T(s)-TGGGATTCAATAACCTTGCAGACAGTGGAGV̄GAAGGCCTTTGGCGTGATACCACAGG-(s)T(s)G(s) (SEQ ID NO:109) or a functional fragment thereof that is suitable and sufficient to correct a mutation in CFTR, wherein the bolded and underlined nucleotides are inserted mutations for gene correction, and "(s)" indicates an optional phosphorothioate internucleoside linkage. See also, FIGS. 8A-8C, W1282X.

iii. G542X Mutation Site

In some embodiments, the triplex-forming molecule includes the nucleic acid sequence TCTTTTT (SEQ ID NO:110), preferable includes the sequence TCTTTTT (SEQ ID NO:110) linked to the sequence TTTTTCT (SEQ ID NO:111), or more preferable includes the sequence TCTTTTT (SEQ ID NO:110) linked to the sequence TTTTTCTGTAATTTTAA (SEQ ID NO:112); or the triplex-forming molecule includes the nucleic acid sequence TCTCTTTCT (SEQ ID NO:113), preferable includes the sequence TCTCTTTCT (SEQ ID NO:113) linked to the sequence TCTTTCTCT (SEQ ID NO:114), or more preferable includes the sequence TCTCTTTCT (SEQ ID NO:113) linked to the sequence TCTTTCTCTGCAAACTT (SEQ ID NO:115); or the triplex-forming molecule includes the nucleic acid sequence TTTCTTT (SEQ ID NO:116), preferable includes the sequence TTTCTTT (SEQ ID NO:116) linked to the sequence TTTCTTT (SEQ ID NO:116), or more preferable includes the sequence TTTCTTT (SEQ ID NO:116) linked to the sequence TTTCTTTAAGAACGAGCA (SEQ ID NO:117).

In preferred embodiments, the triple forming nucleic acid is a peptide nucleic acid including the sequence TJTTTTT (SEQ ID NO:118) linked to the sequence TTTTTCT (SEQ ID NO:111) or TTTTTCTGTAATTTTAA (SEQ ID NO:112); or a peptide nucleic acid including the sequence TJTJTTTJT (SEQ ID NO:119) linked to the sequence TCTTTCTCT (SEQ ID NO:114) or linked to the sequence TCTTTCTCTGCAAACTT (SEQ ID NO:115); or a peptide nucleic acid including the sequence TTTJTTT (SEQ ID NO:120) linked to the sequence TTTCTTT (SEQ ID NO:116) or linked to the sequence TTTCTTTAAGAACGAGCA (SEQ ID NO:117);

optionally, but preferably wherein one or more of the PNA monomers is a γPNA.

In specific embodiments, the triplex forming nucleic acid is a peptide nucleic acid including the sequence lys-lys-lys-TJTTTTT-OOO-T<u>TTTTCTGTAATTTTAA</u>-lys-lys-lys (SEQ ID NO:121) (tcPNA-302); or lys-lys-lys-TJTJTTTJT-OOO-TC<u>TT</u>TCTCTGC<u>AAA</u>CTT-lys-lys-lys (SEQ ID NO:122) (tcPNA-529); or lys-lys-lys-TTTJTTT-OOO-T<u>TT</u>CTTT<u>A</u>AG<u>A</u>ACG<u>A</u>GCA-lys-lys-lys (SEQ ID NO:123) (tcPNA-586);

optionally, but preferably wherein one or more of the PNA monomers is a γPNA. In even more specific embodiments, the bolded and underlined residues are miniPEG-containing γPNA.

In some embodiments, a donor that can be used for CFTR gene correction, particularly in combination with the foregoing triplex forming molecules, includes the sequence T(s)C(s)C(s)-AAGTTTGCAGAGAAAGATAATATAGTCCTTGGAGAAGGAGGAATCACCCTGAGTGG A-G(s)G(s)T(s) (SEQ ID NO:124), or a functional fragment thereof that is suitable and sufficient to correct a mutation in CFTR, wherein the bolded and underlined nucleotides are inserted mutations for gene correction, and "(s)" indicates an optional phosphorothioate internucleoside linkage. See also, FIGS. 9A-9C, G542X.

3. HIV

The gene editing compositions can be used to treat infections, for example those caused by HIV.

a. Exemplary Target Sites

The target sequence for the triplex-forming molecules is within or adjacent to a human gene that encodes a cell surface receptor for human immunodeficiency virus (HIV). Preferably, the target sequence of the triplex-forming molecules is within or is adjacent to a portion of a HIV receptor gene important to its function in HIV entry into cells, such as sequences that are involved in efficient expression of the receptor, transport of the receptor to the cell surface, stability of the receptor, viral binding by the receptor, or endocytosis of the receptor. Target sequences can be within the coding DNA sequence of the gene or within introns. Target sequences can also be within DNA sequences that regulate expression of the target gene, including promoter or enhancer sequences.

The target sequence can be within or adjacent to any gene encoding a cell surface receptor that facilitates entry of HIV into cells. The molecular mechanism of HIV entry into cells involves specific interactions between the viral envelope glycoproteins (env) and two target cell proteins, CD4 and the chemokine receptors. HIV cell tropism is determined by the specificity of the env for a particular chemokine receptor, a 7 transmembrane-spanning, G protein-coupled receptor (Steinberger, et al., *Proc. Natl. Acad. Sci. USA.* 97: 805-10 (2000)). The two major families of chemokine receptors are the CXC chemokine receptors and the CC chemokine receptors (CCR) so named for their binding of CXC and CC chemokines, respectively. While CXC chemokine receptors traditionally have been associated with acute inflammatory responses, the CCRs are mostly expressed on cell types found in connection with chronic inflammation and T-cell-mediated inflammatory reactions: eosinophils, basophils, monocytes, macrophages, dendritic cells, and T cells (Nansen, et al. 2002, Blood 99:4). In one embodiment, the target sequence is within or adjacent to the human genes encoding chemokine receptors, including, but not limited to, CXCR4, CCR5, CCR2b, CCR3, and CCR1.

In a preferred embodiment, the target sequence is within or adjacent to the human CCR5 gene. The CCR5 chemokine receptor is the major co-receptor for R5-tropic HIV strains, which are responsible for most cases of initial, acute HIV infection. Individuals who possess a homozygous inactivating mutation, referred to as the Δ32 mutation, in the CCR5 gene are almost completely resistant to infection by R5-tropic HIV-1 strains. The Δ32 mutation produces a 32 base pair deletion in the CCR5 coding region.

Another naturally occurring mutation in the CCR5 gene is the m303 mutation, characterized by an open reading frame single T to A base pair transversion at nucleotide 303 which indicates a cysteine to stop codon change in the first extracellular loop of the chemokine receptor protein at amino acid 101 (C101X) (Carrington et al. 1997). Mutagenesis assays have not detected the expression of the m303 co-receptor on the surface of CCR5 null transfected cells which were found to be non-susceptible to HIV-1 R5-isolates in infection assays (Blanpain, et al. (2000).

Compositions and methods for targeted gene therapy using triplex-forming oligonucleotides and peptide nucleic acids for treating infectious diseases such as HIV are described in U.S. Application No. 2008/050920 and WO 2011/133803. Each provides sequences of triplex foiming molecules, target sequences, and donor oligonucleotides that can be utilized in the compositions and methods provided herein.

For example, individuals having the homozygous Δ32 inactivating mutation in the CCR5 gene display no significant adverse phenotypes, suggesting that this gene is largely dispensable for normal human health. This makes the CCR5 gene a particularly attractive target for targeted mutagenesis using the triplex-forming molecules disclosed herein. The gene for human CCR5 is known in the art and is provided at GENBANK accession number NM_000579. The coding region of the human CCR5 gene is provided by nucleotides 358 to 1416 of GENBANK accession number NM_000579.

In some embodiments, the target region is a polypurine site within or adjacent to a gene encoding a chemokine receptor including CXCR4, CCR5, CCR2b, CCR3, and CCR1. In a preferred embodiment, the target region is a polypurine or homopurine site within the coding region of the human CCR5 gene. Three homopurine sites in the coding region of the CCR5 gene that are especially useful as target sites for triplex-forming molecules are from positions 509-518, 679-690 and 900-908 relative to the ATG start codon.

The homopurine site from 679-690 partially encompasses the site of the nonsense mutation created by the 432 mutation. Triplex-forming molecules that bind to this target site are particularly useful.

b. Exemplary Triplex Forming Sequences

In some embodiments, the triplex-forming molecule includes the nucleic acid sequence CTCTTCTTCT (SEQ ID NO:125), preferable includes the sequence CTCTTCTTCT (SEQ ID NO:125) linked to the sequence TCTTCTTCTC (SEQ ID NO:126), or more preferable includes the sequence CTCTTCTTCT (SEQ ID NO:125) linked to the sequence TCTTCTTCTCATTTC (SEQ ID NO:127).

In some embodiments, the triplex-forming molecule includes the nucleic acid sequence CTTCT (SEQ ID NO:128), preferable includes the sequence CTTCT (SEQ ID NO:128) linked to the sequence TCTTC (SEQ ID NO:129) or TCTTCTTCTC (SEQ ID NO:130), or more preferable includes the sequence CTTCT (SEQ ID NO:128) linked to the sequence TCTTCTTCTCATTTC (SEQ ID NO:131).

In preferred embodiments, the triplex forming nucleic acid is a peptide nucleic acid including the sequence JTJTTJTTJT (SEQ ID NO:132) linked to the sequence TCTTCTTCTC (SEQ ID NO:126) or TCTTCTTCTCATTTC (SEQ ID NO:127);

or JTTJT (SEQ ID NO:133) linked to the sequence TCTTC (SEQ ID NO:129) or TCTTCTTCTC (SEQ ID NO:130) or more preferably TCTTCTTCTCATTTC (SEQ ID NO:131);

optionally, but preferably wherein one or more of the PNA monomers is a γPNA.

In specific embodiments, the triplex forming nucleic acid is a peptide nucleic acid including the sequence Lys-Lys-Lys-JTJTTJTTJT-OOO-T<u>C</u>TT<u>C</u>TT<u>C</u>T<u>C</u>ATT<u>TC</u>-Lys-Lys-Lys (SEQ ID NO:134) (PNA-679);

or Lys-Lys-Lys-JTTJT-OOO-T<u>C</u>TT<u>C</u>TT<u>C</u>T<u>C</u>ATT<u>TC</u>-Lys-Lys-Lys (SEQ ID NO:135) (tcPNA-684) optionally, but preferably wherein one or more of the PNA monomers is a γPNA. In even more specific embodiments, the bolded and underlined residues are miniPEG-containing γPNA.

c. Exemplary Donor Sequences

In some embodiments, the triplex forming molecules are used in combination with one or more donor oligonucleotides such as donor 591 having the sequence: 5' AT TCC CGA GTA GCA GAT GAC CAT GAC AGC TTA GGG CAG GAC CAG CCC CAA GAT GAC TAT C 3' (SEQ ID NO:136), or donor 597 having the sequence 5' TT TAG GAT TCC CGA GTA GCA GAT GAC CCC TCA GAG CAG CGG CAG GAC CAG CCC CAA GAT G 3' (SEQ ID NO:137), which can be used in combination to induce two different non-sense mutations, one in each allele of the CCR5 gene, in the vicinity of the Δ32 deletion (mutation sites are bolded); or a functional fragment thereof that is suitable and sufficient to introduce a non-sense mutation in at least one allele of the CCR5 gene.

In another preferred embodiment, donor oligonucleotides are designed to span the Δ32 deletion site (see, e.g., FIG. 1 of WO 2011/133803) and induce changes into a wildtype CCR5 allele that mimic the Δ32 deletion. Donor sequences designed to target the Δ32 deletion site may be particularly usefully to facilitate knockout of the single wildtype CCR5 allele in heterozygous cells.

Preferred donor sequences designed to target the Δ32 deletion site include, but are not limited to, Donor DELTA32JDC:
(SEQ ID NO: 138)
5'GATGACTATCTTTAATGTCTGGAAATTCTTCCAGAATTAATTAAG

ACTGTATGGAAAATGAGAGC 3';

Donor DELTAJDC2:
(SEQ ID NO: 139)
5'CCCCAAGATGACTATCTTTAATGTCTGGAACGATCATCAGAATTG ATACTGACTGTATGGAAAATG 3';
and Donor DELTA32RSB:
(SEQ ID NO: 140)
5'GATGACTATCTTTAATGTCTGGAAATTCTACTAGAATTGATACTG

ACTGTATGGAAAATGAGAGC 3', or a functional fragment of SEQ ID NO:138, 139, or 140 that is suitable and sufficient to introduce mutation CCR5 gene.

4. Lysosomal Storage Diseases

The disclosed compositions and methods compositions can also be used to treat lysosomal storage diseases. Lysosomal storage diseases (LSDs) are a group of more than 50 clinically-recognized, rare inherited metabolic disorders that result from defects in lysosomal function (Walkley, *J Inherit. Metab. Dis.*, 32(2):181-9 (2009)). Lysosomal storage disorders are caused by dysfunction of the cell's lysosome orangelle, which is part of the larger endosomal/lysosomal system. Together with the ubiquitin-proteosomal and autophagosomal systems, the lysosome is essential to substrate degradation and recycling, homeostatic control, and signaling within the cell. Lysosomal dysfunction is usually the result of a deficiency of a single enzyme necessary for the metabolism of lipids, glycoproteins (sugar containing proteins) or mucopolysaccharides (long unbranched polysaccharides consisting of a repeating disaccharide unit; also known as glycosaminoglycans, or GAGs) which are fated for breakdown or recycling. Enzyme deficiency reduces or prevents break down or recycling of the unwanted lipids, glycoproteins, and GAGs, and results in buildup or "storage" of these materials within the cell. Most lysosomal diseases show widespread tissue and organ involvement, with brain, viscera, bone and connective tissues often being affected. More than two-thirds of lysosomal diseases affect the brain. Neurons appear particularly vulnerable to lysosomal dysfunction, exhibiting a range of defects from specific axonal and dendritic abnormalities to neuron death.

Individually, LSDs occur with incidences of less than 1:100,000, however, as a group the incidence is as high as 1 in 1,500 to 7,000 live births (Staretz-Chacham, et al., *Pediatrics*, 123(4):1191-207 (2009)). LSDs are typically the result of inborn genetic errors. Most of these disorders are autosomal recessively inherited, however a few are X-linked recessively inherited, such as Fabry disease and Hunter syndrome (MPS II). Affected individuals generally appear normal at birth, however the diseases are progressive. Develop of clinical disease may not occur until years or decades later, but is typically fatal. Lysosomal storage diseases affect mostly children and they often die at a young and unpredictable age, many within a few months or years of birth. Many other children die of this disease following years of suffering from various symptoms of their particular disorder. Clinical disease may be manifest as mental retardation and/or dementia, sensory loss including blindness or deafness, motor system dysfunction, seizures, sleep and behavioral disturbances, and so forth. Some people with Lysosomal storage disease have enlarged livers (hepatomegaly) and enlarged spleens (splenomegaly), pulmonary and cardiac problems, and bones that grow abnormally.

Treatment for many LSDs is enzyme replacement therapy (ERT) and/or substrate reduction therapy (SRT), as wells as treatment or management of symptoms. The average annual cost of ERT in the United States ranges from $90,000 to $565,000. While ERT has significant systemic clinical efficacy for a variety of LSDs, little or no effects are seen on central nervous system (CNS) disease symptoms, because the recombinant proteins cannot penetrate the blood-brain barrier. Allogeneic hematopoietic stem cell transplantation (HSCT) represents a highly effective treatment for selected LSDs. It is currently the only means to prevent the progression of associated neurologic sequelae. However, HSCT is expensive, requires an HLA-matched donor and is associated with significant morbidity and mortality. Recent gene therapy studies suggest that LSDs are good targets for this type of treatment.

Compositions and methods for targeted gene therapy using triplex-forming oligonucleotides and peptide nucleic acids for treating lysosomal storage diseases are described in WO 2011/133802, which provides sequences of triplex forming molecules, target sequences, and donor oligonucleotides that can be utilized in the compositions and methods provided herein.

For example, the disclosed compositions and methods can be are employed to treat Gaucher's disease (GD). Gaucher's disease, also known as Gaucher syndrome, is the most common lysosomal storage disease. Gaucher's disease is an inherited genetic disease in which lipid accumulates in cells and certain organs due to deficiency of the enzyme glucocerebrosidase (also known as acid β-glucosidase) in lysosomes. Glucocerebrosidase enzyme contributes to the degradation of the fatty substance glucocerebroside (also known as glucosylceramide) by cleaving b-glycoside into b-glucose and ceramide subunits (Scriver C R, Beaudet A L, Valle D, Sly W S. *The metabolic and molecular basis of inherited disease.* 8th ed. New York: McGraw-Hill Pub, 2001: 3635-3668). When the enzyme is defective, the substance accumulates, particularly in cells of the mononuclear cell lineage, and organs and tissues including the spleen, liver, kidneys, lungs, brain and bone marrow.

There are two major forms: non-neuropathic (type 1, most commonly observed type in adulthood) and neuropathic (type 2 and 3). GBA (GBA glucosidase, beta, acid), the only known human gene responsible for glucosidase-mediated GD, is located on chromosome 1, location 1q21. More than 200 mutations have been defined within the known genomic sequence of this single gene (NCBI Reference Sequence: NG_009783.1). The most commonly observed mutations are N370S, L444P, RecNcil, 84GG, R463C, recTL and 84 GG is a null mutation in which there is no capacity to synthesize enzyme. However, N370S mutation is almost always related with type 1 disease and milder forms of disease. Very rarely, deficiency of sphingolipid activator protein (Gaucher factor, SAP-2, saposin C) may result in GD. In some embodiments, triplex-forming molecules are used to induce recombination of donor oligonucleotides designed to correct mutations in GBA.

In another embodiment, compositions and the methods disclosed herein are used to treat Fabry disease (also known as Fabry's disease, Anderson-Fabry disease, angiokeratoma corporis diffusum and alpha-galactosidase A deficiency), a rare X-linked recessive disordered, resulting from a deficiency of the enzyme alpha galactosidase A (a-GAL A, encoded by GLA). The human gene encoding GLA has a known genomic sequence (NCBI Reference Sequence: NG_007119.1) and is located at Xp22 of the X chromosome. Mutations in GLA result in accumulation of the glycolipid globotriaosylceramide (abbreviated as Gb3, GL-3, or ceramide trihexoside) within the blood vessels, other tissues, and organs, resulting in impairment of their proper function (Karen, et al., *Dermatol. Online J.,* 11 (4): 8 (2005)). The condition affects hemizygous males (i.e. all males), as well as homozygous, and potentially heterozygous (carrier), females. Males typically experience severe symptoms, while women can range from being asymptomatic to having severe symptoms. This variability is thought to be due to X-inactivation patterns during embryonic development of the female. In some embodiments, triplex-forming molecules are used to induce recombination of donor oligonucleotides designed to correct mutations in GLA.

In preferred embodiments, the disclosed compositions and methods are used to treat Hurler syndrome (HS). Hurler syndrome, also known as mucopolysaccharidosis type I (MPS I), α-L-iduronidase deficiency, and Hurler's disease, is a genetic disorder that results in the buildup of mucopolysaccharides due to a deficiency of α-L iduronidase, an enzyme responsible for the degradation of mucopolysaccharides in lysosomes (Dib and Pastories, *Genet. Mol. Res.,* 6(3):667-74 (2007)). MPS I is divided into three subtypes based on severity of symptoms. All three types result from an absence of, or insufficient levels of, the enzyme α-L-iduronidase. MPS I H or Hurler syndrome is the most severe of the MPS I subtypes. The other two types are MPS I S or Scheie syndrome and MPS I H-S or Hurler-Scheie syndrome. Without α-L-iduronidase, heparan sulfate and dermatan sulfate, the main components of connective tissues, build-up in the body. Excessive amounts of glycosaminoglycans (GAGs) pass into the blood circulation and are stored throughout the body, with some excreted in the urine. Symptoms appear during childhood, and can include developmental delay as early as the first year of age. Patients usually reach a plateau in their development between the ages of two and four years, followed by progressive mental decline and loss of physical skills (Scott et al., *Hum. Mutat.* 6: 288-302 (1995)). Language may be limited due to hearing loss and an enlarged tongue, and eventually site impairment can results from clouding of cornea and retinal degeneration. Carpal tunnel syndrome (or similar compression of nerves elsewhere in the body) and restricted joint movement are also common.

a. Exemplary Target Sites

The human gene encoding alpha-L-iduronidase (α-L-iduronidase; IDUA) is found on chromosome 4, location 4p16.3, and has a known genomic sequence (NCBI Reference Sequence: NG 008103.1). Two of the most common mutations in IDUA contributing to Hurler syndrome are the Q70X and the W420X, non-sense point mutations found in exon 2 (nucleotide 774 of genomic DNA relative to first nucleotide of start codon) and exon 9 (nucleotide 15663 of genomic DNA relative to first nucleotide of start codon) of IDUA respectively. These mutations cause dysfunction alpha-L-iduronidase enzyme. Two triplex-forming molecule target sequences including a polypurine:polypyrimidine stretches have been identified within the IDUA gene. One target site with the polypurine sequence 5' CTGCTCGGAAGA 3' (SEQ ID NO:141) and the complementary polypyrimidine sequence 5' TCTTCCGAGCAG 3' (SEQ ID NO:142) is located 170 base pairs downstream of the Q70X mutation. A second target site with the polypurine sequence 5' CCTTCACCAAGGGGA 3' (SEQ ID NO:143) and the complementary polypyrimidine sequence 5' TCCCCTTGGTGAAGG 3' (SEQ ID NO:144) is located 100 base pairs upstream of the W402X mutation. In preferred embodiments, triplex-forming molecules are designed to bind/hybridize in or near these target locations.

b. Exemplary Triplex Forming Sequences and Donors i. W402X mutation

In some embodiments, a triplex-forming molecule binds to the target sequence upstream of the W402X mutation includes the nucleic acid sequence TTCCCCT (SEQ ID NO:145), preferable includes the sequence TTCCCCT (SEQ ID NO:145) linked to the sequence TCCCCTT (SEQ ID NO:146), or more preferable includes the sequence TTCCCCT (SEQ ID NO:145) linked to the sequence TCCCCTTGGTGAAGG (SEQ ID NO:147).

In some preferred embodiments, the triplex forming nucleic acid is a peptide nucleic acid that binds to the target sequence upstream of the W402X mutation including the sequence TTJJJJT (SEQ ID NO:148), linked to the sequence TCCCCTT (SEQ ID NO:146) or TCCCCTTGGTGAAGG (SEQ ID NO:147), optionally, but preferably wherein one or more of the PNA monomers is a γPNA.

In specific embodiments, the triplex forming nucleic acid is a peptide nucleic acid having the sequence Lys-Lys-Lys-TTJJJJT-OOO-T<u>CCCC</u>T<u>TGGTGAAG</u>G-Lys-Lys-Lys (SEQ ID NO:159) (IDUA402tc715) optionally, but preferably wherein one or more of the PNA monomers is a γPNA. In even more specific embodiments, the bolded and underlined residues are miniPEG-containing γPNA.

In the most preferred embodiments, triplex-forming molecules are administered according to the disclosed methods in combination with one or more donor oligonucleotides designed to correct the point mutations at Q70X or W402X mutations sites. In some embodiments, in addition to containing sequence designed to correct the point mutation at Q70X or W402X mutation, the donor oligonuclotides may also contain 7 to 10 additional, synonymous (silent) mutations. The additional silent mutations can facilitate detection of the corrected target sequence using allele-specific PCR of genomic DNA isolated from treated cells.

In some embodiments, the donor oligonucleotide with the sequence 5' AGGACGGTCCCGGCCTGCGACACTTC-CGCCCATAATTGTTCTTCATCT GCGGGGCGGGG-GGGGG 3' (SEQ ID NO:149), or a functional fragment thereof that is suitable and sufficient to correct the W402X mutation is administered with triplex-forming molecules designed to target the binding site upstream of W402X to correct the W402X mutation in cells.

ii. Q70X Mutation

In some embodiments, a triplex-forming molecule that binds to the target sequence downstream of the Q70X mutation includes the nucleic acid sequence CCTTCT (SEQ ID NO:150), preferable includes the sequence CCTTCT (SEQ ID NO:150) linked to the sequence TCTTCC (SEQ ID NO:151), or more preferable includes the sequence CCTTCT (SEQ ID NO:150) linked to the sequence TCTTCCGAGCAG (SEQ ID NO:152).

In preferred embodiments, the triplex forming nucleic acid is a peptide nucleic acid that binds to the target sequence downstream of the Q70X mutation including the sequence JJTTJT (SEQ ID NO:153) linked to the sequence TCTTCC (SEQ ID NO:151) or TCTTCCGAGCAG (SEQ ID NO:152) optionally, but preferably wherein one or more of the PNA monomers is a γPNA.

In a specific embodiment, a tcPNA with a sequence of Lys-Lys-Lys-JJTTJT-OOO-TC<u>TTCC</u>G<u>AGCA</u>G-Lys-Lys-Lys (SEQ ID NO:153) (IDUA402tc715) optionally, but preferably wherein one or more of the PNA monomers is a γPNA. In even more specific embodiments, the bolded and underlined residues are miniPEG-containing γPNA.

A donor oligonucleotide can have the sequence 5'GGGACGGCGCCCACATAGGCCAAATTCAATTGCTGATCCCAGCTTA AGACGTACTGGTCAGCCTGGC 3' (SEQ ID NO:154), or a functional fragment thereof that is suitable and sufficient to correct the Q70X mutation is administered with triplex-forming molecules designed to target the binding site downstream of Q70X to correct the of Q70X mutation in cells.

X. Combination Therapies

Each of the different components of gene editing and potentiation disclosed here can be administered alone or in any combination and further in combination with one or more additional active agents. In all cases, the combination of agents can be part of the same admixture, or administered as separate compositions. In some embodiments, the separate compositions are administered through the same route of administration. In other embodiments, the separate compositions are administered through different routes of administration.

A. Conventional Therapeutic Agents

Examples of preferred additional active agents include other conventional therapies known in the art for treating the desired disease or condition. For example, in the treatment of sickle cell disease, the additional therapy may be hydroxurea.

In the treatment of cystic fibrosis, the additional therapy may include mucolytics, antibiotics, nutritional agents, etc. Specific drugs are outlined in the Cystic Fibrosis Foundation drug pipeline and include, but are not limited to, CFTR modulators such as KALYDECO® (invascaftor), ORKAMBI™ (lumacaftor+ivacaftor), ataluren (PTC124), VX-661+ invacaftor, riociguat, QBW251, N91115, and QR-010; agents that improve airway surface liquid such as hypertonic saline, bronchitol, and P-1037; mucus alteration agents such as PULMOZYME® (dornase alfa); anti-inflammatories such as ibuprofen, alpha 1 anti-trypsin, CTX-4430, and JBT-101; anti-infective such as inhaled tobramycin, azithromycin, CAYSTON® (aztreonam for inhalation solution), TOBI inhaled powder, levofloxacin, ARIKACE® (nebulized liposomal amikacin), AEROVANC® (vancomycin hydrochloride inhalation powder), and gallium; and nutritional supplements such as aquADEKs, pancrelipase enzyme products, liprotamase, and burlulipase.

In the treatment of HIV, the additional therapy maybe an antiretroviral agents including, but not limited to, a non-nucleoside reverse transcriptase inhibitor (NNRTIs), a nucleoside reverse transcriptase inhibitor (NRTIs), a protease inhibitors (PIs), a fusion inhibitors, a CCR5 antagonists (CCR5s) (also called entry inhibitors), an integrase strand transfer inhibitors (INSTIs), or a combination thereof.

In the treatment of lysosomal storage disease, the additional therapy could include, for example, enzyme replacement therapy, bone marrow transplantation, or a combination thereof.

B. Additional Mutagenic Agents

The compositions can be used in combination with other mutagenic agents. In a preferred embodiment, the additional mutagenic agents are conjugated or linked to gene editing technology or a delivery vehicle (such as a nanoparticle) thereof. Additional mutagenic agents that can be used in combination with gene editing technology, particularly triplex forming molecules, include agents that are capable of directing mutagenesis, nucleic acid crosslinkers, radioactive agents, or alkylating groups, or molecules that can recruit DNA-damaging cellular enzymes. Other suitable mutagenic agents include, but are not limited to, chemical mutagenic agents such as alkylating, bialkylating or intercalating agents. A preferred agent for co-administration is psoralen-linked molecules as described in PCT/US/94/07234 by Yale University.

It may also be desirable to administer gene editing compositions in combination with agents that further enhance the frequency of gene modification in cells. For example, the disclosed compositions can be administered in combination with a histone deacetylase (HDAC) inhibitor, such as suberoylanilide hydroxamic acid (SAHA), which has been found to promote increased levels of gene targeting in asynchronous cells.

The nucleotide excision repair pathway is also known to facilitate triplex-forming molecule-mediated recombination. Therefore, the disclosed compositions can be administered in combination with an agent that enhances or increases the nucleotide excision repair pathway, for example an agent that increases the expression, or activity, or localization to the target site, of the endogenous damage recognition factor XPA.

Compositions may also be administered in combination with a second active agent that enhances uptake or delivery of the gene editing technology. For example, the lysosomotropic agent chloroquine has been shown to enhance delivery of PNAs into cells (Abes, et al., *J Controll. Rel.*, 110:595-604 (2006). Agents that improve the frequency of gene modification are particularly useful for in vitro and ex vivo application, for example ex vivo modification of hematopoietic stem cells for therapeutic use.

XI. Methods for Determining Triplex Formation and Gene Modification

A. Methods for Determining Triplex Formation

A useful measure of triple helix formation is the equilibrium dissociation constant, $K_d$, of the triplex, which can be estimated as the concentration of triplex-forming molecules at which triplex formation is half-maximal. Preferably, the molecules have a binding affinity for the target sequence in the range of physiologic interactions. Preferred triplex-forming molecules have a $K_d$ less than or equal to approximately $10^{-7}$ M. Most preferably, the $K_d$ is less than or equal to $2 \times 10^{-8}$ M in order to achieve significant intramolecular interactions. A variety of methods are available to determine the $K_d$ of triplex-forming molecules with the target duplex. In the examples which follow, the $K_d$ was estimated using a gel mobility shift assay (R. H. Durland et al., *Biochemistry* 30, 9246 (1991)). The dissociation constant ($K_d$) can be determined as the concentration of triplex-forming molecules in which half was bound to the target sequence and half was unbound.

B. Methods for Determining Gene Modification

Sequencing and allele-specific PCR are preferred methods for determining if gene modification has occurred. PCR primers are designed to distinguish between the original allele, and the new predicted sequence following recombination. Other methods of determining if a recombination event has occurred are known in the art and may be selected based on the type of modification made. Methods include, but are not limited to, analysis of genomic DNA, for example by sequencing, allele-specific PCR, or restriction endonuclease selective PCR (REMS-PCR); analysis of mRNA transcribed from the target gene for example by Northern blot, in situ hybridization, real-time or quantitative reverse transcriptase (RT) PCT; and analysis of the polypeptide encoded by the target gene, for example, by immunostaining, ELISA, or FACS. In some cases, modified cells will be compared to parental controls. Other methods may include testing for changes in the function of the RNA transcribed by, or the polypeptide encoded by the target gene. For example, if the target gene encodes an enzyme, an assay designed to test enzyme function may be used.

XII. Kits

Medical kits are also disclosed. The medical kits can include, for example, a dosage supply of gene editing technology or a potentiating agent thereof, or a combination thereof in separately or together in the same admixture. The active agents can be supplied alone (e.g., lyophilized), or in a pharmaceutical composition. The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

EXAMPLES

Example 1: Triplex-Forming PNA Design and Nanoparticle Formulation for Gene Editing of a β-Globin Mutation Materials and Methods
Oligonucleotides
$^{MP}$γPNA monomers were prepared as reported (Sahu, et al., *J. Org. Chem.*, 76:5614-5627 (2011)). PNA oligomers were synthesized on solid support using Boc chemistry, as described (Bahal, et al., *ChemBioChem*, 13:56-60 (2012)). The sequences of PNAs used in this study are:

tcPNA1:
(SEQ ID NO: 33)
H-KKK-JTTTJTTTJTJT-OOO-TCTCTTTCTTTCAGGGCA-KKK-NH$_2$ tcPNA2:
(SEQ ID NO: 34)
H-KKK-TTTTJJJ------OOO-CCCTTTTGCTAATCATGT-KKK-NH$_2$ tcPNA3:
(SEQ ID NO: 35)
H-KKK-TTTJTJJ------OOO-CCTCTTTGCACCATTCT-KKK-NH$_2$

γtcPNA4:
(SEQ ID NO: 162)
H-KKK-JTTTJTTTJTJT-OOO-TCTCTTTCTTTCAGGGCA-KKK-NH$_2$

γtcPNA4-Scr.:
(SEQ ID NO: 158)
H-KKK-TTJTTTJTTJTJ-OOO-CTCTTCTTTCTTGACAGG-KKK-NH$_2$

Sequences of tcPNAs and γtcPNAs used in this study to bind to positions 577 to 595 (tcPNA1 and γtcPNA4), 611 to 629 (tcPNA2), and 807 to 825 (tcPNA3) in β-globin intron 2 within the β-globin/GFP fusion gene and within the human β-globin gene in the thalassemic mouse model. γtcPNA4-Scr is a scrambled version of γtcPNA4 with the same base composition. Bold and underline indicates γPNA residues. All PNAs have three lysine residues conjugated to each end. "J" indicates pseudoisocytosine substituted for C to allow pH-independent triplex formation. "O" represents 8-amino-2,6,10-trioxaoctanoic acid residues that are used to form flexible linkers connecting the Hoogsteen and Watson-Crick binding domains of the tcPNAs.

The single-stranded donor DNA oligomer was prepared by standard DNA synthesis except for the inclusion of 3 phosphorothioate internucleoside linkages at each end to protect from nuclease degradation. The sequence of the donor DNA matches positions 624 to 684 in β-globin intron 2 and is as follows, with the correcting IVS2-654 nucleotide underlined:

(SEQ ID NO: 65)
5'AAAGAATAACAGTGATAATTTCTGGGTTAAGGCAATAGCAATATC
TCTGCATATAAATAT3'.

PLGA Nanoparticle Synthesis and Characterization
PLGA nanoparticles containing the PNAs and DNAs were formulated using a double-emulsion solvent evaporation method and characterized as previously described (McNeer, et al., *Molecular Therapy*, 19(1):172-180 (2011), and). Release profiles were analyzed as previously described (McNeer, et al., *Mol. Ther.*, 19:172-180 (2011)).

DNA Binding Gel Shift Assays
For gel electrophoresis, synthetic 120 bp dsDNA targets were incubated with indicated oligomers at 37 C in low ionic strength buffer (10 mM NaPi, pH 7.4). The samples were separated on 10% non-denaturing polyacrylamide gels in 1×TBE buffer. The gels were run at 100 V/cm for 1.5 hr. After electrophoresis, the gels were stained with 1×SYBR-Gold (catalog #S11494, Invitrogen) for 10 min, washed 2× with 1×TBE buffer, and then imaged using a gel documentation system (BioDoc-It System). The images were then inverted using Adobe Photoshop 6.0.

Results
To assay for gene editing in a robust and quantitative manner, a transgenic mouse model was utilized with a β-globin/GFP fusion transgene of human β-globin intron 2 carrying a thalassemia-associated IVS2-654 (C→T) mutation embedded within the GFP coding sequence, resulting in incorrect splicing of β-globin/GFP mRNA and lack of GFP expression (Sazani, et al., *Nat. Biotechnol.*, 20:1228-1233 (2002)). PNA-mediated triplex-formation induces DNA repair and recombination of the genomic site with a 60-nucleotide sense donor DNA that is homologous to a portion of the β-globin intron 2 sequence except for providing a wild-type nucleotide at the IVS2-654 position. Via recombination, the splice-site mutation is corrected and expression of functional GFP occurs (FIG. 1A) (McNeer, et al., *Gene Therapy*, 20:658-669 (2013); Bahal, et al., *Curr. Gene Ther.*, 14:331-342 (2014)). Hence, GFP expression provides a direct phenotypic assessment of genome editing frequencies that can be quantified by flow cytometry.

Figure 1B:
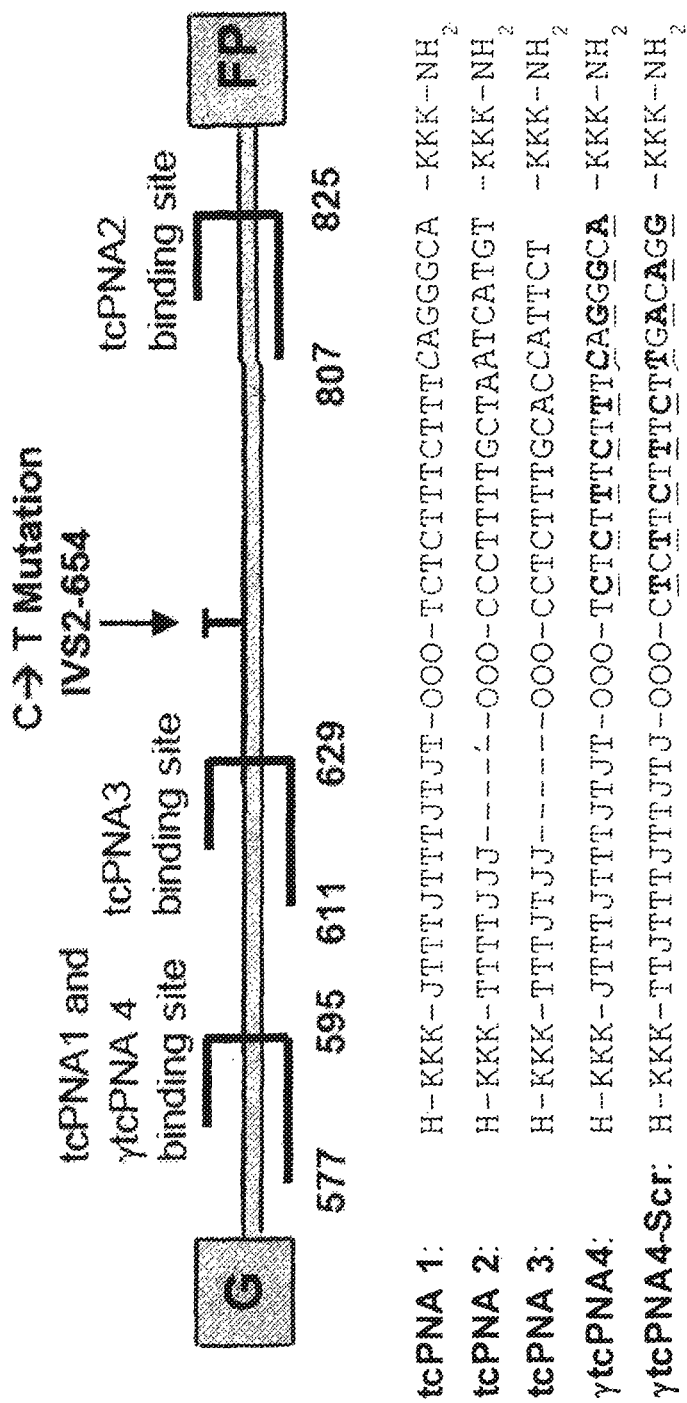
FIG. 1B is an illustration showing tcPNA and γtcPNA oligomers (SEQ ID NOS:33-35, 162, and 158, respectively) designed to bind to the homopurine regions within intron 2 of the human β-globin gene in the vicinity of the thalassemia-associated mutation IVS2-654 (C→T), and a scrambled control sequence (SEQ ID NO:158).
Figure 1C:
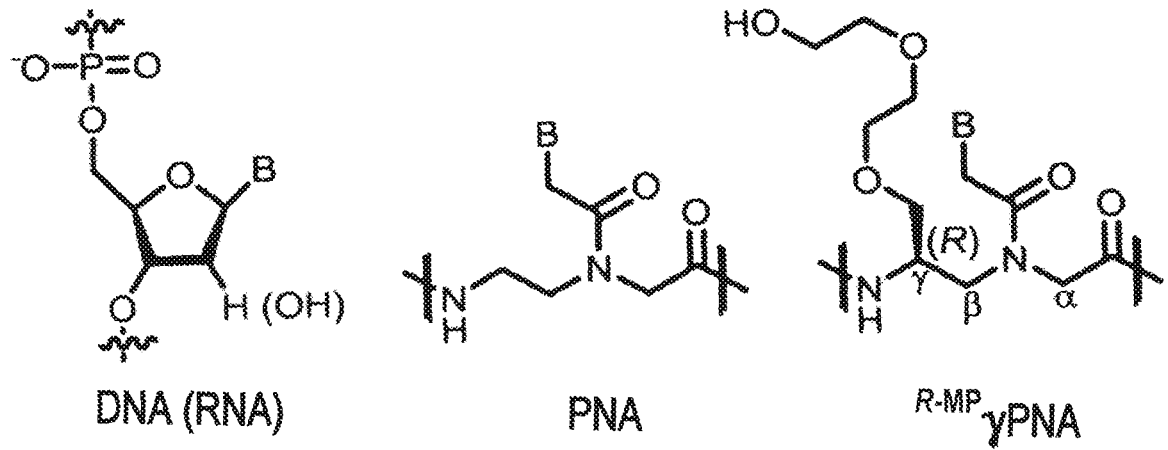
FIG. 1C is the chemical structures of DNA, unmodified PNA and miniPEG gamma PNA ($^{MP}$γPNA) units.

A series of tcPNAs were designed to bind to selected polypurine stretches in the β-globin intron in the vicinity of the IVS2-654 mutation (FIG. 1B). Two of the tcPNAs were synthesized to contain partial substitution with a minipolyethylene-glycol (mini-PEG) group at the γ position ($^{MP}$γPNA) (FIG. 1C, and sequences above). Gamma substitutions in PNAs have been shown to enhance strand invasion and DNA binding affinity in the Watson-Crick binding mode due to helical pre-organization enforced by the modification (Bahal, et al., ChemBioChem, 13:56-60 (2012)). γtcPNA4 matches the sequence of tcPNA1 except that it contains γ units at alternating positions in the Watson-Crick domain (see sequences above). Scrambled γtcPNA (γtcPNA4-Scr) had the same base composition as γtcPNA4 but a scrambled sequence. All tcPNA oligomers were synthesized with 3 lysines at both termini to improve solubility and increase binding affinity to genomic DNA (see sequences above).

Gel shift assays to assess the binding of the tcPNAs to 120-bp DNA duplexes containing the respective target sequences showed that all of the tcPNAs bound specifically to their target sites in duplex DNA under physiological conditions. No binding was seen in the case of the scrambled sequence γtcPNA4-Scr oligomer.

Poly(lactic-co-glycolic acid) (PLGA) NPs can effectively deliver PNA/donor DNA combinations into primary human and mouse hematopoietic cells with essentially no toxicity (McNeer, et al., Gene Therapy, 20:658-669 (2013); Schleifinan, et al., Mol. Ther.—Nucleic Acids, 2:e135 (2013); McNeer, et al., Mol. Ther., 19:172-180 (2011)). Here, tcPNAs and donor DNAs, at a molar ratio of 2:1, were incorporated into PLGA NPs. The NP formulations were evaluated by scanning electron microscopy (SEM) and dynamic light scattering (DLS). All the NPs exhibited sizes within the expected range and showed a uniform charge distribution as calculated from their zeta potential.

TABLE 1

Hydrodynamic diameter of formulated PLGA nanoparticles measured using dynamic light scattering in PBS buffer.

| Sample | Diameter (nm) |
| --- | --- |
| tcPNA 1/donor DNA | 293.1 ± 6.1 |
| tcPNA 2/donor DNA | 610.6 ± 27.7 |
| tcPNA 3/donor DNA | 373.0 ± 4.3 |
| γtcPNA 4/donor DNA | 291.0 ± 4.7 |
| γtcPNA 4-Scr/donor DNA | 458.6 ± 8.2 |
| Donor DNA | 907.3 ± 200 |

TABLE 2

Zeta potential of formulated PLGA nanoparticles.

| Sample | Zeta Potential (mV) |
| --- | --- |
| tcPNA1/donor DNA | −24.6 ± 0.4 |
| tcPNA2/donor DNA | −16.5 ± 0.5 |
| tcPNA3/donor DNA | −23.6 ± 0.5 |
| γtcPNA4/donor DNA | −23.4 ± 0.5 |
| γtcPNA 4-Scr/donor DNA | −19.5 ± 1.3 |
| Donor DNA | −29.1 ± 0.4 |

Figure 1D:
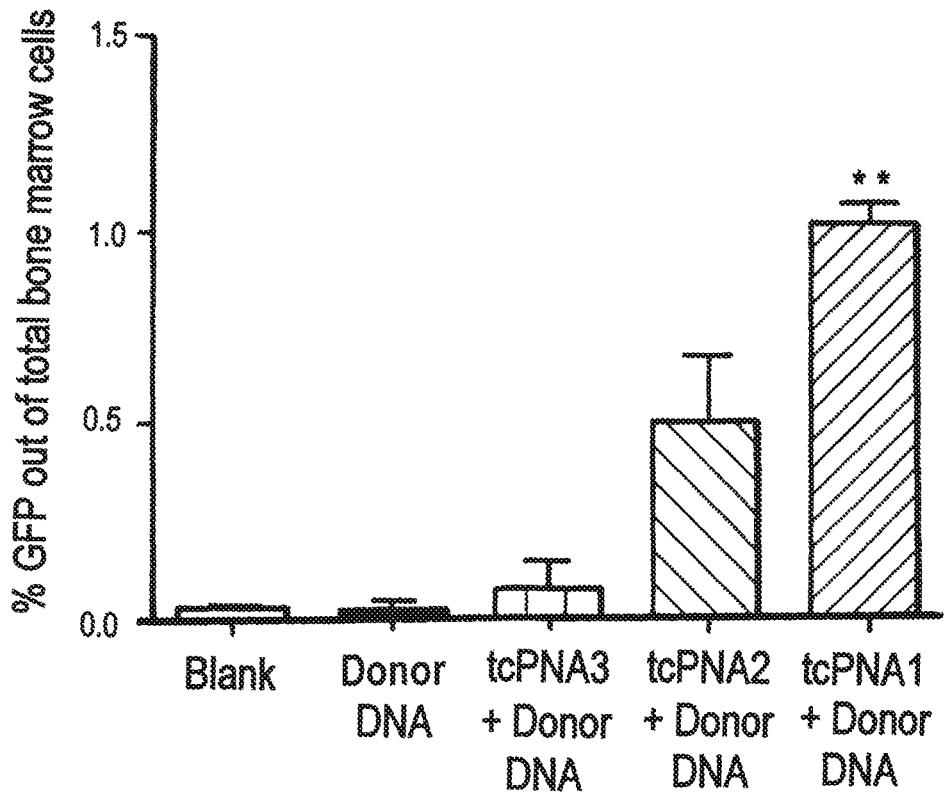
FIG. 1D is a bar graph showing gene correction of the IVS2-654 (C→T) mutation within the β-globin/GFP fusion gene in mouse bone marrow cells treated ex vivo with blank NPs and NPs containing donor DNA (SEQ ID NO:65) alone or in combination with tcPNA3 (SEQ ID NO:35), tcPNA2 (SEQ ID NO:34), or tcPNA1 (SEQ ID NO:33). The % GFP+ cells among mouse bone marrow cells was determined by flow cytometry and indicates successful gene editing. Data are shown as mean±s.e., n=3; statistical analysis was performed with student's t-test, asterisk, p<0.05.
Figure 1E:
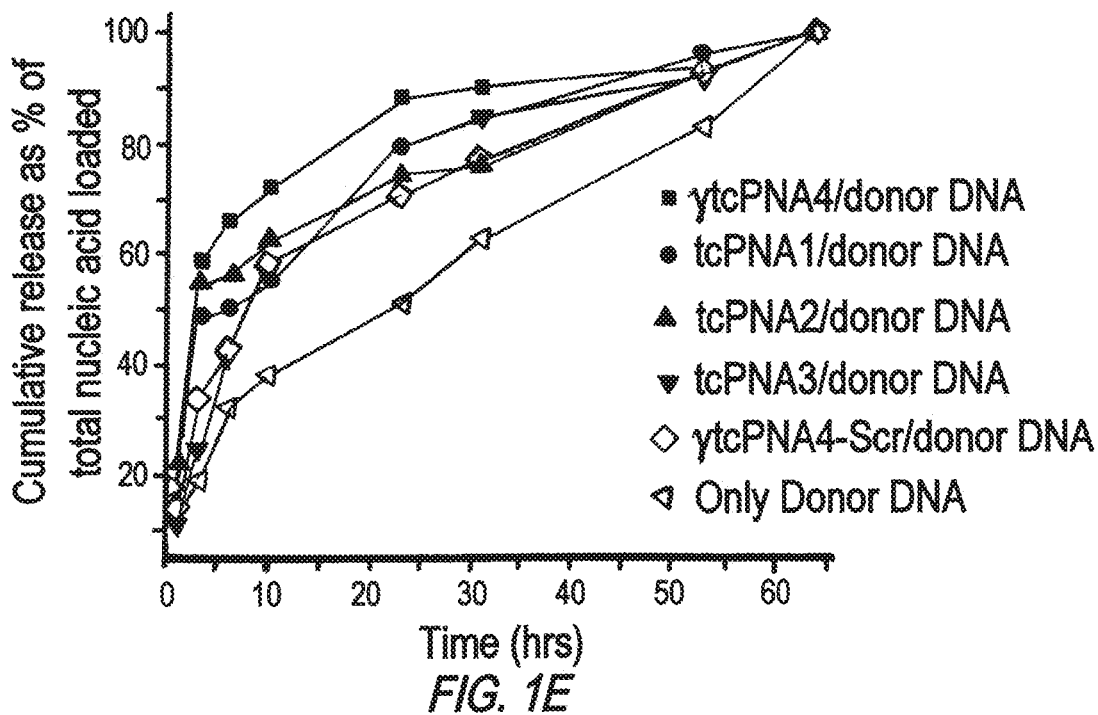
FIG. 1E is a line graph showing release of total nucleic acids (PNAs in combination with donor DNA (SEQ ID NO:65): γtcPNA4 (SEQ ID NO:162), tcPNA1 (SEQ ID NO:33), tcPNA2 (SEQ ID NO:34), tcPNA3 (SEQ ID NO:35) or γtcPNA4-Scr (SEQ ID NO:158); or DNA donor (SEQ ID NO:65) alone) from PLGA nanoparticles during incubation at 37° C. in PBS. At 64 hrs, the residual nucleic acid in the NP pellet was extracted and the total nucleic acid load was calculated as a sum of absorbance obtained from the pellet and supernatant.

Nucleic acid release profiles in aqueous solution were consistent with previous studies, indicating no deleterious impact of the γ modifications on release from NPs (FIG. 1E).

Example 2: γtcPNA Edit Bone Marrow Cell Genome Ex Vivo

Materials and Methods

Ex Vivo Experiments

Bone marrow cells were harvested by flushing of femurs and tibias from β-globin/GFP transgenic mice with Roswell Park Memorial Institute (RPMI)/10% FBS media. Two mg/ml of nanoparticles were used to treat approximately 300,000-500,000 cells for 48 hr in RPMI/10% FBS media containing glutamine, in triplicate samples. After 48 hr, cells were fixed by using 4% paraformaldehyde, and flow cytometry analyses were performed. Cells treated with blank nanoparticles were included as a control.

For CD117+ cell experiments, Iscove's Modified Dulbecco's Media (IMDM) media containing insulin (10 ng/ml), FCS (10%) and erythropoietin (1 U/ml) was used to culture CD117+ cells after isolation using magnetic separation. Where indicated, 3 μg/ml of SCF (Recombinant murine SCF, catalog #250-03, PeproTech, Rocky Hill, N.J.;) was added prior to nanoparticle treatment. 2 mg/ml of NPs were used to treat 50,000-100,000 CD117+ cells in triplicate for 48 hrs in the above media, followed by flow cytometry analyses as above. Inhibitors were used at concentrations of 200 nM (dasatinib), 1.0 μM (MEK162) and 3.0 μM (BKM120). Dasatanib was obtained from Cayman Chemical (Ann Arbor, Mich.; item #11498) and dissolved according to manufacturer's protocol. MEK162 and BKM120 were obtained from Dr. Harriet Kluger, Yale University.

Comet Assay 400,000 bone marrow cells/well were plated on 6-well plates in 1 mL media, then treated with 2 mg/mL of PLGA nanoparticles with or without PNA and donor DNA. After 48 hours, cells were scraped and harvested, and prepared using the Trevigen Comet Assay kit per manufacturer's protocol (Trevigen, Gaithersburg, Md.). Briefly, cells were suspended in agarose, added to comet slides, allowed to set, incubated 1 hr in lysis solution, placed in electrophoresis solution for 30 min, then run at 21 V for 45 min, placed in acetate solution for 30 min, transferred to 70% ethanol solution for 30 min, dried, stained with Sybr Green for 30 min, then visualized using an EVOS microscope. TriTek Comet Score freeware was used to analyze images.

Results

Figure 1F:
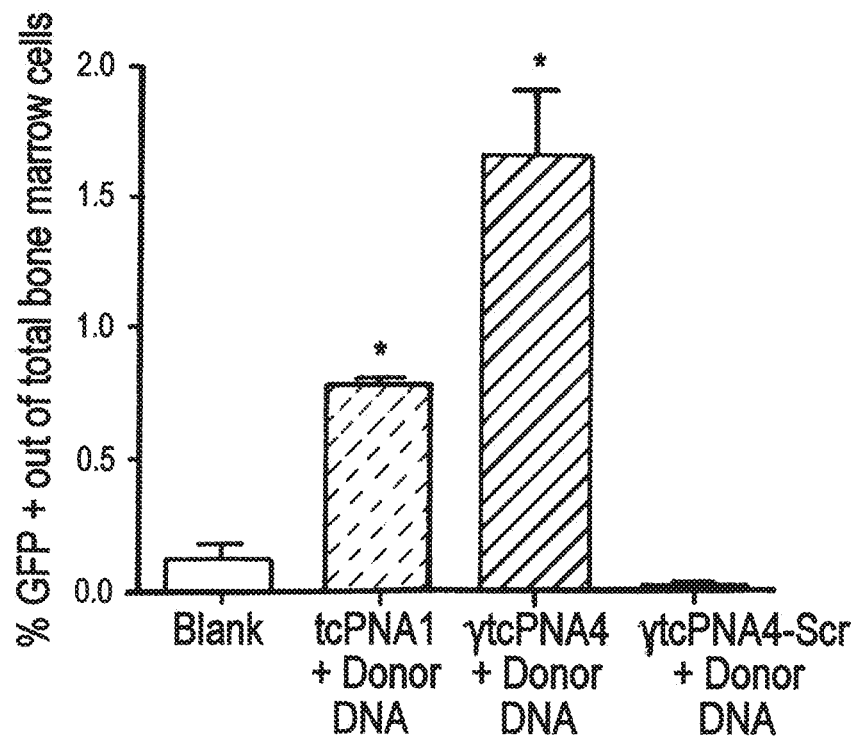
FIG. 1F is a bar graph showing % GFP+ cells determined by flow cytometry among mouse bone marrow cells (from β-globin/GFP transgenic mice) after ex vivo treatment with PLGA NPs containing tcPNA1 (SEQ ID NO:33), γtcPNA4 (SEQ ID NO:162), or γtcPNA4-Scr (SEQ ID NO:158) plus donor DNAs (SEQ ID NOS:65). Replicates and statistics as above for FIG. 1D.

Bone marrow cells harvested from β-globin/GFP transgenic mice were treated ex vivo with PLGA NPs containing tcPNA1/donor DNA, tcPNA2/donor DNA and tcPNA3/donor DNA combinations. After 48 hr, the percentage of GFP+ (corrected) cells was quantified via flow cytometry, revealing that tcPNA1/donor DNA, tcPNA2/donor and tcPNA3/donor DNA-containing NPs induced genome modification at frequencies of ~1.0%, 0.51% and 0.1% respectively (FIG. 1D). The higher gene editing activity of tcPNA1 is likely due to its longer Hoogsteen binding domain, as previously observed (Schleifman, et al., Chem. Biol. (Cambridge, Mass., U.S.), 18:1189-1198 (2011))). NPs containing the γ-substituted tcPNA (γtcPNA4) and donor DNA yielded significantly higher gene modification (1.62%) (FIG. 1F), showing that the $^{MP}$γ substitutions confer increased biological activity that correlates with their improved binding properties. NPs with the γ-substituted but scrambled sequence γtcPNA4-Scr produced no modification (FIG. 1F).

Figure 1G:
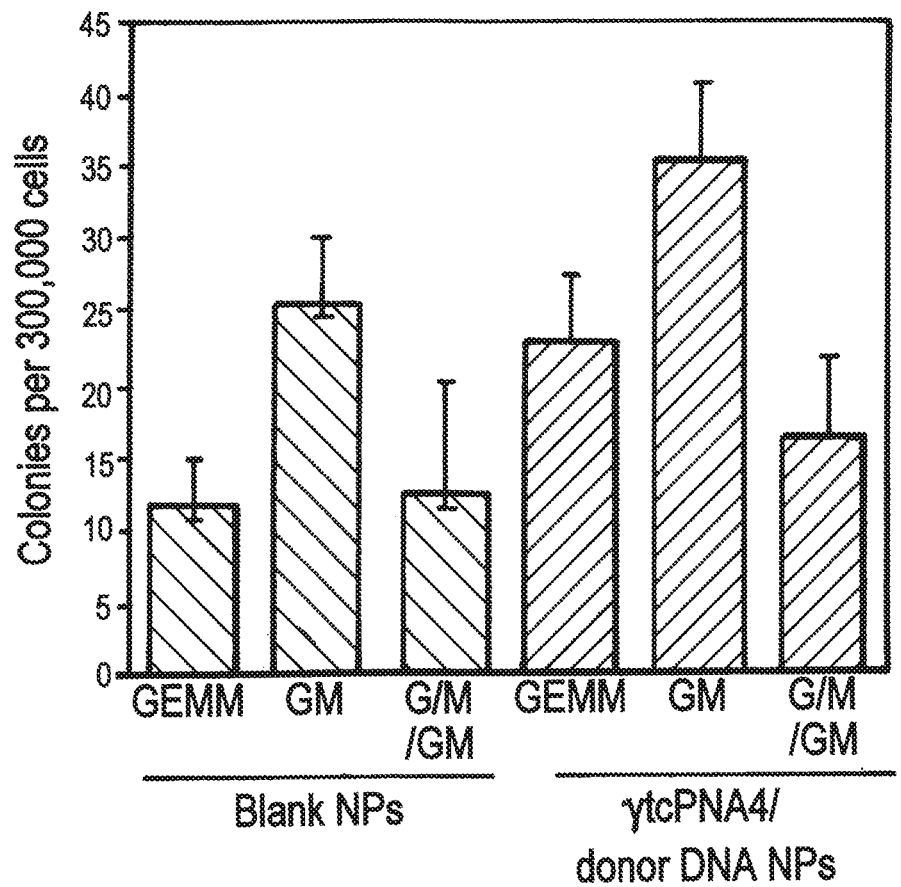
FIG. 1G is a bar graph showing mouse total bone marrow cells were treated with either blank NPs or NPs containing γtcPNA4 (SEQ ID NO:162) and donor DNA (SEQ ID NO:65) and were plated for a colony-forming cell assay in methylcellulose medium with selected cytokines for growth of granulocyte/macrophage colonies (CFU-G, CFU-M and CFU-GM) or combined colonies (CFU-GEMM, granulocyte, erythroid, monocyte/macrophage, megakaryocyte. Numbers of each type of colony per 300,000 plated cells are shown. Data are shown as mean±s.d., n=3.
Figure 1H:
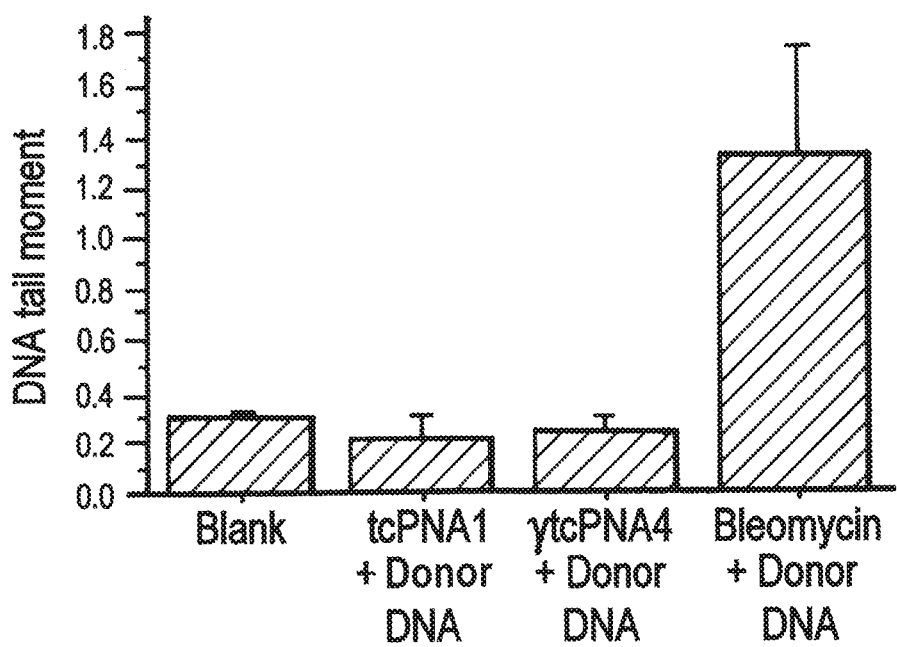
FIG. 1H is a bar graph showing the results of a comet assay to measure DNA breaks in NP-treated bone marrow cells. Cells were treated with NPs containing either tcPNA1/donor DNA (SEQ ID NOS:33 and 65), γtcPNA4/donor DNA (SEQ ID NOS:162 and 65), or bleomycin/donor DNA (SEQ ID NO:65), as indicated. DNA tail moment provides a measurement of the extent of breaks. Data are shown as mean±s.e., n=3.

Bone marrow cells treated with either blank NPs or NPs containing γtcPNA4/donor DNA were plated in methylcellulose medium supplemented with selected cytokines for growth of granulocyte/macrophage colonies (CFU-G, CFU-M and CFU-GM) or combined colonies (CFU- GEMM, granulocyte, erythroid, monocyte/macrophage, megakaryocyte). The two sets of treated cells formed myeloid and erythroid colonies at similar frequencies, indicating that treatment with γtcPNA4 and donor DNA does not impair the ability of the progenitor cells to proliferate and differentiate (FIG. 1G). Sequencing analysis of genomic DNA from selected GFP-positive methylcellulose colonies confirmed the presence of the targeted gene modification in the β-globin/GFP transgene at the IVS2-654 base pair. In other assays for toxicity, there was no increase in DNA double-strand breaks (DSBs) in the cells treated with γtcPNA4/donor DNA-containing NPs compared to blank NPs based on a single-cell gel electrophoresis assay (Comet assay) (FIG. 1H) and there was no induction of the inflammatory cytokines, TNF-alpha or interleukin-6 (IL-6), in the treated bone marrow cells, consistent with prior work with NPs containing standard PNAs (McNeer, et al., *Gene Therapy*, 20:658-669 (2013); Schleifman, et al., *Mol. Ther.—Nucleic Acids*, 2:e135 (2013); McNeer, et al., *Mol. Ther.*, 19:172-180 (2011)).

Figure 2A:
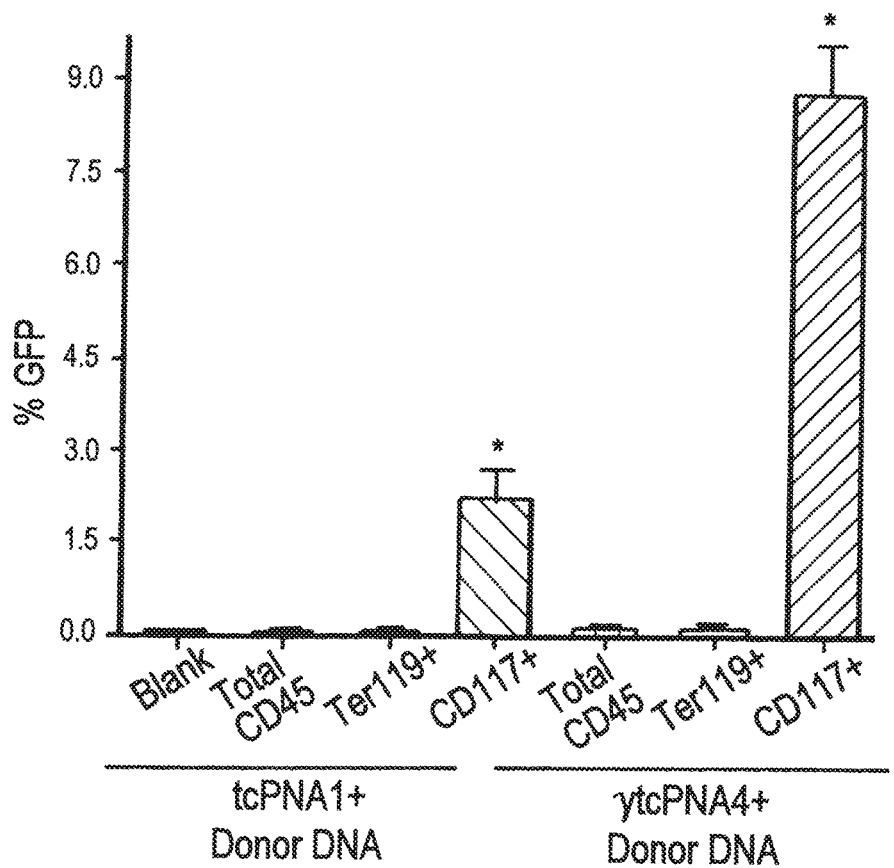
FIG. 2A is a bar graph showing % GFP expression in treated mouse bone marrow cells based on selected hematopoietic cell surface markers. Total bone marrow was treated with NPs containing either tcPNA1/donor DNA (SEQ ID NOS:33 and 65) or γtcPNA4/donor DNA (SEQ ID NOS:162 and 65), and then the cells were stained using antibodies specific for the indicated markers and assayed by flow cytometry for marker and GFP expression. Data are shown as mean±s.e., n=3; statistical analysis was performed with student's t-test, asterisk, p<0.05.

Example 3: Gene Modification is Elevated by γtcPNAs in CD117+ Hematopoietic Cells Materials and Methods
Cell Sorting and Flow Cytometry
BD Bioscience kit catalog #558451 (BDImag™ Hematopoietic Progenitor Stem Cell Enrichment Set—DM) was used to isolate CD117 cells. Enrichment for CD117 was confirmed by flow cytometry. CD117+ enriched cells were labeled with CD117-APC (BD Pharmingen™ catalog #558451) antibody. Cells were co-labelled with control IgG antibody (BD Pharmingen™ catalog #555746) for gating purposes. To quantify GFP expression, after CD117 co-labelling, flow cytometry was performed using FACScaliburS by resuspending cells in PBS/1% FBS where green fluorescent cells are measured in the F11 channel and APC stained cells are in the F14 channel Antibodies for other markers were Ter119 (BD Pharmingen™ catalog #561033) and CD45 APC (BD Pharmingen™ catalog #561018).
Results
Previous work indicated that there might be increased activation of PNA-mediated DNA repair in certain colony-forming progenitors (McNeer, et al., *Gene Therapy*, 20:658-669 (2013)). To test this, whole bone marrow cells were treated with either blank NPs, NPs containing tcPNA1/donor DNA, or NPs containing γtcPNA4/donor DNA. Two days later, flow cytometry was performed to assess the frequency of GFP+ cells within selected sub-populations. Substantially elevated gene editing was observed in CD117+ cells compared to the total CD45+ cell population (FIG. 2A), with a frequency of 8.6% in CD117+ cells after a single treatment with the γtcPNA4/donor DNA NPs. The less potent tcPNA1/donor DNA NPs still yielded an elevated correction frequency of 2.1% in the CD117+ cells. The Ter119+ population, which includes more mature cells committed to the erythroid lineage, showed minimal susceptibility to gene editing with either PNA.

Figure 2B:
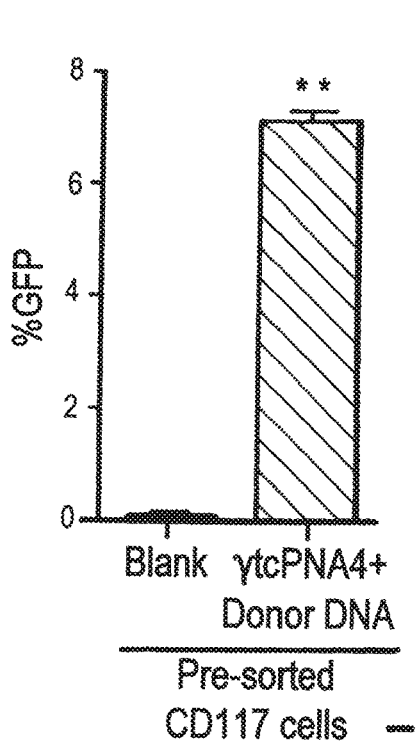
FIG. 2B is a bar graph showing % GFP expressing CD117 (c-Kit+) cells after ex vivo treatment with NPs carrying γtcPNAs and donor DNAs (SEQ ID NOS:162 and 65) versus with blank NPs. Data are shown as mean±s.e., n=3; statistical analysis was performed with student's t-test, asterisk, p<0.05.

Next, the predisposition of CD117+ cells to increased gene editing was tested by first sorting for CD117+ cells prior to treatment with the NPs (FIG. 2B). An elevated percentage of modification (7.2%) was again seen in the CD117+ cells after a single treatment (FIG. 2B).

Example 4: The c-Kit Pathway Mediates Increased Gene Modification in CD117+ Cells CD117 (also known as mast/stem cell growth factor receptor or proto-oncogene c-Kit protein) is a receptor tyrosine kinase expressed on the surface of hematopoietic stem and progenitor cells as well as other cell types. Stem cell factor (SCF), the ligand for c-Kit, causes dimerization of the receptor and activates its tyrosine kinase activity to trigger downstream signaling pathways that can impact survival, proliferation, and differentiation.

To explore the mechanism of the increased gene editing in CD117+ cells, the requirement of c-Kit-dependent signaling for elevated gene correction or whether CD117 simply serves as a marker for the increased susceptibility to gene editing was distinguished. To do this, γtcPNA4/donor DNA NP-mediated gene editing was assayed in pre-sorted CD117+ cells in the presence or absence of selected kinase inhibitors (FIG. 2D). Dasatinib, which inhibits the c-Kit kinase in addition to the BCR/Abl and Src kinases, reduced the gene editing from 7% to 2.0%. Inhibitors of signaling factors downstream of c-Kit, including mitogen/extracellular signal-regulated kinase (MEK) (Binimetinib; MEK162) and phosphatidylinositol-3-kinase (PI3K) (BKM120), also decreased the gene editing frequencies in CD117+ cells to 2.6% and 4.1%, respectively (FIG. 2D).

Figure 2C:
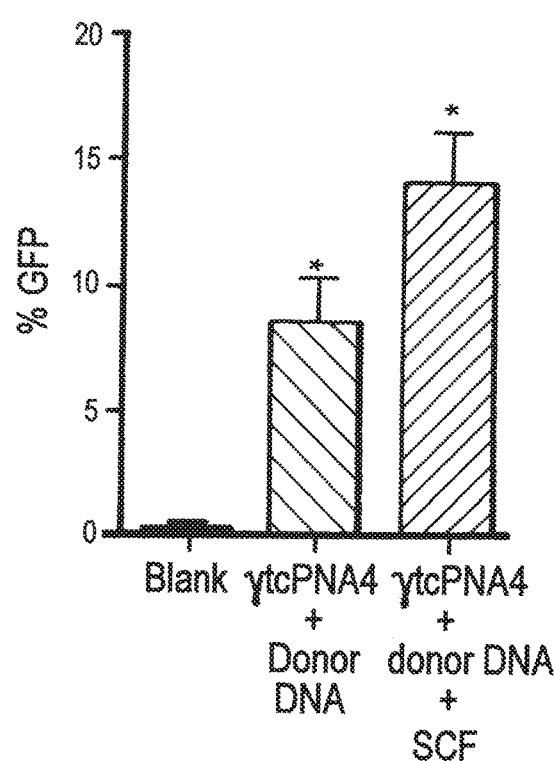
FIG. 2C is a bar graph showing % GFP expressing CD117+ cells from β-globin/GFP transgenic mice after ex vivo treatment with NPs containing γtcPNA4/donor DNA (SEQ ID NOS:162 and 65) with or without prior treatment with the c-Kit ligand, SCF. Data are shown as mean±s.e., n=3; statistical analysis was performed with student's t-test, asterisk, p<0.05.
Figure 2D:
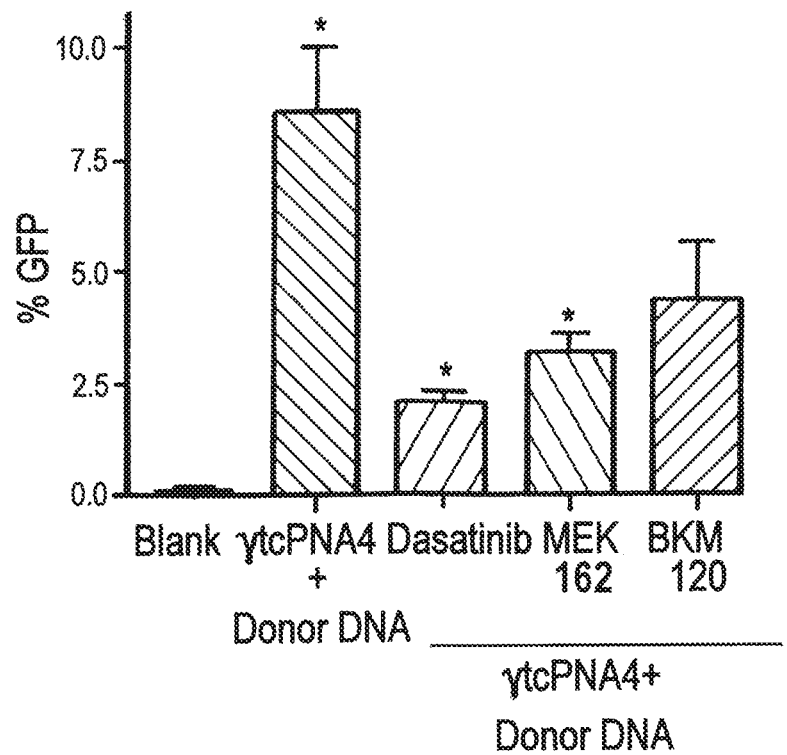
FIG. 2D is a bar graph showing % GFP expressing CD117+ cells isolated from β-globin/GFP transgenic mice after ex vivo treatment with NPs containing γtcPNA4/donor DNA (SEQ ID NOS:162 and 65) in the presence or absence of selected c-Kit pathway kinase inhibitors: dasatinib (inhibits c-Kit), MEK162 (inhibits mitogen/extracellular signal-regulated kinase, MEK) and BKM120 (inhibits phosphatidylinositol-3-kinase, PI3K). Data are shown as mean±s.e., n=3; statistical analysis was performed with student's t-test, asterisk, p<0.05.

On the other hand, when the CD117+ cells were treated with the c-Kit ligand, SCF, a significant increase in γtcPNA4/donor DNA-mediated gene editing (up to almost 15%) was observed (FIG. 2C). These results indicate that the SCF/c-Kit signaling can enhance gene editing and identify SCF as a potential agent to stimulate PNA-mediated gene editing.

Example 5: Expression of DNA Repair Genes are Increased Upon Activation of the c-Kit+ Pathway Materials and Methods
Microarray Analysis
Microarray analyses were performed on CD117+ and CD117-cells obtained from bone marrow of three separate β-globin/GFP mice at Yale Center of genomic analysis at Yale west campus. Each replicate cell sample was obtained from a separate mouse. RNA was extracted from $2 \times 10^6$ for each sample using the RNeasy Mini Plus kit from Qiagen, as per the manufacturer's protocol. Following DNase treatment, total RNA was sequenced and analyzed at the Yale Center for Genome Analysis. Heat maps were generated using variance stabilizing transformations of the count data on the basis of a parametric fit to the overall mean dispersions.
RT-PCR Analysis
Cells were harvested, pelleted, and stored frozen in RNA stabilization reagent (Qiagen), until ready for RNA extraction. RNA was extracted from the cell pellets using the RNAeasy Mini Plus kit from Qiagen, as per the manufacturer's protocol. The Invitrogen SuperScript III kit was used to generate cDNA from the RNA, as per the manufacturer's protocol, using 500 ng of RNA per reaction. PCR reactions contained cDNA, 20% Betaine, 0.2 mM dNTPS, Advantage 2 Polymerase Mix, 0.2 µM of each primer, 2% Platinum Taq, and Brilliant SYBR Green. Primers and ROX reference dye were obtained from Stratagene and analysis was conducted using a Mx3000p realtime cycler. Cycler conditions were 94° C. for 2 min, 40 cycles of 94° C. 30 s/50° C. 30 s/72° C. 1 min, then 95° C. 1 min. Relative expression were calculated using the 2ΔΔCt method (Ct<36) and then normalized. Mouse BRCA2 primers were designed using Primer3 database: BRCA2-3F: 5' GTTCAT-AACCGTGGGGCTTA (SEQ ID NO:203) and BRCA2-3R: 5' TTGGGAAATTTTTAAGGCGA (SEQ ID NO:176). For BRCA2 data analysis GAPDH were used as control using following primers: 5'-TGATGACATC AAGAAGGTGGT-GAAG-3' (SEQ ID NO:177) and 5'-TCCTTGGAGG CCATGTGGGCCAT-3' (SEQ ID NO:178). For RAD51 analysis, Rad51 mRNA was quantified by using TaqMan® Gene Expression Assay (Life technologies, Mm00487905_m1) kit and using gene 18S (Life technologies, Mm03928990_g1) as a control.

Western Blot Analysis

CD117+ and CD117-cells were isolated from β-globin/GFP mice and protein was extracted with Radio-Immunoprecipitation Assay (RIPA) lysis buffer. 50-100 µg total protein was run on SDS/PAGE gels and transferred to nitrocellulose membranes. Antibodies used were: Anti-BRCA2 (Ab-1) mouse mAb (EMD Millipore, OP95-100 ug) anti-RAD51-antibody (Santa Cruz biotechnology, SC 8349)).

Results

The increased gene editing in the c-Kit+(CD117) cells was not explained by differential uptake of the NPs, as there were no detectable differences in uptake across several bone marrow cell sub-populations. Gene expression patterns in the c-Kit+ cells were evaluated for increased DNA repair gene expression. Gene expression analyses were performed on sorted CD117+ and CD117-cells from whole bone marrow from the β-globin/GFP mice using Illumina arrays.

TABLE 3

Selected genes that were up-regulated in CD117+ enriched cells as compared to CD117- cells with increased expression of transcripts expected to be associated with CD117 including c-Kit, VEGF (vascular endothelial growth factor), Sca1 (stem cell antigen-1), and Erdr1 (erythroid differentiation regulator 1).

| Gene | CD117 Negative | CD117 Positive | Fold Change CD117 negative/ CD117 positive | P value |
| --- | --- | --- | --- | --- |
| c-Kit | 593.98 | 2368.32 | −3.98715 | 0.0051 |
| VEGF | 344.34 | 1109.97 | −3.22341 | 0.0084 |
| Sca1 | 208.24 | 490.86 | −2.35711 | 0.0126 |
| Erdr1 | 1011.81 | 2760.26 | 2.72805 | 0.0319 |

Figure 2E:
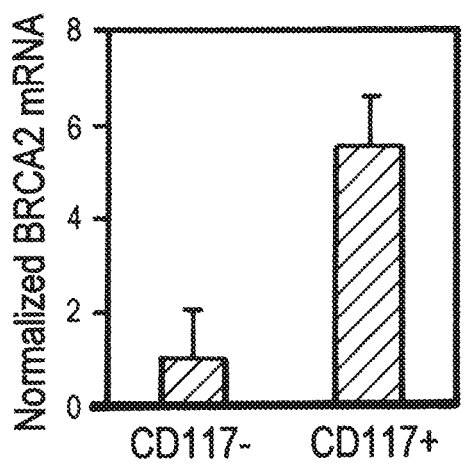
FIGS. 2E and 2F are bar graphs showing qPCR determination of mRNA expression levels of BRCA2 (2E) and Rad51 (2I) in CD117- and CD117+ cells.
Figure 2F:
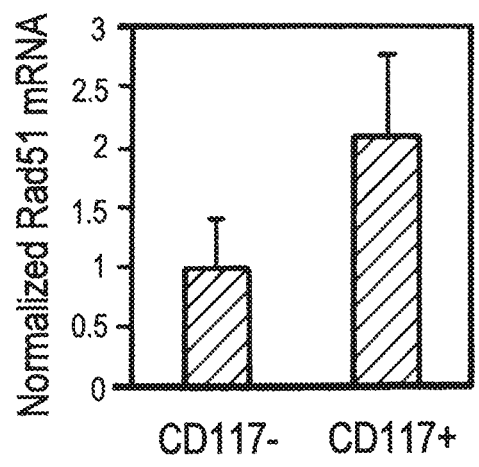

Numerous genes involved in DNA repair, including BRCA1, BRCA2, Rad51, ERCC2, XRCC2, XRCC3, showed higher levels of expression in CD117+ cells. Two key HDR genes expected to play a role in PNA-induced recombination, BRCA2 and Rad51, were among the upregulated genes detected by the array. Increased expression of these genes was confirmed in CD117+ cells at the mRNA level by quantitative RT-PCR (FIGS. 2E and 2F) and at the protein level by western blot.

Figure 2G:
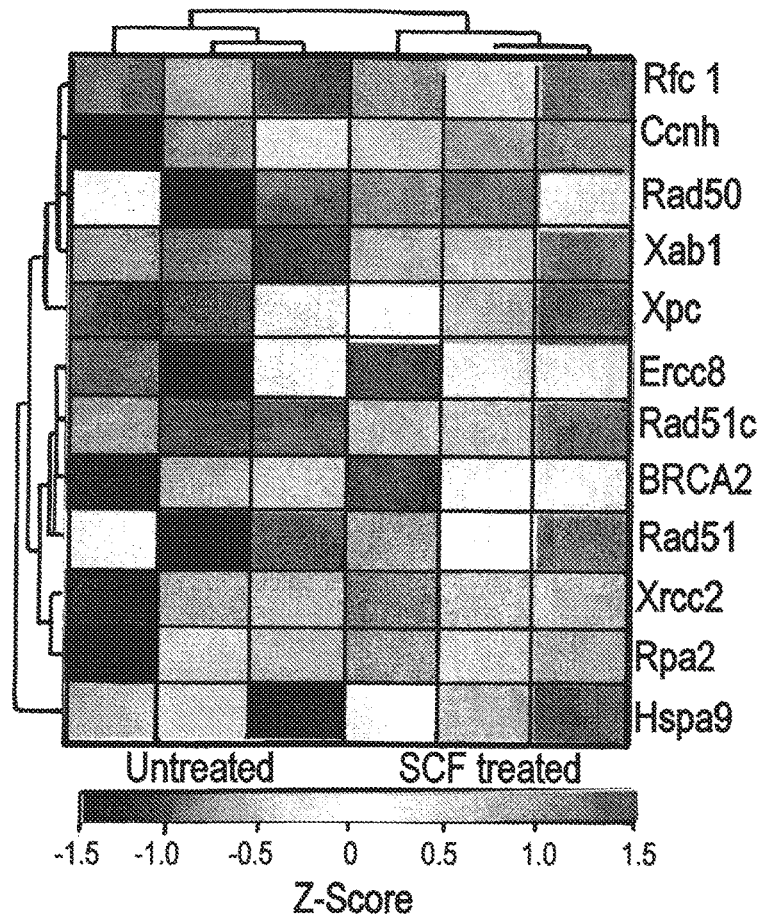
FIG. 2G is a heat map showing up-regulated genes involved in DNA repair pathways in CD117+ cells with or without treatment with SCF; rows are clustered by Euclidean distance measure.

Based on these findings, activation of the c-Kit pathway by SCF treatment to further increase DNA repair gene expression was examined Gene expression profiling on SCF-treated CD117+ cells versus untreated CD117+ cells showed additional up-regulation of numerous DNA repair genes (FIG. 2G), again including Rad51 and BRCA2.

Example 6: The c-Kit Pathway Induces Functionally Elevated DNA Repair

Materials and Methods

Reporter Gene Assay for Homology-Dependent Repair

An inactivating I-Sce1 site was cloned 56 amino acids into the firefly luciferase open reading frame under the control of a CMV promoter. The reporter construct also contains a promoterless luciferase gene used as a template for homologous recombination. A double-strand break in the luciferase reporter is created by in vitro digestion with the I-Sce I restriction enzyme (NEB #R0694L). Plasmid DNA was digested with I-Sce 1 for 1 hour at 37° C. at a ratio of 10 units enzyme to 1 µg DNA and then the enzyme was inactivated at 65° C. for 20 minutes. The linearization of the plasmid was confirmed for each digestion via gel electrophoresis and the linear plasmid was purified using the Qiagen Qiaquick spin columns. After separation CD117+ and CD117-cells from bone marrow of β-globin/GFP transgenic mice, cells were transfected using the Lonza 2b Nucleofector Device. $5 \times 10^5$ cells were transfected with 1 µg of either the luciferase reporter vector or a positive control firefly luciferase expression vector, along with 50 ng of a renilla luciferase expression plasmid as a transfection efficiency control. All transfections were performed in triplicate. After transfection the cells were plated at a density of $5 \times 10^5$ cells/ml in 12-well plates. After 24 hours incubation post transfection, luciferase activity was measured using the Promega Dual Luciferase Assay Kit. In each sample firefly luciferase activity was normalized to the renilla luciferase transfection control. Reporter reactivation was calculated as a ratio of normalized firefly luciferase activity in the cells transfected with the reporter plasmid to the positive control.

Results

Figure 2H:
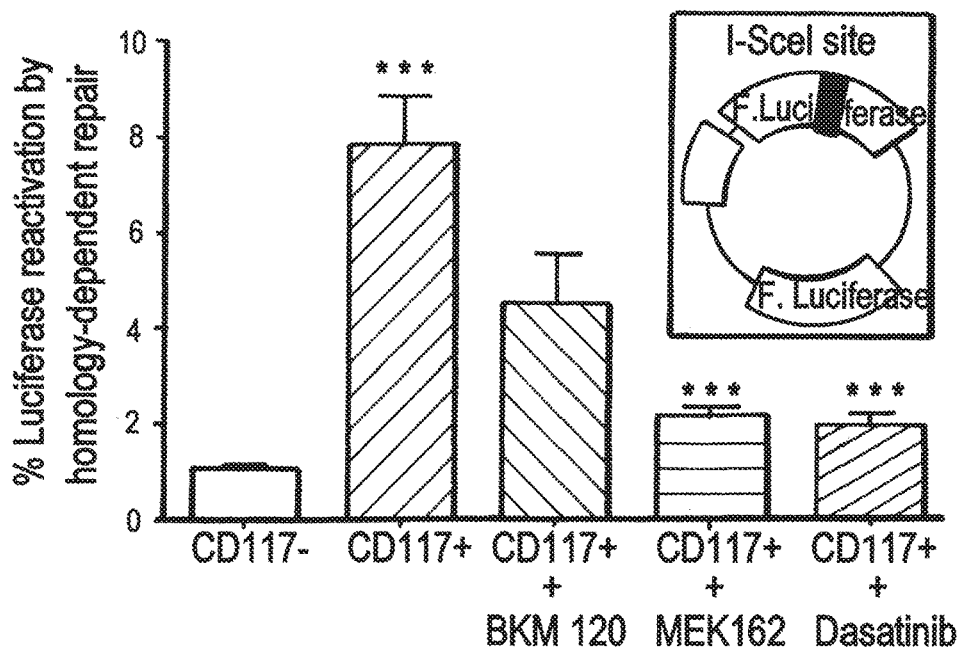
FIG. 2H is a bar graph showing the results of a gene assay for homology-dependent repair (HDR) activity in the presence or absence of selected c-Kit pathway kinase inhibitors: dasatinib (inhibits c-Kit), MEK162 (inhibits mitogen/extracellular signal-regulated kinase, MEK) and BKM120 (inhibits phosphatidylinositol-3-kinase, PI3K). Inset shows a diagram of the luciferase reporter gene assay for repair of a nuclease-induced double-strand break by homology-dependent repair (HDR). Luciferase expression occurs only after homologous recombination and is scored as % reactivation of the DSB-damaged plasmid, normalized to a transfection control.
Figure 2I:
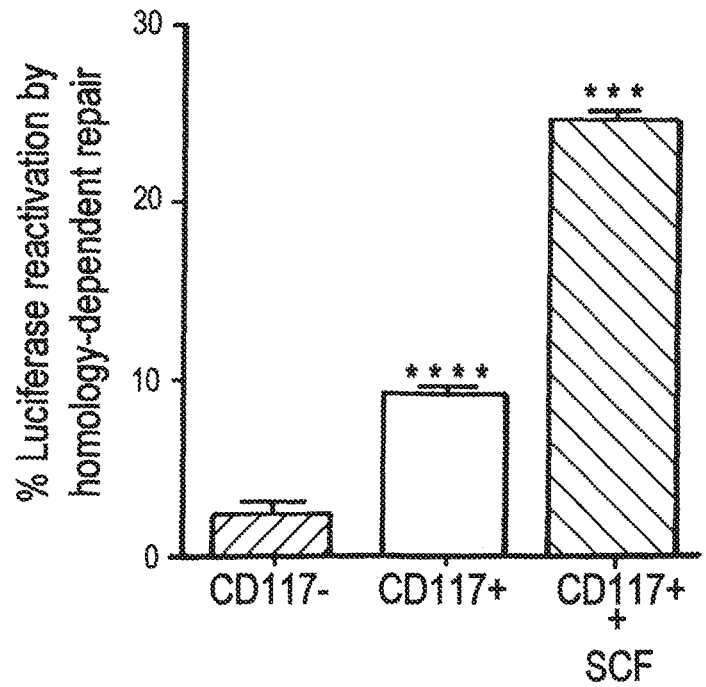
FIG. 2I is a bar graph showing the results of an HDR assay in CD117+ cells with or without the addition of SCF. Data are shown as mean±s.e., n=3; statistical analysis was performed with student's t-test, asterisk, p<0.05.
Figure 2J:
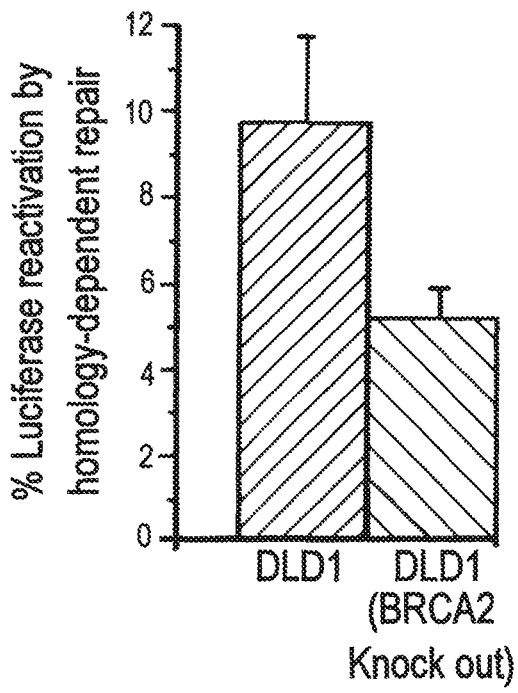
FIG. 2J is a bar graph showing the results of an HDR assay in DLD-1 cells either proficient or deficient in the homology dependent repair factor BRCA2 as a validation of the assay. Data are shown as mean±s.e., n=3; statistical analysis was performed with student's t-test, asterisk, p<0.05.

To test whether the above increases in DNA repair gene expression could be correlated with functional differences in DNA repair, a luciferase-based assay was used to quantify repair of DNA double-strand breaks (DSBs) by HDR. In this assay, repair of a DSB in a reporter plasmid via intramolecular homologous recombination creates ("reactivates") a functional luciferase gene (FIG. 2H), and so the assay provides a measure of HDR capacity (FIG. 2J). The results show increased luciferase reactivation in CD117+ compared to CD117-cells (FIG. 2H). The repair activity in the CD117+ cells was diminished by treatment with the kinase inhibitors MEK162, BKM120 and dasatnib (FIG. 2H); conversely, it was further boosted by SCF treatment (FIG. 2I). These results indicate that a functional c-Kit signaling pathway mediates increased HDR.

Example 7: In Vivo Gene Editing by Intravenous Injections of PNA/DNA NPs is Enhanced by SCF Treatment Materials and Methods Mouse Models and In Vivo Treatments All animal use was in accordance with the guidelines of the Animal Care and Use Committee of Yale University and conformed to the recommendations in the Guide for the Care and Use of Laboratory Animals (Institute of Laboratory Animal Resources, National Research Council, National Academy of Sciences, 1996).

The β-globin/GFP transgenic mice were obtained from Ryszard Kole, University of North Carolina (Sazani, et al., Nat. Biotechnol., 20:1228-1233 (2002)). For treatment of the mice, where indicated SCF (15.6 ug per mouse, Recombinant Mouse SCF, carrier-free, R&D catalog #455-mc-050/CF) was injected intraperitoneally 3 hrs prior to treatment with 4 mg of NPs in 150 µl PBS delivered via retro-orbital intravenous injection. In some cases, mice were sacrificed 48 hrs after the NP injections and bone marrow and spleen cells were harvested for further analysis. The bone marrow and spleen cells (500,000 each) were co-labelled with APC conjugated antibodies as described above and flow cytometry was performed as above. For deep sequencing analyses, CD117+ cells were isolated based on magnetic separation methods according to BD Bioscience protocol (BDImag™

Hematopoietic Progenitor Stem Cell Enrichment Set—DM), and genomic DNA from three mice was pooled followed by sequence analysis as described (McNeer, et al., *Gene Therapy*, 20:658-669 (2013)).

The IVS2-654 β-thalassemic mice were also obtained from Ryszard Kole, University of North Carolina (Svasti, et al., *Proc Natl Acad Sci USA*, 106:1205-1210 (2009)). For treatment of the mice, where indicated SCF (15.6 ug per mouse, Recombinant Mouse SCF, carrier-free, R&D catalog #455-mc-050/CF) was injected intraperitoneally 3 hrs prior to treatment with 4 mg of NPs in 150 µl PBS delivered via retro-orbital intravenous injection. Each mouse received 4 treatments given at 48 hr intervals. Mice were anesthetized with isoflurane followed by retro-orbital bleeding (~100 µL) using ethylenediaminetetraacetic acid-treated glass capillary tubes. The blood was evacuated into tubes with 5 µL of 0.5 M EDTA acid in heparinized coated tubes. Complete blood counts were performed using a Hemavet 950FS (Drew Scientific, Oxford, Conn.) according to the manufacturer's protocol. Slides containing blood smears were stained with Wright and Giemsa stain for microscopy. Methylene blue staining was used for reticulocyte counts. Spleen images and weights were taken after selected mice were sacrificed on day 36 after the last treatment. Harvested spleens were fixed in 10% neutral buffered formalin and processed by Yale Pathology Tissue Services for H&E, CD61 and E cadherin staining.

For assigning animals into treatment groups as listed above, littermate animals were genotyped, and then the pups carrying the required genotypes (either β-globin/GFP transgenic mice or IVS2-654 β-thalassemic mice) were randomized into the several treatment groups in cohorts of 3 to 6, as indicated. The investigators were not blinded as to treatment groups.

Genomic DNA Extraction and Deep Sequence Analysis

Genomic DNA from mouse cells treated ex vivo or in vivo, as indicated, was harvested using the Wizard Genomic Purification Kit (Promega), and then electrophoresed in a 1% low melting point agarose gel in TAE, to separate genomic DNA from possible residual PNA and/or DNA oligonucleotide. The high-molecular weight species, representing genomic DNA, was cut from the agarose gel and extracted using the Wizard SV Gel and PCR Clean-Up System (Promega) according to manufacturer's instructions. Once genomic DNA was isolated from treated cells or mouse tissue, PCR reactions were performed with high fidelity TAQ polymerase. Each PCR tube consisted of 28.2 µL dH2O, 5 µL 10×HiFi Buffer, 3 µL 50 mM MgCl2, 1 µL DNTP, 1 µL each of forward and reverse primer, 0.8 µL High Fidelity Platinum Taq Polymerase (Invitrogen, Carlsbad Calif.) and 10 µL DNA template. PCR products were prepared by end-repair and adapter ligation according to Illumina protocols (San Diego, Calif.), and samples sequenced by the Illumina HiSeq with 75 paired-end reads at the Yale Center for Genome Analysis. Samples were analyzed as previously described (McNeer, et al., *Gene Therapy*, 20:658-669 (2013)). Primers for deep sequencing were designed using Primer3 data base. The primers used for β-globin intron 2 were as follows: forward primer: 5' TAT-CATGCCTCTTTGCACCA (SEQ ID NO:179); reverse primer: 5' AGCAATATGAAACCTCTTACATCA (SEQ ID NO:180). Primers for off-target sites of partial homology were as follows; forward primer is listed first:

Vascular cell adhesion protein precursor 1

(5' AGATAATTATTGCCTCCCACTGC (SEQ ID NO: 181) and

5' AATGGAAGGGCATGCAGTCA (SEQ ID NO: 182));

Polypyrimidine tract binding protein (5' CCCAATCCTGAATCCTGGCT (SEQ ID NO: 183) and

5' CATACTGATGTCTGTGGCTTGA (SEQ ID NO: 184));

Protocadherin fat 4 precursor (5' AAGCTCAAACCTACCAGACCA (SEQ ID NO: 185) and

5' AGCTGGAAGCTTCTTCAGTCA (SEQ ID NO: 186));

Olfactory receptor 266

(5' CCCTCTGTGGACTGAGGAAG (SEQ ID NO: 187) and

5' TGATGAGCTACGGGTATGTGA (SEQ ID NO: 188));

Syntaxin binding protein (5' CAAAAAGCCTTAAGCAAACACTC (SEQ ID NO: 189) and

5' TCTCTCCCTCAGCATCTATTCC (SEQ ID NO: 190));

Muscleblind like protein (5' TGTGTTTGTTTATGGATACTTGAGC (SEQ ID NO: 191) and

5' GCATGCACAATAAAGGCACT (SEQ ID NO: 192));

Ceruloplasmin isoform (5' CATGGGAAACAGTCAAAAGAAA (SEQ ID NO: 193) and

5' TGTAGGTTTCCCCACAGCTT (SEQ ID NO: 194)).

Results

Figure 3A:
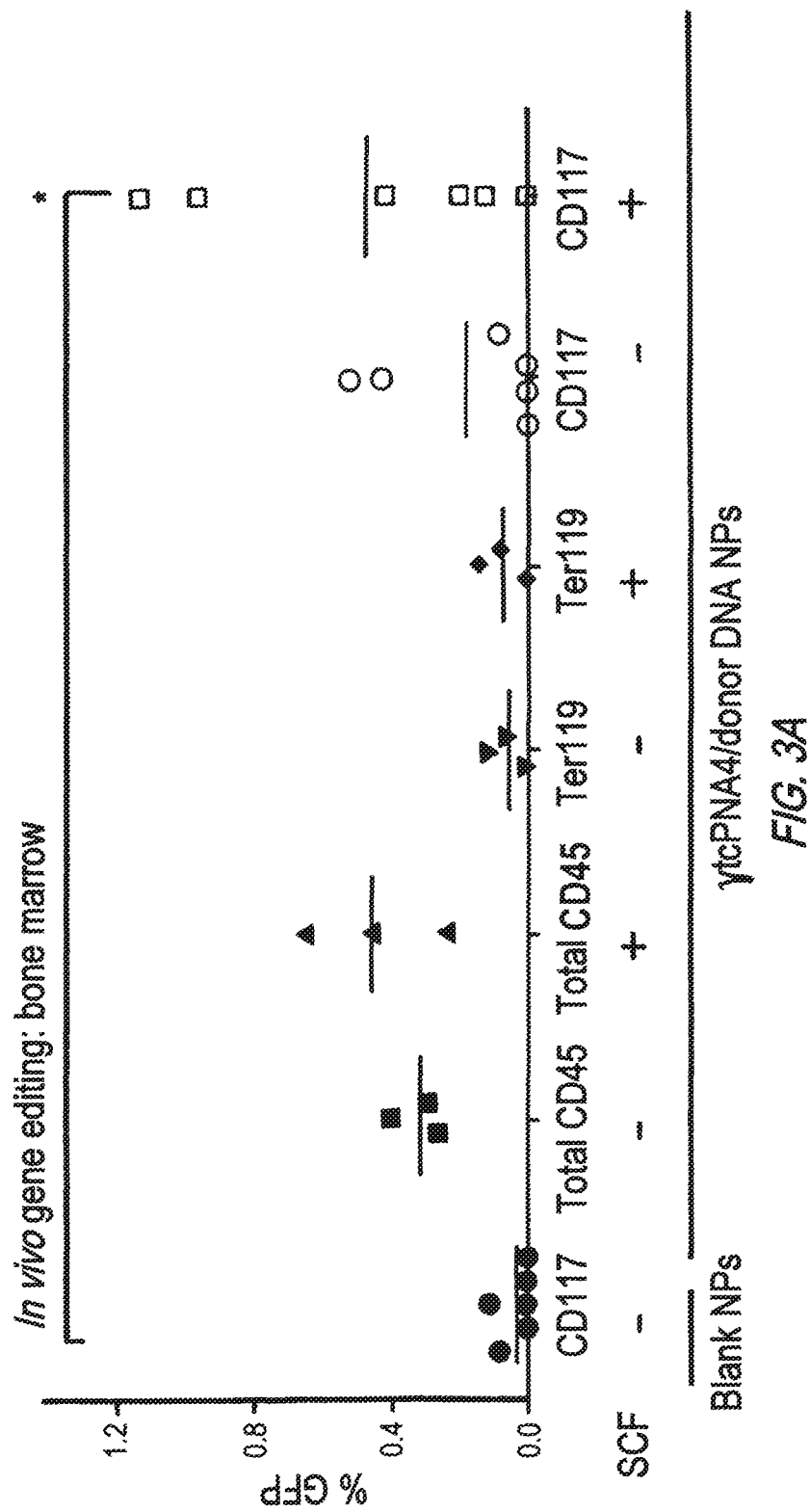
FIGS. 3A and 3B are dot plots showing frequencies of gene editing (GFP expression) in bone marrow (3A) and spleen (3B) cells from β-globin/GFP transgenic mice (6 mice per group) injected or not (as indicated) with 15.6 µg of SCF i.p. followed by a single treatment of 4 mg of NPs injected intravenously. Each group received either blank NPs or NPs containing γtcPNA4 and donor DNA (SEQ ID NOS:162 and 65), with or without SCF and were harvested and analysed two days later. Each data point represents analysis of cells from a single mouse. Statistical analyses were performed using student's t-test: asterisk, p<0.05.
Figure 3B:
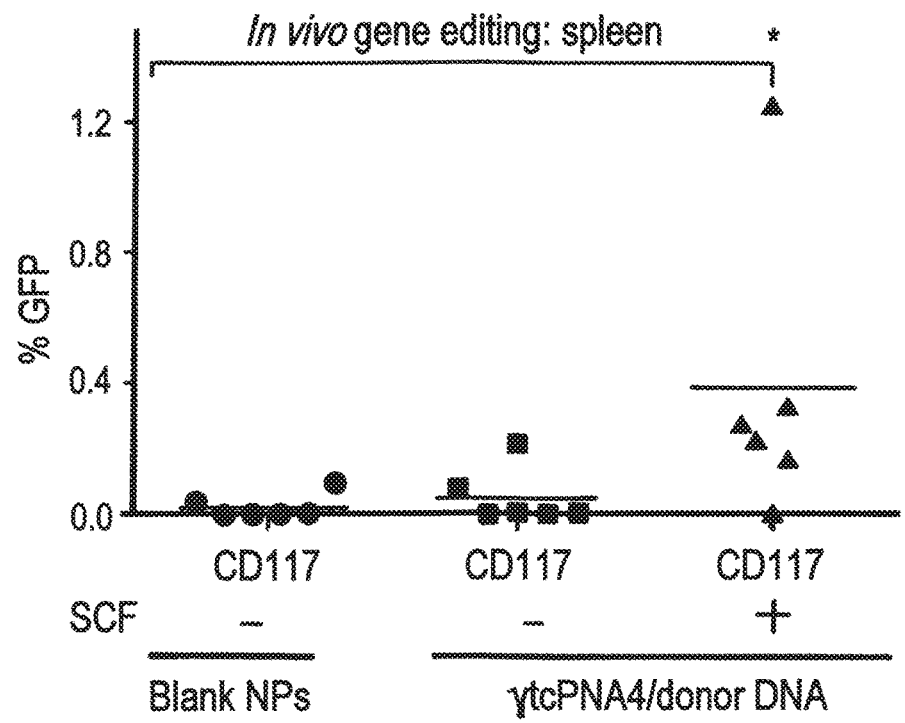

The potential for in vivo gene editing in the β-globin/GFP transgenic mice was explored by intravenous injection of NPs containing γtcPNA4 and donor DNA. The ability of SCF treatment to enhance gene editing in vivo was also tested. Mice were treated with a single intravenous dose of 4 mg NPs in 150 µl PBS, and 2 days later the mice were sacrificed for analysis of gene editing in cells from the bone marrow and spleen. Some mice also received murine SCF (15.6µg) given by intraperitoneal injection 3 hr prior to the NP injection, as indicated. In vivo gene editing was scored by GFP expression in marker-sorted cell populations from bone marrow and spleen (FIGS. 3A and B). The highest levels of gene editing were seen in CD117+ cells from bone marrow and spleen of the SCF-treated mice, with frequencies in the range of 1% in several mice, and average frequencies in the 0.4% to 0.5% range.

Figure 3C:
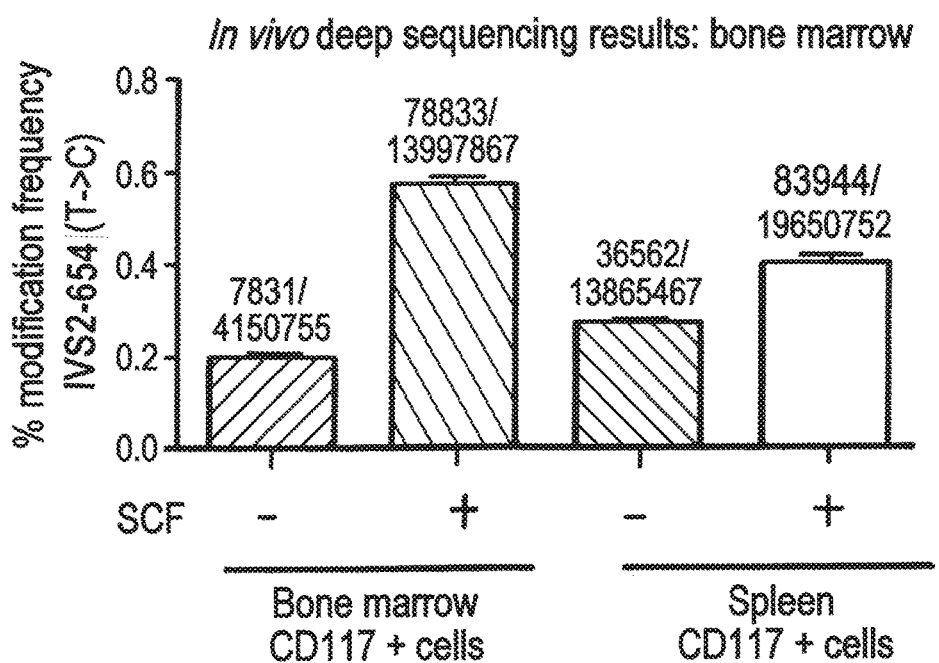
FIG. 3C is a bar graph showing the results of deep-sequencing analysis to quantify the frequency of targeted gene editing (% modification frequency IVS2-654 (T→C)) in vivo in CD117+ cells from bone marrow and spleen of β-globin/ GFP mice treated as described for FIGS. 3A and 3B. Error bars indicate standard error of proportions.

These results were confirmed by performing deep sequencing analysis on genomic DNA from CD117+ cells isolated from bone marrow and spleen of treated mice (FIG. 3C), which revealed gene editing frequencies in the range of 0.2% in the bone marrow of mice treated with NPs alone and 0.6% in mice receiving SCF along with the NPs, consistent with the frequencies of gene correction quantified by GFP expression. Deep-sequencing was also used to assess off-target effects in the bone marrow cells of the mice that were treated with SCF and γtcPNA4 and donor DNA NPs (Table 4). By BLAST analysis, seven off-target sites with partial homology to the target site of γtcPNA4 in β-globin intron 2 were identified. Mutation frequencies at these sites were quantified via deep sequencing. Extremely low frequencies of off-target effects were found in the γtcPNA4/donor DNA treated mice, with six sites showing no detectable sequence changes out of millions of reads and two sites showing modification frequencies of only 0.0074% and 0.00018% compared to 0.56% at the targeted β-globin site. (Table 4). The overall off-target modification frequency at all seven sites combined was 0.00034%, 1,647-fold lower than the frequency of the targeted gene editing.

TABLE 4

Off-target effects in bone marrow cells following intravenous treatment of β-globin/GFP mice with γtcPNA4/donor DNA NPs.

| Gene locus | Sequences of partial homology (5' to 3') | Size of region sequenced | Alleles sequenced | Number modified | Frequency % |
|---|---|---|---|---|---|
| β-globin | TGCCCTGAAAGAAAGAGA (SEQ ID NO: 195) | 128 | 1399786 | 78833 | 0.56 |
| Vascular cell adhesion protein precursor 1 | AGCCCTGAAAGAAAGAGA (SEQ ID NO: 196) | 111 | 480013 | 0 | 0 |
| Polypyrimidine tract binding protein | GAACCTGAAAGAAAGAGA (SEQ ID NO: 197) | 101 | 349723 | 26 | 0.0074 |
| Protocadherin fat 4 precursor | CACCCTGAAAGAAAGAAA (SEQ ID NO: 198) | 115 | 73245 | 0 | 0 |
| Olfactory receptor 266 | AAGCCTGAAAGAAAGAGT (SEQ ID NO: 199) | 172 | 1092990 | 2 | 0.00018 |
| Syntaxin binding protein | AGAAATGAAAGAAAGAGA (SEQ ID NO: 200) | 150 | 2478636 | 0 | 0 |
| Muscleblind like protein | GGTGGTGAAAGAAAGAGA (SEQ ID NO: 201) | 165 | 2331971 | 0 | 0 |
| Ceruloplasmin isoform | AGGACTGAAAGAAAGAGT (SEQ ID NO: 202) | 154 | 1390439 | 0 | 0 |
| Total off-target | | | 8197017 | 28 | 0.00034 |

The top seven gene loci with partial homology to the 18 bp γtcPNA4 target site in β-globin intron 2 were identified, with the sequences as indicated. β-globin/GFP mice were treated with SCF followed by intravenous infusion with NPs containing γtcPNA4/donor DNA, and genomic DNA from c-Kit+ bone marrow cells was subject to deep sequencing analysis at these loci. The size of the region sequenced around each site is listed, along with the number of alleles sequenced and the number of alleles with modified sequences.

Example 8: SCF and PNA NP Treatment can Correct a Genomic Mutation in a Mouse β-Thalassemia Disease Model To test the extent to which combined SCF and PNA NP treatment in vivo could correct a human β-thalassemia mutation in a mouse disease model, a transgenic mouse line was utilized in which the two (cis) murine adult beta globin genes were replaced with a single copy of the human β-globin gene with the thalassemia-associated IVS2-654 mutation (Svasti, et al., Proc Natl Acad Sci USA, 106:1205-1210 (2009)). Homozygous mice do not survive, and heterozygotes have a moderate form of β-thalassemia, with marked hemolytic anemia, microcytosis, and increased MCHC and red cell distribution width reflecting reduced amounts of mouse β-globin and no human β-globin (Lewis, et al., Blood, 91:2152-2156 (1998); Svasti, et al., Proc Natl Acad Sci USA, 106:1205-1210 (2009)). Blood smears from these mice show erythrocyte morphologies consistent with β-thalassemia. Treatment groups for this experiment included (1) blank NPs; (2) SCF treatment alone (no NPs); (3) SCF plus γtcPNA4/donor DNA NPs; and (4) SCF plus γtcPNA4-Scr/donor DNA. SCF injections were given i.p., and NPs were given i.v. via retro-orbital injection. Each treatment group consisted of six mice, and each mouse received four treatments at two-day intervals. Blood smears examined at day 0 (before treatment) and at day 36 after the last treatment showed marked improvement in RBC morphology on day 36 in the γtcPNA4/donor DNA treated mice but not in the mice treated with either blank NPs, SCF alone, or SCF plus γtcPNA4-Scr/donor DNA. Compared to wild-type, the untreated group (and corresponding control animals) exhibit extreme poikilocytosis which is typical of β-thalassemia, as well as the presence of numerous target cells, cabot rings, anisochromasia, and ovalocytosis, changes characteristic of β-thalassemia. Treatment with γtcPNA4/donor DNA and SCF ameliorates the poikilocytosis and yields a reduction in anisocytosis, ovalocytosis, and target cells indicative of reduced alpha-globin precipitation in the RBCs.

CBC analyses performed on blood samples taken at 30, 45, 60, and 75 days post-treatment from mice in each group showed persistent correction of the anemia in the mice treated with SCF plus the γtcPNA4/donor DNA NPs (FIG. 4A-4C), with elevation of the blood hemoglobin levels into the normal range. Only the SCF plus γtcPNA4/donor DNA-treated mice achieved and maintained hemoglobin levels within the normal range during the duration of the experiment, reflecting the increased hemoglobin stability conferred by the gene editing.

Figure 4D:
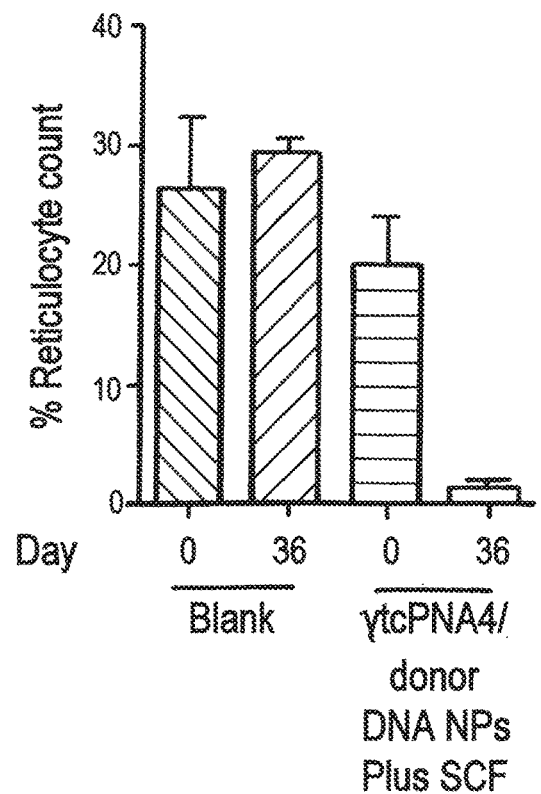
FIG. 4D is a bar graph showing reticulocyte counts (% of total RBCs) calculated in blood smears from thalassemic mice treated with either blank NPs or with NPs containing γtcPNA4/donor DNA (SEQ ID NOS:162 and 65) plus SCF on days 0 and 36 post treatment.
Figure 4E:
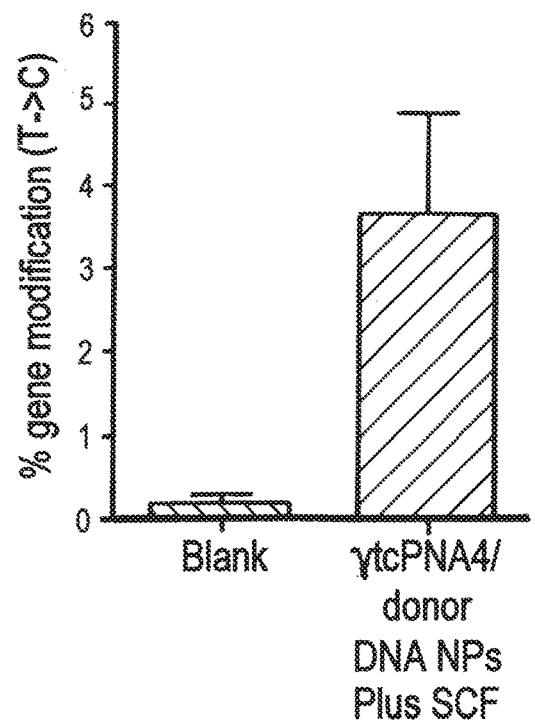
FIG. 4E is a bar graphs showing the % gene modification (T→C) as determined by deep-sequencing analysis of genomic DNA from bone marrow cells after treatment of thalassemic mice with either blank NPs or with NPs containing and γtcPNA4/donor DNA (SEQ ID NOS: 162 and 65) plus SCF.

The anemia was not improved in any of the controls. Reticulocyte counts were observed in mice treated with SCF plus the γtcPNA4/donor DNA NPs but not in the mice treated with blank NPs (FIG. 4D). Deep sequencing analyses were performed on genomic DNA extracted from bone marrow cells of three mice from each group that were sacrificed on day 36 post-treatment. Correction of the targeted mutation was seen at a frequency of almost 4% in the γtcPNA4/donor DNA treated group (FIG. 4E), whereas no correction was seen in the mice treated with blank NPs. In addition, in keeping with the correction of the anemia and suppression of the reticulocytosis, the γtcPNA4/donor DNA treated mice also showed reduced splenomegaly at 36 days post-treatment.

Consistent with the reduced splenomegaly, histologic examination of the spleens of mice sacrificed on day 36 showed substantially improved splenic architecture specifically in the γtcPNA4/donor DNA treated mice. The regular splenic histologic pattern of white pulp (lymphoid follicles) surrounded by rims of red pulp as seen in the wild-type spleen is disrupted in the β-thalassemic animals (blank NPs, SCF alone, SCF plus scrambled γtcPNA4-Scr/donor DNA NPs) due to extramedullary hematopoiesis, which results in an expansion in the red pulp (causing the splenomegaly) and disruption of the white pulp. The CD61 and Ecad immunohistochemical stains highlight the increased cellularity characteristic of extramedullary hematopoiesis and demonstrate that the expanded red pulp in the β-thalassemic animals includes elevated numbers of megakaryocytes and erythroid precursors, respectively. This increased cellularity is substantially ameliorated in the γtcPNA4/donor DNA treated mice.

Deep-sequencing was also used to assess off-target effects in the bone marrow of the in vivo treated thalassemic mice. As above, seven off-target sites with partial homology to the binding site of γtcPNA4 in the β-globin gene were analyzed. Only extremely low frequencies of off-target effects were found in the γtcPNA4/donor DNA-treated thalassemic mice (Table 5), similar to the results in the β-globin/GFP transgenic mice (Table 4). The overall off-target modification frequency in this case was 0.0032%, 1,218-fold lower than the frequency off β-globin gene editing.

TABLE 5

Off-target effects in bone marrow cells following intravenous treatment of β-thalassemic mice with SCF and γtcPNA4/donor DNA NPs.

| Gene locus | Sequences of partial homology (5' to 3') | Size of region sequenced | Alleles sequenced | Number modified | Frequency % |
| --- | --- | --- | --- | --- | --- |
| β-globin | TGCCCTGAAAGAAA GAGA (SEQ ID NO: 195) | 128 | 8615313 | 337192 | 3.9 |
| Vascular cell adhesion protein precursor 1 | AGCCCTGAAAGAAA GAGA (SEQ ID NO: 196) | 111 | 482051 | 0 | 0 |
| Polypyrimidine tract binding protein | GAACCTGAAAGAAA GAGA (SEQ ID NO: 197) | 101 | 355567 | 2 | .00056 |
| Protocadherin fat 4 precursor | CACCCTGAAAGAAA GAAA (SEQ ID NO: 198) | 115 | 123158 | 0 | 0 |
| Olfactory receptor 266 | AAGCCTGAAAGAAA GAGT (SEQ ID NO: 199) | 172 | 1099880 | 262 | 0.0231 |
| Syntaxin binding protein | AGAAATGAAAGAAA GAGA (SEQ ID NO: 200) | 150 | 2493024 | 0 | 0 |
| Muscleblind like protein | GGTGGTGAAAGAAA GAGA (SEQ ID NO: 201) | 165 | 2336715 | 0 | 0 |
| Ceruloplasmin isoform | AGGACTGAAAGAAA GAGT (SEQ ID NO: 202) | 154 | 1397271 | 0 | 0 |
| Total off-target | | | 8287666 | 268 | .0032 |

The top seven gene loci with partial homology to the 18 bp γtcPNA4 target site in β-globin intron 2 were identified, with the sequences as indicated. Thalassemic mice were treated with SCF followed by intravenous infusion with NPs containing γtcPNA4/donor DNA, and genomic DNA from c-Kit+ bone marrow cells was subject to deep sequencing analysis at these loci. The size of the region sequenced around each site is listed, along with the number of alleles sequenced and the number of alleles with modified sequences.

In sum the results above demonstrate that chemically modified γPNAs and donor DNAs delivered intravenously via polymer NPs, and given in combination with SCF treatment, can mediate gene editing in vivo at a level sufficient to ameliorate the disease phenotype in the thalassemic mice. Sustained reversal of the anemia, with normalization of serum hemoglobin concentrations and suppression of the reticulocytosis were induced. A morphologic improvement in RBC cytology, indicative of improved RBC stability, along with reduced extramedullary hematopoiesis and reduction in splenomegaly were observed. This constellation of findings indicates that the disclosed therapeutic approach has the potential to deliver a substantial clinical response that would relieve the morbidity and mortality associated with β-thalassemia.

There are at least two important advances for gene editing in this work. One advance is the incorporation of next generation PNA chemistry by substitution within the polyamide backbone at the gamma position to consistently yield increases in gene editing frequencies compared to standard PNAs. This increased efficacy correlates with the enhanced DNA binding properties of γPNAs, which take on a preorganized helical conformation enforced by the miniPEG γ substitution.

Another advance is the finding that the SCF/c-Kit pathway promotes increased gene editing by triplex-forming PNAs and donor DNAs. Upon ex vivo treatment of bone marrow cells with γPNAs, the gene editing frequency in c-Kit+ cells was as high as 8%. The combination of SCF treatment with the γPNAs yielded even higher frequencies in the c-Kit+ cells, with just over 15% in a single treatment. In vivo, treatment of transgenic mice carrying a β-globin/GFP reporter transgene by i.p. injection of SCF followed by intravenous administration of NPs containing γPNAs and donor DNAs yielded gene editing in CD117+ cells in the bone marrow and spleen at frequencies up to 1% in a single treatment. Prompted by these results in reporter mice, gene editing was tested in the thalassemic mouse model via simple intravenous injection of the optimized combination of SCF and γPNA/donor DNA NPs given four times at two-day intervals. This regimen yielded gene editing at a frequency of almost 4% in total bone marrow cells and produced sustained amelioration of the disease phenotype, achieved in a minimally invasive manner without the need for stem cell harvest or transplantation.

Importantly, in a series of ex vivo and in vivo assays for hematopoietic colony formation, for induction of inflammatory cytokines, for generation of strand breaks, and for off-target mutagenesis by deep sequencing, there was essentially no measurable cellular toxicity and very low off-target genome effects from the γPNA-containing NPs, providing a possible safety advantage relative to other gene editing approaches (Cradick, et al., *Nucleic Acids Res.,* 41:9584-9592 (2013)).

CD117 is the product of the c-Kit gene and is a receptor tyrosine kinase that mediates downstream signalling to multiple cellular pathways. The results discussed above indicate that activation of this pathway promotes gene editing, rather than CD117 simply being a marker for the phenotype. Inhibition of the c-Kit kinase with dasatinib reduces the frequency by almost 4-fold, whereas treatment with SCF almost doubles the frequency. Mechanistically, CD117+ bone marrow cells, in comparison to CD117-cells, have elevated levels of expression of numerous DNA repair genes, including factors in the HDR pathway that prior work has shown is required for triplex-induced gene editing (Vasquez, et al., *Science,* 290:530-533 (2000); Rogers, et al., *Proc. Natl. Acad. Sci. USA,* 99:16695-16700 (2002); Datta, et al., *J Biol Chem,* 276:18018-18023 (2001); Vasquez, et al., *Proc Natl Acad Sci USA,* 99:5848-5853 (2002)). When CD117+ cells are treated with SCF, expression of these DNA repair genes is increased even more, correlating with a further increase in gene editing.

In addition, the results show that the elevated expression of DNA repair genes in CD117+ cells is associated with functionally increased HDR activity using an assay for recombination between reporter gene constructs. Treatment of the CD117+ cells with SCF produced a further 2-fold increase in HDR, whereas dasatinib and the other inhibitors yielded reductions in HDR activity. These results show the functional importance of the c-Kit pathway in promoting HDR and provide further mechanistic insight into gene editing pathways.

The 4% frequency of bone marrow gene editing achieved in the thalassemic mice was sufficient to achieve a clear improvement in phenotype, with blood hemoglobin levels rising into the normal range, suppression of the reticulocytosis, and reduction in the splenomegaly that is otherwise associated with extramedullary hematopoiesis. The observation that gene correction at a frequency of 4% could confer a phenotypic impact is consistent with transplantation studies in thalassemic mice and in patients in which mixed chimerism at one ratio of wild-type donor to thalassemic recipient cells in the marrow has produced much higher proportions of donor RBCs in the periphery (Andreani, et al., *Bone Marrow Transplant,* 7(Suppl 2):75 (1991); Felfly, et al., *Mol Ther,* 15:1701-1709 (2007)). This effect has been attributed to increased survival and enrichment of genetically corrected erythroblasts during erythropoiesis, decreased ineffective erythropoiesis, and increased survival in the circulation of corrected erythrocytes relative to thalassemic RBCs (Miccio, et al., *Proc Natl Acad Sci USA,* 105:10547-10552 (2008)).

Overall, these results support the feasibility of NP-mediated delivery of γPNAs and donor DNAs as a therapeutic strategy to achieve in vivo gene editing for treatment of human genetic disorders. The results described above demonstrate effective NP-mediated gene editing in bone marrow, but other recent work has shown that NP delivery to lung airway epithelia is also possible as a potential means to achieve correction of the CFTR gene mutation associated with cystic fibrosis (Fields, et al., *Adv Healthc Mater* (2014); McNeer, et al., *Nature Communications in press* (2015)).

The finding that SCF stimulates gene editing identifies SCF as a possible pharmacologic means to boost gene editing, a strategy that may be applicable not just to PNA-mediated gene editing as shown here but possibly also to editing by other methods, such as CRISPR/Cas9, SFHR, or ZFNs. Furthermore, even though the γPNAs show consistently improved gene editing potency, the level of off-target effects in the genome remains extremely low. This is in keeping with the lack of any intrinsic nuclease activity in the PNAs (in contrast to ZFNs or CRISPR/Cas9), and reflects the mechanism of triplex-induced gene editing, which acts by creating an altered helix at the target-binding site that engages endogenous high fidelity DNA repair pathways. The SCF/c-Kit pathway also stimulates these same pathways, providing for enhanced gene editing without increasing off-target risk or cellular toxicity.

Example 9: Repair Proteins Modulate Triplex-Forming PNA Mediated Gene Editing

Materials and Methods

Figure 5A:
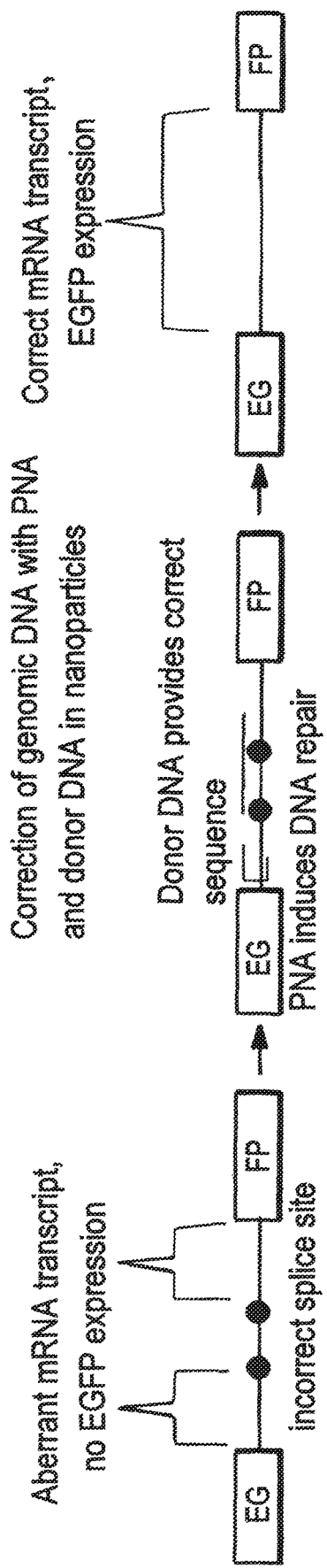
FIG. 5A is a flow diagram illustrating a GFP/beta globin gene correction assay.

Skin fibroblasts were isolated from the β-globin/GFP mice (intron 2 of human β-globin inserted with in the GFP coding regions) and grown in culture in DMEM medium plus 10% FCS. The intron contains the IVS2-654 (C→T) mutation. The gene correction assay is illustrated in FIG. 5A.

The fibroblasts were treated ex vivo with nanoparticles containing tcPNA1+ Donor DNA and 72 hours later flow cytometry analysis was performed to quantify the % gene correction based on the frequency of GFP positive cells. In some cases, DNA repair inhibitors or other small molecule inhibitors were given 48 hours before the nanoparticle treatment.

```
tcPNA1:
                                    (SEQ ID NO: 35)
H-KKK-TTTJTJJ-OOO-CCTCTTTGCACCATTCT-KKK-NH2

Donor DNA:
                                   (SEQ ID NO: 175)
5'A(s)A(s)A(s)GAATAACAGTGATAATTTCTGGGTTAAGGCAAT AGCAATATCTCTGCATATAAA(s)T(s)A(s)T 3'
```

TABLE 6

ATR pathway inhibitors

| Drug | Inhibits | Working Concentration |
| --- | --- | --- |
| MIRIN | Mre11 | 20 μM |
| KU55933 | ATM | 20 μM |
| VE-821 | ATR | 10 μM |
| NU7441 | DNAPKcs | 20 μM |
| LCA | Polymerase β | 50 μM |
| L189 | DNA ligase I III IV | 50 μM |

TABLE 7

CHK1, DNA polymerase alpha, and polyADP ribose polymerase inhibitors

| Drug | Inhibits | Working Concentration |
| --- | --- | --- |
| Aphidicolin | Polymerase α | 1 μg/ml |
| SB218075 | Chk1 | 1 μM |
| AZD | PARP | 20 μM |

Results

Figure 5B:
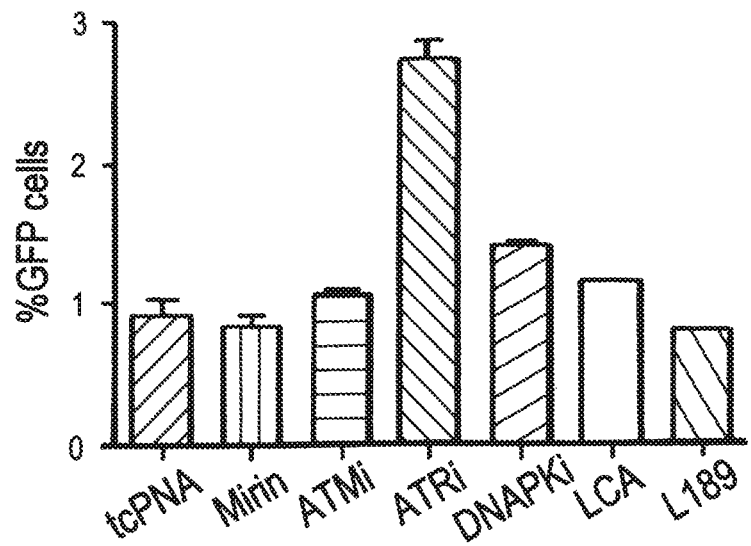
FIG. 5B is a bar graph showing gene correction of cells treated with nanoparticles containing tcPNA1 (SEQ ID NO:191) and donor DNA (SEQ ID NO:65) alone, or in combination with an ataxia telangiectasia and Rad3-related protein (ATR) pathway inhibitor (MIRIN, KU5593, VE-821, NU7441, LCA, or L189).

Inhibition of ATR boosts gene editing in the GFP/beta globin gene correction assay in mouse fibroblasts. The results are presented in FIG. 5B.

Figure 5C:
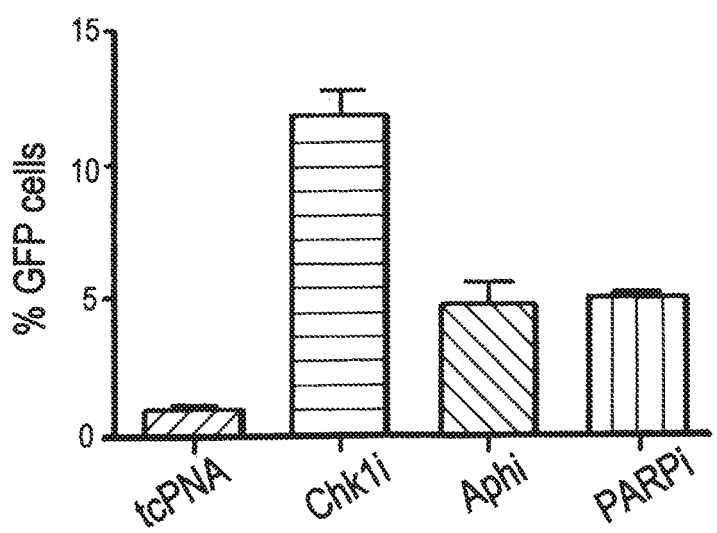
FIG. 5C is a bar graph showing gene correction of cells treated with nanoparticles containing tcPNA1 (SEQ ID NO:191) and donor DNA (SEQ ID NO:65) alone, or in combination with a Checkpoint Kinase 1 inhibitor (Chk1i) (SB218075), a DNA polymerase alpha inhibitor (Aphi) (aphidicolin) or a polyADP ribose polymerase (PARPi) (AZD-2281 (olaparib)).

Inhibition of CHK1 substantially boosts gene editing in GFP/beta globin gene correction assay Inhibition of DNA polymerase alpha (by aphidicolin) or of polyADP ribose polymerase by AZD-2281 (olaparib) also boosts gene editing. The results are presented in FIG. 5C.

Inhibition of heat shock protein 90 (HSP90) by STA-9090/Ganetespib enhances gene editing in the GFP/beta globin gene correction assay. The results are presented in FIG. 5D.

Example 10: Partial γ Substitution in the Hoogsteen Domain Increases Gene Correction Efficiency Materials and Methods

```
                                    (SEQ ID NO: 93)
lys-lys-lys-TJTJJTTT-OOO-TTTCCTCTATGGGTAAG-lyslys-lys
                                    (SEQ ID NO: 69)
lys-lys-lys-TJTJJTTT-OOO-TTTCCTCTATGGGTAAG-lyslys-lys
```

Results

Figure 7A:
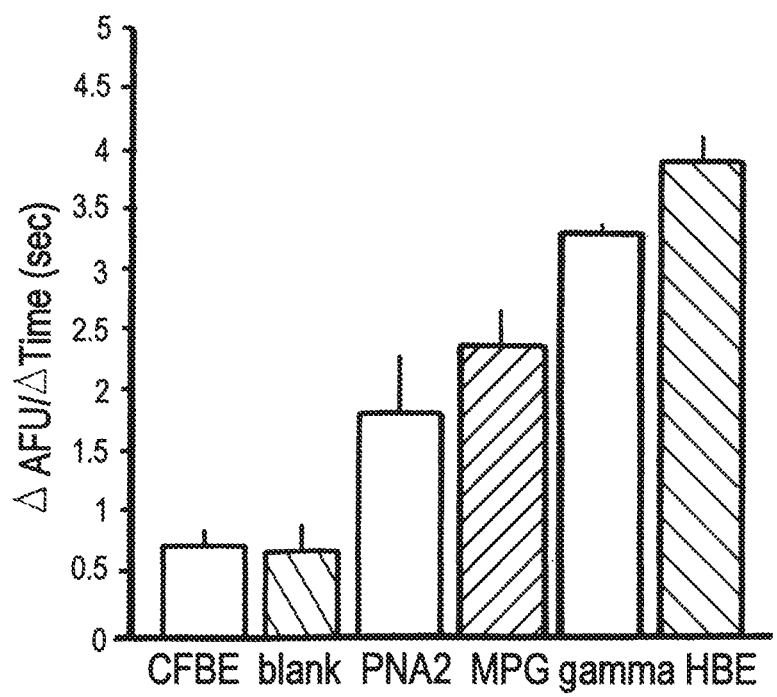
FIG. 7A is a bar graph showing the results of a MQAE (N-(Ethoxycarbonylmethyl)-6-Methoxyquinolinium Bromide) assay (delta(AFU)/(delta(Time (sec))) measuring chloride flux for negative control CFBE cells; CFBE cells treated with blank nanoparticles, PNA2: lys-lys-lys-TJTJJTTT-OOO-TTTCCTCTATGGGTAAG-lys-lys-lys (SEQ ID NO:93)-loaded nanoparticles, PNA2 (SEQ ID NO:93)-loaded nanoparticles with an MPG peptide, γPNA2 lys-lys-lys-TJTJJTTT-OOO-TTTCCTCTATGGGTAAG-lys-lys-lys (SEQ ID NO:69)-loaded nanoparticles; and untreated positive control wildtype 16HBE14o-cells.
Figure 7B:
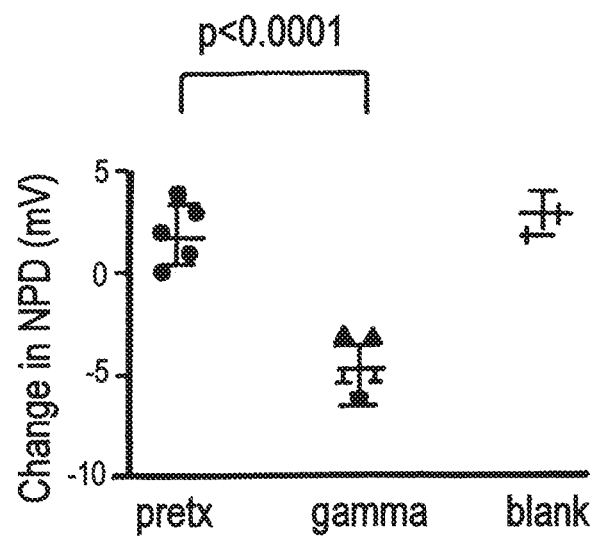
FIG. 7B is a dot pot showing nasal potential difference (NPD) (pretreatment, after treatment with γPNA2 (SEQ ID NO:69)-loaded nanoparticles, and after treatment with blank nanoparticles) measured using a non-invasive assay used to detect chloride potential differences in vivo.

A substantial increase in gene editing in F508del CFTR using γtcPNAs with just partial γ substitution and only in the Hoogsteen domain of CF PNA2. As shown in FIGS. 7A and 7B, with only 4 γ residues in the Hoogsteen domain, a more than 50% increase in activity for CFTR gene correction was achieved in CFBE cells (via NPs containing γtcPNAs) as judged by the MQAE assay (FIG. 7A). A substantial increase in activity with γtcPNA containing NPs was also achieved in vivo in CF mice following intranasal delivery, as determined by NPD measurements (FIG. 7B).

Example 11: Nanoparticle Delivered tcPNA and Donor Oligonucleotide Correct a Sickle Cell Mutation In Vivo Materials and Methods
PNAs

```
SCD-tcPNA 1:
                                    (SEQ ID NO: 59)
H-KKK-JJTJTTJ-OOO-CTTCTCCACAGGAGTCAG-KKK-NH2

SCD-tcPNA 2:
                                   (SEQ ID NO: 213)
H-KKK-TTJJTJT-OOO-TCTCCTTAAACCTGTCTT-KKK-NH2

SCD-tcPNA 3:
                                    (SEQ ID NO: 60)
H-KKK-TJTJTTJT-OOO-TCTTCTCTGTCTCCACAT-KKK-NH2.
```

K indicates lysine; J, pseudoisocytosine (for C) for pH-independent triplex formation. O,8-amino-2,6,10-trioxaoctanoic acid linkers connecting the Hoogsteen and Watson-Crick domains of the tcPNAs.
Donor

```
                                   (SEQ ID NO: 161)
5'-T(s)T(s)G(s)CCCCACAGGGCAGTAACGGCAGACTTCTCCTCAGG

AGTCAGGTGCACCATGGTGTCTGTT(s)T(s)G(s)-3',
``` wherein the bolded and underlined residue is the correction and "(s)" indicates a phosphorothioate internucleoside linkage.

Mouse Models for Sickle Cells Disease

In sickle cell disease (SCD), the mutation (GAG→GTG) at codon 6 results in glutamic acid changed to valine. For correction of this SCD mutation site in vivo, in vivo studies were performed in two mouse models:

(1) sickle cell gene knock in murine model also known as the Berkeley mouse model introduced by Pászty C, Brion C M, Manci E, Witkowska H E, Stevens M E, Mohandas N, Rubin E M., "Transgenic knockout mice with exclusively human sickle hemoglobin and sickle cell disease." *Science.* 1997 Oct. 31; 278(5339):876-8. PMID: 9346488 and (2) the Townes mouse model developed by Ryan™, Ciavatta D J, Townes T M., "Knockout-transgenic mouse model of sickle cell disease." *Science.* 1997 Oct. 31; 278 (5339):873-6. PMID: 9346487.

Both of these mouse models express exclusively human sickle hemoglobin (HbS). They were produced by generating transgenic mice expressing human α-, γ-, and β$^s$-globin that were then bred with knockout mice that had deletions of the murine α- and β-globin genes. Thus the resulting progeny no longer express mouse α- and β-globin. Instead, they express exclusively human α- and β$^s$-globin. Hence, the mice express human sickle hemoglobin and possess many of the major hematologic and histopathologic features of individuals with SCD.

Nanoparticles tcPNAs and donor DNAs, at a molar ratio of 2:1, were incorporated into PLGA NPs. The NP formulations were evaluated by scanning electron microscopy (SEM) and dynamic light scattering (DLS).

Treatment Protocol

Three each (i.e., n=3) of Berkley and Townes mice were treated with (1) Blank PLGA nanoparticles, (2) 4 treatments of sc-tcPNA1/donor DNA in PLGA nanoparticles, (3) 4 treatments of sc-tcPNA2/donor DNA in PLGA nanoparticles, (4) 4 treatments of sc-tcPNA3/donor DNA in PLGA nanoparticles. Mice were injected intravenously with 2 mg of NPs containing the PNAs and donor DNAs every two days for a total of 4 injections. After the last treatment, bone marrow and spleen were collected for histology, deep sequencing, and restriction enzyme digest.

Results

Figure 10A:
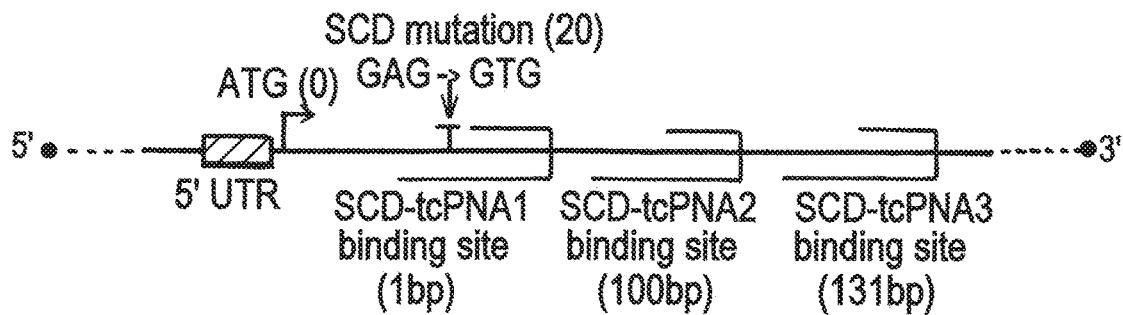
FIG. 10A is an illustration of Strategy for targeted correction of a β-globin gene containing SCD mutation (A→T) mutation and tcPNAs designed to bind to homopurine regions near the mutation.

Three polypurine sites in the β-globin gene in the vicinity of the SCD codon. Triplex formation can catalyze recombination at sites up to several hundred base pairs away. A series of tcPNAs were designed to bind to selected polypurine stretches in the β-globin gene in the vicinity of the SCD mutation and synthesized (FIG. 10A). A sense donor DNA (a single-stranded 60-mer matching nucleotides in β-globin gene and end-protected from degradation by 3 terminal phosphorothioate internucleoside linkages was also designed.

More specifically, gel mobility shift assays demonstrated binding of SCDtcPNA1, SCDtcPNA2, SCDtcPNA3 to 120 bp double-stranded DNA fragments containing β-globin sequences. Each 120 bp dsDNA contained the binding site for the respective tcPNAs. The binding assays revealed that all synthesized SCD tcPNAs bind specifically to double-stranded genomic DNA under physiological conditions.

Figure 10B:
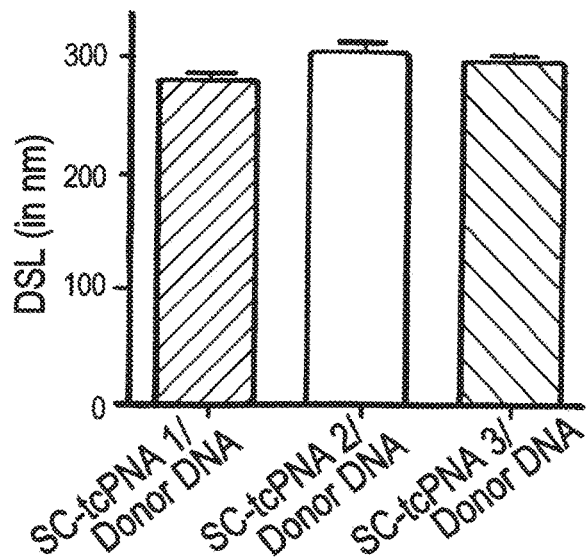
FIGS. 10B-10C are bar graphs showing hydrodynamic diameter of formulated PLGA nanoparticles measured using dynamic light scattering in PBS buffer (FIG. 10B) and zeta potential of formulated PLGA nanoparticles (FIG. 10C). Data in both graphs are presented as mean±s.e.m., n=3.
Figure 10C:
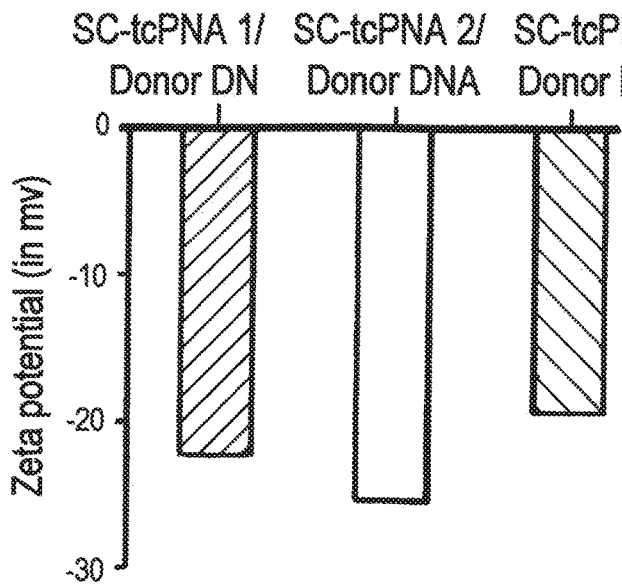

Poly (lactic-co-glycolic acid) (PLGA) NPs can effectively deliver PNA/donor DNA combinations into primary human and mouse hematopoietic cells with essentially no toxicity. Here, tcPNAs and donor DNAs, at a molar ratio of 2:1, were incorporated into PLGA NPs. The NP formulations were evaluated by scanning electron microscopy (SEM) and dynamic light scattering (DLS). All the NPs exhibited sizes within the expected range and showed uniform charge distribution (FIGS. 10B-10C).

Next, correction of SCD mutation in the two disease mouse models was carried out as described above. Treatment groups included (1) blank NPs; (2) SCD tcPNA1/donor DNA; (3) SCD tcPNA2/donor DNA; and (4) SCD tcPNA3/donor DNA. Mice were injected intravenously with 2 mg of NPs containing the PNAs and DNAs every two days for a total of 4 injections.

Figure 10D:
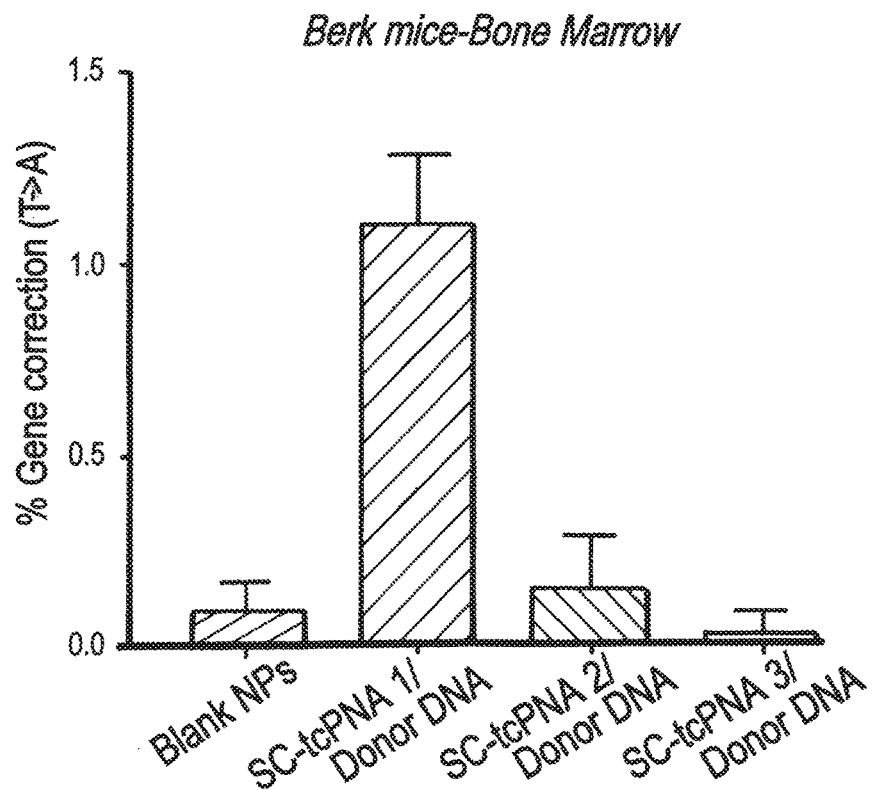
FIGS. 10D-10E are bar graphs showing the results of deep-sequencing analysis to quantify the frequency of targeted gene editing in vivo in bone marrow cells of Berkley "Berk" mice (FIG. 10D) and Townes mice (FIG. 10E). Error bars indicate standard error of proportions.
Figure 10E:
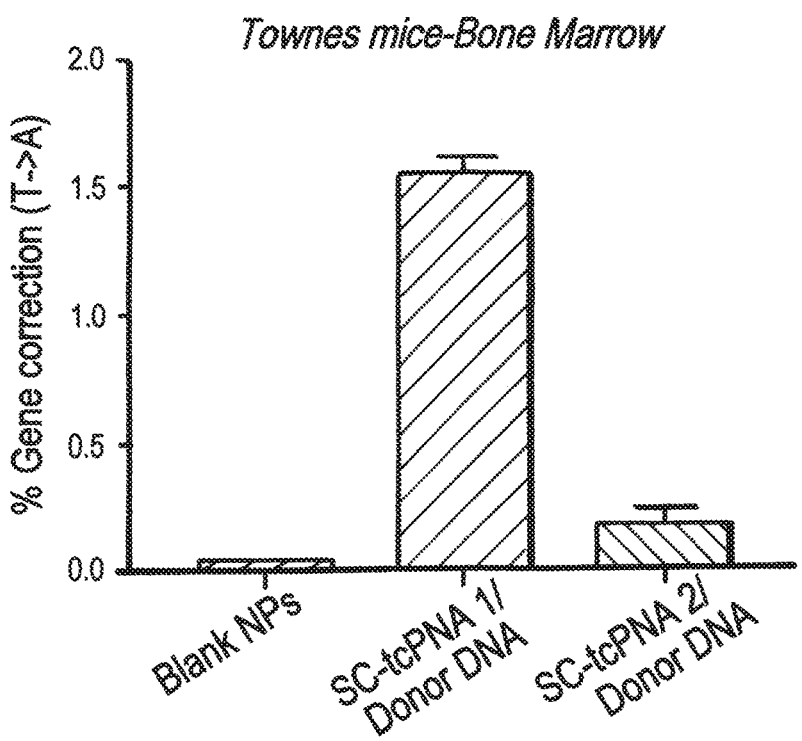

Deep sequencing analyses of the human beta globin alleles were performed on genomic DNA taken from total bone marrow cells of mice on day 36 post-treatment. Correction of the SCD mutation was seen at a frequency of almost 1.5% in the SCD tcPNA1/donor DNA treated group in the Townes mice (FIG. 10D) and 1.2% gene correction in the Berkley mice (FIG. 10E), whereas no correction was seen in the mice treated with blank NPs. The results were confirmed using restriction enzyme (Bsu361) digestion which cuts only when the sequence at codon 6 has been edited from the SCD mutation to the wild-type sequence.

Sequences with γPNA substitutions based on the above SCD PNAs can be and have been designed, and include, for example, partial or complete γPNA substitution in the Watson-Crick domain, partial or complete substitutions in the Hoogsteen domain, or a combination thereof. Exemplary sequences include, but are not limited to,

```
SCD-tcPNA 1A:
                                   (SEQ ID NO: 59)
H-KKK-JJTJTTJ-OOO-CTTCTCCACAGGAGTCAG-KKK-NH2

SCD-tcPNA 1B:
                                  (SEQ ID NO: 211)
H-KKK-JJTJTTJ-OOO-CTTCTCCACAGGAGTCAG-KKK-NH2

SCD-tcPNA 1C:
                                  (SEQ ID NO: 210)
H-KKK-JJTJTTJ-OOO-CTTCTCCACAGGAGTCAG-KKK-NH2

SCD-tcPNA 1D:
                                  (SEQ ID NO: 208)
H-KKK-JJTJTTJ-OOO-CTTCTCCACAGGAGTCAGGTGC-KKK-
NH2

SCD-tcPNA 1E:
                                  (SEQ ID NO: 207)
H-KKK-JJTJTTJ-OOO-CTTCTCCACAGGAGTCAGGTGC-KKK-
NH2

SCD-tcPNA 1F:
                                  (SEQ ID NO: 206)
H-KKK-JJTJTTJ-OOO-CTTCTCCACAGGAGTCAGGTGC-KKK-
NH2
```

Underlined residues include a gamma modification, for example, miniPEG γPNA substitution. K indicates lysine; J, pseudoisocytosine (for C) for pH-independent triplex formation. O,8-amino-2,6,10-trioxaoctanoic acid linkers connecting the Hoogsteen and Watson-Crick domains of the tcPNAs.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of modifying the genomes of CD117+ cells comprising contacting the CD117+ cells with an effective amount of
   (i) a gene editing potentiating agent selected from the group consisting of receptor tyrosine kinase C-kit ligands, ATR-Chk1 cell cycle checkpoint pathway inhibitors, and heat shock protein 90 inhibitors (HSP90i), and
   (ii) a gene editing technology that can induce genomic modification through a mechanism comprising a DNA repair pathway endogenous to the CD117+ cells,
   to modify the genomes of the CD117+ cells contacted with both (i) and (ii) at a higher frequency than an equivalent population of cells contacted with (ii) in the absence of (i).

2. The method of claim 1 further comprising contacting the cells with a donor oligonucleotide comprising a sequence that corrects a mutation(s) in the cells' genomes by insertion or recombination induced or enhanced by the gene editing technology.

3. The method of claim 2, wherein the cells' genomes have a mutation underlying a disease or disorder.

4. The method of claim 3, wherein the disease is a globinopathy.

5. The method of claim 3, wherein the disease is a lysosomal storage disease.

6. The method of claim 1 further comprising contacting the cells with a donor oligonucleotide comprising a sequence that induces a mutation(s) in the cells' genomes by insertion or recombination induced or enhanced by the gene editing technology.

7. The method of claim 2, wherein the cells are hematopoietic stem cells.

8. The method of claim 2, wherein the contacting occurs in vivo following administration of (i), (ii), and the donor oligonucleotide to a subject in need thereof.

9. The method of claim 8, wherein the subject has a disease or disorder.

10. The method of claim 8, wherein (i), (ii), the donor oligonucleotide or a combination thereof are packaged together or separately in nanoparticles.

11. The method of claim 10, wherein the nanoparticles comprise poly(lactic-co-glycolic acid) (PLGA).

12. The method of claim 1, wherein the gene editing potentiating agent is a receptor tyrosine kinase C-kit ligand.

13. A method of modifying the genomes of CD117+ cells comprising contacting the CD117+ cells with an effective amount of
   (i) a gene editing potentiating agent selected from the group consisting of receptor tyrosine kinase C-kit ligands, ATR-Chk1 cell cycle checkpoint pathway inhibitors, and heat shock protein 90 inhibitors (HSP90i), and
   (ii) a triplex forming composition comprising a peptide nucleic acid (PNA), wherein one or more of the PNA monomers is a γPNA,
   to modify the genomes of the cells contacted with both (i) and (ii) at a higher frequency than an equivalent population of cells contacted with (ii) in the absence of (i).

14. An isolated population of cells treated according to the method of claim 2.

15. The method of claim 1, wherein the gene editing technology is a triplex forming molecule.

16. The method of claim 15, wherein the triplex forming molecule comprises a peptide nucleic acid (PNA) comprising:
   (a) a Hoogsteen binding PNA segment;
   (b) a Watson-Crick binding PNA segment; and
   (c) a γPNA monomer.

17. The method of claim 16, wherein (a) and (b) are linked by a linker.

18. The method of claim 16, wherein the PNA comprises a polyethylene glycol moiety.

19. The method of claim 16, wherein the triplex forming molecule is a tail-clamp PNA.

20. The method of claim 16, wherein the Hoogsteen binding segment comprises a chemically modified cytosine.

21. The method of claim 15, wherein the cells comprise a genome encoding a human beta-globin gene,
   the triplex forming molecule forms a triplex at the cells' genomic beta-globin locus and, the triplex forming molecule comprises a Hoogsteen binding peptide nucleic acid (PNA) segment and a Watson-Crick binding PNA segment, wherein
(i) the Hoogsteen binding segment comprises the sequence JTTTJTTTJTJT (SEQ ID NO:30) and the Watson-Crick binding segment comprises the sequence TCTCTTTCTTTC (SEQ ID NO:22) or TCTCTTTCTTTCAGGGCA (SEQ ID NO:23);
(ii) the Hoogsteen binding segment comprises the sequence TTTTJJJ (SEQ ID NO:31) and the Watson-Crick binding segment comprises the sequence CCCTTTT (SEQ ID NO:25) or CCCTTTTGCTAATCATGT (SEQ ID NO:26);
(iii) the Hoogsteen binding segment comprises the sequence TTTJTJJ (SEQ ID NO:32) and the Watson-Crick binding segment comprises the sequence CCTCTTT (SEQ ID NO:28) or CCTCTTTGCACCATTCT (SEQ ID NO:29);
(iv) the Hoogsteen binding segment comprises the sequence TJTTTTJTTJ (SEQ ID NO:36) and the Watson-Crick binding segment comprises the sequence CTTCTTTTCT (SEQ ID NO:37);
(v) the Hoogsteen binding segment comprises the sequence TTJTTJTTTJ (SEQ ID NO:38) and the Watson-Crick binding segment comprises the sequence CTTTCTTCTT (SEQ ID NO:39);
(vi) the Hoogsteen binding segment comprises the sequence JJJTJJTTJT (SEQ ID NO:40) and the Watson-Crick binding segment comprises TCTTCCTCCC (SEQ ID NO:41);
(vii) the Hoogsteen binding segment comprises the sequence JJTJTTJ (SEQ ID NO:56) and the Watson-Crick binding segment comprises the sequence CTTCTCC (SEQ ID NO:46) or CTTCTCCAAAGGAGT (SEQ ID NO:47) or CTTCTCCACAGGAGTCAG (SEQ ID NO:48) or CTTCTCCACAGGAGTCAGGTGC (SEQ ID NO:205);
(viii) the Hoogsteen binding segment comprises the sequence TTJJTJT (SEQ ID NO:214) and the Watson-Crick binding segment comprises the sequence TCTCCTT (SEQ ID NO:50) or TCTCCTTAAACCTGT (SEQ ID NO:51) or TCTCCTTAAACCTGTCTT (SEQ ID NO:212); or
(ix) the Hoogsteen binding segment comprises the sequence TJTJTTJT (SEQ ID NO:215) and the Watson-Crick binding segment comprises the sequence TCTTCTCT (SEQ ID NO:53) or TCTTCTCTGTCTCCAC (SEQ ID NO:54) or TCTTCTCTGTCTCCACAT (SEQ ID NO:55);
wherein "J" is pseudoisocytosine, and
wherein the two segments are optionally linked by a linker.

22. The method of 21, wherein the triplex forming molecule comprises a sequence selected from:

(i)
(SEQ ID NO: 33)
lys-lys-lys-JTTTJTTTJTJT-OOO-T<u>CT</u>C<u>TTT</u>C<u>TTT</u>C<u>A</u>GGGC<u>A</u>-lys-lys-lys;

(ii)
(SEQ ID NO: 34)
lys-lys-lys-TTTTJJJ-OOO-C<u>CC</u>T<u>TTT</u>G<u>CT</u>AAT<u>C</u>A<u>TGT</u>-lys-lys;

(iii)
(SEQ ID NO: 35)
lys-lys-lys-TTTJTJJ-OOO-C<u>CT</u>C<u>TTT</u>G<u>C</u>AC<u>C</u>A<u>TTC</u>T-lys-lys-lys, (iv)
(SEQ ID NO: 42)
lys-lys-lys-TJTTTTJTTJ-OOO-C<u>TT</u>C<u>TTTT</u>C<u>T</u>-lys-lys-lys (IVS2-24);

(v)
(SEQ ID NO: 43)
lys-lys-lys-TTJTTJTTTJ-OOO-C<u>TTT</u>C<u>TT</u>C<u>TT</u>-lys-lys-lys (IVS2-512);

(vi)
(SEQ ID NO: 44)
lys-lys-lys-JJJTJJTTJT-OOO-T<u>CTT</u>CC<u>T</u>CC<u>C</u>-lys-lys-lys (IVS2-830);

(vii)
(SEQ ID NO: 160)
lys-lys-lys-JJTJTTJ-OOO-C<u>TT</u>C<u>T</u>CC<u>AAAGG</u>A<u>G</u>T-lys-lys-lys;

(viii)
(SEQ ID NO: 57)
lys-lys-lys-TTJJTJT-OOO-T<u>C</u>T<u>CC</u>T<u>T</u>A<u>AACC</u>T<u>G</u>T-lys-lys-lys;

(ix)
(SEQ ID NO: 213)
lys-lys-lys-TTJJTJT-OOO-T<u>C</u>T<u>CC</u>T<u>T</u>A<u>AACC</u>T<u>G</u>T<u>C</u>T<u>T</u>-lys-lys-lys (x)
(SEQ ID NO: 58)
lys-lys-lys-TJTJTTJT-OOO-T<u>C</u>T<u>T</u>C<u>T</u>C<u>TG</u>T<u>C</u>T<u>CC</u>A<u>C</u>-lys-lys-lys (tc816);

(xi)
(SEQ ID NO: 59)
lys-lys-lys-JJTJTTJ-OOO-C<u>TT</u>C<u>T</u>CC<u>A</u>C<u>A</u>GG<u>A</u>G<u>T</u>C<u>A</u>G-lys-lys-lys;

(xii)
(SEQ ID NO: 59)
lys-lys-lys-JJTJTTJ-OOO-<u>CTT</u>C<u>T</u>CC<u>A</u>C<u>A</u>GG<u>A</u>G<u>T</u>C<u>A</u>G-lys-lys (SCD-tcPNA 1A);

(xiii)
(SEQ ID NO: 59)
lys-lys-lys-JJTJTTJ-OOO-<u>CTTCTCCACAGGAGTCAG</u>-lys-lys (SCD-tcPNA 1B);

(xiv)
(SEQ ID NO: 59)
lys-lys-lys-JJ<u>TJTTJ</u>-OOO-<u>CTTCTCCACAGGAGTCAG</u>-lys-lys (SCD-tcPNA 1C);

(xv)
(SEQ ID NO: 209)
lys-lys-lys-JJTJTTJ-OOO-<u>CTTCTCCACAGGAGTCAGGTGC</u>-lys-lys-lys (SCD-tcPNA 1D);

-continued (xvi)
(SEQ ID NO: 209)
lys-lys-lys-JJTJTTJ-OOO-CTTCTCCACAGGAGTCAGGTGC- lys-lys-lys (SCD-tcPNA 1E);

(xvii)
(SEQ ID NO: 209)
lys-lys-lys-JJTJTTJ-OOO-CTTCTCCACAGGAGTCAGGTGC- lys-lys-lys (SCD-tcPNA 1F);

(xviii)
(SEQ ID NO: 60)
lys-lys-lys-TJTJTTJT-OOO-TCTTCTCTGTCTCCACAT-lyslys-lys;

wherein each "lys" is the amino acid lysine, each "J" is pseudoisocytosine, each "O" is selected from 8-amino-3,6-dioxaoctanoic acid, 6-aminohexanoic acid, and 8-amino-2,6,10-trioxaoctanoic acid, and the bolded and underlined residues are miniPEG-containing γPNA residues.

binding segment comprises the sequence TTTTTCT (SEQ ID NO:111) or TTTTTCTGTAATTTTTAA (SEQ ID NO:112);

(v) the Hoogsteen binding segment comprises the sequence TJTJTTTJT (SEQ ID NO:119) and the Watson-Crick binding segment comprises the sequence TCTTTCTCT (SEQ ID NO:114) or TCTTTCTCTGCAAACTT (SEQ ID NO:115); or (vi) the Hoogsteen binding segment comprises the sequence TTTJTTT (SEQ ID NO:120) and the Watson-Crick binding segment comprises the sequence TTTCTTT (SEQ ID NO:116) or TTTCTTTAAGAACGAGCA (SEQ ID NO:117);

wherein "J" is pseudoisocytosine, and wherein the two segments are optionally linked by a linker.

24. The method of claim 23, wherein the triplex forming molecule comprises a sequence selected from:

```
(i)    lys-lys-lys-JTTJJTJTTT-OOO-TTTCTCCTTCAGTGTTCA-lys-lys-lys;    (SEQ ID NO: 155)
(ii)   lys-lys-lys-TTTTJJT-OOO-TCCTTTTGCTCACCTGTGGT-lys-lys-lys;     (SEQ ID NO: 156)
(iii)  lys-lys-lys-TJTTTTTTJJ-OOO-CCTTTTTTCTGGCTAAGT-lys-lys-lys;    (SEQ ID NO: 157)
(iv)   lys-lys-lys-TJTTTTT-OOO-TTTTTCTGTAATTTTTAA-lys-lys-lys;       (SEQ ID NO: 121)
(v)    lys-lys-lys-TJTJTTTJT-OOO-TCTTTCTCTGCAAACTT-lys-lys-lys;      (SEQ ID NO: 122)
(vi)   lys-lys-lys-TTTJTTT-OOO-TTTCTTTAAGAACGAGCA-lys-lys-lys; and   (SEQ ID NO: 123)
(vii)  lys-lys-lys-TJTJJTTT-OOO-TTTCCTCTATGGGTAAG-lys-lys-lys        (SEQ ID NO: 93)
```

23. The method of claim 15, wherein the cells comprise a genome encoding a human cystic fibrosis transmembrane conductance regulator (CFTR) gene,
the triplex forming molecule forms a triplex at the genomic locus of the CFTR gene and
the triplex forming molecule comprises a Hoogsteen binding peptide nucleic acid (PNA) segment and a Watson-Crick binding PNA segment, wherein
(i) the Hoogsteen binding segment comprises the sequence JTTJJTJTTT (SEQ ID NO:106) and the Watson-Crick binding segment comprises the sequence TTTCTCCTTC (SEQ ID NO:98) or TTTCTCCTTCAGTGTTCA (SEQ ID NO:99);
(ii) the Hoogsteen binding segment comprises the sequence TTTTJJT (SEQ ID NO:107) and the Watson-Crick binding segment comprises the sequence TCCTTTT (SEQ ID NO:101) or TCCTTTTGCTCACCTGTGGT (SEQ ID NO:102);
(iii) the Hoogsteen binding segment comprises the sequence TJTTTTTTJJ (SEQ ID NO:108) and the Watson-Crick binding segment comprises the sequence CCTTTTTCT (SEQ ID NO:104) or CCTTTTTTCTGGCTAAGT (SEQ ID NO:105);
(iv) the Hoogsteen binding segment comprises the sequence TJTTTTT (SEQ ID NO:118) Watson-Crick wherein each "lys" is the amino acid lysine, each "J" is pseudoisocytosine, each "O" is selected from 8-amino-3,6-dioxaoctanoic acid, 6-aminohexanoic acid, and 8-amino-2,6,10-trioxaoctanoic acid, and the bolded and underlined residues are miniPEG-containing γPNA residues.

25. The method of claim 3, wherein the disease is cystic fibrosis.

26. The method of claim 1, wherein DNA repair pathway is the homology-dependent repair (HDR) pathway.

27. The method of claim 1, wherein the gene editing technology comprises an enzyme that induces a single or double strand break in cells' genomes.

28. The method of claim 27, wherein the enzyme is a Cas endonuclease, zinc finger nuclease (ZFN), transcription activator-like effector nucleases (TALEN), or intron encoded meganuclease.

29. The method of claim 13, further comprising contacting the cells with a donor oligonucleotide comprising a sequence that introduces or corrects a mutation(s) in the cells' genomes by insertion or recombination induced or enhanced by the triplex forming composition.

30. The method of claim 13, wherein the gene editing potentiating agent is a receptor tyrosine kinase C-kit ligand.

* * * * *

SEQUENCE LISTING

<160> NUMBER OF SEQ ID NOS: 216

<210> SEQ ID NO 1
<211> LENGTH: 273
<212> TYPE: PRT
<213> ORGANISM: Homo sapiens

<400> SEQUENCE: 1

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val

<210> SEQ ID NO 2
<211> LENGTH: 165
<212> TYPE: PRT
<213> ORGANISM: Homo sapiens

<400> SEQUENCE: 2

Met Glu Gly Ile Cys Arg Asn Arg Val Thr Asn Asn Val Lys Asp Val
1               5                   10                  15

Thr Lys Leu Val Ala Asn Leu Pro Lys Asp Tyr Met Ile Thr Leu Lys
            20                  25                  30

Tyr Val Pro Gly Met Asp Val Leu Pro Ser His Cys Trp Ile Ser Glu
        35                  40                  45

```
Met Val Val Gln Leu Ser Asp Ser Leu Thr Asp Leu Leu Asp Lys Phe
         50                  55                  60

Ser Asn Ile Ser Glu Gly Leu Ser Asn Tyr Ser Ile Ile Asp Lys Leu
 65                  70                  75                  80

Val Asn Ile Val Asp Asp Leu Val Glu Cys Val Lys Glu Asn Ser Ser
                 85                  90                  95

Lys Asp Leu Lys Lys Ser Phe Lys Ser Pro Glu Pro Arg Leu Phe Thr
                100                 105                 110

Pro Glu Glu Phe Phe Arg Ile Phe Asn Arg Ser Ile Asp Ala Phe Lys
                115                 120                 125

Asp Phe Val Val Ala Ser Glu Thr Ser Asp Cys Val Val Ser Ser Thr
        130                 135                 140

Leu Ser Pro Glu Lys Asp Ser Arg Val Ser Val Thr Lys Pro Phe Met
145                 150                 155                 160

Leu Pro Pro Val Ala
                165

<210> SEQ ID NO 3
<211> LENGTH: 273
<212> TYPE: PRT
<213> ORGANISM: Mus musculus

<400> SEQUENCE: 3

Met Lys Lys Thr Gln Thr Trp Ile Ile Thr Cys Ile Tyr Leu Gln Leu
 1               5                  10                  15

Leu Leu Phe Asn Pro Leu Val Lys Thr Lys Glu Ile Cys Gly Asn Pro
                 20                  25                  30

Val Thr Asp Asn Val Lys Asp Ile Thr Lys Leu Val Ala Asn Leu Pro
                 35                  40                  45

Asn Asp Tyr Met Ile Thr Leu Asn Tyr Val Ala Gly Met Asp Val Leu
         50                  55                  60

Pro Ser His Cys Trp Leu Arg Asp Met Val Ile Gln Leu Ser Leu Ser
 65                  70                  75                  80

Leu Thr Thr Leu Leu Asp Lys Phe Ser Asn Ile Ser Glu Gly Leu Ser
                 85                  90                  95

Asn Tyr Ser Ile Ile Asp Lys Leu Gly Lys Ile Val Asp Asp Leu Val
                100                 105                 110

Leu Cys Met Glu Glu Asn Ala Pro Lys Asn Ile Lys Glu Ser Pro Lys
        115                 120                 125

Arg Pro Glu Thr Arg Ser Phe Thr Pro Glu Gly Phe Phe Ser Ile Phe
130                 135                 140

Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Ala Lys Ala Pro
                195                 200                 205

Glu Asp Ser Gly Leu Gln Trp Thr Ala Met Ala Leu Pro Ala Leu Ile
        210                 215                 220

Ser Leu Val Ile Gly Phe Ala Phe Gly Ala Leu Tyr Trp Lys Lys Lys
225                 230                 235                 240

Gln Ser Ser Leu Thr Arg Ala Val Glu Asn Ile Gln Ile Asn Glu Glu
```

```
                        245                 250                 255
Asp Asn Glu Ile Ser Met Leu Gln Gln Lys Glu Arg Glu Phe Gln Glu
                260                 265                 270
Val

<210> SEQ ID NO 4
<211> LENGTH: 165
<212> TYPE: PRT
<213> ORGANISM: Mus musculus

<400> SEQUENCE: 4

Met Lys Glu Ile Cys Gly Asn Pro Val Thr Asp Asn Val Lys Asp Ile
1               5                   10                  15

Thr Lys Leu Val Ala Asn Leu Pro Asn Asp Tyr Met Ile Thr Leu Asn
            20                  25                  30

Tyr Val Ala Gly Met Asp Val Leu Pro Ser His Cys Trp Leu Arg Asp
        35                  40                  45

Met Val Ile Gln Leu Ser Leu Ser Leu Thr Thr Leu Leu Asp Lys Phe
    50                  55                  60

Ser Asn Ile Ser Glu Gly Leu Ser Asn Tyr Ser Ile Ile Asp Lys Leu
65                  70                  75                  80

Gly Lys Ile Val Asp Asp Leu Val Leu Cys Met Glu Glu Asn Ala Pro
                85                  90                  95

Lys Asn Ile Lys Glu Ser Pro Lys Arg Pro Glu Thr Arg Ser Phe Thr
            100                 105                 110

Pro Glu Glu Phe Phe Ser Ile Phe Asn Arg Ser Ile Asp Ala Phe Lys
        115                 120                 125

Asp Phe Met Val Ala Ser Asp Thr Ser Asp Cys Val Leu Ser Ser Thr
    130                 135                 140

Leu Gly Pro Glu Lys Asp Ser Arg Val Ser Val Thr Lys Pro Phe Met
145                 150                 155                 160

Leu Pro Pro Val Ala
                165

<210> SEQ ID NO 5
<211> LENGTH: 273
<212> TYPE: PRT
<213> ORGANISM: Mus musculus

<400> SEQUENCE: 5

Met Lys Lys Thr Gln Thr Trp Ile Ile Thr Cys Ile Tyr Leu Gln Leu
1               5                   10                  15

Leu Leu Phe Asn Pro Leu Val Lys Thr Gln Glu Ile Cys Arg Asn Pro
            20                  25                  30

Val Thr Asp Asn Val Lys Asp Ile Thr Lys Leu Val Ala Asn Leu Pro
        35                  40                  45

Asn Asp Tyr Met Ile Thr Leu Asn Tyr Val Ala Gly Met Asp Val Leu
    50                  55                  60

Pro Ser His Cys Trp Leu Arg Asp Met Val Thr His Leu Ser Val Ser
65                  70                  75                  80

Leu Thr Thr Leu Leu Asp Lys Phe Ser Asn Ile Ser Glu Gly Leu Ser
                85                  90                  95

Asn Tyr Ser Ile Ile Asp Lys Leu Gly Lys Ile Val Asp Asp Leu Val
            100                 105                 110

Ala Cys Met Glu Glu Asn Ala Pro Lys Asn Val Lys Glu Ser Leu Lys
        115                 120                 125
```

-continued

Lys Pro Glu Thr Arg Asn Phe Thr Pro Glu Glu Phe Phe Ser Ile Phe
            130                 135                 140

Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Ala Lys Ser Pro
            195                 200                 205

Glu Asp Pro Gly Leu Gln Trp Thr Ala Met Ala Leu Pro Ala Leu Ile
210                 215                 220

Ser Leu Val Ile Gly Phe Ala Phe Gly Ala Leu Tyr Trp Lys Lys Lys
225                 230                 235                 240

Gln Ser Ser Leu Thr Arg Ala Val Glu Asn Ile Gln Ile Asn Glu Glu
                245                 250                 255

Asp Asn Glu Ile Ser Met Leu Gln Gln Lys Glu Arg Glu Phe Gln Glu
                260                 265                 270

Val

<210> SEQ ID NO 6
<211> LENGTH: 165
<212> TYPE: PRT
<213> ORGANISM: Rattus rattus

<400> SEQUENCE: 6

Met Gln Glu Ile Cys Arg Asn Pro Val Thr Asp Asn Val Lys Asp Ile
1               5                   10                  15

Thr Lys Leu Val Ala Asn Leu Pro Asn Asp Tyr Met Ile Thr Leu Asn
            20                  25                  30

Tyr Val Ala Gly Met Asp Val Leu Pro Ser His Cys Trp Leu Arg Asp
                35                  40                  45

Met Val Thr His Leu Ser Val Ser Leu Thr Thr Leu Leu Asp Lys Phe
50                  55                  60

Ser Asn Ile Ser Glu Gly Leu Ser Asn Tyr Ser Ile Ile Asp Lys Leu
65                  70                  75                  80

Gly Lys Ile Val Asp Asp Leu Val Ala Cys Met Glu Glu Asn Ala Pro
                85                  90                  95

Lys Asn Val Lys Glu Ser Leu Lys Lys Pro Glu Thr Arg Asn Phe Thr
            100                 105                 110

Pro Glu Glu Phe Phe Ser Ile Phe Asn Arg Ser Ile Asp Ala Phe Lys
            115                 120                 125

Asp Phe Met Val Ala Ser Asp Thr Ser Asp Cys Val Leu Ser Ser Thr
            130                 135                 140

Leu Gly Pro Glu Lys Asp Ser Arg Val Ser Val Thr Lys Pro Phe Met
145                 150                 155                 160

Leu Pro Pro Val Ala
                165

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 7

Tyr Gly Arg Lys Lys Arg Arg Gln Arg Arg Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Arg Lys Lys Arg Arg Gln Arg Arg Arg
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 10

His His His His Arg Lys Lys Arg Arg Gln Arg Arg Arg His His
1               5                   10                  15

His His His

<210> SEQ ID NO 11
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 11

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 12
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 12

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

```
<210> SEQ ID NO 13
<211> LENGTH: 6060
<212> TYPE: DNA
<213> ORGANISM: Homo sapiens

<400> SEQUENCE: 13
aaagctcttg ctttgacaat tttggtcttt cagaatacta taaatataac ctatattata     60
atttcataaa gtctgtgcat tttctttgac ccaggatatt tgcaaaagac atattcaaac    120
ttccgcagaa cactttattt cacatataca tgcctcttat atcagggatg tgaaacaggg    180
tcttgaaaac tgtctaaatc taaaacaatg ctaatgcagg tttaaattta ataaaataaa    240
atccaaaatc taacagccaa gtcaaatctg tatgttttaa catttaaaat attttaaaga    300
cgtcttttcc caggattcaa catgtgaaat cttttctcag ggatacacgt gtgcctagat    360
cctcattgct ttagtttttt acagaggaat gaatataaaa agaaaatact taaattttat    420
ccctcttacc tctataatca tacataggca taatttttta acctaggctc cagatagcca    480
tagaagaacc aaaactttc tgcgtgtgtg agaataatca gagtgagatt ttttcacaag    540
tacctgatga gggttgagac aggtagaaaa agtgagagat ctctatttat ttagcaataa    600
tagagaaagc atttaagaga ataaagcaat ggaaataaga aatttgtaaa tttccttctg    660
ataactagaa atagaggatc cagtttcttt tggttaacct aaattttatt tcattttatt    720
gttttatttt attttatttt attttatttt gtgtaatcgt agtttcagag tgttagagct    780
gaaaggaaga agtaggagaa acatgcaaag taaaagtata acactttcct tactaaaccg    840
actgggtttc caggtagggg caggattcag gatgactgac agggccctta gggaacactg    900
agaccctacg ctgacctcat aaatgcttgc tacctttgct gttttaatta catcttttaa    960
tagcaggaag cagaactctg cacttcaaaa gttttcctc acctgaggag ttaatttagt   1020 acaagggaa aaagtacagg gggatgggag aaaggcgatc acgttgggaa gctatagaga   1080
aagaagagta aattttagta aaggaggttt aaacaaacaa aatataaaga gaataggaa    1140 cttgaatcaa ggaaatgatt ttaaaacgca gtattcttag tggactagag gaaaaaaata   1200
atctgagcca agtagaagac cttttccccct cctaccccta cttctaagt cacagaggct   1260 ttttgttccc ccagacactc ttgcagatta gtccaggcag aaacagttag atgtccccag   1320
ttaacctcct atttgacacc actgattacc ccattgatag tcacactttg ggttgtaagt   1380
gactttttat ttatttgtat ttttgactgc attaagaggt ctctagtttt ttatctcttg   1440
tttcccaaaa cctaataagt aactaatgca cagagcacat tgatttgtat ttattctatt   1500
tttagacata atttattagc atgcatgagc aaattaagaa aaacaacaac aaatgaatgc   1560
atatatatgt atatgtatgt gtgtatatat acacatatat atatatattt tttttctttt   1620
cttaccagaa ggttttaatc caaataagga gaagatatgc ttagaactga ggtagagttt   1680
tcatccattc tgtcctgtaa gtattttgca tattctggag acgcaggaag agatccatct   1740
acatatccca aagctgaatt atggtagaca aagctcttcc acttttagtg catcaatttc   1800
ttatttgtgt aataagaaaa ttgggaaaac gatcttcaat atgcttacca agctgtgatt   1860
ccaaatatta cgtaaataca cttgcaaagg aggatgtttt tagtagcaat ttgtactgat   1920 ggtatgggc caagagatat atcttagagg gagggctgag ggtttgaagt ccaactccta   1980
agccagtgcc agaagagcca aggacaggta cggctgtcat cacttagacc tcaccctgtg   2040
gagccacacc ctagggttgg ccaatctact cccaggagca gggagggcag gagccagggc   2100
tgggcataaa agtcagggca gagccatcta ttgcttacat ttgcttctga cacaactgtg   2160
```

```
ttcactagca acctcaaaca gacaccatgg tgcacctgac tcctgaggag aagtctgccg    2220
ttactgccct gtggggcaag gtgaacgtgg atgaagttgg tggtgaggcc ctgggcaggt    2280
tggtatcaag gttacaagac aggtttaagg agaccaatag aaactgggca tgtggagaca    2340
gagaagactc ttgggtttct gataggcact gactctctct gcctattggt ctattttccc    2400
acccttaggc tgctggtggt ctaccettgg acccagaggt tctttgagtc ctttggggat    2460
ctgtccactc ctgatgctgt tatgggcaac cctaaggtga aggctcatgg caagaaagtg    2520
ctcggtgcct ttagtgatgg cctggctcac ctggacaacc tcaagggcac ctttgccaca    2580
ctgagtgagc tgcactgtga caagctgcac gtggatcctg agaacttcag ggtgagtcta    2640
tgggacccett gatgttttct tcccettct tttctatggt taagttcatg tcataggaag    2700
gggagaagta acagggtaca gtttagaatg gaaacagac gaatgattgc atcagtgtgg    2760
aagtctcagg atcgttttag tttcttttat ttgctgttca taacaattgt tttcttttgt    2820
ttaattcttg cttctttttt ttttcttctc cgcaattttt actattatac ttaatgcctt    2880
aacattgtgt ataacaaaag gaaatatctc tgagatacat taagtaactt aaaaaaaaac    2940
tttacacagt ctgcctagta cattactatt tggaatatat gtgtgcttat ttgcatattc    3000
ataatctccc tactttattt tcttttattt ttaattgata cataatcatt atacatattt    3060
atgggttaaa gtgtaatgtt ttaatatgtg tacacatatt gaccaaatca gggtaatttt    3120
gcatttgtaa ttttaaaaaa tgcttttcttc ttttaatata ctttttttgtt tatcttattt    3180
ctaatacttt ccctaatctc tttctttcag ggcaataatg atacaatgta tcatgcctct    3240
ttgcaccatt ctaaagaata acagtgataa tttctgggtt aaggcaatag caatatttct    3300
gcatataaat atttctgcat ataaattgta actgatgtaa gaggtttcat attgctaata    3360
gcagctacaa tccagctacc attctgcttt tatttttatgg ttgggataag gctggattat    3420
tctgagtcca agctaggccc ttttgctaat catgttcata cctcttatct tcctcccaca    3480
gctcctgggc aacgtgctgg tctgtgtgct ggcccatcac tttggcaaag aattcacccc    3540
accagtgcag gctgcctatc agaaagtggt ggctggtgtg ctaatgccc tggcccacaa    3600
gtatcactaa gctcgctttc ttgctgtcca atttctatta aaggttcctt tgttccctaa    3660
gtccaactac taaactgggg gatattatga agggccttga gcatctggat tctgcctaat    3720
aaaaaacatt tattttcatt gcaatgatgt atttaaatta tttctgaata ttttactaaa    3780
aagggaatgt gggaggtcag tgcatttaaa acataaagaa atgaagagct agttcaaacc    3840
ttgggaaaat acactatatc ttaaactcca tgaaagaagg tgaggctgca aacagctaat    3900
gcacattggc aacagccctg atgcctatgc cttattcatc cctcagaaaa ggattcaagt    3960
agaggcttga tttggaggtt aaagttttgc tatgctgtat tttacattac ttattgtttt    4020
agctgtcctc atgaatgtct tttcactacc catttgctta tcctgcatct ctcagccttg    4080
actccactca gttctcttgc ttagagatac ccactttccc ctgaagtgtt ccttccatgt    4140
tttacggcga gatggtttct cctcgcctgg ccactcagcc ttagttgtct ctgttgtctt    4200
atagaggtct acttgaagaa ggaaaaacag ggggcatggt ttgactgtcc tgtgagccct    4260
tcttccctgc ctcccccact cacagtgacc cggaatctgc agtgctagtc tcccggaact    4320
atcactcttt cacagtctgc tttggaagga ctgggcttag tatgaaaagt taggactgag    4380
aagaatttga aagggggctt tttgtagctt gatattcact actgtcttat taccctatca    4440
taggcccacc ccaaatggaa gtcccattct tcctcaggat gtttaagatt agcattcagg    4500
aagagatcag aggtctgctg gctccettat catgtcccett atggtgcttc tggctctgca    4560
```

```
gttattagca tagtgttacc atcaaccacc ttaacttcat ttttcttatt caatacctag    4620
gtaggtagat gctagattct ggaaataaaa tatgagtctc aagtggtcct tgtcctctct    4680
cccagtcaaa ttctgaatct agttggcaag attctgaaat caaggcatat aatcagtaat    4740
aagtgatgat agaagggtat atagaagaat tttattatat gagagggtga aacctaaaat    4800
gaaatgaaat cagacccttg tcttacacca taaacaaaaa taaatttgaa tgggttaaag    4860
aattaaacta agacctaaaa ccataaaaat ttttaaagaa atcaaaagaa gaaaattcta    4920
atattcatgt tgcagccgtt ttttgaattt gatatgagaa gcaaaggcaa caaaaggaaa    4980
aataaagaag tgaggctaca tcaaactaaa aaatttccac acaaaaaaga aaacaatgaa    5040
caaatgaaag gtgaaccatg aaatggcata tttgcaaacc aaatatttct taaatatttt    5100
ggttaatatc caaatatat aagaaacaca gatgattcaa taacaaacaa aaaattaaaa    5160
ataggaaaat aaaaaaatta aaagaagaa atcctgcca tttatgcgag aattgatgaa    5220
cctggaggat gtaaaactaa gaaaataag cctgacacaa aaagacaaat actacacaac    5280
cttgctcata tgtgaaacat aaaaaagtca ctctcatgga aacagacagt agaggtatgg    5340
tttccagggg ttgggggtgg gagaatcagg aaactattac tcaagggta taaaatttca    5400 gttatgtggg atgaataaat tctagatatc taatgtacag catcgtgact gtagttaatt    5460
gtactgtaag tatatttaaa atttgcaaag agagtagatt ttttttgtttt tttagatgga    5520 gttttgctct tgttgtccag gctggagtgc aatggcaaga tcttggctca ctgcaacctc    5580
cgcctcctgg gttcaagcaa atctcctgcc tcagcctccc gagtagctgg gattacaggc    5640
atgcgacacc atgcccagct aattttgtat ttttagtaga cgggggtttt ctccatgttg    5700
gtcaggctga tccgcctcct cggccaccaa agggctggga ttacaggcgt gaccaccggg    5760
cctggccgag agtagatctt aaaagcattt accacaagaa aaaggtaact atgtgagata    5820
atgggtatgt taattagctt gattgtggta atcatttcac aaggtataca tatattaaaa    5880
catcatgttg tacaccttaa atatatacaa ttttttatttg tgaatgatac ctcaataaag    5940
ttgaagaata ataaaaaaga atagacatca catgaattaa aaaactaaaa aataaaaaaa    6000
tgcatcttga tgattagaat tgcattcttg attttcaga tacaaatatc catttgactg    6060
```

<210> SEQ ID NO 14
<211> LENGTH: 850
<212> TYPE: DNA
<213> ORGANISM: Homo sapiens

<400> SEQUENCE: 14

```
gtgagtctat gggacccttg atgttttctt tccccttctt ttctatggtt aagttcatgt      60
cataggaagg ggagaagtaa cagggtacag tttagaatgg gaaacagacg aatgattgca     120
tcagtgtgga agtctcagga tcgttttagt ttcttttatt tgctgttcat aacaattgtt     180
ttcttttgtt taattcttgc tttctttttt tttcttctcc gcaattttta ctattatact     240
taatgcctta acattgtgta taacaaaagg aaatatctct gagatacatt aagtaactta     300
aaaaaaaact ttacacagtc tgcctagtac attactattt ggaatatatg tgtgcttatt     360
tgcatattca taatctccct actttatttt cttttatttt taattgatac ataatcatta     420
tacatattta tgggttaaag tgtaatgttt taatatgtgt acacatattg accaaatcag     480
ggtaattttg catttgtaat tttaaaaat gctttcttct tttaatatac ttttttgttt     540
atcttatttc taatactttc cctaatctct ttctttcagg gcaataatga tacaatgtat     600
```

-continued

```
catgcctctt tgcaccattc taaagaataa cagtgataat ttctgggtta aggcaatagc      660
aatatttctg catataaata tttctgcata taaattgtaa ctgatgtaag aggtttcata      720
ttgctaatag cagctacaat ccagctacca ttctgctttt attttatggt tgggataagg      780
ctggattatt ctgagtccaa gctaggccct tttgctaatc atgttcatac ctcttatctt      840
cctcccacag                                                             850

<210> SEQ ID NO 15
<211> LENGTH: 12
<212> TYPE: DNA
<213> ORGANISM: Artificial Sequence
<220> FEATURE:
<223> OTHER INFORMATION: Synthetic Primer

<400> SEQUENCE: 15
gaaagaaaga ga                                                           12

<210> SEQ ID NO 16
<211> LENGTH: 18
<212> TYPE: DNA
<213> ORGANISM: Artificial Sequence
<220> FEATURE:
<223> OTHER INFORMATION: Synthetic Primer

<400> SEQUENCE: 16
tgccctgaaa gaaagaga                                                     18

<210> SEQ ID NO 17
<211> LENGTH: 7
<212> TYPE: DNA
<213> ORGANISM: Artificial Sequence
<220> FEATURE:
<223> OTHER INFORMATION: Synthetic Primer

<400> SEQUENCE: 17 ggagaaa                                                                  7

<210> SEQ ID NO 18
<211> LENGTH: 17
<212> TYPE: DNA
<213> ORGANISM: Artificial Sequence
<220> FEATURE:
<223> OTHER INFORMATION: Synthetic Primer

<400> SEQUENCE: 18
agaatggtgc aaagagg                                                      17

<210> SEQ ID NO 19
<211> LENGTH: 7
<212> TYPE: DNA
<213> ORGANISM: Artificial Sequence
<220> FEATURE:
<223> OTHER INFORMATION: Synthetic Primer

<400> SEQUENCE: 19 aaaaggg                                                                  7

<210> SEQ ID NO 20
<211> LENGTH: 18
<212> TYPE: DNA
<213> ORGANISM: Artificial Sequence
<220> FEATURE:
<223> OTHER INFORMATION: Synthetic Primer

<400> SEQUENCE: 20
```
acatgattag caaaaggg                                                   18

<210> SEQ ID NO 21
<211> LENGTH: 12
<212> TYPE: DNA
<213> ORGANISM: Artificial Sequence
<220> FEATURE:
<223> OTHER INFORMATION: Synthetic Primer

<400> SEQUENCE: 21
ctttctttct ct                                                         12

<210> SEQ ID NO 22
<211> LENGTH: 12
<212> TYPE: DNA
<213> ORGANISM: Artificial Sequence
<220> FEATURE:
<223> OTHER INFORMATION: Synthetic Primer

<400> SEQUENCE: 22
tctctttctt tc                                                         12

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
tctctttctt tcagggca                                                   18

<210> SEQ ID NO 24
<211> LENGTH: 6
<212> TYPE: DNA
<213> ORGANISM: Artificial Sequence
<220> FEATURE:
<223> OTHER INFORMATION: Synthetic Primer

<400> SEQUENCE: 24 tttccc                                                                 6

<210> SEQ ID NO 25
<211> LENGTH: 7
<212> TYPE: DNA
<213> ORGANISM: Artificial Sequence
<220> FEATURE:
<223> OTHER INFORMATION: Synthetic Primer

<400> SEQUENCE: 25 ccctttt                                                                7

<210> SEQ ID NO 26
<211> LENGTH: 18
<212> TYPE: DNA
<213> ORGANISM: Artificial Sequence
<220> FEATURE:
<223> OTHER INFORMATION: Synthetic Primer

<400> SEQUENCE: 26
cccttttgct aatcatgt                                                   18

<210> SEQ ID NO 27
<211> LENGTH: 7
<212> TYPE: DNA

```
<213> ORGANISM: Artificial Sequence
<220> FEATURE:
<223> OTHER INFORMATION: Synthetic Primer

<400> SEQUENCE: 27 tttctcc                                                                    7

<210> SEQ ID NO 28
<211> LENGTH: 7
<212> TYPE: DNA
<213> ORGANISM: Artificial Sequence
<220> FEATURE:
<223> OTHER INFORMATION: Synthetic Primer

<400> SEQUENCE: 28 cctcttt                                                                    7

<210> SEQ ID NO 29
<211> LENGTH: 17
<212> TYPE: DNA
<213> ORGANISM: Artificial Sequence
<220> FEATURE:
<223> OTHER INFORMATION: Synthetic Primer

<400> SEQUENCE: 29
cctctttgca ccattct                                                        17

<210> SEQ ID NO 30
<211> LENGTH: 12
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (5)..(5)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (11)..(11)
<223> OTHER INFORMATION: n = Pseudoisocytosine

<400> SEQUENCE: 30
ntttntttnt nt                                                             12

<210> SEQ ID NO 31
<211> LENGTH: 7
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(7)
<223> OTHER INFORMATION: n = Pseudoisocytosine

<400> SEQUENCE: 31 ttttnnn                                                                    7

<210> SEQ ID NO 32
<211> LENGTH: 7
```

```
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (6)..(7)
<223> OTHER INFORMATION: n = Pseudoisocytosine

<400> SEQUENCE: 32 tttntnn                                                              7

<210> SEQ ID NO 33
<211> LENGTH: 30
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (5)..(5)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (11)..(11)
<223> OTHER INFORMATION: n = Pseudoisocytosine
<220> FEATURE:
<221> NAME/KEY: misc_feature
<222> LOCATION: (12)..(13)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (30)..(30)
<223> OTHER INFORMATION: Linked to lys-lys-lys

<400> SEQUENCE: 33
ntttntttnt nttctctttc tttcagggca                                     30

<210> SEQ ID NO 34
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (5)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
```

```
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 34
ttttnnnccc ttttgctaat catgt                                            25

<210> SEQ ID NO 35
<211> LENGTH: 24
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (6)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (24)..(24)
<223> OTHER INFORMATION: Linked to lys-lys-lys

<400> SEQUENCE: 35
tttntnncct ctttgcacca ttct                                             24

<210> SEQ ID NO 36
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (10)..(10)
<223> OTHER INFORMATION: n = Pseudoisocytosine

<400> SEQUENCE: 36 tnttttnttn                                                             10

<210> SEQ ID NO 37
<211> LENGTH: 10
<212> TYPE: DNA
<213> ORGANISM: Artificial Sequence
<220> FEATURE:
<223> OTHER INFORMATION: Synthetic Primer

<400> SEQUENCE: 37
cttcttttct                                                             10
```

<210> SEQ ID NO 38
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (10)..(10)
<223> OTHER INFORMATION: n = Pseudoisocytosine

<400> SEQUENCE: 38 ttnttntttn                                                          10

<210> SEQ ID NO 39
<211> LENGTH: 10
<212> TYPE: DNA
<213> ORGANISM: Artificial Sequence
<220> FEATURE:
<223> OTHER INFORMATION: Synthetic Primer

<400> SEQUENCE: 39
ctttcttctt                                                          10

<210> SEQ ID NO 40
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(3)
<223> OTHER INFORMATION: n = Pseudoisocytosine
<220> FEATURE:
<221> NAME/KEY: misc_feature
<222> LOCATION: (5)..(6)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine

<400> SEQUENCE: 40 nnntnnttnt                                                          10

<210> SEQ ID NO 41
<211> LENGTH: 10
<212> TYPE: DNA
<213> ORGANISM: Artificial Sequence
<220> FEATURE:
<223> OTHER INFORMATION: Synthetic Primer

<400> SEQUENCE: 41
tcttcctccc                                                          10

<210> SEQ ID NO 42
<211> LENGTH: 20
<212> TYPE: DNA
<213> ORGANISM: Artificial Sequence
<220> FEATURE:

```
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (10)..(10)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (20)..(20)
<223> OTHER INFORMATION: Linked to lys-lys-lys

<400> SEQUENCE: 42
tnttttnttn cttcttttct                                            20

<210> SEQ ID NO 43
<211> LENGTH: 20
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(3)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (10)..(10)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (20)..(20)
<223> OTHER INFORMATION: Linked to lys-lys-lys

<400> SEQUENCE: 43 tnttnttn ctttcttctt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
```

```
<222> LOCATION: (1)..(1)
<223> OTHER INFORMATION: Linked to lys-lys-lys
<220> FEATURE:
<221> NAME/KEY: misc_feature
<222> LOCATION: (1)..(3)
<223> OTHER INFORMATION: n = Pseudoisocytosine
<220> FEATURE:
<221> NAME/KEY: misc_feature
<222> LOCATION: (5)..(6)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (20)..(20)
<223> OTHER INFORMATION: Linked to lys-lys-lys

<400> SEQUENCE: 44
nnntnnttnt tcttcctccc                                            20

<210> SEQ ID NO 45
<211> LENGTH: 7
<212> TYPE: DNA
<213> ORGANISM: Artificial Sequence
<220> FEATURE:
<223> OTHER INFORMATION: Synthetic Primer

<400> SEQUENCE: 45 cctcttc                                                           7

<210> SEQ ID NO 46
<211> LENGTH: 7
<212> TYPE: DNA
<213> ORGANISM: Artificial Sequence
<220> FEATURE:
<223> OTHER INFORMATION: Synthetic Primer

<400> SEQUENCE: 46 cttctcc                                                           7

<210> SEQ ID NO 47
<211> LENGTH: 15
<212> TYPE: DNA
<213> ORGANISM: Artificial Sequence
<220> FEATURE:
<223> OTHER INFORMATION: Synthetic Primer

<400> SEQUENCE: 47
cttctccaaa ggagt                                                 15

<210> SEQ ID NO 48
<211> LENGTH: 18
<212> TYPE: DNA
<213> ORGANISM: Artificial Sequence
<220> FEATURE:
<223> OTHER INFORMATION: Synthetic Primer

<400> SEQUENCE: 48
cttctccaca ggagtcag                                              18

<210> SEQ ID NO 49
```

```
<211> LENGTH: 7
<212> TYPE: DNA
<213> ORGANISM: Artificial Sequence
<220> FEATURE:
<223> OTHER INFORMATION: Synthetic Primer

<400> SEQUENCE: 49 ttcctct                                                                        7

<210> SEQ ID NO 50
<211> LENGTH: 7
<212> TYPE: DNA
<213> ORGANISM: Artificial Sequence
<220> FEATURE:
<223> OTHER INFORMATION: Synthetic Primer

<400> SEQUENCE: 50 tctcctt                                                                        7

<210> SEQ ID NO 51
<211> LENGTH: 15
<212> TYPE: DNA
<213> ORGANISM: Artificial Sequence
<220> FEATURE:
<223> OTHER INFORMATION: Synthetic Primer

<400> SEQUENCE: 51
tctccttaaa cctgt                                                              15

<210> SEQ ID NO 52
<211> LENGTH: 8
<212> TYPE: DNA
<213> ORGANISM: Artificial Sequence
<220> FEATURE:
<223> OTHER INFORMATION: Synthetic Primer

<400> SEQUENCE: 52 tctcttct                                                                       8

<210> SEQ ID NO 53
<211> LENGTH: 8
<212> TYPE: DNA
<213> ORGANISM: Artificial Sequence
<220> FEATURE:
<223> OTHER INFORMATION: Synthetic Primer

<400> SEQUENCE: 53 tcttctct                                                                       8

<210> SEQ ID NO 54
<211> LENGTH: 16
<212> TYPE: DNA
<213> ORGANISM: Artificial Sequence
<220> FEATURE:
<223> OTHER INFORMATION: Synthetic Primer

<400> SEQUENCE: 54
tcttctctgt ctccac                                                             16

<210> SEQ ID NO 55
<211> LENGTH: 18
<212> TYPE: DNA
<213> ORGANISM: Artificial Sequence
<220> FEATURE:
<223> OTHER INFORMATION: Synthetic Primer

<400> SEQUENCE: 55
```

```
tcttctctgt ctccacat                                                       18

<210> SEQ ID NO 56
<211> LENGTH: 7
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine

<400> SEQUENCE: 56 nntnttn                                                                    7

<210> SEQ ID NO 57
<211> LENGTH: 22
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(4)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (22)..(22)
<223> OTHER INFORMATION: Linked to lys-lys-lys

<400> SEQUENCE: 57
ttnntnttct ccttaaacct gt                                                  22

<210> SEQ ID NO 58
<211> LENGTH: 24
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
```

```
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (24)..(24)
<223> OTHER INFORMATION: Linked to lys-lys-lys

<400> SEQUENCE: 58
tntnttnttc ttctctgtct ccac                                           24

<210> SEQ ID NO 59
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 59
nntnttnctt ctccacagga gtcag                                          25

<210> SEQ ID NO 60
<211> LENGTH: 26
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
```

```
<222> LOCATION: (7)..(7)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (26)..(26)
<223> OTHER INFORMATION: Linked to lys-lys-lys

<400> SEQUENCE: 60
tntnttnttc ttctctgtct ccacat                                              26

<210> SEQ ID NO 61
<211> LENGTH: 51
<212> TYPE: DNA
<213> ORGANISM: Artificial Sequence
<220> FEATURE:
<223> OTHER INFORMATION: Synthetic Primer

<400> SEQUENCE: 61
gttcagcgtg tccggcgagg gcgaggtgag tctatgggac ccttgatgtt t                  51

<210> SEQ ID NO 62
<211> LENGTH: 51
<212> TYPE: DNA
<213> ORGANISM: Artificial Sequence
<220> FEATURE:
<223> OTHER INFORMATION: Synthetic Primer

<400> SEQUENCE: 62
aaacatcaag ggtcccatag actcacctcg ccctcgccgg acacgctgaa c                  51

<210> SEQ ID NO 63
<211> LENGTH: 70
<212> TYPE: DNA
<213> ORGANISM: Artificial Sequence
<220> FEATURE:
<223> OTHER INFORMATION: Synthetic Primer

<400> SEQUENCE: 63
cttgccccac agggcagtaa cggcagattt ttcttccggc gttaaatgca ccatggtgtc         60
tgtttgaggt                                                                70

<210> SEQ ID NO 64
<211> LENGTH: 51
<212> TYPE: DNA
<213> ORGANISM: Artificial Sequence
<220> FEATURE:
<223> OTHER INFORMATION: Synthetic Primer

<400> SEQUENCE: 64
acagacacca tggtgcacct gactcctgag gagaagtctg ccgttactgc c                  51

<210> SEQ ID NO 65
<211> LENGTH: 60
<212> TYPE: DNA
<213> ORGANISM: Artificial Sequence
<220> FEATURE:
<223> OTHER INFORMATION: Synthetic Primer

<400> SEQUENCE: 65
aaagaataac agtgataatt tctgggttaa ggcaatagca atatctctgc atataaatat         60
```

```
<210> SEQ ID NO 66
<211> LENGTH: 22
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (22)..(22)
<223> OTHER INFORMATION: Linked to lys-lys-lys

<400> SEQUENCE: 66
nntnttnctt ctccaaagga gt                                          22

<210> SEQ ID NO 67
<211> LENGTH: 22
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(4)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (22)..(22)
<223> OTHER INFORMATION: Linked to lys-lys-lys

<400> SEQUENCE: 67
ttnntnttct ccttaaacct gt                                          22

<210> SEQ ID NO 68
<211> LENGTH: 24
<212> TYPE: DNA
<213> ORGANISM: Artificial Sequence
<220> FEATURE:
<223> OTHER INFORMATION: Synthetic Peptide Nucleic Acid
```

```
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid moleculess
<220> FEATURE:
<221> NAME/KEY: misc_feature
<222> LOCATION: (24)..(4)
<223> OTHER INFORMATION: Linked to lys-lys-lys

<400> SEQUENCE: 68
tntnttnttc ttctctgtct ccac                                            24

<210> SEQ ID NO 69
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 69
tntnnttttt tcctctatgg gtaag                                           25

<210> SEQ ID NO 70
<211> LENGTH: 8
<212> TYPE: DNA
<213> ORGANISM: Artificial Sequence
<220> FEATURE:
<223> OTHER INFORMATION: Synthetic Primer

<400> SEQUENCE: 70 tttcctct                                                               8

<210> SEQ ID NO 71
```

```
<211> LENGTH: 17
<212> TYPE: DNA
<213> ORGANISM: Artificial Sequence
<220> FEATURE:
<223> OTHER INFORMATION: Synthetic Primer

<400> SEQUENCE: 71
tttcctctat gggtaag                                                  17

<210> SEQ ID NO 72
<211> LENGTH: 8
<212> TYPE: DNA
<213> ORGANISM: Artificial Sequence
<220> FEATURE:
<223> OTHER INFORMATION: Synthetic Primer

<400> SEQUENCE: 72 agaggaaa                                                             8

<210> SEQ ID NO 73
<211> LENGTH: 17
<212> TYPE: DNA
<213> ORGANISM: Artificial Sequence
<220> FEATURE:
<223> OTHER INFORMATION: Synthetic Primer

<400> SEQUENCE: 73
cttacccata gaggaaa                                                  17

<210> SEQ ID NO 74
<211> LENGTH: 8
<212> TYPE: DNA
<213> ORGANISM: Artificial Sequence
<220> FEATURE:
<223> OTHER INFORMATION: Synthetic Primer

<400> SEQUENCE: 74 agaagagg                                                             8

<210> SEQ ID NO 75
<211> LENGTH: 17
<212> TYPE: DNA
<213> ORGANISM: Artificial Sequence
<220> FEATURE:
<223> OTHER INFORMATION: Synthetic Primer

<400> SEQUENCE: 75
atgccaacta gaagagg                                                  17

<210> SEQ ID NO 76
<211> LENGTH: 8
<212> TYPE: DNA
<213> ORGANISM: Artificial Sequence
<220> FEATURE:
<223> OTHER INFORMATION: Synthetic Primer

<400> SEQUENCE: 76 cctcttct                                                             8

<210> SEQ ID NO 77
<211> LENGTH: 17
<212> TYPE: DNA
<213> ORGANISM: Artificial Sequence
<220> FEATURE:
<223> OTHER INFORMATION: Synthetic Primer

<400> SEQUENCE: 77
```

```
cctcttctag ttggcat                                                  17

<210> SEQ ID NO 78
<211> LENGTH: 9
<212> TYPE: DNA
<213> ORGANISM: Artificial Sequence
<220> FEATURE:
<223> OTHER INFORMATION: Synthetic Primer

<400> SEQUENCE: 78 ctttcccttt                                                           9

<210> SEQ ID NO 79
<211> LENGTH: 18
<212> TYPE: DNA
<213> ORGANISM: Artificial Sequence
<220> FEATURE:
<223> OTHER INFORMATION: Synthetic Primer

<400> SEQUENCE: 79
ctttcccttg tatctttt                                                 18

<210> SEQ ID NO 80
<211> LENGTH: 9
<212> TYPE: DNA
<213> ORGANISM: Artificial Sequence
<220> FEATURE:
<223> OTHER INFORMATION: Synthetic Primer

<400> SEQUENCE: 80 aagggaaag                                                            9

<210> SEQ ID NO 81
<211> LENGTH: 18
<212> TYPE: DNA
<213> ORGANISM: Artificial Sequence
<220> FEATURE:
<223> OTHER INFORMATION: Synthetic Primer

<400> SEQUENCE: 81
aaaagataca agggaaag                                                 18

<210> SEQ ID NO 82
<211> LENGTH: 8
<212> TYPE: DNA
<213> ORGANISM: Artificial Sequence
<220> FEATURE:
<223> OTHER INFORMATION: Synthetic Primer

<400> SEQUENCE: 82 tctccttt                                                             8

<210> SEQ ID NO 83
<211> LENGTH: 8
<212> TYPE: DNA
<213> ORGANISM: Artificial Sequence
<220> FEATURE:
<223> OTHER INFORMATION: Synthetic Primer

<400> SEQUENCE: 83 tttcctct                                                             8

<210> SEQ ID NO 84
<211> LENGTH: 17
<212> TYPE: DNA
```

```
<213> ORGANISM: Artificial Sequence
<220> FEATURE:
<223> OTHER INFORMATION: Synthetic Primer

<400> SEQUENCE: 84
tttcctctat gggtaag                                                        17

<210> SEQ ID NO 85
<211> LENGTH: 8
<212> TYPE: DNA
<213> ORGANISM: Artificial Sequence
<220> FEATURE:
<223> OTHER INFORMATION: Synthetic Primer

<400> SEQUENCE: 85 tcttctcc                                                                   8

<210> SEQ ID NO 86
<211> LENGTH: 8
<212> TYPE: DNA
<213> ORGANISM: Artificial Sequence
<220> FEATURE:
<223> OTHER INFORMATION: Synthetic Primer

<400> SEQUENCE: 86 cctcttct                                                                   8

<210> SEQ ID NO 87
<211> LENGTH: 17
<212> TYPE: DNA
<213> ORGANISM: Artificial Sequence
<220> FEATURE:
<223> OTHER INFORMATION: Synthetic Primer

<400> SEQUENCE: 87
cctcttctag ttggcat                                                        17

<210> SEQ ID NO 88
<211> LENGTH: 9
<212> TYPE: DNA
<213> ORGANISM: Artificial Sequence
<220> FEATURE:
<223> OTHER INFORMATION: Synthetic Primer

<400> SEQUENCE: 88 ttccctttc                                                                  9

<210> SEQ ID NO 89
<211> LENGTH: 9
<212> TYPE: DNA
<213> ORGANISM: Artificial Sequence
<220> FEATURE:
<223> OTHER INFORMATION: Synthetic Primer

<400> SEQUENCE: 89 ctttcccctt                                                                 9

<210> SEQ ID NO 90
<211> LENGTH: 18
<212> TYPE: DNA
<213> ORGANISM: Artificial Sequence
<220> FEATURE:
<223> OTHER INFORMATION: Synthetic Primer

<400> SEQUENCE: 90
ctttcccttg tatcttt                                                        18
```

<210> SEQ ID NO 91
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine

<400> SEQUENCE: 91 tntnnttt                                                                8

<210> SEQ ID NO 92
<211> LENGTH: 9
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(5)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine

<400> SEQUENCE: 92 ttnnntttn                                                               9

<210> SEQ ID NO 93
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 93
tntnnttttt tcctctatgg gtaag                                             25

<210> SEQ ID NO 94
<211> LENGTH: 25
<212> TYPE: DNA

```
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (5)..(5)
<223> OTHER INFORMATION: n = Pseudoisocytosine
<220> FEATURE:
<221> NAME/KEY: misc_feature
<222> LOCATION: (7)..(8)
<223> OTHER INFORMATION: n = Pseudoisocytosine
<220> FEATURE:
<221> NAME/KEY: misc_feature
<222> LOCATION: (8)..(9)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 94
tnttntnncc tcttctagtt ggcat                                          25

<210> SEQ ID NO 95
<211> LENGTH: 27
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(5)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (9)..(10)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (27)..(27)
<223> OTHER INFORMATION: Linked to lys-lys-lys

<400> SEQUENCE: 95
ttnnntttnc tttcccttgt atctttt                                        27

<210> SEQ ID NO 96
<211> LENGTH: 61
<212> TYPE: DNA
<213> ORGANISM: Artificial Sequence
<220> FEATURE:
<223> OTHER INFORMATION: Synthetic Primer

<400> SEQUENCE: 96
ttctgtatct atattcatca taggaaacac caaagataat gttctcctta atggtgccag    60
``` g                                                              61

<210> SEQ ID NO 97
<211> LENGTH: 10
<212> TYPE: DNA
<213> ORGANISM: Artificial Sequence
<220> FEATURE:
<223> OTHER INFORMATION: Synthetic Primer

<400> SEQUENCE: 97
cttcctcttt                                                     10

<210> SEQ ID NO 98
<211> LENGTH: 10
<212> TYPE: DNA
<213> ORGANISM: Artificial Sequence
<220> FEATURE:
<223> OTHER INFORMATION: Synthetic Primer

<400> SEQUENCE: 98
tttctccttc                                                     10

<210> SEQ ID NO 99
<211> LENGTH: 18
<212> TYPE: DNA
<213> ORGANISM: Artificial Sequence
<220> FEATURE:
<223> OTHER INFORMATION: Synthetic Primer

<400> SEQUENCE: 99
tttctccttc agtgttca                                            18

<210> SEQ ID NO 100
<211> LENGTH: 7
<212> TYPE: DNA
<213> ORGANISM: Artificial Sequence
<220> FEATURE:
<223> OTHER INFORMATION: Synthetic Primer

<400> SEQUENCE: 100 ttttcct                                                         7

<210> SEQ ID NO 101
<211> LENGTH: 7
<212> TYPE: DNA
<213> ORGANISM: Artificial Sequence
<220> FEATURE:
<223> OTHER INFORMATION: Synthetic Primer

<400> SEQUENCE: 101 tcctttt                                                         7

<210> SEQ ID NO 102
<211> LENGTH: 20
<212> TYPE: DNA
<213> ORGANISM: Artificial Sequence
<220> FEATURE:
<223> OTHER INFORMATION: Synthetic Primer

<400> SEQUENCE: 102 tcctttgct cacctgtggt                                           20

<210> SEQ ID NO 103
<211> LENGTH: 10
<212> TYPE: DNA

```
<213> ORGANISM: Artificial Sequence
<220> FEATURE:
<223> OTHER INFORMATION: Synthetic Primer

<400> SEQUENCE: 103
tcttttttcc                                                              10

<210> SEQ ID NO 104
<211> LENGTH: 10
<212> TYPE: DNA
<213> ORGANISM: Artificial Sequence
<220> FEATURE:
<223> OTHER INFORMATION: Synthetic Primer

<400> SEQUENCE: 104
ccttttttct                                                              10

<210> SEQ ID NO 105
<211> LENGTH: 18
<212> TYPE: DNA
<213> ORGANISM: Artificial Sequence
<220> FEATURE:
<223> OTHER INFORMATION: Synthetic Primer

<400> SEQUENCE: 105
ccttttttct ggctaagt                                                     18

<210> SEQ ID NO 106
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine

<400> SEQUENCE: 106 nttnntnttt                                                              10

<210> SEQ ID NO 107
<211> LENGTH: 7
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(6)
<223> OTHER INFORMATION: n = Pseudoisocytosine

<400> SEQUENCE: 107 ttttnnt                                                                  7

<210> SEQ ID NO 108
<211> LENGTH: 10
<212> TYPE: DNA
<213> ORGANISM: Artificial Sequence
<220> FEATURE:
<223> OTHER INFORMATION: Synthetic Primer
```

```
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (9)..(10)
<223> OTHER INFORMATION: n = Pseudoisocytosine

<400> SEQUENCE: 108 tnttttttnn                                                              10

<210> SEQ ID NO 109
<211> LENGTH: 58
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: Optional phosphorothioate internucleoside
      linkage
<220> FEATURE:
<221> NAME/KEY: misc_feature
<222> LOCATION: (2)..(3)
<223> OTHER INFORMATION: Optional phosphorothioate internucleoside
      linkage
<220> FEATURE:
<221> NAME/KEY: misc_feature
<222> LOCATION: (3)..(4)
<223> OTHER INFORMATION: Optional phosphorothioate internucleoside
      linkage
<220> FEATURE:
<221> NAME/KEY: misc_feature
<222> LOCATION: (55)..(56)
<223> OTHER INFORMATION: Optional phosphorothioate internucleoside
      linkage
<220> FEATURE:
<221> NAME/KEY: misc_feature
<222> LOCATION: (56)..(57)
<223> OTHER INFORMATION: Optional phosphorothioate internucleoside
      linkage
<220> FEATURE:
<221> NAME/KEY: misc_feature
<222> LOCATION: (57)..(58)
<223> OTHER INFORMATION: Optional phosphorothioate internucleoside
      linkage

<400> SEQUENCE: 109
tgggattcaa taaccttgca gacagtggag gaaggccttt ggcgtgatac cacaggtg        58

<210> SEQ ID NO 110
<211> LENGTH: 7
<212> TYPE: DNA
<213> ORGANISM: Artificial Sequence
<220> FEATURE:
<223> OTHER INFORMATION: Synthetic Primer

<400> SEQUENCE: 110 tcttttt                                                                  7

<210> SEQ ID NO 111
<211> LENGTH: 7
<212> TYPE: DNA
<213> ORGANISM: Artificial Sequence
<220> FEATURE:
<223> OTHER INFORMATION: Synthetic Primer

<400> SEQUENCE: 111 tttttct                                                                  7
```

```
<210> SEQ ID NO 112
<211> LENGTH: 18
<212> TYPE: DNA
<213> ORGANISM: Artificial Sequence
<220> FEATURE:
<223> OTHER INFORMATION: Synthetic Primer

<400> SEQUENCE: 112
tttttctgta atttttaa                                                 18

<210> SEQ ID NO 113
<211> LENGTH: 9
<212> TYPE: DNA
<213> ORGANISM: Artificial Sequence
<220> FEATURE:
<223> OTHER INFORMATION: Synthetic Primer

<400> SEQUENCE: 113 tctctttct                                                            9

<210> SEQ ID NO 114
<211> LENGTH: 9
<212> TYPE: DNA
<213> ORGANISM: Artificial Sequence
<220> FEATURE:
<223> OTHER INFORMATION: Synthetic Primer

<400> SEQUENCE: 114 tctttctct                                                            9

<210> SEQ ID NO 115
<211> LENGTH: 17
<212> TYPE: DNA
<213> ORGANISM: Artificial Sequence
<220> FEATURE:
<223> OTHER INFORMATION: Synthetic Primer

<400> SEQUENCE: 115
tctttctctg caaactt                                                  17

<210> SEQ ID NO 116
<211> LENGTH: 7
<212> TYPE: DNA
<213> ORGANISM: Artificial Sequence
<220> FEATURE:
<223> OTHER INFORMATION: Synthetic Primer

<400> SEQUENCE: 116 tttcttt                                                              7

<210> SEQ ID NO 117
<211> LENGTH: 18
<212> TYPE: DNA
<213> ORGANISM: Artificial Sequence
<220> FEATURE:
<223> OTHER INFORMATION: Synthetic Primer

<400> SEQUENCE: 117
tttctttaag aacgagca                                                 18

<210> SEQ ID NO 118
<211> LENGTH: 7
<212> TYPE: DNA
<213> ORGANISM: Artificial Sequence
<220> FEATURE:
<223> OTHER INFORMATION: Synthetic Primer
```

```
<220> FEATURE:
<221> NAME/KEY: misc_feature
<222> LOCATION: (2)..(2)
<223> OTHER INFORMATION: n = Pseudoisocytosine

<400> SEQUENCE: 118 tntttt                                                                      7

<210> SEQ ID NO 119
<211> LENGTH: 9
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (8)..(8)
<223> OTHER INFORMATION: n = Pseudoisocytosine

<400> SEQUENCE: 119 tntntttnt                                                                   9

<210> SEQ ID NO 120
<211> LENGTH: 7
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: n = Pseudoisocytosine

<400> SEQUENCE: 120 tttnttt                                                                     7

<210> SEQ ID NO 121
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 121 tnttttttt ttctgtaatt tttaa                                                 25
```

```
<210> SEQ ID NO 122
<211> LENGTH: 26
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (8)..(8)
<223> OTHER INFORMATION: n = Pseudoisocytosine
<220> FEATURE:
<221> NAME/KEY: misc_feature
<222> LOCATION: (9)..(10)
<223> OTHER INFORMATION: Linked by three 8-amino-2, 6, 10-trioxaoctanoic
     acid, three 8-amino-3,6-dioxaoctanoic acid, or three 6-
     aminohexanoic acid molecules
<220> FEATURE:
<221> NAME/KEY: misc_feature
<222> LOCATION: (26)..(26)
<223> OTHER INFORMATION: Linked to lys-lys-lys

<400> SEQUENCE: 122
tntntttntt ctttctctgc aaactt                                          26

<210> SEQ ID NO 123
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
     acid, three 8-amino-3,6-dioxaoctanoic acid, or three 6-
     aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 123
tttntttttt ctttaagaac gagca                                           25

<210> SEQ ID NO 124
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: Optional phosphorothioate internucleoside
```

```
          linkage
<220> FEATURE:
<221> NAME/KEY: misc_feature
<222> LOCATION: (2)..(3)
<223> OTHER INFORMATION: Optional phosphorothioate internucleoside
      linkage
<220> FEATURE:
<221> NAME/KEY: misc_feature
<222> LOCATION: (3)..(4)
<223> OTHER INFORMATION: Optional phosphorothioate internucleoside
      linkage
<220> FEATURE:
<221> NAME/KEY: misc_feature
<222> LOCATION: (57)..(58)
<223> OTHER INFORMATION: Optional phosphorothioate internucleoside
      linkage
<220> FEATURE:
<221> NAME/KEY: misc_feature
<222> LOCATION: (58)..(59)
<223> OTHER INFORMATION: Optional phosphorothioate internucleoside
      linkage
<220> FEATURE:
<221> NAME/KEY: misc_feature
<222> LOCATION: (59)..(60)
<223> OTHER INFORMATION: Optional phosphorothioate internucleoside
      linkage

<400> SEQUENCE: 124
aagtttgcag agaaagataa tatagtcctt ggagaaggag gaatcaccct gagtggaggt    60

<210> SEQ ID NO 125
<211> LENGTH: 10
<212> TYPE: DNA
<213> ORGANISM: Artificial Sequence
<220> FEATURE:
<223> OTHER INFORMATION: Synthetic Primer

<400> SEQUENCE: 125
ctcttcttct                                                           10

<210> SEQ ID NO 126
<211> LENGTH: 10
<212> TYPE: DNA
<213> ORGANISM: Artificial Sequence
<220> FEATURE:
<223> OTHER INFORMATION: Synthetic Primer

<400> SEQUENCE: 126
tcttcttctc                                                           10

<210> SEQ ID NO 127
<211> LENGTH: 15
<212> TYPE: DNA
<213> ORGANISM: Artificial Sequence
<220> FEATURE:
<223> OTHER INFORMATION: Synthetic Primer

<400> SEQUENCE: 127
tcttcttctc atttc                                                     15

<210> SEQ ID NO 128
<211> LENGTH: 5
<212> TYPE: DNA
<213> ORGANISM: Artificial Sequence
<220> FEATURE:
<223> OTHER INFORMATION: Synthetic Primer

<400> SEQUENCE: 128 cttct                                                                 5
```

```
<210> SEQ ID NO 129
<211> LENGTH: 5
<212> TYPE: DNA
<213> ORGANISM: Artificial Sequence
<220> FEATURE:
<223> OTHER INFORMATION: Synthetic Primer

<400> SEQUENCE: 129 tcttc                                                                    5

<210> SEQ ID NO 130
<211> LENGTH: 10
<212> TYPE: DNA
<213> ORGANISM: Artificial Sequence
<220> FEATURE:
<223> OTHER INFORMATION: Synthetic Primer

<400> SEQUENCE: 130
tcttcttctc                                                              10

<210> SEQ ID NO 131
<211> LENGTH: 15
<212> TYPE: DNA
<213> ORGANISM: Artificial Sequence
<220> FEATURE:
<223> OTHER INFORMATION: Synthetic Primer

<400> SEQUENCE: 131
tcttcttctc atttc                                                        15

<210> SEQ ID NO 132
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (3)..(3)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine

<400> SEQUENCE: 132 ntnttnttnt                                                              10

<210> SEQ ID NO 133
<211> LENGTH: 5
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
```

<400> SEQUENCE: 133 nttnt                                                                                      5

<210> SEQ ID NO 134
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (3)..(3)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 134
ntnttnttnt tcttcttctc atttc                                                                25

<210> SEQ ID NO 135
<211> LENGTH: 20
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (5)..(6)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (20)..(20)
<223> OTHER INFORMATION: Linked to lys-lys-lys

<400> SEQUENCE: 135

```
nttnttcttc ttctcatttc                                          20
```

<210> SEQ ID NO 136
<211> LENGTH: 60
<212> TYPE: DNA
<213> ORGANISM: Artificial Sequence
<220> FEATURE:
<223> OTHER INFORMATION: Synthetic Primer

<400> SEQUENCE: 136

```
attcccgagt agcagatgac catgacagct tagggcagga ccagccccaa gatgactatc    60
```

<210> SEQ ID NO 137
<211> LENGTH: 60
<212> TYPE: DNA
<213> ORGANISM: Artificial Sequence
<220> FEATURE:
<223> OTHER INFORMATION: Synthetic Primer

<400> SEQUENCE: 137

```
tttaggattc ccgagtagca gatgacccct cagagcagcg gcaggaccag ccccaagatg    60
```

<210> SEQ ID NO 138
<211> LENGTH: 65
<212> TYPE: DNA
<213> ORGANISM: Artificial Sequence
<220> FEATURE:
<223> OTHER INFORMATION: Synthetic Primer

<400> SEQUENCE: 138

```
gatgactatc tttaatgtct ggaaattctt ccagaattaa ttaagactgt atggaaaatg    60
agagc                                                               65
```

<210> SEQ ID NO 139
<211> LENGTH: 66
<212> TYPE: DNA
<213> ORGANISM: Artificial Sequence
<220> FEATURE:
<223> OTHER INFORMATION: Synthetic Primer

<400> SEQUENCE: 139

```
ccccaagatg actatcttta atgtctggaa cgatcatcag aattgatact gactgtatgg    60
aaaatg                                                              66
```

<210> SEQ ID NO 140
<211> LENGTH: 65
<212> TYPE: DNA
<213> ORGANISM: Artificial Sequence
<220> FEATURE:
<223> OTHER INFORMATION: Synthetic Primer

<400> SEQUENCE: 140

```
gatgactatc tttaatgtct ggaaattcta ctagaattga tactgactgt atggaaaatg    60
agagc                                                               65
```

<210> SEQ ID NO 141
<211> LENGTH: 12
<212> TYPE: DNA
<213> ORGANISM: Artificial Sequence
<220> FEATURE:
<223> OTHER INFORMATION: Synthetic Primer

<400> SEQUENCE: 141

```
ctgctcggaa ga                                                       12
```

```
<210> SEQ ID NO 142
<211> LENGTH: 12
<212> TYPE: DNA
<213> ORGANISM: Artificial Sequence
<220> FEATURE:
<223> OTHER INFORMATION: Synthetic Primer

<400> SEQUENCE: 142
tcttccgagc ag                                                         12

<210> SEQ ID NO 143
<211> LENGTH: 15
<212> TYPE: DNA
<213> ORGANISM: Artificial Sequence
<220> FEATURE:
<223> OTHER INFORMATION: Synthetic Primer

<400> SEQUENCE: 143
ccttcaccaa gggga                                                      15

<210> SEQ ID NO 144
<211> LENGTH: 15
<212> TYPE: DNA
<213> ORGANISM: Artificial Sequence
<220> FEATURE:
<223> OTHER INFORMATION: Synthetic Primer

<400> SEQUENCE: 144 tcccttggt gaagg                                                       15

<210> SEQ ID NO 145
<211> LENGTH: 7
<212> TYPE: DNA
<213> ORGANISM: Artificial Sequence
<220> FEATURE:
<223> OTHER INFORMATION: Synthetic Primer

<400> SEQUENCE: 145 ttcccct                                                               7

<210> SEQ ID NO 146
<211> LENGTH: 7
<212> TYPE: DNA
<213> ORGANISM: Artificial Sequence
<220> FEATURE:
<223> OTHER INFORMATION: Synthetic Primer

<400> SEQUENCE: 146 tcccctt                                                               7

<210> SEQ ID NO 147
<211> LENGTH: 15
<212> TYPE: DNA
<213> ORGANISM: Artificial Sequence
<220> FEATURE:
<223> OTHER INFORMATION: Synthetic Primer

<400> SEQUENCE: 147 tcccctttggt gaagg                                                     15

<210> SEQ ID NO 148
<211> LENGTH: 7
<212> TYPE: DNA
<213> ORGANISM: Artificial Sequence
<220> FEATURE:
```

```
<223> OTHER INFORMATION: Synthetic Primer
<220> FEATURE:
<221> NAME/KEY: misc_feature
<222> LOCATION: (3)..(6)
<223> OTHER INFORMATION: n = Pseudoisocytosine

<400> SEQUENCE: 148 ttnnnnt                                                               7

<210> SEQ ID NO 149
<211> LENGTH: 63
<212> TYPE: DNA
<213> ORGANISM: Artificial Sequence
<220> FEATURE:
<223> OTHER INFORMATION: Synthetic PRimer

<400> SEQUENCE: 149
aggacggtcc cggcctgcga cacttccgcc cataattgtt cttcatctgc ggggcggggg    60
ggg                                                                  63

<210> SEQ ID NO 150
<211> LENGTH: 6
<212> TYPE: DNA
<213> ORGANISM: Artificial Sequence
<220> FEATURE:
<223> OTHER INFORMATION: Synthetic Primer

<400> SEQUENCE: 150 ccttct                                                                6

<210> SEQ ID NO 151
<211> LENGTH: 6
<212> TYPE: DNA
<213> ORGANISM: Artificial Sequence
<220> FEATURE:
<223> OTHER INFORMATION: Synthetic Primer

<400> SEQUENCE: 151 tcttcc                                                                6

<210> SEQ ID NO 152
<211> LENGTH: 12
<212> TYPE: DNA
<213> ORGANISM: Artificial Sequence
<220> FEATURE:
<223> OTHER INFORMATION: Synthetic Primer

<400> SEQUENCE: 152
tcttccgagc ag                                                        12

<210> SEQ ID NO 153
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (5)..(5)
<223> OTHER INFORMATION: n = Pseudoisocytosine
```

```
<220> FEATURE:
<221> NAME/KEY: misc_feature
<222> LOCATION: (6)..(7)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (18)..(18)
<223> OTHER INFORMATION: Linked to lys-lys-lys

<400> SEQUENCE: 153
nnttnttctt ccgagcag                                                    18

<210> SEQ ID NO 154
<211> LENGTH: 67
<212> TYPE: DNA
<213> ORGANISM: Artificial Sequence
<220> FEATURE:
<223> OTHER INFORMATION: Synthetic Primer

<400> SEQUENCE: 154
gggacggcgc ccacataggc caaattcaat tgctgatccc agcttaagac gtactggtca     60
gcctggc                                                                67

<210> SEQ ID NO 155
<211> LENGTH: 28
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (28)..(28)
<223> OTHER INFORMATION: Linked to lys-lys-lys

<400> SEQUENCE: 155
nttnntnttt tttctccttc agtgttca                                         28

<210> SEQ ID NO 156
<211> LENGTH: 27
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
```

```
<221> NAME/KEY: misc_feature
<222> LOCATION: (5)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (27)..(27)
<223> OTHER INFORMATION: Linked to lys-lys-lys

<400> SEQUENCE: 156
ttttnnttcc ttttgctcac ctgtggt                                            27

<210> SEQ ID NO 157
<211> LENGTH: 28
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (9)..(10)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (28)..(28)
<223> OTHER INFORMATION: Linked to lys-lys-lys

<400> SEQUENCE: 157
tnttttttnn cctttttttct ggctaagt                                          28

<210> SEQ ID NO 158
<211> LENGTH: 30
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(3)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (10)..(10)
<223> OTHER INFORMATION: n = Pseudoisocytosine
<220> FEATURE:
<221> NAME/KEY: misc_feature
<222> LOCATION: (12)..(12)
<223> OTHER INFORMATION: n = Pseudoisocytosine
```

```
<220> FEATURE:
<221> NAME/KEY: misc_feature
<222> LOCATION: (12)..(13)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (30)..(30)
<223> OTHER INFORMATION: Linked to lys-lys-lys

<400> SEQUENCE: 158
ttntttnttn tnctcttctt tcttgacagg                                    30

<210> SEQ ID NO 159
<211> LENGTH: 22
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (22)..(22)
<223> OTHER INFORMATION: Linked to lys-lys-lys

<400> SEQUENCE: 159
ttnnnnttcc ccttggtgaa gg                                            22

<210> SEQ ID NO 160
<211> LENGTH: 22
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (22)..(22)
<223> OTHER INFORMATION: Linked to lys-lys-lys
```

```
<400> SEQUENCE: 160 nntnttncttctccaaaggagt                                          22

<210> SEQ ID NO 161
<211> LENGTH: 65
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: phosphorothioate internucleoside linkage
<220> FEATURE:
<221> NAME/KEY: misc_feature
<222> LOCATION: (2)..(3)
<223> OTHER INFORMATION: phosphorothioate internucleoside linkage
<220> FEATURE:
<221> NAME/KEY: misc_feature
<222> LOCATION: (3)..(4)
<223> OTHER INFORMATION: phosphorothioate internucleoside linkage
<220> FEATURE:
<221> NAME/KEY: misc_feature
<222> LOCATION: (62)..(63)
<223> OTHER INFORMATION: phosphorothioate internucleoside linkage
<220> FEATURE:
<221> NAME/KEY: misc_feature
<222> LOCATION: (63)..(64)
<223> OTHER INFORMATION: phosphorothioate internucleoside linkage
<220> FEATURE:
<221> NAME/KEY: misc_feature
<222> LOCATION: (64)..(65)
<223> OTHER INFORMATION: phosphorothioate internucleoside linkage

<400> SEQUENCE: 161
ttgccccaca gggcagtaac ggcagacttc tcctcaggag tcaggtgcac catggtgtct    60
gtttg                                                                65

<210> SEQ ID NO 162
<211> LENGTH: 30
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (5)..(5)
<223> OTHER INFORMATION: n = Pseudoisocytosine
<220> FEATURE:
<221> NAME/KEY: misc_feature
<222> LOCATION: (9)..(9)
<223> OTHER INFORMATION: n = Pseudoisocytosine
<220> FEATURE:
<221> NAME/KEY: misc_feature
<222> LOCATION: (11)..(11)
<223> OTHER INFORMATION: n = Pseudoisocytosine
<220> FEATURE:
<221> NAME/KEY: misc_feature
<222> LOCATION: (12)..(13)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (30)..(30)
<223> OTHER INFORMATION: Linked to lys-lys-lys
```

-continued

<400> SEQUENCE: 162
ntttntttnt nttctctttc tttcagggca                               30

<210> SEQ ID NO 163
<211> LENGTH: 10
<212> TYPE: DNA
<213> ORGANISM: Artificial Sequence
<220> FEATURE:
<223> OTHER INFORMATION: Synthetic Primer

<400> SEQUENCE: 163
gaaggagaaa                                                    10

<210> SEQ ID NO 164
<211> LENGTH: 7
<212> TYPE: DNA
<213> ORGANISM: Artificial Sequence
<220> FEATURE:
<223> OTHER INFORMATION: Synthetic Primer

<400> SEQUENCE: 164 aaaagga                                                        7

<210> SEQ ID NO 165
<211> LENGTH: 9
<212> TYPE: DNA
<213> ORGANISM: Artificial Sequence
<220> FEATURE:
<223> OTHER INFORMATION: Synthetic Primer

<400> SEQUENCE: 165 agaaaaaag                                                      9

<210> SEQ ID NO 166
<211> LENGTH: 7
<212> TYPE: DNA
<213> ORGANISM: Artificial Sequence
<220> FEATURE:
<223> OTHER INFORMATION: Synthetic Primer

<400> SEQUENCE: 166 agaaaaa                                                        7

<210> SEQ ID NO 167
<211> LENGTH: 9
<212> TYPE: DNA
<213> ORGANISM: Artificial Sequence
<220> FEATURE:
<223> OTHER INFORMATION: Synthetic Primer

<400> SEQUENCE: 167 agagaaaga                                                      9

<210> SEQ ID NO 168
<211> LENGTH: 7
<212> TYPE: DNA
<213> ORGANISM: Artificial Sequence
<220> FEATURE:
<223> OTHER INFORMATION: Synthetic Primer

<400> SEQUENCE: 168 aaagaaa                                                        7

<210> SEQ ID NO 169

```
<211> LENGTH: 28
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(1)
<223> OTHER INFORMATION: n = Pseudoisocytosine
<220> FEATURE:
<221> NAME/KEY: misc_feature
<222> LOCATION: (4)..(5)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (28)..(28)
<223> OTHER INFORMATION: Linked to lys-lys-lys

<400> SEQUENCE: 169
nttnntnttt tttctccttc agtgttca                                        28

<210> SEQ ID NO 170
<211> LENGTH: 27
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (5)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (27)..(27)
<223> OTHER INFORMATION: Linked to lys-lys-lys

<400> SEQUENCE: 170
ttttnnttcc ttttgctcac ctgtggt                                         27

<210> SEQ ID NO 171
<211> LENGTH: 28
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
```

```
<222> LOCATION: (2)..(2)
<223> OTHER INFORMATION: n = Pseudoisocytosine
<220> FEATURE:
<221> NAME/KEY: misc_feature
<222> LOCATION: (9)..(10)
<223> OTHER INFORMATION: n = Pseudoisocytosine
<220> FEATURE:
<221> NAME/KEY: misc_feature
<222> LOCATION: (10)..(11)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (28)..(28)
<223> OTHER INFORMATION: Linked to lys-lys-lys

<400> SEQUENCE: 171 tntttttnn ccttttttct ggctaagt                                          28

<210> SEQ ID NO 172
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 172 tnttttttt ttctgtaatt tttaa                                             25

<210> SEQ ID NO 173
<211> LENGTH: 26
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (8)..(8)
<223> OTHER INFORMATION: n = Pseudoisocytosine
<220> FEATURE:
<221> NAME/KEY: misc_feature
<222> LOCATION: (9)..(10)
<223> OTHER INFORMATION: Linked by three 8-amino-2, 6, 10-trioxaoctanoic
      acid, three 8-amino-3,6-dioxaoctanoic acid, or three 6-
``` aminohexanoic acid molecules
<220> FEATURE:
<221> NAME/KEY: misc_feature
<222> LOCATION: (26)..(26)
<223> OTHER INFORMATION: Linked to lys-lys-lys

<400> SEQUENCE: 173
tntntttntt ctttctctgc aaactt                                              26

<210> SEQ ID NO 174
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
    acid, three 8-amino-3,6-dioxaoctanoic acid, or three 6-
    aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 174
tttntttttt ctttaagaac gagca                                               25

<210> SEQ ID NO 175
<211> LENGTH: 60
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: Optional phosphorothioate internucleoside
    linkage
<220> FEATURE:
<221> NAME/KEY: misc_feature
<222> LOCATION: (2)..(3)
<223> OTHER INFORMATION: Optional phosphorothioate internucleoside
    linkage
<220> FEATURE:
<221> NAME/KEY: misc_feature
<222> LOCATION: (3)..(4)
<223> OTHER INFORMATION: Optional phosphorothioate internucleoside
    linkage
<220> FEATURE:
<221> NAME/KEY: misc_feature
<222> LOCATION: (57)..(58)
<223> OTHER INFORMATION: Optional phosphorothioate internucleoside
    linkage
<220> FEATURE:
<221> NAME/KEY: misc_feature
<222> LOCATION: (58)..(59)
<223> OTHER INFORMATION: Optional phosphorothioate internucleoside
    linkage
<220> FEATURE:
<221> NAME/KEY: misc_feature
<222> LOCATION: (59)..(60)
<223> OTHER INFORMATION: Optional phosphorothioate internucleoside
    linkage

<400> SEQUENCE: 175
aaagaataac agtgataatt tctgggttaa ggcaatagca atatctctgc atataaatat    60

<210> SEQ ID NO 176
<211> LENGTH: 20
<212> TYPE: DNA
<213> ORGANISM: Artificial Sequence
<220> FEATURE:
<223> OTHER INFORMATION: Synthetic Primer

<400> SEQUENCE: 176
ttgggaaatt tttaaggcga    20

<210> SEQ ID NO 177
<211> LENGTH: 25
<212> TYPE: DNA
<213> ORGANISM: Artificial Sequence
<220> FEATURE:
<223> OTHER INFORMATION: Synthetic Primer

<400> SEQUENCE: 177
tgatgacatc aagaaggtgg tgaag    25

<210> SEQ ID NO 178
<211> LENGTH: 23
<212> TYPE: DNA
<213> ORGANISM: Artificial Sequence
<220> FEATURE:
<223> OTHER INFORMATION: Synthetic Primer

<400> SEQUENCE: 178
tccttggagg ccatgtgggc cat    23

<210> SEQ ID NO 179
<211> LENGTH: 20
<212> TYPE: DNA
<213> ORGANISM: Artificial Sequence
<220> FEATURE:
<223> OTHER INFORMATION: Synthetic Primer

<400> SEQUENCE: 179
tatcatgcct ctttgcacca    20

<210> SEQ ID NO 180
<211> LENGTH: 24
<212> TYPE: DNA
<213> ORGANISM: Artificial Sequence
<220> FEATURE:
<223> OTHER INFORMATION: Synthetic Primer

<400> SEQUENCE: 180
agcaatatga aacctcttac atca    24

<210> SEQ ID NO 181
<211> LENGTH: 23
<212> TYPE: DNA
<213> ORGANISM: Artificial Sequence
<220> FEATURE:
<223> OTHER INFORMATION: Synthetic Primer

<400> SEQUENCE: 181
agataattat tgcctcccac tgc    23

<210> SEQ ID NO 182
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 182
aatggaaggg catgcagtca                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic Primer

<400> SEQUENCE: 183
cccaatcctg aatcctggct                                               20

<210> SEQ ID NO 184
<211> LENGTH: 22
<212> TYPE: DNA
<213> ORGANISM: Artificial Sequence
<220> FEATURE:
<223> OTHER INFORMATION: Synthetic Primer

<400> SEQUENCE: 184
catactgatg tctgtggctt ga                                            22

<210> SEQ ID NO 185
<211> LENGTH: 21
<212> TYPE: DNA
<213> ORGANISM: Artificial Sequence
<220> FEATURE:
<223> OTHER INFORMATION: Synthetic Primer

<400> SEQUENCE: 185
aagctcaaac ctaccagacc a                                             21

<210> SEQ ID NO 186
<211> LENGTH: 21
<212> TYPE: DNA
<213> ORGANISM: Artificial Sequence
<220> FEATURE:
<223> OTHER INFORMATION: Synthetic Primer

<400> SEQUENCE: 186
agctggaagc ttcttcagtc a                                             21

<210> SEQ ID NO 187
<211> LENGTH: 20
<212> TYPE: DNA
<213> ORGANISM: Artificial Sequence
<220> FEATURE:
<223> OTHER INFORMATION: Synthetic Primer

<400> SEQUENCE: 187
ccctctgtgg actgaggaag                                               20

<210> SEQ ID NO 188
<211> LENGTH: 21
<212> TYPE: DNA
<213> ORGANISM: Artificial Sequence
<220> FEATURE:
<223> OTHER INFORMATION: Synthetic Primer

<400> SEQUENCE: 188
tgatgagcta cgggtatgtg a                                             21
```

<210> SEQ ID NO 189
<211> LENGTH: 23
<212> TYPE: DNA
<213> ORGANISM: Artificial Sequence
<220> FEATURE:
<223> OTHER INFORMATION: Synthetic Primer

<400> SEQUENCE: 189
caaaaagcct taagcaaaca ctc                                              23

<210> SEQ ID NO 190
<211> LENGTH: 22
<212> TYPE: DNA
<213> ORGANISM: Artificial Sequence
<220> FEATURE:
<223> OTHER INFORMATION: Synthetic Primer

<400> SEQUENCE: 190
tctctccctc agcatctatt cc                                               22

<210> SEQ ID NO 191
<211> LENGTH: 25
<212> TYPE: DNA
<213> ORGANISM: Artificial Sequence
<220> FEATURE:
<223> OTHER INFORMATION: Synthetic Primer

<400> SEQUENCE: 191
tgtgtttgtt tatggatact tgagc                                            25

<210> SEQ ID NO 192
<211> LENGTH: 20
<212> TYPE: DNA
<213> ORGANISM: Artificial Sequence
<220> FEATURE:
<223> OTHER INFORMATION: Synthetic Primer

<400> SEQUENCE: 192
gcatgcacaa taaaggcact                                                  20

<210> SEQ ID NO 193
<211> LENGTH: 22
<212> TYPE: DNA
<213> ORGANISM: Artificial Sequence
<220> FEATURE:
<223> OTHER INFORMATION: Synthetic Primer

<400> SEQUENCE: 193
catgggaaac agtcaaaaga aa                                               22

<210> SEQ ID NO 194
<211> LENGTH: 20
<212> TYPE: DNA
<213> ORGANISM: Artificial Sequence
<220> FEATURE:
<223> OTHER INFORMATION: Synthetic Primer

<400> SEQUENCE: 194
tgtaggtttc cccacagctt                                                  20

<210> SEQ ID NO 195
<211> LENGTH: 18
<212> TYPE: DNA
<213> ORGANISM: Artificial Sequence
<220> FEATURE:

<223> OTHER INFORMATION: Synthetic Primer

<400> SEQUENCE: 195
tgccctgaaa gaaagaga                                                 18

<210> SEQ ID NO 196
<211> LENGTH: 18
<212> TYPE: DNA
<213> ORGANISM: Artificial Sequence
<220> FEATURE:
<223> OTHER INFORMATION: Synthetic Primer

<400> SEQUENCE: 196
agccctgaaa gaaagaga                                                 18

<210> SEQ ID NO 197
<211> LENGTH: 18
<212> TYPE: DNA
<213> ORGANISM: Artificial Sequence
<220> FEATURE:
<223> OTHER INFORMATION: Synthetic Primer

<400> SEQUENCE: 197
gaacctgaaa gaaagaga                                                 18

<210> SEQ ID NO 198
<211> LENGTH: 18
<212> TYPE: DNA
<213> ORGANISM: Artificial Sequence
<220> FEATURE:
<223> OTHER INFORMATION: Synthetic Primer

<400> SEQUENCE: 198
caccctgaaa gaaagaaa                                                 18

<210> SEQ ID NO 199
<211> LENGTH: 18
<212> TYPE: DNA
<213> ORGANISM: Artificial Sequence
<220> FEATURE:
<223> OTHER INFORMATION: Synthetic Peptide

<400> SEQUENCE: 199
aagcctgaaa gaaagagt                                                 18

<210> SEQ ID NO 200
<211> LENGTH: 18
<212> TYPE: DNA
<213> ORGANISM: Artificial Sequence
<220> FEATURE:
<223> OTHER INFORMATION: Synthetic Primer

<400> SEQUENCE: 200
agaaatgaaa gaaagaga                                                 18

<210> SEQ ID NO 201
<211> LENGTH: 18
<212> TYPE: DNA
<213> ORGANISM: Artificial Sequence
<220> FEATURE:
<223> OTHER INFORMATION: Synthetic Primer

<400> SEQUENCE: 201
ggtggtgaaa gaaagaga                                                 18

```
<210> SEQ ID NO 202
<211> LENGTH: 18
<212> TYPE: DNA
<213> ORGANISM: Artificial Sequence
<220> FEATURE:
<223> OTHER INFORMATION: Synthetic Primer

<400> SEQUENCE: 202
aggactgaaa gaaagagt                                                 18

<210> SEQ ID NO 203
<211> LENGTH: 20
<212> TYPE: DNA
<213> ORGANISM: Artificial Sequence
<220> FEATURE:
<223> OTHER INFORMATION: Synthetic Primer

<400> SEQUENCE: 203
gttcataacc gtggggctta                                               20

<210> SEQ ID NO 204
<211> LENGTH: 65
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(2)
<223> OTHER INFORMATION: Optional phosphorothioate internucleoside
      linkage
<220> FEATURE:
<221> NAME/KEY: misc_feature
<222> LOCATION: (2)..(3)
<223> OTHER INFORMATION: Optional phosphorothioate internucleoside
      linkage
<220> FEATURE:
<221> NAME/KEY: misc_feature
<222> LOCATION: (3)..(4)
<223> OTHER INFORMATION: Optional phosphorothioate internucleoside
      linkage
<220> FEATURE:
<221> NAME/KEY: misc_feature
<222> LOCATION: (62)..(63)
<223> OTHER INFORMATION: Optional phosphorothioate internucleoside
      linkage
<220> FEATURE:
<221> NAME/KEY: misc_feature
<222> LOCATION: (63)..(64)
<223> OTHER INFORMATION: Optional phosphorothioate internucleoside
      linkage
<220> FEATURE:
<221> NAME/KEY: misc_feature
<222> LOCATION: (64)..(65)
<223> OTHER INFORMATION: Optional phosphorothioate internucleoside
      linkage

<400> SEQUENCE: 204
ttgccccaca gggcagtaac ggcagacttc tcctcaggag tcaggtgcac catggtgtct   60
gtttg                                                               65

<210> SEQ ID NO 205
<211> LENGTH: 22
<212> TYPE: DNA
<213> ORGANISM: Artificial Sequence
<220> FEATURE:
<223> OTHER INFORMATION: Synthetic Primer

<400> SEQUENCE: 205
cttctccaca ggagtcaggt gc                                            22
```

```
<210> SEQ ID NO 206
<211> LENGTH: 29
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (29)..(29)
<223> OTHER INFORMATION: Linked to lys-lys-lys

<400> SEQUENCE: 206
nntnttnctt ctccacagga gtcaggtgc                                    29

<210> SEQ ID NO 207
<211> LENGTH: 29
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (29)..(29)
<223> OTHER INFORMATION: Linked to lys-lys-lys

<400> SEQUENCE: 207
nntnttnctt ctccacagga gtcaggtgc                                    29

<210> SEQ ID NO 208
<211> LENGTH: 29
```

```
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (29)..(29)
<223> OTHER INFORMATION: Linked to lys-lys-lys

<400> SEQUENCE: 208 nntnttncttctccacaggagtcaggtgc                                             29

<210> SEQ ID NO 209
<211> LENGTH: 29
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (29)..(29)
<223> OTHER INFORMATION: Linked to lys-lys-lys

<400> SEQUENCE: 209 nntnttncttctccacaggagtcaggtgc                                             29

<210> SEQ ID NO 210
<211> LENGTH: 25
<212> TYPE: DNA
<213> ORGANISM: Artificial Sequence
<220> FEATURE:
```

<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 210 nntnttncttctccacagga gtcag         25

<210> SEQ ID NO 211
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (1)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 211 nntnttncttctccacagga gtcag         25

<210> SEQ ID NO 212
<211> LENGTH: 18
<212> TYPE: DNA
<213> ORGANISM: Artificial Sequence
<220> FEATURE:
<223> OTHER INFORMATION: Synthetic Primer

<400> SEQUENCE: 212
tctccttaaa cctgtctt                                          18

<210> SEQ ID NO 213
<211> LENGTH: 25
<212> TYPE: DNA
<213> ORGANISM: Artificial Sequence
<220> FEATURE:
<223> OTHER INFORMATION: Synthetic Peptide Nucleic Acid
<220> FEATURE:
<221> NAME/KEY: misc_feature
<222> LOCATION: (1)..(1)
<223> OTHER INFORMATION: Linked to lys-lys-lys
<220> FEATURE:
<221> NAME/KEY: misc_feature
<222> LOCATION: (3)..(4)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine
<220> FEATURE:
<221> NAME/KEY: misc_feature
<222> LOCATION: (7)..(8)
<223> OTHER INFORMATION: Linked by three 8-amino-2, 6, 10-trioxaoctanoic
      acid, three 8-amino-3,6-dioxaoctanoic acid, or three 6-
      aminohexanoic acid molecules
<220> FEATURE:
<221> NAME/KEY: misc_feature
<222> LOCATION: (25)..(25)
<223> OTHER INFORMATION: Linked to lys-lys-lys

<400> SEQUENCE: 213
ttnntnttct ccttaaacct gtctt                                  25

<210> SEQ ID NO 214
<211> LENGTH: 7
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (3)..(4)
<223> OTHER INFORMATION: n = Pseudoisocytosine
<220> FEATURE:
<221> NAME/KEY: misc_feature
<222> LOCATION: (6)..(6)
<223> OTHER INFORMATION: n = Pseudoisocytosine

<400> SEQUENCE: 214 ttnntnt                                                      7

<210> SEQ ID NO 215
<211> LENGTH: 8
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (4)..(4)
<223> OTHER INFORMATION: n = Pseudoisocytosine
<220> FEATURE:
<221> NAME/KEY: misc_feature
<222> LOCATION: (7)..(7)
<223> OTHER INFORMATION: n = Pseudoisocytosine

<400> SEQUENCE: 215

```
tntnttnt                                                          8

<210> SEQ ID NO 216
<211> LENGTH: 8
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (2)..(2)
<223> OTHER INFORMATION: n = Pseudoisocytosine
<220> FEATURE:
<221> NAME/KEY: misc_feature
<222> LOCATION: (5)..(5)
<223> OTHER INFORMATION: n = Pseudoisocytosine
<220> FEATURE:
<221> NAME/KEY: misc_feature
<222> LOCATION: (7)..(8)
<223> OTHER INFORMATION: n = Pseudoisocytosine

<400> SEQUENCE: 216 tnttntnn                                                          8
```